US008952042B2

(12) United States Patent
Kremoser et al.

(10) Patent No.: US 8,952,042 B2
(45) Date of Patent: Feb. 10, 2015

(54) FXR (NR1H4) BINDING AND ACTIVITY MODULATING COMPOUNDS

(75) Inventors: Claus Kremoser, Heidelberg (DE); Ulrich Abel, Bad Homburg (DE); Christoph Steeneck, Dossenheim (DE); Olaf Kinzel, Heidelberg (DE)

(73) Assignee: Phenex Pharmaceuticals AG, Ludwigshafen (DE)

( * ) Notice: Subject to any disclaimer, the term of this patent is extended or adjusted under 35 U.S.C. 154(b) by 367 days.

(21) Appl. No.: 13/390,499

(22) PCT Filed: Aug. 19, 2010

(86) PCT No.: PCT/EP2010/005093
§ 371 (c)(1),
(2), (4) Date: Apr. 26, 2012

(87) PCT Pub. No.: WO2011/020615
PCT Pub. Date: Feb. 24, 2011

(65) Prior Publication Data
US 2012/0232116 A1  Sep. 13, 2012

Related U.S. Application Data

(60) Provisional application No. 61/235,117, filed on Aug. 19, 2009.

(30) Foreign Application Priority Data

Aug. 19, 2009  (EP) ..................... 09010676

(51) Int. Cl.
C07D 413/04 (2006.01)
C07D 413/14 (2006.01)
C07D 413/12 (2006.01)
C07D 261/08 (2006.01)
C07D 249/06 (2006.01)
A61K 31/4439 (2006.01)
A61K 31/422 (2006.01)
A61K 31/423 (2006.01)
A61K 31/4192 (2006.01)
A61K 31/42 (2006.01)

(52) U.S. Cl.
CPC ............ *C70D 261/08* (2013.01); *A61K 31/423* (2013.01); *A61K 31/4192* (2013.01); *A61K 31/42* (2013.01); *A61K 31/4439* (2013.01); *A61K 31/422* (2013.01); *C07D 249/06* (2013.01); *C07D 413/04* (2013.01); *C07D 413/12* (2013.01); *C07D 413/14* (2013.01)
USPC ........... 514/378; 514/341; 514/340; 514/359; 514/406; 546/272.1; 546/272.4; 546/275.4; 548/247; 548/255; 548/376.1

(58) Field of Classification Search
CPC .. C07D 413/04; C07D 413/14; C07D 413/12; C07D 261/08; C07D 249/06; A61K 31/4439; A61K 31/422; A61K 31/423; A61K 31/4192; A61K 31/42

USPC ........................ 514/341, 340, 378, 359, 406; 546/272.1, 272.4, 275.4; 548/247, 255, 548/376.1
See application file for complete search history.

(56) References Cited

FOREIGN PATENT DOCUMENTS

| WO | WO 00/37077 A1 | 6/2000 |
|---|---|---|
| WO | WO 03/015771 A1 | 2/2003 |
| WO | WO 03/080803 A2 | 10/2003 |
| WO | WO 2004/048349 A1 | 6/2004 |
| WO | WO 2004/087076 A2 | 10/2004 |
| WO | WO 2007/076260 A2 | 7/2007 |
| WO | WO 2007/092751 A2 | 8/2007 |
| WO | WO 2007/140174 A2 | 12/2007 |
| WO | WO 2007/140183 A1 | 12/2007 |
| WO | WO 2008/025539 A1 | 3/2008 |
| WO | WO 2008/025540 A1 | 3/2008 |
| WO | WO 2008/051942 A2 | 5/2008 |
| WO | WO 2008/157270 A1 | 12/2008 |
| WO | WO 2009/005998 A1 | 1/2009 |
| WO | WO 2009/012125 A1 | 1/2009 |

OTHER PUBLICATIONS

Hollman et al. Biochimica et Biophysica Acta 2012, 1821, 1443-1452.*
Niu et al. Acta Pharmaceutica Sinica B 2011, 1, 73-79.*
Cariou et al. Trends in Pharmacological Sciences 2007, 28, 236-243.*
Luo et al. Cell, 2009, 136, pp. 823-837.*
(Continued)

Primary Examiner — Joseph Kosack
Assistant Examiner — Matthew Coughlin
(74) Attorney, Agent, or Firm — Seed IP Law Group PLLC

(57) ABSTRACT

The present invention relates to compounds of formula (1):

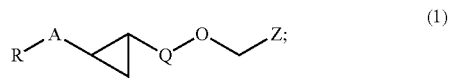

where R, A, Q and Z are defined herein, or an enantiomer, diastereomer, tautomer, solvate, prodrug or pharmaceutical acceptable salt thereof. These compounds bind to the NR1H4 receptor (FXR) and act as agonists of the NR1H4 receptor (FXR). The invention further relates to the use of the compounds for the preparation of a medicament for the treatment of diseases and/or conditions through binding of said nuclear receptor by said compounds, and to a process for the synthesis of said compounds.

9 Claims, 21 Drawing Sheets

(56) References Cited

OTHER PUBLICATIONS

De Gottardi et al. Molecular Cancer 2006, 48, 5, 1-10.*
Fujino et al. J. Biochem. 2012, 15, 677-586.*
Swales et al. Cancer Res. 2006, 66, 10120-10126.*
American Cancer Society, Breast Cancer Overview, obtained from http://www.cancer.org/cancer/breastcancer/overviewguide/breast-cancer-overview-prevention on Jun. 4, 2014.*
MayoClinic, Cirrhosis—Prevention, obtained from http://www.mayoclinic.org/diseases-conditions/cirrhosis/basics/prevention/con20031617 on Jun. 4, 2014.*
Abel et al., "Synthesis and pharmacological validation of a novel series of non-steroidal FXR agonists," *Bioorganic & Medicinal Chemistry Letters 20*: 4911-4917, 2010.
Akwabi-Ameyaw et al., "Conformationally constrained farnesoid X receptor (FXR) agonists: Naphthoic acid-based analogs of GW 4064," *Bioorg. Med. Chem. Lett. 18*(15): 4339-4343 (2008), doi:10.1016/j.bmcl.2008.06.073, 5 pages.
Alvarez et al., "Reduced hepatic expression of farnesoid X receptor in hereditary cholestasis associated to mutation in ATP8B1," *Human Molecular Genetics 13*(20): 2451-2460, 2004.
Anand et al., "Downregulation of TACO gene transcription restricts mycobacterial entry/survival within human macrophages," *FEMS Microbiology Letters 250*(1): 137-144, 2005, doi:10.1016/j.femsle.2005.06.056, 8 pages.
Ananthanarayanan et al., "Human Bile Salt Export Pump Promoter Is Transactivated by the Farnesoid X Receptor/Bile Acid Receptor," *The Journal of Biological Chemistry 276*(31): 28857-28865, Aug. 3, 2001.
Aranda et al., "Nuclear Hormone Receptors and Gene Expression," *Physiological Reviews 81*(3): 1269-1304, Jul. 2001.
Bilz et al., "Activation of the farnesoid X receptor improves lipid metabolism in combined hyperlipidemic hamsters," *Am. J. Physiol. Endocrinol. Metab 290*(4) E716-722, 2006, doi:10.1152/ajpendo.00355.2005, 24 pages.
Brzozowski et al., "Molecular basis of agonism and antagonism in the oestrogen receptor," *Nature 389*: 753-758, Oct. 16, 1997.
Buijsman et al., "Non-Steroidal Steroid Receptor Modulators," *Current Medicinal Chemistry 12*(9): 1017-1075, 2005.
Cai et al., "FXR: a target for cholestatic syndromes?" *Expert Opin. Ther. Targets 10*(3): 409-421, 2006.
Cariou et al., "The Farnesoid X Receptor Modulates Adiposity and Peripheral Insulin Sensitivity in Mice," *The Journal of Biological Chemistry 281*(16): 11039-11049, Apr. 21, 2006.
Chen et al., "Progressive Familial Intrahepatic Cholestasis, Type 1, Is Associated With Decreased Farnesoid X Receptor Activity," *Gastroenterology 126*: 756-764, Mar. 2004.
Claudel et al., "The Farnesoid X Receptor: A Molecular Link Between Bile Acid and Lipid and Glucose Metabolism," *Arteriosclerosis, Thrombosis, and Vascular Biology 25*(10): 2020-2031, 2005, obtained from URL=http://atvb.ahajournals.org, download date Jan. 19, 2012, 13 pages.
Doggrell, "New targets in and potential treatments for cholesterol gallstone disease," *Current Opinion in Investigational Drugs 7*(4): 344-348, 2006.
Duran-Sandoval et al., "Potential regulatory role of the farnesoid X receptor in the metabolic syndrome," *Biochimie 87*: 93-98, 2005.
Dyer et al., "A Noncommercial Dual Luciferase Enzyme Assay System for Reporter Gene Analysis," *Analytical Biochemistry 282*: 158-161, 2000.
Evans, "The Nuclear Receptor Superfamily: A Rosetta Stone for Physiology," *Molecular Endocrinology 19*(6): 1429-1438, Jun. 2005.
Figge et al., "Hepatic Overexpression of Murine Abcb11 Increases Hepatobiliary Lipid Secretion and Reduces Hepatic Steatosis," *The Journal of Biological Chemistry 279*(4): 2790-2799, Jan. 23, 2004.
Fiorucci et al., "The Nuclear Receptor SHP Mediates Inhibition of Hepatic Stellate Cells by FXR and Protects Against Liver Fibrosis," *Gastroenterology 127*(5): 1497-1512, Nov. 2004.
Fiorucci et al., "A Farnesoid X Receptor-Small Heterodimer Partner Regulatory Cascade Modulates Tissue Metalloproteinase Inhibitor-1 and Matrix Metalloprotease Expression in Hepatic Stellate Cells and Promotes Resolution of Liver Fibrosis," *The Journal of Pharmacology and Experimental Therapeutics 314*(2): 584-595, 2005.
Fiorucci et al., "Protective Effects of 6-Ethyl Chenodeoxycholic Acid, a Farnesoid X Receptor Ligand, in Estrogen-Induced Cholestasis," *The Journal of Pharmacology and Experimental Therapeutics 313*(2): 604-612, 2005.
Folch et al., "A Simple Method for the Isolation and Purification of Total Lipides From Animal Tissues," *The Journal of Biological Chemistry 226*(1): 497-509, May 1957.
Forman et al., "Identification of a Nuclear Receptor That Is Activated by Farnesol Metabolites," *Cell 81*: 687-693, Jun. 2, 1995.
Goodwin et al., "A Regulatory Cascade of the Nuclear Receptors FXR, SHP-1, and LRH-1 Represses Bile Acid Biosynthesis," *Molecular Cell 6*: 517-526, Sep. 2000.
Hanniman et al., "Loss of functional farnesoid X receptor increases atherosclerotic lesions in apolipoprotein E-deficient mice," *Journal of Lipid Research 46*: 2595-2604, 2005.
He et al., "Downregulation of Endothelin-1 by Farnesoid X Receptor in Vascular Endothelial Cells," *Circulation Research 98*(2): 192-199, 2006, plus online supplement, obtained from URL=http://circres.ahajournals.org, download date Jun. 11, 2012, 14 pages.
Heery et al., "A signature motif in transcriptional co-activators mediates binding to nuclear receptors," *Nature 387*: 733-736, Jun. 12, 1997.
Heinzel et al., "A complex containing N-CoR, mSin3 and histone deacetylase mediates transcriptional repression," *Nature 387*: 43-48, May 1, 1997.
Holt et al., "Definition of a novel growth factor-dependent signal cascade for the suppression of bile acid biosynthesis," *Genes & Development 17*: 1581-1591, 2003.
Huang et al., "Farnesoid X Receptor Activates Transcription of the Phospholipid Pump MDR3," *The Journal of Biological Chemistry 278*(51): 51085-51090, Dec. 19, 2003.
Huang et al., "Nuclear Receptor-Dependent Bile Acid Signaling Is Required for Normal Liver Regeneration," *Science 312*: 233-236, Apr. 14, 2006.
Inagaki et al., "Fibroblast growth factor 15 functions as an enterohepatic signal to regulate bile acid homeostasis," *Cell Metabolism 2*: 217-225, Oct. 2005.
Inagaki et al., "Regulation of antibacterial defense in the small intestine by the nuclear bile acid receptor," *Proc. Natl. Acad. Sci USA 103*(10): 3920-3905, 2006, doi:10.1073/pnas.0509592103, 6 pages.
Journe et al., "Association between farnesoid X receptor expression and cell proliferation in estrogen receptor-positive luminal-like breast cancer from postmenopausal patients," *Breast Cancer Res. Treat. 115*(3): 523-534, 2009, doi: 10.1007/s10549-008-0094-2, 13 pages.
Kast et al., "Farnesoid X-Activated Receptor Induces Apolipoprotein C-II Transcription: a Molecular Mechanism Linking Plasma Triglyceride Levels to Bile Acids," *Molecular Endocrinology 15*(10): 1720-1728, Oct. 2001.
Kast et al., "Regulation of Multidrug Resistance-associated Protein 2 (ABCC2) by the Nuclear Receptors Pregnane X Receptor, Farnesoid X-activated Receptor, and Constitutive Androstane Receptor," *The Journal of Biological Chemistry 277*(4): 2908-2915, Jan. 25, 2002.
Kim et al., "Spontaneous hepatocarcinogenesis in farnesoid X receptor-null mice," *Carcinogenesis 28*(5): 940-946, 2007.
Kuo et al., "Induction of Drug-Metabolizing Enzymes and Toxicity of *trans*-Stilbene Oxide in Rat Liver and Kidney," *Toxicology 22*: 149-160, 1981.
Lambert et al., "The Farnesoid X-receptor Is an Essential Regulator of Cholesterol Homeostasis," *The Journal of Biological Chemistry 278*(4): 2563-2570, Jan. 24, 2003.
Lebel et al., "Stereoselective Cyclopropanation Reactions," *Chemical Reviews 103*(4): 977-1050, 2003.
Liu et al., "Hepatoprotection by the farnesoid X receptor agonist GW4064 in rat models of intra-and extrahepatic cholestasis," *The Journal of Clinical Investigation 112*(11): 1678-1687, 2003, doi:10.1172/JCI200318945, 10 pages.
Lu et al., "Molecular Basis for Feedback Regulation of Bile Acid Synthesis by Nuclear Receptors," *Molecular Cell 6*: 507-515, Sep. 2000.

(56) References Cited

OTHER PUBLICATIONS

Ma et al., "Farnesoid X receptor is essential for normal glucose homeostasis," *The Journal of Clinical Investigation* 116(4): 1102-1109, 2006, doi:10.1172/JCI25604.

Makishima et al., "Identification of a Nuclear Receptor for Bile Acids," *Science* 284: 1362-1365, May 21, 1999.

Maloney et al., "Identification of a Chemical Tool for the Orphan Nuclear Receptor FXR," *Journal of Medicinal Chemistry* 43(16): 2971-2974, Aug. 10, 2000.

Mangelsdorf et al., "The Nuclear Receptor Superfamily: The Second Decade," *Cell* 83: 835-839, Dec. 15, 1995.

Maran et al., "FXR Deficiency in Mice Leads to Increased Intestinal Epithelial Cell Proliferation and Tumor Development," *American Society for Pharmacology and Experimental Therapeutics*, Published on Nov. 3, 2008 as DOI:10.1124/jpet.108.145409, 35 pages.

Miyata et al., "Role of Farnesoid X Receptor in the Enhancement of Canalicular Bile Acid Output and Excretion of Unconjugated Bile Acids: A Mechanism for Protection against Cholic Acid-Induced Liver Toxicity," *The Journal of Pharmacology and Experimental Therapeutics* 312(2): 759-766, 2005.

Modica et al., "Nuclear Bile Acid Receptor FXR Protects against Intestinal Tumorigenesis," *Cancer Res* 68(23): 9589-9594, Dec. 1, 2008.

Moschetta et al., "Prevention of cholesterol gallstone disease by FXR agonists in a mouse model," *Nature Medicine* 10(12): 1352-1358, Dec. 2004.

Nettles et al., "Ligand Control of Coregulator Recruitment to Nuclear Receptors," *Annu. Rev. Physiol.* 67: 309-333, 2005.

Parks et al., "Bile Acids: Natural Ligands for an Orphan Nuclear Receptor," *Science* 284: 1365-1368, May 21, 1999.

Pellicciari et al., "6α-Ethyl-Chenodeoxycholic Acid (6-ECDCA), a Potent and Selective FXR Agonist Endowed with Anticholestatic Activity," *Journal of Medicinal Chemistry* 45(17): 3569-3572, Aug. 15, 2002.

Plass et al., "Farnesoid X Receptor and Bile Salts Are Involved in Transcriptional Regulation of the Gene Encoding the Human Bile Salt Export Pump," *Hepatology* 35: 589-596, Mar. 2002.

Rizzo et al., "Role of FXR in Regulating Bile Acid Homeostasis and Relevance for Human Diseases," *Current Drug Targets—Immune, Endocrine & Metabolic Disorders* 5(3): 289-303, 2005.

Schena et al., "Mammalian Glucocorticoid Receptor Derivatives Enhance Transcription in Yeast," *Science* 241: 965-967, Aug. 19, 1988.

Sinal et al., "Targeted Disruption of the Nuclear Receptor FXR/BAR Impairs Bile Acid and Lipid Homeostasis," *Cell* 102: 731-744, Sep. 15, 2000.

Stayrook et al., "Regulation of Carbohydrate Metabolism by the Farnesoid X Receptor," *Endocrinology* 146(3): 984-991, 2005.

Sugihara et al., "Metabolic Activation of the Proestrogens *trans*-Stilbene and *trans*-Stilbene Oxide by Rat Liver Microsomes," *Toxicology and Applied Pharmacology* 167: 46-54, 2000.

Swales et al., "The Farnesoid X Receptor Is Expressed in Breast Cancer and Regulates Apoptosis and Aromatase Expression," *Cancer Res.* 66(20): 10120-10126, Oct. 15, 2006.

Tomlinson et al., "Transgenic Mice Expressing Human Fibroblast Growth Factor-19 Display Increased Metabolic Rate and Decreased Adiposity," *Endocrinology* 143(5): 1741-1747, May 2002.

Urizar et al., "The Farnesoid X-activated Receptor Mediates Bile Acid Activation of Phospholipid Transfer Protein Gene Expression," *The Journal of Biological Chemistry* 275(50): 39313-39317, Dec. 15, 2000.

Urizar et al., "A Natural Product That Lowers Cholesterol As an Antagonist Ligand for FXR," *Science* 296: 1703-1706, May 31, 2002.

Wang et al., "FXR: a metabolic regulator and cell protector," *Cell Research* 18(11): 1087-1095, 2008, doi: 10.1038/cr.2008.289, 9 pages.

Watanabe et al., "Bile acids lower triglyceride levels via a pathway involving FXR, SHP, and SREBP-1c," *The Journal of Clinical Investigation* 113(10): 1408-1418, May 2004.

Willson et al., "Chemical Genomics: Functional Analysis of Orphan Nuclear Receptors in the Regulation of Bile Acid Metabolism," *Medicinal Research Reviews* 21(6): 513-522, 2001.

Wittenburg et al., "FXR and ABCG5/ABCG8 as Determinants of Cholesterol Gallstone Formation From Quantitative Trait Locus Mapping in Mice," *Gastroenterology* 1256: 868-881, Sep. 2003.

Yang et al., "Spontaneous Development of Liver Tumors in the Absence of the Bile Acid Receptor Farnesoid X Receptor," *Cancer Res* 67(3): 863-867, Feb. 1, 2007.

Zhang et al., "Activation of the nuclear receptor FXR improves hyperglycemia and hyperlipidemia in diabetic mice," *PNAS* 103(4): 1006-1011, Jan. 24, 2006.

Zollner et al., "Role of Nuclear Receptors in the Adaptive Response to Bile Acids and Cholestasis: Pathogenetic and Therapeutic Considerations," *Molecular Pharmaceutics* 3(3): 231-251, 2006.

Pellicciari et al., "Potential therapeutic applications of farnesoid X receptor (FXR) modulators," *Expert Opin. Ther. Patents* 16(3): 333-341, 2006.

Colerangle, "Regulatory non-clinical photosafety evaluation—An attempt to merge the FDA and EMEA photosafety testing strategies," *Regul Toxicol Pharmacol.* Jul. 16, 2009, Abstract only, 1 page.

Cariou, "The farnesoid X receptor (FXR) as a new target in non-alcoholic steatohepatitis," *Diabetes & Metabolism* 34: 685-691, 2008.

Chen et al., "FXR Agonist, GW4064, Reverses Metabolic Defects in High-Fat Diet Fed Mice," American Diabetes Association (ADA) 66th annual scientific sessions, Jun. 2006, Abstract No. 856-P, 1 page.

Henry et al., "Can light absorption and photostability data be used to assess the photosafety risks in patients for a new drug molecule?," *Journal of Photochemistry and Photobiology B: Biology* 96: 57-62, 2009.

Lívero et al., "The FXR agonist 6ECDCA reduces hepatic steatosis and oxidative stress induced by ethanol and low-protein diet in mice," *Chemico-Biological Interactions* 217: 19-27, 2014.

Ma et al., "Synthetic FXR Agonist GW4064 Prevents Diet-Induced Hepatic Steatosis and Insulin Resistance," *Pharm. Res.* 30: 1447-1457, 2013.

Maran et al., "FXR Deficiency in Mice Leads to Increased Intestinal Epithelial Cell Proliferation and Tumor Development," *JPET Fast Forward* #145409, published on Nov. 3, 2008 as DOI:10.1124/jpet.108.145409, 35 pages.

McMahan et al., "Bile Acid Receptor Activation Modulates Hepatic Monocyte Activity and Improves Nonalcoholic Fatty Liver Disease," *The Journal of Biological Chemistry* 288(17): 11761-11770, Apr. 26, 2013.

Wermuth (ed.), *The Practice of Medicinal Chemistry*, Academic Press, London, England, 1996, Chapter 13, "Molecular Variations Based on Isosteric Replacements," pp. 221-222, Chapter 17, "Specific Substituent Effects," p. 326, 7 pages.

Wang et al., "FXR: a metabolic regulator and cell protector," *Cell Research* advance online publication Sep. 30, 2008; doi: 10.1038/cr.2008.289, 9 pages.

Wu et al., "Activation of farnesoid X receptor attenuates hepatic injury in a murine model of alcoholic liver disease," *Biochemical and Biophysical Research Communications* 443: 68-73, 2014.

Zhang et al., "Farnesoid X receptor agonist WAY-362450 attenuates liver inflammation and fibrosis in murine model of non-alcoholic steatohepatitis," *Journal of Hepatology* 51: 380-388, 2009.

\* cited by examiner

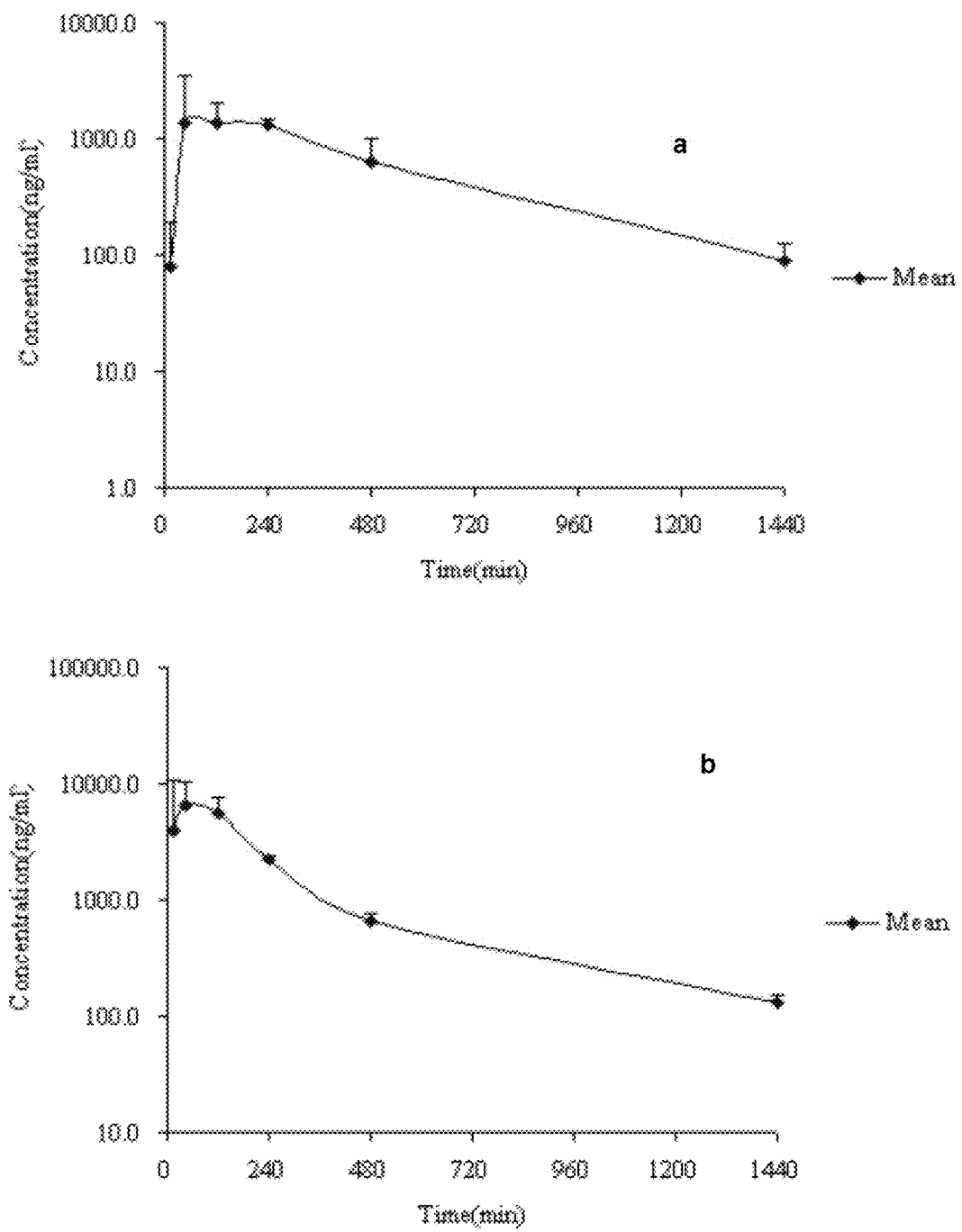
*Figure 1a and b*

GW4064

PX20535

Example 4

FXR (NR1H4) BINDING AND ACTIVITY MODULATING COMPOUNDS

This application is a U.S. National Phase Application of International Application No. PCT/EP2010/005093, filed Aug. 19, 2010, which claims priority to European Patent Application No. 09010676.6, filed Aug. 19, 2009, and U.S. Provisional Patent Application No. 61/235,117, filed Aug. 19, 2009.

The present invention relates to compounds which bind to the NR1H4 receptor (FXR) and act as agonists or modulators of the NR1H4 receptor (FXR). The invention further relates to the use of the compounds for the treatment and/or prophylaxis of diseases and/or conditions through binding of said nuclear receptor by said compounds.

Multicellular organisms are dependent on advanced mechanisms of information transfer between cells and body compartments. The information that is transmitted can be highly complex and can result in the alteration of genetic programs involved in cellular differentiation, proliferation, or reproduction. The signals, or hormones, are often low molecular weight molecules, such as peptides, fatty acid, or cholesterol derivatives.

Many of these signals produce their effects by ultimately changing the transcription of specific genes. One well-studied group of proteins that mediate a cell's response to a variety of signals is the family of transcription factors known as nuclear receptors, hereinafter referred to often as "NR". Members of this group include receptors for steroid hormones, vitamin D, ecdysone, cis and trans retinoic acid, thyroid hormone, bile acids, cholesterol-derivatives, fatty acids (and other peroxisomal proliferators), as well as so-called orphan receptors, proteins that are structurally similar to other members of this group, but for which no ligands are known. Orphan receptors may be indicative of unknown signalling pathways in the cell or may be nuclear receptors that function without ligand activation. The activation of transcription by some of these orphan receptors may occur in the absence of an exogenous ligand and/or through signal transduction pathways originating from the cell surface (D. Mangelsdorf et al. "The nuclear receptor superfamily: the second decade", Cell 1995, 83(6), 835-839; R. Evans "The nuclear receptor superfamily: a rosetta stone for physiology" Mol. Endocrinol. 2005, 19(6), 1429-1438).

In general, three functional domains have been defined in NRs. An amino terminal domain is believed to have some regulatory function. It is followed by a DNA-binding domain hereinafter referred to as "DBD" which usually comprises two zinc finger elements and recognizes a specific Hormone Responsive Element hereinafter referred to as "HRE" within the promoters of responsive genes. Specific amino acid residues in the "DBD" have been shown to confer DNA sequence binding specificity (M. Schena "Mammalian glucocorticoid receptor derivatives enhance transcription in yeast", Science 1988, 241(4868), 965-967). A ligand-binding-domain hereinafter referred to as "LBD" is at the carboxy-terminal region of known NRs.

In the absence of hormone, the LBD appears to interfere with the interaction of the DBD with its HRE. Hormone binding seems to result in a conformational change in the NR and thus opens this interference (A. Brzozowski et al. "Molecular basis of agonism and antagonism in the oestrogen receptor" Nature 1997, 389(6652), 753-758). A NR without the LBD constitutively activates transcription but at a low level.

Coactivators or transcriptional activators are proposed to bridge between sequence specific transcription factors, the basal transcription machinery and in addition to influence the chromatin structure of a target cell. Several proteins like SRC-1, ACTR, and Grip1 interact with NRs in a ligand enhanced manner (D. Heery et al. "A signature motif in transcriptional co-activators mediates binding to nuclear receptors" Nature 1997, 387(6634), 733-736; T. Heinzel et al. "A complex containing N—CoR, mSin3 and histone deacetylase mediates transcriptional repression" Nature 1997, 387(6628), 16-17; K. Nettles, G. Greene "Ligand control of coregulator recruitment to nuclear receptors" Annu. Rev. Physiol. 2005, 67, 309-333).

Nuclear receptor modulators like steroid hormones affect the growth and function of specific cells by binding to intracellular receptors and forming nuclear receptor-ligand complexes. Nuclear receptor-hormone complexes then interact with a hormone response element (HRE) in the control region of specific genes and alter specific gene expression (A. Aranda, A. Pascual "Nuclear hormone receptors and gene expression" Physiol. Rev. 2001, 81(3), 1269-1304).

The Farnesoid X Receptor alpha (hereinafter also often referred to as NR1H4 when referring to the human receptor) is a prototypical type 2 nuclear receptor which activates genes upon binding to promoter region of target genes in a heterodimeric fashion with Retinoid X Receptor (B. Forman et al. "Identification of a nuclear receptor that is activated by farnesol metabolites" Cell 1995, 81(5), 687-693). The relevant physiological ligands of NR1H4 are bile acids (D. Parks et al. "Bile acids: natural ligands for an orphan nuclear receptor" Science 1999, 284(5418), 1365-1368; M. Makishima et al. "Identification of a nuclear receptor for bile acids" Science 1999, 284(5418), 1362-1365). The most potent one is chenodeoxycholic acid (CDCA), which regulates the expression of several genes that participate in bile acid homeostasis. Farnesol and derivatives, together called farnesoids, are originally described to activate the rat orthologue at high concentration but they do not activate the human or mouse receptor. FXR is expressed in the liver, throughout the entire gastrointestinal tract including the esophagus, stomach, duodenum, small intestine, colon, ovary, adrenal gland and kidney. Beyond controlling intracellular gene expression, FXR seems to be also involved in paracrine and endocrine signalling by upregulating the expression of the cytokine Fibroblast Growth Factor 15 (rodents or 19 (monkeys, humans, J. Holt et al. "Definition of a novel growth factor-dependent signal cascade for the suppression of bile acid biosynthesis" Genes Dev. 2003, 17(13), 1581-1591; T. Inagaki et al. "Fibroblast growth factor 15 functions as an enterohepatic signal to regulate bile acid homeostasis" Cell Metab. 2005, 2(4), 217-225).

There is one publication which proposes a direct impact of FXR activation on the survival of infectious organisms such as bacteria or protozoic parasites via the upregulation of the lysosomal fate/survival factor Taco-2 in macrophages (P. Anand et al. "Downregulation of TACO gene transcription restricts mycobacterial entry/survival within human macrophages" FEMS Microbiol. Lett. 2005, 250(1), 137-144). This might pave the way for further studies that assess the suitability of FXR to act as drug target for the treatment of intracellular bacterial or parasitic infections such as Tuberculosis, Lepra, Leishmaniosis or Trypanosomiasis, e.g. Chagas Disease.

Small molecule compounds which act as FXR modulators have been disclosed in the following publications: WO 2000/037077, WO 2003/015771, WO 2004/048349, WO 2007/076260, WO 2007/092751, WO 2007/140174, WO 2007/140183, WO 2008/051942, WO 2008/157270, WO 2009/005998, WO 2009/012125, WO 2008/025539, and WO 2008/025540. Further small molecule FXR modulators have been recently reviewed (R. C. Buijsman et al. "Non-Steroidal Steroid Receptor Modulators" Curr. Med. Chem. 2005, 12, 1017-1075).

WO 2000/037077 discloses compounds of the following general formula

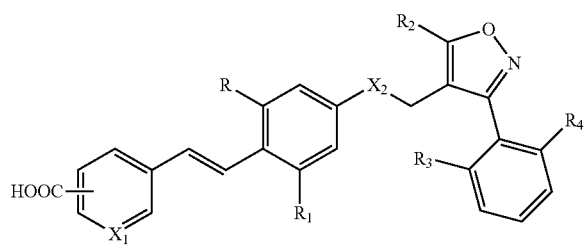

wherein $X_1$ is CH, N; $X_2$ is O or NH; R and $R_1$ are independently H, lower alkyl, halogen, or $CF_3$; $R_2$ is lower alkyl; $R_3$ and $R_4$ are independently H, lower alkyl, halogen, $CF_3$, OH, O-alkyl, or O-polyhaloalkyl.

In a more preferred embodiment WO 2000/037077 discloses compound GW4064

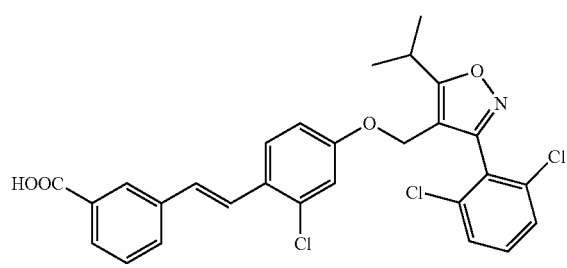 [SMILES: CC(C)c1onc(-c2c(Cl)cccc2Cl)c1COc1ccc(/C=C/c2cccc(C(=O)O)c2)c(Cl)c1]

which was also published first in Maloney et al. "Identification of a chemical tool for the orphan nuclear receptor FXR" J. Med. Chem. 2000, 43(16), 2971-2974. Akwabi-Ameyaw et al. "Conformationally constrained Farnesoid X Receptor Agonists: Naphtoic acid-based analogs of GW4064", Bioorg. Med. Chem. Lett. 2008, 18(15), 4339-4343 mentions the potential liabilities of this FXR agonist. According to the publication, GW4064 exhibits poor pharmacokinetics with a low oral bioavailability and a low plasma exposure together with a short plasma half life. Moreover, the trans-stilbene moiety of this molecule and related FXR agonists from WO 2000/037077 pose the issue of a potential toxicophore as addressed in Kuo et al. "Induction of drug-metabolizing enzymes and toxicity of trans-stilbene oxide in rat liver and kidney." Toxicology 1981, 22(2), 149-160 and in Sugihara et al. "Metabolic activation of the proestrogens trans-stilbene and trans-stilbene oxide by rat liver microsomes.", Toxicol. Appl. Pharmacol. 2000, 167(1), 46-54. Finally, the authors of Akwabi-Ameyaw et al. mention that GW4064's trans-stilbene moiety is responsible for its ultraviolet light instability. Photoinstability may turn into phototoxicity if the compound when administered to humans is exposed to UV-light e.g. by deposition or accumulation in the skin (see Colerangle J B. "Regulatory non-clinical photosafety evaluation—An attempt to merge the FDA and EMEA photosafety testing strategies." Regul. Toxicol. Pharmacol. 2009, Jul. 16. [Epub ahead of print] and Henry et al. "Can light absorption and photostability data be used to assess the photosafety risks in patients for a new drug molecule?" J. Photochem. Photobiol. B. 2009, 96(1), 57-62).

On the other hand, this conjugated trans-stilbene is the basis for GW4064's activity since the authors mention that the simple reduction of the double bond to an ethylene group results in a reduction in the FXR ligand binding properties.

Accordingly it is the object of the present invention to provide a technical solution to overcoming the liabilities of the trans-stilbene moiety containing FXR agonists disclosed in WO 2000/037077 while maintaining or even improving the binding potency to FXR as opposed to the reduction in FXR binding activity that is observed with the naphtoic acid analogs of GW4064 that are described in Akwabi-Ameyaw et al.

This object has been solved by providing the compounds of claim 1. Preferred embodiments are disclosed in the claims as well as in the following description. The present invention uses the conversion of the trans-stilbene double bond into a cyclopropyl moiety, which may be achieved by carbene addition, yielding compounds that show a suprisingly complete elimination of the UV induced photolability while overcoming the potentially toxic properties of the trans-stilbene at the same time. The racemic mixtures that are obtained display FXR agonist properties that are similar to the values that are obtained with the respective trans-stilbene containing molecules. Moreover, the chiral separation of the racemic mixtures yielded single enantiomers that showed even superior FXR binding and transactivation properties as opposed to the corresponding trans-stilbene containing molecules or the related naphtoic acid analogs that are published in Akwabi-Ameyaw et al. Hence the present invention provides for a superior solution to the technical liability problem that is exerted by trans-stilbene containing FXR compounds as opposed to other technical solutions as published in Akwabi-Ameyaw et al.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1a shows the mean concentration-time curve of Example 12 after oral administration in monkeys (12 mg/kg; n=3).

FIG. 1b shows the mean concentration-time curve of Example 4 after oral administration in monkeys (12 mg/kg; n=3).

FIG. 3l shows the $^1$H-NMR spectra of Example 4 at t=70 h of UV irradiation at 254 nm.

Figure 1C:
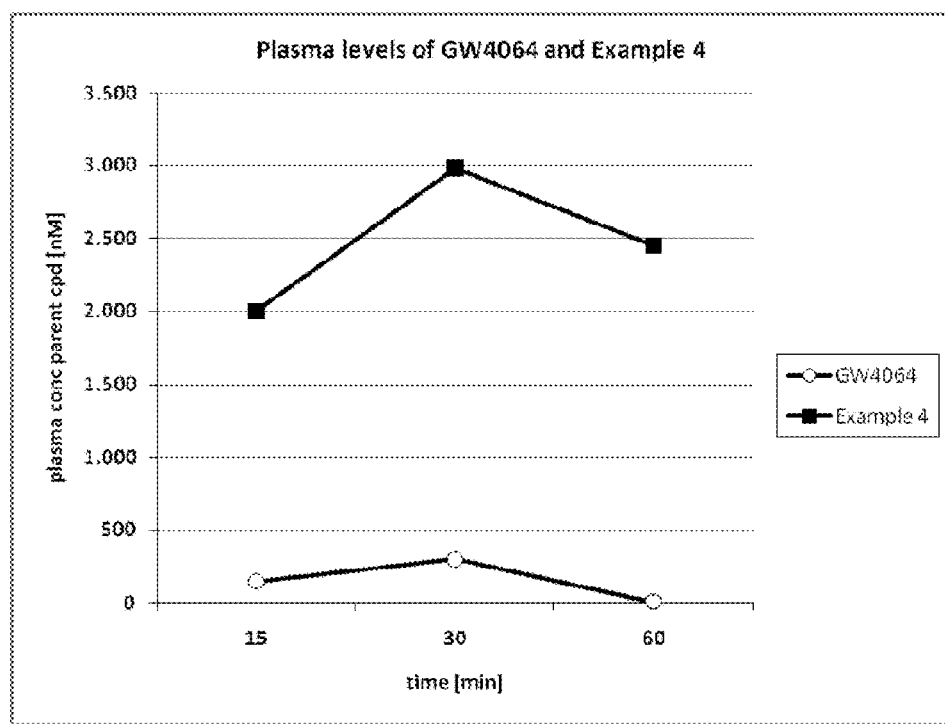
FIG. 1c shows the plasma parent compound level in [nM] after a single dose gavage of 5 mg/kg of GW4064 and Example 4 individually into C57 BLKS lepr$^{-/-}$ db/db mice. Data represent the mean of 3 individual mouse plasma measurements.
Figure 2A:
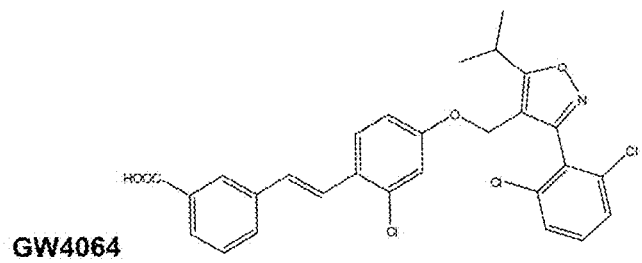
FIG. 2a shows the UV spectrum and chemical structure of GW4064.
Figure 2A:
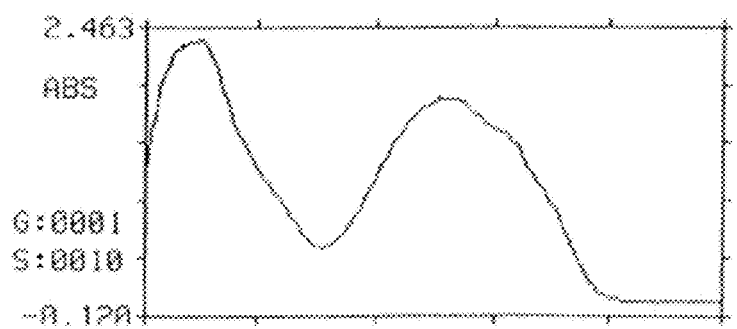
Figure 2B:
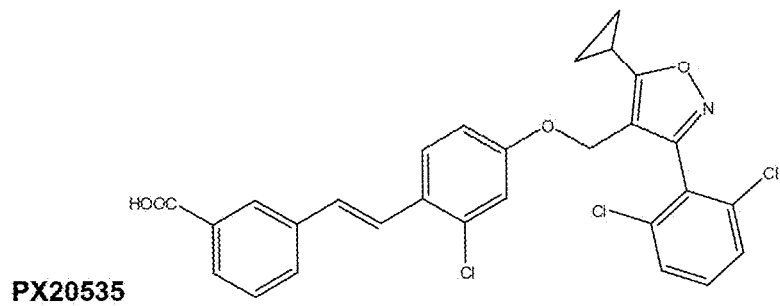
FIG. 2b shows the UV spectrum and chemical structure of Px20535.
Figure 2B:
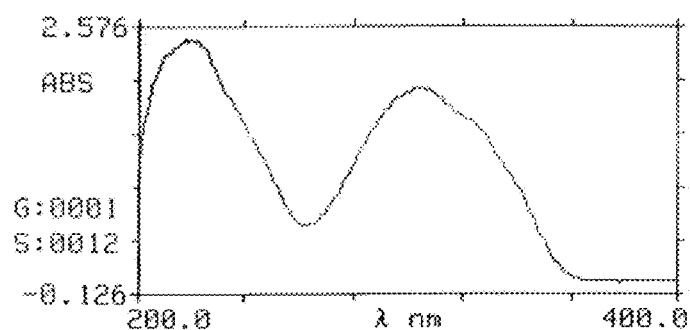
Figure 2C:
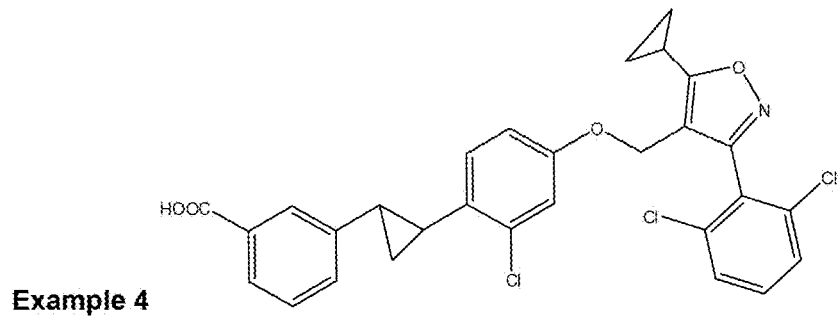
FIG. 2c shows the UV spectrum and chemical structure of Example 4.
Figure 2C:
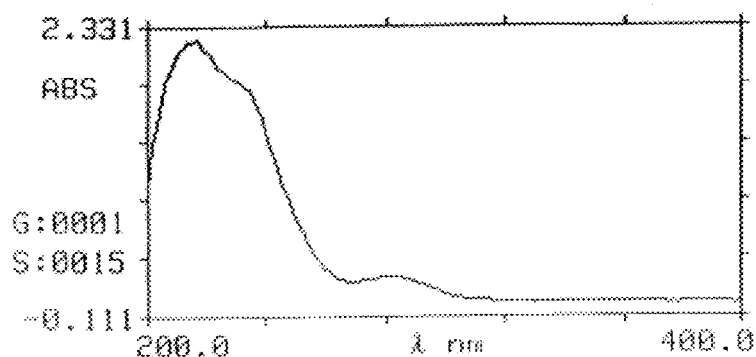

The compounds of the present invention share a common chemical structure according to formula (1).

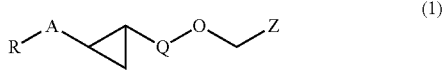
(1)

wherein

R is selected from the group consisting of COOR$_6$, CONR$_7$R$_8$, tetrazolyl or H, with R$_6$ independently selected from the group consisting of H, or lower alkyl, and R$_7$ and R$_8$ independently from each other selected from the group consisting of H, lower alkyl, C$_{1-6}$ haloalkyl, C$_{1-6}$ alkylene-R$_9$, SO$_2$—C$_{1-6}$ alkyl wherein R$_9$ is selected from the group consisting of COOH, OH, or SO$_3$H;

A is selected from the group consisting of phenyl, pyridyl, pyrazolyl, indolyl, thienyl, benzothienyl, indazolyl, benzisoxazolyl, benzofuranyl, benzotriazolyl, furanyl, benzothiazolyl, thiazolyl, each optionally substituted with one or two groups independently selected from the group consisting of OH, lower alkyl, lower cycloalkyl, or halogen;

Q is selected from the group consisting of phenyl, pyridyl, thiazolyl, thiophenyl, pyrimidyl, each optionally substituted with one or two groups independently selected from the group consisting of lower alkyl, halogen or CF$_3$;

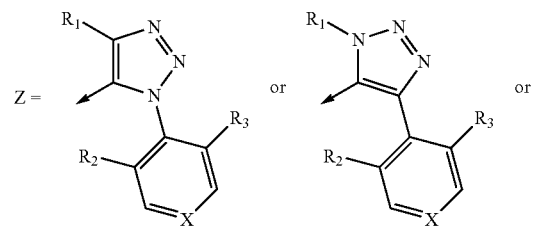

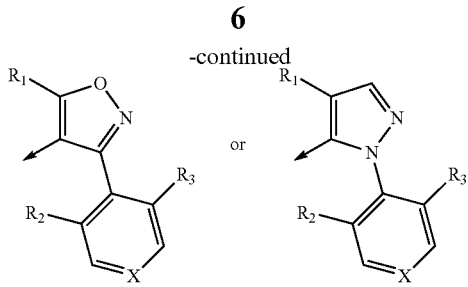

wherein

X=CH, N, NO;

R$_1$ is selected from the group consisting of hydrogen, C$_1$-C$_3$ alkyl, C$_3$-C$_6$ cycloalkyl, C$_4$-C$_5$ alkylcycloalkyl, wherein C$_{1-3}$ alkyl is optionally substituted with 1 to 3 substituents independently selected from halogen, hydroxy or C$_{1-6}$ alkoxy;

R$_2$ and R$_3$ are independently selected from the group consisting of hydrogen, C$_1$-C$_3$ alkyl, C$_1$-C$_3$ haloalkyl, C$_1$-C$_3$ alkoxy, C$_1$-C$_3$ haloalkoxy and halogen.

In the present invention the term lower alkyl defines an alkyl group which may be straight or branched, preferable straight and contains from 1 to 6, preferable from 1 to 4 carbon atoms. Preferred examples are methyl and ethyl, isopropyl and t-butyl. The term lower cycloalkyl defines a cycloalkyl group with from 3 to 6 carbon atoms. Cyclopropyl is particularly preferred. Examples of halogen atoms employed in the present invention as substituents as listed above are F, Cl and Br, with Cl being preferred.

In a preferred embodiment in combination with any embodiments above and below, compounds of the present invention are represented by a structure according to formula (1).

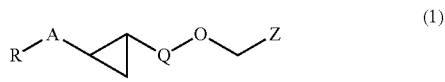
(1)

wherein

R is selected from the group consisting of COOR$_6$, CONR$_7$R$_6$, tetrazolyl or H, with R$_6$, R$_7$ and R$_3$ independently selected from the group consisting of H, lower alkyl;

A is selected from the group consisting of phenyl, pyridyl, indolyl, thienyl, benzothienyl, indazolyl, benzisoxazolyl, benzofuranyl, benzotriazolyl, furanyl, benzothiazolyl, thiazolyl, each optionally substituted with one or two groups independently selected from the group consisting of OH, lower alkyl, lower cycloalkyl;

Q is selected from the group consisting of phenyl, pyridyl, thiazolyl, thiophenyl, pyrimidyl, each optionally substituted with one or two groups independently selected from the group consisting of lower alkyl, halogen or CF$_3$;

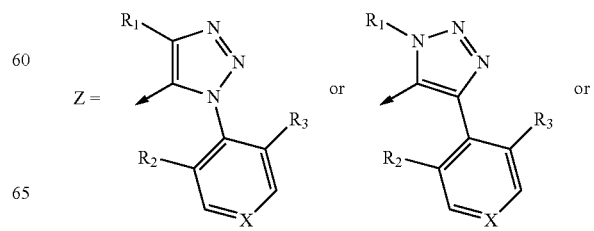

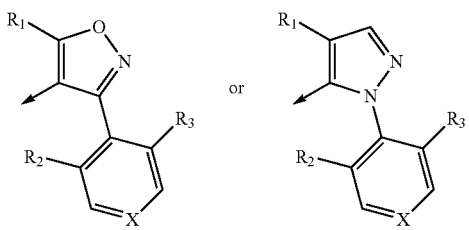 or 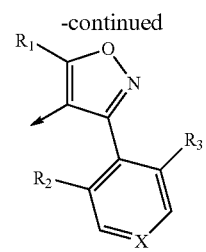

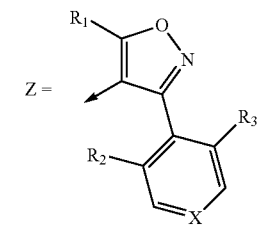

wherein

X=CH, N, NO;

$R_1$ is selected from the group consisting of hydrogen, $C_1$-$C_3$ alkyl, $C_1$-$C_3$ haloalkyl, $C_3$-$C_6$ cycloalkyl, $C_4$-$C_5$ alkylcycloalkyl;

$R_2$ and $R_3$ are independently selected from the group consisting of hydrogen, $C_1$-$C_3$ alkyl, $C_1$-$C_3$ haloalkyl, $C_1$-$C_3$ alkoxy, $C_1$-$C_3$ haloalkoxy and halogen.

Preferably R is selected among $COOR_6$ and $CONR_7R_8$ wherein $R_6$, $R_7$ and $R_8$ are as defined above, more preferably R is $COOR_6$ wherein $R_6$ is as defined above, preferably $R_6$ is selected among H and lower alkyl.

In an equally more preferred embodiment, R is $CONR_7R_8$ wherein $R_7$ and $R_8$ are as defined above, more preferably $R_7$ and $R_8$ are independently from each other selected from H, lower alkyl, $C_{1-6}$ alkylene-$R_6$, and $SO_2$—$C_{1-6}$ alkyl wherein $R_9$ is selected from the group consisting of COOH and $SO_3H$.

A is preferably selected among those moieties as identified above which are not substituted. More preferably A is phenyl.

In an alternative preferred embodiment in combination with any of the embodiments above and below, A is preferably selected among the heterocyclic moieties pyridyl, pyrazolyl, benzisoxazolyl and indazolyl whereby A is unsubstituted or substituted with one or two groups independently selected from OH, lower alkyl, lower cycloalkyl and halogen.

Q is preferably selected among those moieties as identified above substituted with one substituent. Preferably the substituent is a halogen, more preferably Cl. In particular Q is phenyl substituted with one halogen, preferably Cl.

In an alternative preferred embodiment in combination with any of the embodiments above and below, Q is a pyridyl group which is unsubstituted or substituted with one or two groups, preferably one group independently selected form the group consisting of lower alkyl, halogen and $CF_3$.

In a preferred embodiment in combination with any of the embodiments above and below, Z is selected among the following moieties:

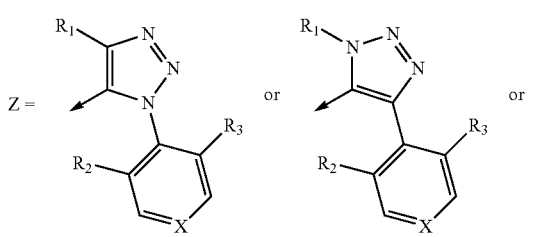

Even more preferably, Z is the following moiety:

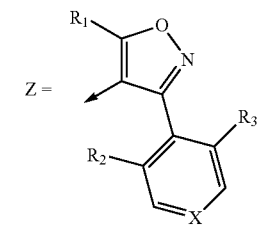

Further, Z is preferably selected among the structures identified above where X is CH. More preferably Z is preferably selected among the structures identified above where X is CH and $R_1$ is a cycloalkyl group, preferably cyclopropyl. Even more preferably Z is preferably selected among the structures identified above where X is CH and $R_1$ is a cycloalkyl group, preferably cyclopropyl, and $R_2$ and $R_3$ each represent halogen, most preferably Cl. The most preferred embodiment for Z is as defined above where the principle heterocyclic skeleton is the third structure identified above, comprising a five membered ring with a O—N moiety.

In an equally preferred embodiment in combination with any of the embodiments above and below, Z is preferably selected among the structures identified above where X is N or NO, more preferably X is N.

In a preferred embodiment in combination with any of the embodiments above and below, $R_1$ is selected from the group consisting of hydrogen, $C_{1-3}$ alkyl, $C_{3-6}$ cycloalkyl, and $C_{4-5}$ alkylcycloalkyl wherein $C_{1-3}$ alkyl is unsubstituted or substituted with 1 to 3 substituents, preferably 1 or 2 substituents, independently selected from halogen or hydroxy.

Preferred combinations of R, A, Q and Z are as defined above and the present invention contemplates all combinations of the preferred embodiments as listed above. In a particular preferred embodiment R is $COOR_5$ wherein $R_6$ is as defined above, preferably $R_6$ is selected among H and lower alkyl; A is phenyl; Q is selected among those moieties as identified above substituted with one substituent, preferably the substituent is a halogen, more preferably Cl, and in particular Q is phenyl substituted with one halogen, preferably Cl; and Z is selected among the structures identified above where X is CH and $R_1$ is a cycloalkyl group, preferably cyclopropyl, and $R_2$ and $R_3$ each represent halogen, most preferably Cl.

In a more preferred embodiment of the present invention, compounds have a common structure according to formula (2)

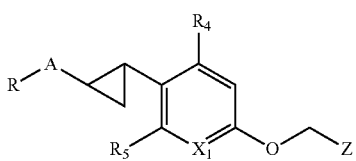

(2)

wherein

X₁ is selected among CH and N, preferably CH;

R₄ and R₅ are independently selected from the group consisting of H, lower alkyl, halogen or CF₃, preferably halogen, more preferably Cl.

Even more preferred compounds of formulae (1) or (2) that share a structure where R-A is selected from

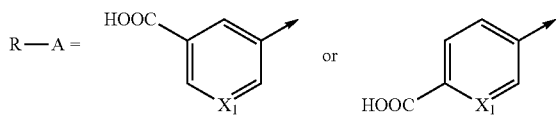

wherein in the formula (1) or (2) R₁ is selected from a group consisting of isopropyl, t-butyl and cyclopropyl;

R₂ and R₃ are independently selected from the group consisting of halogen, C₁-C₃ alkyl, methoxy and trifluoromethoxy, preferably halogen and most preferably Cl.

Most preferred compounds of the invention are as follows.

3-(2-(2-chloro-4-((5-cyclopropyl-3-(2,6-dichlorophenyl-isoxazol-4-yl)methoxy)phenyl)cyclopropyl)benzoic acid, (−)-3-(2-(2-chloro-4-((5-cyclopropyl-3-(2,6-dichlorophenyl)isoxazol-4-yl)methoxy)phenyl)cyclopropyl)benzoic acid, (+)-3-(2-(2-chloro-4-((5-cyclopropyl-3-(2,6-dichlorophenyl)isoxazol-4-yl)methoxy)phenyl)cyclopropyl)benzoic acid, 3-(2-(2-chloro-4-((3-(2,6-dichlorophenyl)-5-isopropylisoxazol-4-yl)methoxy)phenyl)cyclopropyl)benzoic acid, 3-(2-(2-chloro-4-((5-cyclopropyl-3-(3,5-dichloropyridin-4-yl)isoxazol-4-yl)methoxy)phenyl)cyclopropyl)benzoic acid, 4-(4-((4-(2-(3-carboxyphenyl)cyclopropyl)-3-chlorophenoxy)methyl)-5-cyclopropylisoxazol-3-yl)-3,5-dichloropyridine 1-oxide, 3-(2-(2-chloro-4-((1-(2,6-dichlorophenyl)-4-isopropyl-1H-1,2,3-triazol-5-yl)methoxy)phenyl)cyclopropyl)benzoic acid, 4-((4-(2-(6-(1H-tetrazol-5-yl)pyridin-3-yl)cyclopropyl)-3-chlorophenoxy)methyl)-5-cyclopropyl-3-(2,6-dichlorophenyl)isoxazole, or 5-(2-(2-chloro-4-((5-cyclopropyl-3-(2,6-dichlorophenyl)isoxazol-4-yl)methoxy)phenyl)cyclopropyl)picolinic acid.

Equally most preferred are compounds of the invention as follows.

3-(2-(6-((5-cyclopropyl-3-(2,6-dichlorophenyl)isoxazol-4-yl)methoxy)-2-(trifluoromethyl pyridin-3-yl)cyclopropyl)benzoic acid, 4-(2-(2-chloro-4-((5-cyclopropyl-3-(2,6-dichlorophenyl)isoxazol-4-yl)methoxy)phenyl)cyclopropyl)benzoic acid, 1,3-dihydroxy-2-(hydroxymethyl)propan-2-aminium 4-(2-(2-chloro-4-((5-cyclopropyl-3-(2,6-dichlorophenyl)isoxazol-4-yl)methoxy)phenyl)cyclopropyl)benzoate, (+)-4-(2-(2-chloro-4-((5-cyclopropyl-3-(2,6-dichlorophenyl)isoxazol-4-yl)methoxy)phenyl)cyclopropyl)benzoic acid, (−)-4-(2-(2-chloro-4-((5-cyclopropyl-3-(2,6-dichlorophenyl)isoxazol-4-yl)methoxy)phenyl)cyclopropyl)benzoic acid, 6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid, (+)-6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid, (−)-6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid, 4-(2-(2-chloro-4-((5-cyclopropyl-3-(2,6-dichlorophenyl)isoxazol-4-yl)methoxy)phenyl)cyclopropyl)-N-(methylsulfonyl)benzamide, 2-(4-(2-(2-chloro-4-((5-cyclopropyl-3-(2,6-dichlorophenyl)isoxazol-4-yl)methoxy)phenyl)cyclopropyl)benzamido)ethanesulfonic acid, 4-((4-(2-(4-(1H-tetrazol-5-yl)phenyl)cyclopropyl)-3-chlorophenoxy)methyl)-5-cyclopropyl-3-(2,6-dichlorophenyl)isoxazole, 4-(2-(2-chloro-4-((3-(2,6-dichlorophenyl)-5-(2-hydroxypropan-2-yl)isoxazol-4-yl)methoxy)phenyl)cyclopropyl)benzoic acid, 5-(2-(2-chloro-4-((5-cyclopropyl-3-(2,6-dichlorophenyl)isoxazol-4-yl)methoxy)phenyl)cyclopropyl)-1-isopropyl-1H-pyrazole-3-carboxylic acid, 6-(2-(2-chloro-4-((5-cyclopropyl-3-(2,6-dichlorophenyl)isoxazol-4-yl)methoxy)phenyl)cyclopropyl)-1-isopropyl-1H-indazole-3-carboxylic acid, 4-(2-(2-chloro-4-((5-cyclopropyl-3-(2,6-dichlorophenyl)isoxazol-4-yl)methoxy)phenyl)cyclopropyl)-2,6-dimethylbenzoic acid, 4-(2-(2-chloro-4-((5-cyclopropyl-3-(2-(trifluoromethoxy)phenyl)isoxazol-4-yl)methoxy)phenyl)cyclopropyl)benzoic acid, (+)-2-(4-(2-(2-chloro-4-((5-cyclopropyl-3-(2,6-dichlorophenyl)isoxazol-4-yl)methoxy)phenyl)cyclopropyl)benzamido)ethanesulfonic acid, (−)-2-(4-(2-(2-chloro-4-((5-cyclopropyl-3-(2,6-dichlorophenyl)isoxazol-4-yl)methoxy)phenyl)cyclopropyl)benzamido)ethanesulfonic acid, 2-(4-(2-(2-chloro-4-((5-cyclopropyl-3-(2,6-dichlorophenyl)isoxazol-4-yl)methoxy)phenyl)cyclopropyl)benzamido)acetic acid, or 4-(2-(2-chloro-4-((4-(2,6-dichlorophenyl)-1-isopropyl-1H-1,2,3-triazol-5-yl)methoxy)phenyl)cyclopropyl)benzoic acid.

The compounds of the present invention can be in the form of a prodrug compound. "Prodrug compound" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of the prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods.

Other examples of the prodrug are compounds, wherein the carboxylate in a compound of the present invention is, for example, converted into an alkyl-, aryl-, choline-, amino-, acyloxymethylester, linolenoylester.

Metabolites of compounds of the present invention are also within the scope of the present invention.

Where tautomerism, like e.g. keto-enol tautomerism, of compounds of the present invention or their prodrugs may occur, the individual forms, like e.g. the keto and enol form, are each within the scope of the invention as well as their mixtures in any ratio. Same applies for stereoisomers, like e.g. enantiomers, cis/trans isomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials. Another way to obtain pure enantiomers from racemic mixtures would use enantioselective crystallization with chiral counterions.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be present on these groups and can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Further the compounds of the present invention may be present in the form of solvates, such as those which include as solvate water, or pharmaceutically acceptable solvates, such as alcohols, in particular ethanol.

Furthermore, the present invention provides pharmaceutical compositions comprising at least one compound of the present invention, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing at least one compound of the present invention and a pharmaceutically acceptable carrier.

The pharmaceutical composition of the present invention may additionally comprise one or more other compounds as active ingredients like a prodrug compound or other nuclear receptor modulators.

The compositions are suitable for oral, rectal, topical, parenteral (including subcutaneous, intramuscular, and intravenous), ocular (ophthalmic), pulmonary (nasal or buccal inhalation) or nasal administration, although the most suitable route in any given case will depend on the nature and severity of the conditions being treated and on the nature of the active ingredient. They may be conveniently presented in unit dosage form and prepared by any of the methods well-known in the art of pharmacy.

The compounds of the invention may be prepared by a combination of methods known in the art including the procedures described below. Scheme I depicts the reaction of an appropriate compound of formula I with an appropriate heterocyclic compound of formula II.

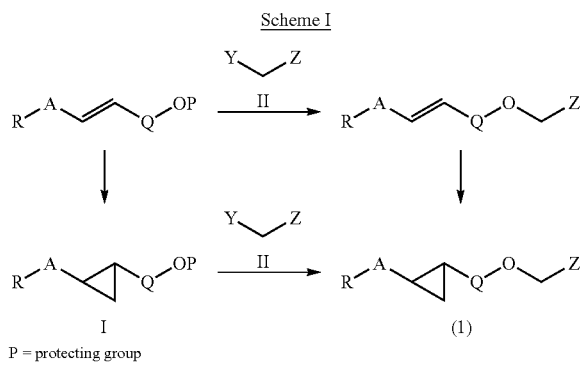

Thus an appropriate compound of formula II in which R1, R2 and R3 are defined as in formula (1) and Y is a leaving group and an appropriate compound of formula I in which R, A and Q are as defined as in formula (1) or a group that gives to R as defined in formula (1) e.g. by formation of an ester, an amide, tetrazol or acid are reacted to form compound of formula (1) with appropriate protections and/or deprotections or other steps known to one skilled in the art or disclosed herein. Suitable leaving groups are well known in the art and include halides, particularly chloro, bromo and iodo, sulfonate esters, such as brosyl, tosyl, methane sulfonyl, and trifluoromethane sulfonyl. A compound of formula I is reacted with a compound of formula II in a suitable solvent such as acetonitrile, dimethylformamide, tetrahydrofuran and the like in the presence of an excess of a suitable base, such as sodium hydride, potassium carbonate, sodium carbonate, triethylamine, diisopropyl-ethylamine, potassium tert-butoxide etc. Such reactions are usually carried out at temperatures from ambient temperature to reflux of the chosen solvent.

Alternatively an appropriate compound of formula I in which R, A and Q are defined as in formula (1) can be condensed with an appropriate heterocyclic compound of formula II in which $R_1$, $R_2$ and $R_3$ are defined as in formula (1) and Y is hydroxyl using a Mitsunobu reaction.

Compounds wherein R is an ester can be converted to compounds of formula (1) wherein R is an acid via methods well known to one skilled in the art. Hydrolysis of simple alkyl esters can be carried out in suitable solvents such as acetonitrile, methanol, ethanol, THF and mixtures thereof with water at temperatures from about 25-100° C. with suitable bases such as sodium hydroxide, potassium hydroxide and lithium hydroxide. In case R is a tert-butyl ester the corresponding acid can be formed under acidic conditions well known to those skilled in the art.

Compounds of formula I and II can be readily prepared by methods that are well known and established in the art including methods and procedures as those described herein.

Compounds of formula I are made from olefin precursors by standard cyclopropanation reactions well known to people skilled in the art (cf. H. Lebel, J-F. Marcoux, C Molinaro, A. B. Charette, Chem. Rev. 2003, 103, 977-1050). For instance, reaction of an optionally substituted stilbene derivative with Simmons-Smith reagent (|ZnCH2I|) in suitable solvents such as ether, THF, hexane, toluene, dichloromethane at temperatures between −20° C. to about reflux of the chosen solvent yield compounds of formula I. Optionally substituted stilbenes can be prepared by Horner-Emmons coupling of an aryl aldehyde and an arylmethylene phosphonate ester or by Heck coupling of an optionally substituted styrene with an optionally substituted arylbromide iodide or triflate in the presence of a palladium catalyst. As depicted in scheme I, cyclopropanation of optionally substituted stilbenes may be carried out after coupling to an optionally substituted heterocycle of formula II.

Compounds of the invention possess chiral centers and may exist in optically active forms. If a stereoisomer is desired it can be prepared by methods well known in the art. For instance the racemic mixture of compounds of formula (1) can be separated by chromatography on a chiral column. Alternatively, a racemic mixture of compounds of formula (1) wherein R is an acid can be separated by crystallization with suitable chiral amines such as a-phenethylamine, brucin, cinchonine. The racemates can also be chemically derivatised with another enantiopure reagent such as a chiral alcohol which could be reacted with the —COOH moiety to turn the racemic mixtures into mixtures of diastereomeric esters that can be separated by conventional chromatographic or other standard separation methods. Separation of the enantiomers can also be performed at the level of the racemic compounds of formula I. The optically active compounds of formula I can then be reacted with a heterocyclic compound of formula II as outlined in Scheme I to give optically active compounds of formula (1).

Synthetic Procedures

Compounds of formula (II) can be prepared as depicted in schemes 1a to 1d. Isoxazole compounds of formula II are prepared by the reaction of optionally substituted benzaldehydes with hydroxylamine in the presence of a suitable base such as triethylamine followed by chlorination with a suitable chlorinating agent such as N-chloro-succinimide. The resulting chloroximes are reacted with an appropriate β-ketoester under basic conditions with a suitable base such as triethylamine or sodium methoxide to yield isoxazole esters. The esters may be reduced to the alcohols of formula II with well known methods such as LAH or DIBAL and converted to a leaving group. 1-Aryl-4-alkyl-triazole compounds of formula II can be prepared by the addition of substituted propargylic alcohols to substituted aromatic azides and subsequent transformation of the hydroxy group to a suitable leaving group. 1-Alkyl-4-aryl-triazole compounds of formula II can be prepared by the addition of an optionally substituted azide to an acetylene ester followed by reduction to the alcohol and conversion to a leaving group. Pyrazole compounds of formula II are prepared by the reaction of an optionally substituted phenyl hydrazine with a 1,3-diketoester followed by reduction and conversion to a leaving group.

The compounds according to this invention were synthesized following one of the Schemes 2 to 14, starting from different chloromethyl-aryl (Cl—$CH_2$—Ar) building blocks which were synthesized according to Schemes 1a-d. As depicted in Scheme 2, reacting one of the chloromethyl-aryl (Cl—$CH_2$—Ar) building blocks A6a-e with the aryl-cyclopropyl-aryl building block B13 and subsequent saponification of the methyl ester to the free acid resulted in compounds from examples 1-6 (Scheme 2). Reacting the chloromethyl-aryl ($C_1$—$CH_2$—Ar) A6e with the (hetero)aryl-cyclopropyl-aryl building block C6 (Scheme 3) yielded the nitrilo-precursor C7 which was either turned into the tetrazole (Example 7) by reaction with $NaN_3$ and $NH_4Cl$ or saponified into the free acid (Example 8, see Scheme 3). Example 9 was prepared according scheme 4. Pyridone D2 was alkylated with building block A6e to intermediate D3. A two step transformation of the ester group into the aldehyde D5 was followed by a HWE reaction to afford the stilbene like intermediate D6. Cyclopropanation and ester hydrolysis gave final compound from example 9. The synthesis of the compound from example 10 is shown in scheme 5. Phosphonate E5 and 3-formyl pyridine were reacted to form the stilbene like intermediate E12, which after deprotection and alkylation with A6e, was cyclopropanated. Final ester hydrolysis afforded the compound from example 10. Compound from example 11 was synthesized according scheme 6. Benzoisoxazole carbaldehyde F5 was reacted with phosphonate F9 to form the stilbene structure containing intermediate F10. Cyclopropanation and deprotection afforded compound from example 11. The compounds from examples 12 to 14 were prepared according scheme 7, similar to scheme 2, but using the 4-methoxycarbonyl phosphonate G1. In scheme 8 is shown the synthesis of compound from example 15. The stilbene like precursor H6 is prepared through a Heck cross coupling reaction of bromo-indazole H4 and olefine H5. Cyclopropanation and ester hydrolysis yielded the final compound from example 15. Example 16 is prepared according to scheme 9. The O-methyl protected trans-stilbene is first cyclopropanated and subsequently the ester group is transformed into a cyano group. O-demethylation and alkylation with A6e provided the cyano intermediate 17 which is reacted with sodium azide to provide the tetrazole example 16. The synthesis of the compound from example 17 is shown in scheme 10. A5a was acetylated followed by bromination in the benzylic position using NBS. Treatment with DBU and $K_2CO_3$ resulted in the formation of intermediate J3 which was OH-protected using TBSOTf. Oxidation using $OsO_4$ and $NaIO_4$ was followed by the addition of methylmagnesium-Grignard and hydroxy deprotection with TBAF to give J7. Mitsunobu reaction with I2a and ester saponification afforded the final compound from example 17. In scheme 11 is shown the synthesis of the compound from example 18. Reaction of J6 with diazomethane followed by TBS deprotection afforded intermediate K2. This intermediate was converted to the final compound of example 18 in a similar manner as that described for example 17. In scheme 12 is shown the synthesis of the compound from example 19. Methyl 3-oxobutanoate was reacted with A3a to form the resulting isoxazole L1. Reaction with DMF-DMA followed by treatment with $SiO_2$ and HCl afforded aldehyde L3, which was reduced to L4 using $NaBH_4$. This was followed by OH-protection with 3,4-dihydropyran, ester reduction with DIBAL-H and Mitsunobu reaction with 12a to afford intermediate L7. Ester saponification and hydroxy deprotection afforded the final compound of example 19.

As a result, the present invention relates to compounds according to the general formula (I) which bind to the NR1H4 receptor (FXR) and act as agonists or modulators of the NR1H4 receptor (FXR).

The invention further relates to the use of said compounds for the treatment and/or prophylaxis of diseases and/or conditions through binding of said nuclear receptor by said compounds. Further the present invention relates to the use of said compounds for the preparation of a medicament for the treatment and/or prophylaxis of diseases and/or conditions through binding of said nuclear receptor by said compounds. Specifically, the present invention relates to the use of compounds according to formula (1) in the preparation of a medicament for the prophylaxis and/or treatment of chronic intrahepatic or some forms of extrahepatic cholestatic conditions, of liver fibrosis resulting from chronic cholestatic conditions, of acute intraheptic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of Type II Diabetes and clinical complications of Type I and Type II Diabetes, of conditions and diseases which result from chronic fatty and fibrotic degeneration of organs due to enforced lipid and specifically triglyceride accumulation and subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistent infections by intracellular bacteria or parasitic protozoae, of non-malignant hyperproliferative disorders, of malignant hyperproliferative disorders, of colon adenocarcinoma and hepatocellular carcinoma in particular, of liver steatosis and associated syndromes, of liver failure or liver malfunction as an outcome of chronic liver diseases or of surgical liver resection, of Hepatitis B infection, of Hepatitis C infection and/or of cholestatic and fibrotic effects that are associated with alcohol-induced cirrhosis or with viral-borne forms of hepatitis.

Medicaments as referred to herein may be prepared by conventional processes, including the combination of a compound according to the present invention and a pharmaceutically acceptable carrier.

FXR is proposed to be a nuclear bile acid sensor. As a result, it modulates both, the synthetic output of bile acids in the liver and their recycling in the intestine (by regulating bile acid binding proteins). But beyond bile acid physiology, FXR seems to be involved in the regulation of many diverse physiological processes which are relevant in the etiology and for the treatment of diseases as diverse as cholesterol gallstones, metabolic disorders such as Type II Diabetes, dyslipidemias or obesity, chronic inflammatory diseases such as Inflammatory Bowel Diseases or chronic intrahepatic forms of cholestasis and many others diseases (T. Claude) et al. "The Farnesoid X receptor: a molecular link between bile acid and lipid and glucose metabolism" Arterioscler. Thromb. Vasc. Biol. 2005, 25(10), 2020-2030; Y. D. Wang et al. "FXR: a metabolic regulator and cell protector." Cell Res. 2008, 18(11), 1087-1095.

FXR regulates a complex pattern of response genes in the liver and in the gastrointestinal tract. The gene products have impact on diverse physiological processes. In the course of functional analysis of FXR, the first regulatory network that was analyzed was the regulation of bile acid synthesis. While the LXRs induce the key enzyme of the conversion of cholesterol into bile acids, Cyp7A1, via the induction of the regulatory nuclear receptor LRH-1, FXR represses the induction of Cyp7A1 via the upregulation of mRNA encoding SHP, a further nuclear receptor that is dominant repressive over LRH-1. Since FXR binds the end products of this pathway, primary bile acids such as cholic acid (CA) or chenodeoxycholic acid (CDCA), this can be regarded as an example of feedback inhibition on the gene expression level (B. Goodwin et al. "A regulatory cascade of the nuclear receptors FXR, SHP-1, and LRH-1 represses bile acid biosynthesis" Mol. Cell. 2000, 6(3), 517-526; T. Lu et al. "Molecular basis for feedback regulation of bile acid synthesis by nuclear receptors" Mol. Cell 2000, 6(3), 507-515). Parallel to the repression of bile acid synthesis via SHP, FXR induces a range of so-called ABC (for ATP-binding cassette) transporters that are responsible for the export of toxic bile acids from the hepatocyte cytosol into the canaliculi, the small bile duct ramifications where the bile originates. This hepatoprotective function of FXR became first apparent with the analysis of FXR knockout mice (C. Sinai at al. "Targeted disruption of the nuclear receptor FXR/BAR impairs bile acid and lipid homeostasis" Cell 2000, 102(6), 731-744). where under- or overexpression of several ABC-transporters in the liver was shown. Further detailed analysis revealed that the major bile salt excretory pump BSEP or ABCB11 (M. Ananthanarayanan et al. "Human bile salt export pump promoter is transactivated by the farnesoid X receptor/bile acid receptor" J. Biol. Chem. 2001, 276(31), 28857-28865; J. Plass et al. "Farnesoid X receptor and bile salts are involved in transcriptional regulation of the gene encoding the human bile salt export pump" Hepatology 2002, 35(3), 589-596) as well as the key enzyme which mediates lipid transfer from lipoproteins to phospholipids, PLTP (N. Urizar et al. "The farnesoid X-activated receptor mediates bile acid activation of phospholipid transfer protein gene expression" J. Biol. Chem. 2000, 275 (50), 39313-39317), and the two key canalicular membrane transporters for phospholipids, MRP-2 (ABCC4) (H. Kast et al. "Regulation of multidrug resistance-associated protein 2 (ABCC2) by the nuclear receptors pregnane X receptor, farnesoid X-activated receptor, and constitutive androstane receptor" J. Biol. Chem. 2002, 277(4), 2908-2915) and MDR-3 (ABCB4); L. Huang et al. "Farnesoid X receptor activates transcription of the phospholipid pump MDR3" J. Biol. Chem. 2003, 278(51), 51085-51090) are direct targets for ligand-directed transcriptional activation by FXR (summarized in: M. Miyata "Role of farnesoid X receptor in the enhancement of canalicular bile acid output and excretion of unconjugated bile acids: a mechanism for protection against cholic acid-induced liver toxicity", J. Pharmacol. Exp. Ther. 2005, 312(2), 759-766; G. Rizzo et al. "Role of FXR in regulating bile acid homeostasis and relevance for human diseases" Curr. Drug Targets Immune Endocr. Metabol. Disord. 2005, 5(3), 289-303.)

The fact that FXR seems to be the major metabolite sensor and regulator for the synthesis, export and re-circulation of bile acids suggested the use of FXR ligands to induce bile flow and change bile acid composition towards more hydrophilic composition. With the development of the first synthetic FXR ligand GW4064 (P. Maloney et al. "Identification of a chemical tool for the orphan nuclear receptor FXR" J. Med. Chem. 2000, 43(16), 2971-2974; T. Willson et al. "Chemical genomics: functional analysis of orphan nuclear receptors in the regulation of bile acid metabolism" Med. Res. Rev. 2001, 21(6) 513-522) as a tool compound and of the semi-synthetic artificial bile acid ligand 6-alpha-ethyl-CDCA, the effects of superstimulation of FXR by potent agonists could be analyzed. It was shown that both ligands induce bile flow in bile duct ligated animals. Moreover, in addition to choleretic effects, also hepatoprotective effects could be demonstrated (R. Pellicciari et al. "6alpha-ethyl-chenodeoxycholic acid (6-ECDCA), a potent and selective FXR agonist endowed with anticholestatic activity" J. Med. Chem. 2002, 45(17), 3569-3572; Y. Liu et al. "Hepatoprotection by the farnesoid X receptor agonist GW4064 in rat models of intra- and extrahepatic cholestasis" J. Clin. Invest. 2003, 112(11), 1678-1687). This hepatoprotective effect was further narrowed down to an anti-fibrotic effect that results from the repression of Tissue Inhibitors of Matrix-Metalloproteinases, TIMP-1 and 2, the induction of collagen-deposit resolving Matrix-Metalloproteinase 2 (MMP-2) in hepatic stellate cells and the subsequent reduction of alpha-collagen mRNA and Transforming growth factor beta (TGF-beta) mRNA which are both pro-fibrotic factors by FXR agonists (S. Fiorucci et al. "The nuclear receptor SHP mediates inhibition of hepatic stellate cells by FXR and protects against liver fibrosis", Gastroenterology 2004, 127(5), 1497-1512; S. Fiorucci et al. "A farnesoid x receptor-small heterodimer partner regulatory cascade modulates tissue metalloproteinase inhibitor-1 and matrix metalloprotease expression in hepatic stellate cells and promotes resolution of liver fibrosis" J. Pharmacol. Exp. Ther. 2005, 314(2), 584-595). Furthermore, anti-cholestatic activity was demonstrated in bile-duct ligated animal models as well as in animal models of estrogen-induced cholestasis (S. Fiorucci et al. "Protective effects of 6-ethyl chenodeoxycholic acid, a farnesoid X receptor ligand, in estrogen-induced cholestasis" J. Pharmacol. Exp. Ther. 2005, 313(2), 604-612).

Genetic studies demonstrate that in hereditary forms of cholestasis (Progressive Familiar Intrahepatic Cholestasis=PFIC, Type I-IV) either nuclear localization of FXR itself is reduced as a consequence of a mutation in the FIC1 gene (in PFIC Type I, also called Byler's Disease) (F. Chen et al. "Progressive familial intrahepatic cholestasis, type 1, is associated with decreased farnesoid X receptor activity" Gastroenterology. 2004, 126(3), 756-764; L. Alvarez et al. "Reduced hepatic expression of farnesoid X receptor in hereditary cholestasis associated to mutation in ATP8B1" Hum. Mol. Genet. 2004, 13(20), 2451-2460) or levels of the FXR target gene encoding MDR-3 phospholipid export pump are reduced (in PFIC Type III). Taken together there is a growing body of evidence that FXR binding compounds will demonstrate substantial clinical utility in the therapeutic regimen of chronic cholestatic conditions such as Primary Biliary Cirrhosis (PBC) or Primary Sclerosing Cholangitis (PSC) (reviewed in: G. Rizzo et al. Curr. Drug Targets Immune Endocr. Metabol. Disord. 2005, 5(3), 289-303; G. Zollner "Role of nuclear receptors in the adaptive response to bile acids and cholestasis: pathogenetic and therapeutic considerations" Mol. Pharm. 2006, 3(3), 231-251; S. Cai et al. "FXR: a target for cholestatic syndromes?" Expert Opin. Ther. Targets 2006, 10(3), 409-421).

The deep impact that FXR activation has on bile acid metabolism and excretion is not only relevant for cholestatic syndromes but even more directly for a therapy against gallstone formation. Cholesterol gallstones form due to low solubility of cholesterol that is actively pumped out of the liver cell into the lumen of the canaliculi. It is the relative percentage of content of the three major components, bile acids, phospholipids and free cholesterol that determines the formation of mixed micelles and hence apparent solubility of free cholesterol in the bile. FXR polymorphisms map as quantitative trait loci as one factor contributing to gallstone disease (H. Wittenburg "FXR and ABCG5/ABCG8 as determinants of cholesterol gallstone formation from quantitative trait locus mapping in mice", Gastroenterology 2003, 125(3), 868-881). Using the synthetic FXR tool compound GW4064 it could be demonstrated that activation of FXR leads to an improvement of the Cholesterol Saturation Index (=CSI) and directly to an abolishment of gallstone formation in C57L gallstone susceptible mice whereas drug treatment in FXR knockout mice shows no effect on gallstone formation (A. Moschetta et al. "Prevention of cholesterol gallstone disease by FXR agonists in a mouse model" Nature Medicine 2004, 10(12), 1352-1358).

These results qualify FXR as a good target for the development of small molecule agonists that can be used to prevent cholesterol gallstone formation or to prevent re-formation of gallstones after surgical removal or shockwave lithotripsy (discussed in: S. Doggrell "New targets in and potential treatments for cholesterol gallstone disease" Curr. Opin. Investig. Drugs 2006, 7(4), 344-348).

Thus, in one embodiment of the invention, the compound according to formula (1) and pharmaceutical compositions comprising said compound is used for the prophylaxis and/or treatment of obstructive or chronic inflammatory disorders that arise out of improper bile composition such as cholelithiasis also known as cholesterol gallstones.

Beyond its strong hepatoprotective and choleretic as well as anti-fibrotic effects that FXR shows upon small molecule stimulated activation in the liver, FXR seems to have a role in protecting the intestine from neoplastic transformation and from the development of polyps and their transition into adenocarcinoma in the gut (S. Modica et al. "Nuclear bile acid receptor FXR protects against intestinal tumorigenesis" Cancer Res. 2008, 68(23), 9589 and R. R. Ma ran et al. "Farnesoid X receptor deficiency in mice leads to increased intestinal epithelial cell proliferation and tumor development" J. Pharmacol. Exp. Ther. 2009, 328(2), 469). Similar to the situation in the intestine absence of FXR leads to a high increase in the formation of Hepatocellular Cacrcinoma (HCC), the most prominent form of liver cancer (I. Kim et al. "Spontaneous hepatocarcinogenesis in farnesoid X receptor-null mice", Carcinogenesis 2007, 28(5), 940 and F. Yang et al. "Spontaneous development of liver tumors in the absence of the bile acid receptor farnesoid X receptor." Cancer Res. 2007, 67(3), 863). Whereas a functional FXR prevents the formation of colon adenocarcinoma and hepatocellular carcinoma, FXR activation induces liver regeneration after hepatectomy (W.

Huang et al. "Nuclear receptor-dependent bile acid signaling is required for normal liver regeneration" Science 2006, 312 (5771), 233).

The combined hepatoprotective, anti-neoplastic and liver regenerative effects associated with FXR activation can be therapeutically exploited for the use of FXR agonists in the treatment of sever liver diseases. In one embodiment, the compounds according to the invention and pharmaceutical compositions comprising said compounds are used in the treatment of liver diseases such as hepatocellular cancer (HCC), stimulation of liver regrowth and amelioration of side effects associated with major liver resection, liver cirrhosis independent of the etiology and prevention or treatment of liver ischemia in the course of liver transplantation or major liver surgery.

Since the discovery of the first synthetic FXR agonist and its administration to rodents it became evident that FXR is a key regulator of serum triglycerides (P. Maloney et al. J. Med. Chem. 2000, 43(16), 2971-2974; T. Willson et al. Med. Res. Rev. 2001, 21(6), 513-522). Over the past six years accumulating evidence has been published that activation of FXR by synthetic agonists leads to significant reduction of serum triglycerides, mainly in the form of reduced VLDL, but also to reduced total serum cholesterol (H. Kast et al. "Farnesoid X-activated receptor induces apolipoprotein C-II transcription: a molecular mechanism linking plasma triglyceride levels to bile acids" Mol. Endocrinol. 2001, 15(10), 1720-1728; N. Urizar et al. "A natural product that lowers cholesterol as an antagonist ligand for FXR" Science 2002, 296(5573), 1703-1706; G. Lambert et al. "The farnesoid X-receptor is an essential regulator of cholesterol homeostasis" J. Biol. Chem. 2003, 278, 2563-2570; M. Watanabe et al. "Bile acids lower triglyceride levels via a pathway involving FXR, SHP, and SREBP-1c" J. Clin. Invest. 2004, 113(10), 1408-1418; A. Figge et al. "Hepatic overexpression of murine Abcb11 increases hepatobiliary lipid secretion and reduces hepatic steatosis" J. Biol. Chem. 2004, 279(4), 2790-2799; S. Bilz et al. "Activation of the farnesoid X receptor improves lipid metabolism in combined hyperlipidemic hamsters" Am. J. Physiol. Endocrinol. Metab. 2006, 290(4), E716-722).

But the lowering of serum triglycerides is not a stand alone effect. Treatment of db/db or ob/ob mice with synthetic FXR agonist GW4064 resulted in marked and combined reduction of serum triglycerides, total cholesterol, free fatty acids, ketone bodies such as 3-OH Butyrate. Moreover, FXR activation engages with the intracellular insulin signaling pathway in hepatocytes, resulting in reduced output of glucose from liver gluconeogenesis but concomitant increase in liver glycogen. Insulin sensitivity as well as glucose tolerance were positively impacted by FXR treatment (K. Stayrook et al. "Regulation of carbohydrate metabolism by the farnesoid X receptor" Endocrinology 2005, 146(3), 984-991; Y. Zhang et al. "Activation of the nuclear receptor FXR improves hyperglycemia and hyperlipidemia in diabetic mice" Proc. Natl. Acad. Sci. USA 2006, 103(4), 1006-1011; B. Cariou et al. "The farnesoid X receptor modulates adiposity and peripheral insulin sensitivity in mice" J. Biol. Chem. 2006, 281, 11039-11049; K. Ma et al. "Farnesoid X receptor is essential for normal glucose homeostasis" J. Clin. Invest. 2006, 116(4), 1102-1109; D. Duran-Sandoval et al. "Potential regulatory role of the farnesoid X receptor in the metabolic syndrome" Biochimie 2005, 87(1), 93-98). An effect on reduction of body weight was also recently observed in mice overfed with a high lipid diet (C. Lihong et al. "FXR Agonist, GW4064, Reverses Metabolic Defects in High-Fat Diet Fed Mice" American Diabetes Association (ADA) 66th annual scientific sessions, June 2006, Abstract Number 856-P). This weight loss effect might results from FXR's induction of FGF-19, a fibroblast growth factor that is known to lead to weight loss and athletic phenotype (J. Holt et al. Genes Dev. 2003, 17(13), 1581-1591; E. Tomlinson et al. "Transgenic mice expressing human fibroblast growth factor-19 display increased metabolic rate and decreased adiposity" Endocrinology 2002, 143 (5), 1741-1747). In recent patent applications, the effect of FXR agonist on reduction of body weight was demonstrated (Stoffel W. et al. "Methods for inhibiting Adipogenesis and for treating Type 2 Diabetes" International Patent Application WO 2004/087076; S. Jones et al "Methods of using FXR Agonists" International Patent Application WO 2003/080803).

Taken together, these pharmacological effects of FXR agonists can be exploited in different therapeutic ways: FXR binding compounds are thought to be good candidates for the treatment of Type II Diabetes because of their insulin sensitization, glycogenogenic, and lipid lowering effects.

In one embodiment, the compounds according to the invention and pharmaceutical compositions comprising said compounds are used in the prophylaxis and/or treatment of Type II Diabetes which can be overcome by FXR-mediated upregulation of systemic insulin sensitivity and intracellular insulin signalling in liver, increased peripheral glucose uptake and metabolisation, increased glycogen storage in liver, decreased output of glucose into serum from liver-borne gluconeogenesis.

In a further embodiment, said compounds and pharmaceutical compositions are used for the prophylaxis and/or treatment of chronic intrahepatic, such as primary biliary cirrhosis (PBC), primary sclerosing cholangitis (PSC), progressive familiar cholestasis (PFIC), alcohol-induced cirrhosis and associated cholestasis, and some forms of extrahepatic cholestatic conditions, or liver fibrosis resulting from chronic cholestatic conditions or acute intrahepatic cholestatic conditions such as estrogen or drug induced cholestasis.

The invention also relates to a compound of formula (I) or to a pharmaceutical composition comprising said compound for the prophylaxis and/or treatment of gastrointestinal conditions with a reduced uptake of dietary fat and fat-soluble dietary vitamins which can be overcome by increased intestinal levels of bile acids and phospholipids.

In a further embodiment, said compound or pharmaceutical composition is used for preventing and/or treating a disease selected from the group consisting of lipid and lipoprotein disorders such as hypercholesterolemia, hypertriglyceridemia, and atherosclerosis as a clinically manifest condition which can be ameliorated by FXR's beneficial effect on lowering total plasma cholesterol, lowering serum triglycerides, increasing conversion of liver cholesterol into bile acids and increased clearance and metabolic conversion of VLDL and other lipoproteins in the liver.

In one further embodiment, said compound and pharmaceutical composition are used for the prophylaxis and/or treatment of diseases where the combined lipid lowering, anti-cholestatic and anti-fibrotic effects of FXR-targeted medicaments can be exploited for the treatment of liver steatosis and associated syndromes such as non-alcoholic steatohepatitis ("NASH"), or for the treatment of cholestatic and fibrotic effects that are associated with alcohol-induced cirrhosis, or with viral-borne forms of hepatitis.

In conjunction with the hypolipidemic effects it was also shown that loss of functional FXR leads to increased atherosclerosis in ApoE knockout mice (E. Hanniman et al. "Loss of functional farnesoid X receptor increases atherosclerotic lesions in apolipoprotein E-deficient mice" J. Lipid Res. 2005, 46(12), 2595-2604). Therefore, FXR agonists might have clinical utility as anti-atherosclerotic and cardioprotective drugs. The downregulation of Endothelin-1 in Vascular Smooth Muscle Cells might also contribute to such beneficial therapeutic effects (F. He et al. "Downregulation of endothelin-1 by farnesoid X receptor in vascular endothelial cells" Circ. Res. 2006, 98(2), 192-199).

The invention also relates to a compound according to formula (I) or a pharmaceutical composition comprising said compound for preventive and posttraumatic treatment of cardiovascular disorders such as acute myocardial infarction, acute stroke, or thrombosis which occur as an endpoint of chronic obstructive atherosclerosis.

Beyond controlling intestinal and colonic polyp formation, FXR seems to be expressed in breast cancer tissue and cell lines but not in healthy breast tissue and seems to interact with the Estrogen Receptor in ER positive breast cancer cells (K. E. Swales at al. "The farnesoid X receptor is expressed in breast cancer and regulates apoptosis and aromatase expression." Cancer Res. 2006, 66(20), 10120 and F. Journe et al. "Association between farnesoid X receptor expression and cell proliferation in estrogen receptor-positive luminal-like breast cancer from postmenopausal patients". Breast Cancer Res. Treat. 2009, 115(3), 523.

This would allow to regard FXR also as a potential target for the treatment of proliferative diseases, especially metastasizing cancer forms that express a small molecule responsive form of FXR.

In a further embodiment, said compounds and pharmaceutical compositions are used for the prophylaxis and/or treatment of malignant hyperproliferative disorders such as different forms of cancer, specifically certain forms of breast, liver or colon cancer) where interference with an FXR ligand will have a beneficial impact.

Finally, FXR seems also to be involved in the control of antibacterial defense in the intestine (T. Inagaki et al. "Regulation of antibacterial defense in the small intestine by the nuclear bile acid receptor" Proc. Natl. Acad. Sci. USA. 2006, 103(10), 3920-3905) although an exact mechanism is not provided. From these published data, however, one can conclude that treatment with FXR agonists might have a beneficial impact in the therapy of Inflammatory Bowel Disorders (IBD), in particular those forms where the upper (ileal) part of the intestine is affected (e.g. ileal Crohn's disease) because this seems to be the site of action of FXR's control on bacterial growth. In IBD the desensitization of the adaptive immune response is somehow impaired in the intestinal immune system. Bacterial overgrowth might then be the causative trigger towards establishment of a chronic inflammatory response. Hence, dampening of bacterial growth by FXR-borne mechanisms might be a key mechanism to prevent acute inflammatory episodes.

Thus, the invention also relates to a compound according to formula (1) or a pharmaceutical composition comprising said compound for preventing and/or treating a disease related to Inflammatory Bowel Diseases such as Crohn's disease or Colitis ulcerosa. FXR-mediated restoration of intestinal barrier function and reduction in non-commensal bacterial load is believed to be helpful in reducing the exposure of bacterial antigens to the intestinal immune system and can therefore reduce inflammatory responses.

The invention further relates to a compound or pharmaceutical composition for the prophylaxis and/or treatment of obesity and associated disorders such as metabolic syndrome (combined conditions of dyslipidemias, diabetes and abnormally high body-mass index) which can be overcome by FXR-mediated lowering of serum triglycerides, blood glucose and increased insulin sensitivity and FXR-mediated weight loss.

In one embodiment, said compound or pharmaceutical composition is for treating persistent infections by intracellular bacteria or parasitic protozoae such as *Mycobacterium* spec. (Treatment of Tuberculosis or Lepra), *Listeria monocytogenes* (Treatment of Listeriosis), *Leishmania* spec. (Leishmaniosis), *Trypanosoma* spec. (Chagas Disease; Trypanosomiasis; Sleeping Sickness).

In a further embodiment, the compounds or pharmaceutical composition of the present invention are useful in preventing and/or treating clinical complications of Type I and Type II Diabetes. Examples of such complications include Diabetic Nephropathy, Diabetic Retinopathy, Diabetic Neuropathies, or Peripheral Arterial Occlusive Disease (PAOD). Other clinical complications of Diabetes are also encompassed by the present invention.

Furthermore, conditions and diseases which result from chronic fatty and fibrotic degeneration of organs due to enforced lipid and specifically triglyceride accumulation and subsequent activation of profibrotic pathways may also be prevented and/or treated by applying the compounds or pharmaceutical composition of the present invention. Such conditions and diseases encompass Non-Alcoholic Steatohepatitis (NASH) and chronic cholestatic conditions in the liver, Glomerulosclerosis and Diabetic Nephropathy in the kidney, Macula Degeneration and Diabetic Retinopathy in the eye and Neurodegenerative diseases such as Alzheimer's Disease in the brain, or Diabetic Neuropathies in the peripheral nervous system.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Since the compounds of the present invention mostly represent carboxylic acids or similar anionic isosters thereof, and since it is well known that salt forms of ionic drug compounds can substantially affect the bioavailability of drug compounds, the compounds of the present invention may also be used as salts with various countercations to yield an orally available formulation. Such pharmaceutically acceptable cations may be amongst others mono- or bivalent ions such as ammonium, the alkaline metals sodium or potassium or the alkaline earth metals magnesium or calcium, certain pharmaceutically acceptable amines such as Tris(hydroxymethyl)aminomethane, ethylendiamine, diethylamine, piperazine or others, or certain cationic amino acids such as Lysine or Arginine.

The compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing FXR mediated conditions for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

Some abbreviations that appear in this application are as follows.

Abbreviations

Abbreviation Designation m-CPBA meta-Chloroperbenzoic acid
DCM Dichloromethane
DIAD Diisopropyl azodicarboxylate
DMF Dimethylformamide
DMSO Dimethylsulfoxide
EtOAc Ethyl acetate
EDTA 2-[2-(Bis(carboxymethyl)amino)ethyl-(carboxymethyl)amino]acetic acid
ESI Electrospray ionisation
FXR Farnesoid X receptor
GST Glutathione-S-transferase
HPLC High-performance liquid chromatography
IPTG Isopropyl $\beta$-D-1-thiogalactopyranoside
LBD Ligand binding domain
LC/MS Liquid chromatography-mass spectroscopy
NMR Nuclear magnetic resonance
PE Petroleum ether
po Perorally
Rf Retention factor
SDS Sodium dodecyl sulfate
THF Tetrahydrofurane
TLC Thin layer chromatography
TMS Tetramethyl silane
TBS tert-butyldimethylsilyl The compounds of the present invention can be prepared according to the procedures of the following Schemes and Examples, using appropriate materials and are further exemplified by the following specific examples. Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described above.

The amine-free bases corresponding to the isolated salts can be generated by neutralization with a suitable base, such as aqueous sodium hydrogen carbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization. The carboxylic free acids corresponding to the isolated salts can be generated by neutralization with a suitable acid, such as aqueous hydrochloric acid, sodium hydrogen sulfate, sodium dihydrogen phosphate, and extraction of the liberated carboxylic-free acid into an organic solvent, followed by evaporation. The carboxylic acid, isolated in this manner, can be further converted into another pharmaceutically acceptable salt by dissolution in an organic solvent, followed by addition of the appropriate base and subsequent evaporation, precipitation or crystallization.

An illustration of the preparation of compounds of the present invention is shown below. Unless otherwise indicated in the schemes, the variables have the same meaning as described above. The examples presented below are intended to illustrate particular embodiments of the invention. Suitable starting materials, building blocks and reagents employed in the synthesis as described below are commercially available from Sigma-Aldrich Chemie GmbH, Munich, Germany, from Acros Organics, Belgium or from Fisher Scientific GmbH, 58239 Schwerte, Germany, for example, or can be routinely prepared by procedures described in the literature, for example in "March's Advanced Organic Chemistry: Reactions, Mechanisms, and Structure", 5th Edition; John Wiley & Sons or Theophil Eicher, Siegfried Hauptmann "The Chemistry of Heterocycles; Structures, Reactions, Synthesis and Application", $2^{nd}$ edition, Wiley-VCH 2003; Fieser et al. "Fiesers' Reagents for organic Synthesis" John Wiley & Sons 2000.

EXAMPLES

Synthesis of Precursors

Scheme 1a:

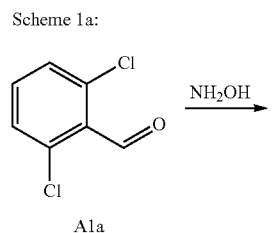

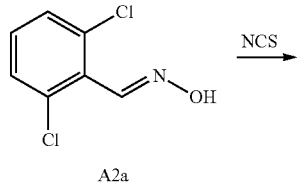

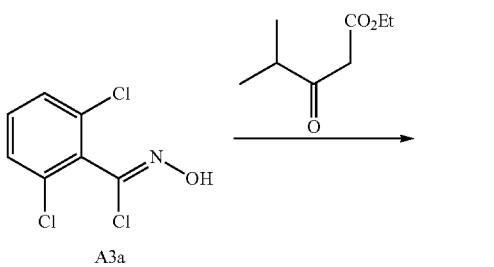

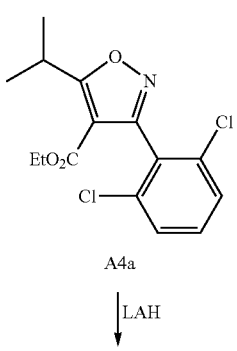

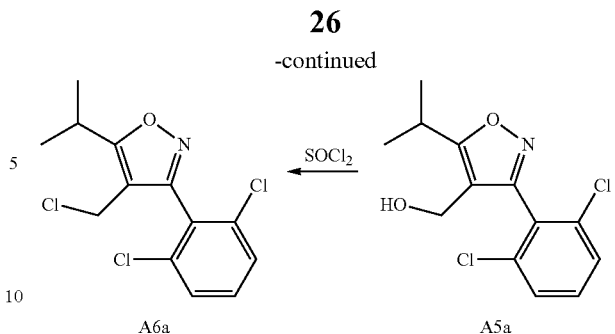

Synthesis of Compound A2a

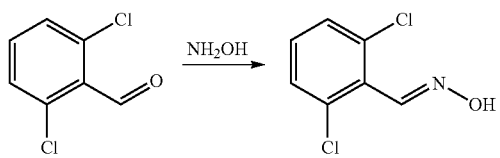

A solution of 2,6-dichlorobenzaldehyde A1a (25 g, 0.14 mol) in 200 mL of ethanol was added to a solution of hydroxylamine hydrochloride (11 g, 0.16 mol) and sodium hydroxide (6.3 g, 0.16 mol) in 100 mL of water. The resulting mixture was stirred at 90° C. for 24 h. The volume was reduced in vacuum by ~30 mL, which induced a precipitate. The flask was then cooled to room temperature and the solid was collected by filtration and washed with water (2×100 mL). The solid was dried under vacuum to give 25.9 g of compound A2a (white solid, yield: 96%).

Synthesis of Compound A3a

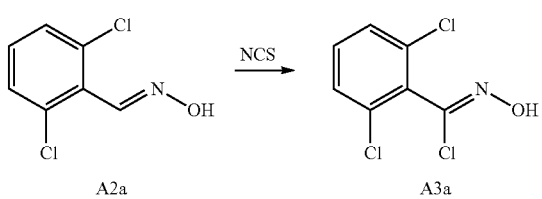 [SMILES: O/N=C/c1c(Cl)cccc1Cl ; "NCS" ; O/N=C(\Cl)c1c(Cl)cccc1Cl]

A 500 mL round bottom flask was charged with a solution of compound A1a (25.9 g, 0.14 mol) in 300 mL of DMF. The flask was placed in an ambient temperature water bath. The flask was then charged with NCS (18.4 g, 0.14 mol). The reaction was stirred an additional hour, then the contents was poured into 400 mL of water and the product was extracted with 500 mL of Et$_2$O. The organic layer was washed with water (2×200 mL) and 100 mL of brine, then dried over MgSO$_4$. After filtration, the solvent was removed under reduced pressure to give 29 g of compound A3a as a yellow oil which was used into the following reaction without further purification.

Synthesis of Compound A4a

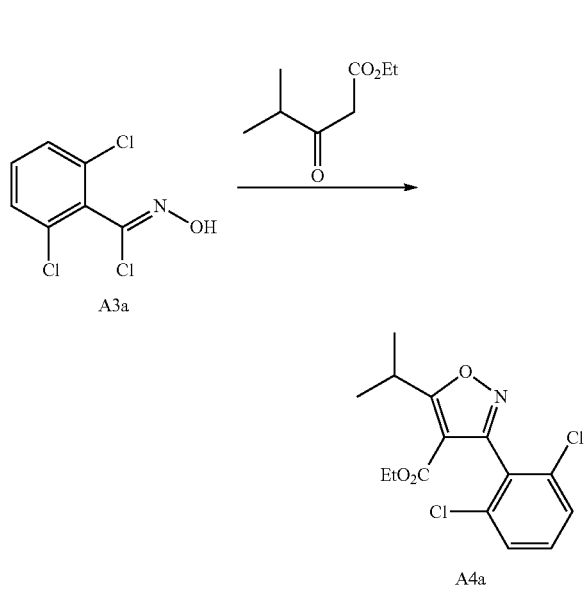

A stirred solution of isobutyryl acetate (16 g, 124.8 mmol) in 120 mL of dry THF was treated with a solution of sodium methoxide (252 mL, 0.5 M in MeOH) followed by a solution of compound A3a (28 g, 124.8 mmol) in 40 mL of dry THF. After stirring at room temperature for 16 h, the solvent was removed under reduced pressure. The residue was partitioned between 800 mL of Et$_2$O and 800 mL of water. The organic layer was washed with brine, dried over Na$_2$SO$_4$, filtered, concentrated and purified by chromatography on silica gel (eluent: PE/EtOAc=10/1) to give 24.8 g of compound A4a as a white solid (Yield: 62%).

Synthesis of Compound A5a

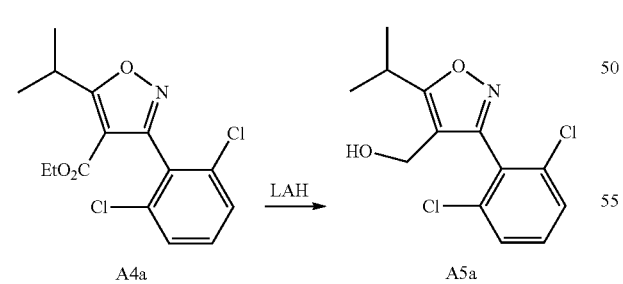

A solution of compound A4a (24.8 g, 79.7 mmol) in 180 mL of dry THF was cooled to 0° C. under nitrogen atmosphere while LAH (3.1 g, 79.7 mmol) was added dropwise. The reaction was allowed to warm slowly to room temperature for 2 h. The flask was again cooled to 0° C. and 5 mL of MeOH was carefully added over a 10 minute period. Sat. Na$_2$SO$_4$ solution was added and the formed solid was filtered over a plug of Celite. Concentrated to give 21 g of compound A5a as a yellow solid (Yield: 93%).

Synthesis of Compound A6a

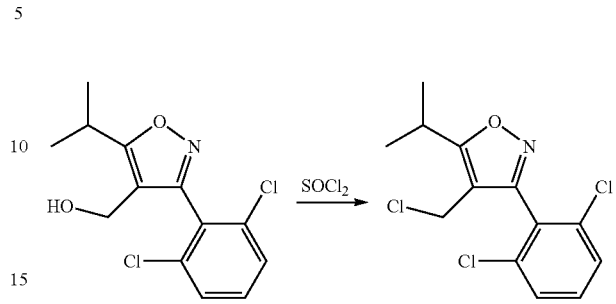

To a solution of benzotrizole (6.77 g, 73.7 mmol) in 100 mL of dry DCM was added SOCl$_2$ (8.76 g, 73.7 mmol) at 0° C., and stirred at room temperature for 1 hour. The resulting mixture was added to the solution of compound A5a (21 g, 73.7 mmol) in 200 mL of dry DCM at room temperature and stirred for 1.5 h. 60 mL of water was added to the mixture to quench the reaction, and the mixture was extracted with DCM. The organic layer was washed with 1 N aq. NaOH solution, dried over Na$_2$SO$_4$, filtered, concentrated and purified by chromatography on silica gel (eluent: PE/EtOAc=10/1) to give 21.7 g of compound A6a as a white solid (Yield: 97.2%).

$^1$H NMR (400 MHz, CDCl$_3$): δ 1.47 (d, J=6.8 Hz, 6H), 3.35 (m, 1H), 4.31 (s, 2H), 7.38-7.48 (m, 3H).

Synthesis of Compound A4e

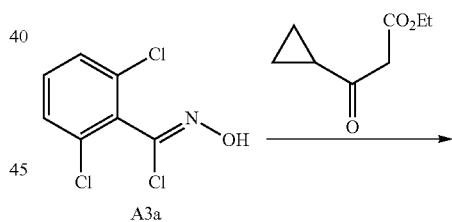

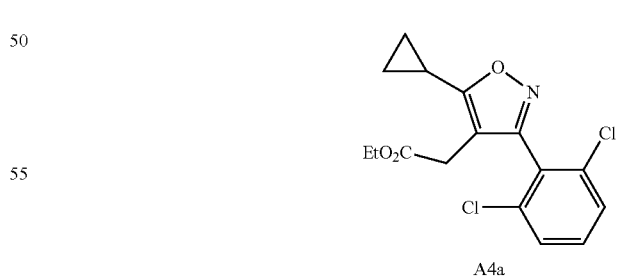

To a solution of compound A3a (105 g, 0.47 mol) in 400 mL of TEA was added ethyl 3-cyclopropyl-3-oxopropanoate (100 g, 0.70 mol). The mixture was stirred at room temperature overnight. The solvent was removed under reduced pressure and purified by chromatography on silica gel (eluent: PE/EA=10/1) to give 87 g of compound A4e as a white solid (Yield: 57%).

Synthesis of Compound A5e

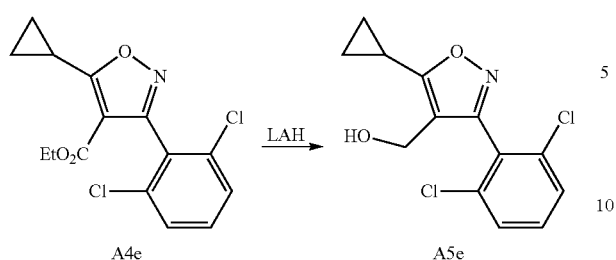

To a solution of compound A4e (80 g, 0.26 mol) in 300 mL of dry THF was added DIBAL-H (360 mL, 0.54 mol) at 0° C. under $N_2$ atmosphere, and stirred at room temperature for 4 h. The reaction was quenched by MeOH (80 mL) and HCl (1 M), extracted with EA and the organic layer was washed by brine. Concentrated under reduced pressure to give 55 g of crude compound A5e used in the following reaction without further purification.

Synthesis of Compound A6e

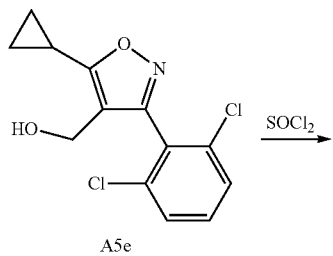

To the solution of benzotrizole (17.85 g, 194.3 mmol) in 100 mL of dry DCM was added $SOCl_2$ (23.09 g, 73.7 mmol) at 0° C., and stirred at room temperature for 1 hour. The resulting mixture was added to the solution of compound A5e (55 g, 194.3 mmol) in 500 mL of dry DCM at room temperature and stirred for 1.5 h. 120 mL of water was added to the mixture for quench, and the mixture was extracted with DCM. The organic layer was washed with 1 N aq. NaOH solution, dried over $Na_2SO_4$, filtered, concentrated and purified by chromatography on silica gel (eluent: PE/EA=10/1) to give 47.4 g of compound A6e as a white solid (Yield: 81%).

$^1$H NMR (400 MHz, $CDCl_3$): δ 1.23-1.33 (m, 4H), 2.14 (m, 1H), 4.40 (s, 2H), 8.31 (s, 2H).

Scheme 1b

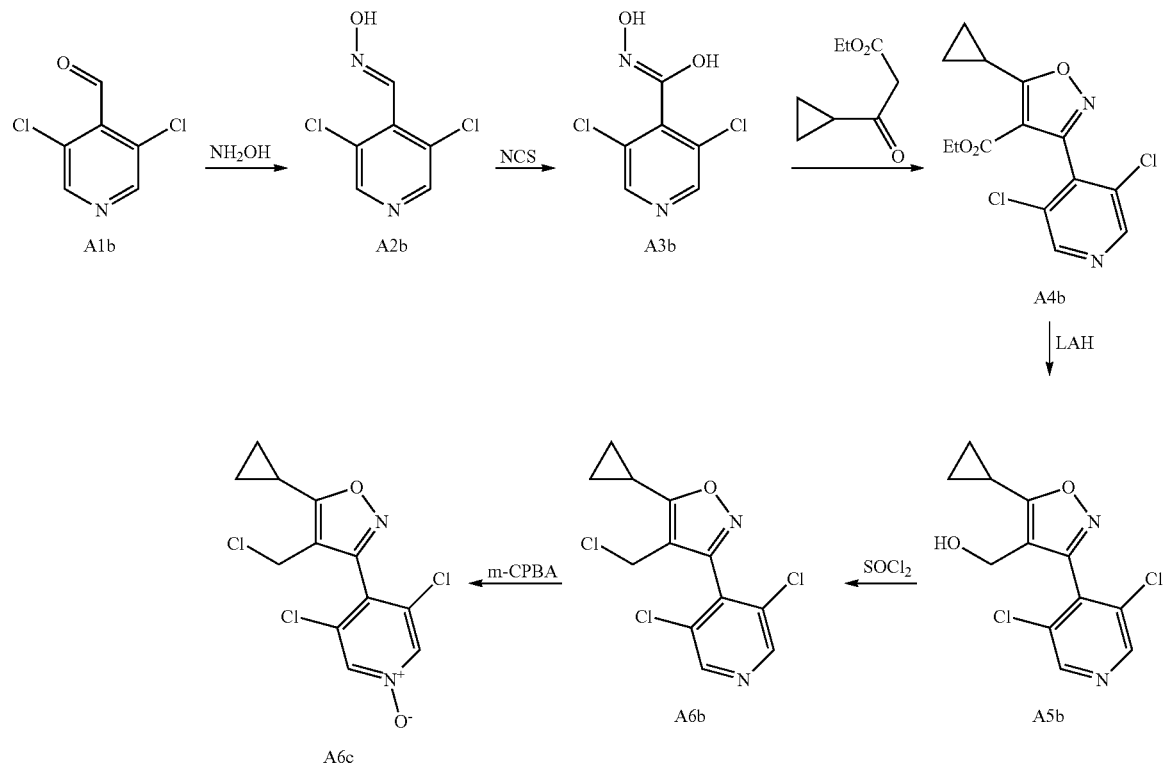

Synthesis of Compound A2b

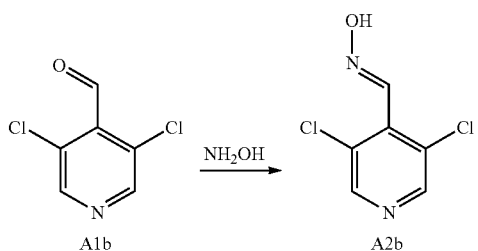

To a solution of compound A1b (5.00 g, 28.4 mmol) in 40 mL of EtOH was added a mixture of NaOH (1.37 g, 34.1 mmol) and $NH_2OH \cdot HCl$ (2.37 g, 34.1 mmol) in 15 mL of $H_2O$. The resulting mixture was stirred at 90° C. for 12 h. The volume was concentrated under reduced pressure by ~10 mL, and the solid was collected by filtration. It was washed with water and dried under vacuum to give 5.0 g of compound A2b as a white solid (Yield: 92%).

Synthesis of Compound A3b

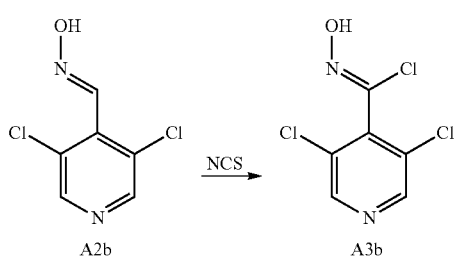

A 100 mL round bottom flask was charged with a solution of compound A2b (5.0 g, 26.2 mmol) in 50 mL of DMF. The flask was placed in an ambient temperature water bath. The flask was then charged with NCS (4.13 g, 31.4 mmol). The reaction was stirred an additional 12 h, then the contents were concentrated under reduced pressure. The residue was diluted with $Et_2O$, washed with water and brine, dried over $Na_2SO_4$, filtered and concentrated to give 5.3 g of compound A3b as a yellow oil which was used into the following reaction without the further purification.

Synthesis of Compound A4b

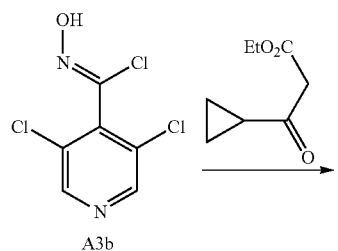

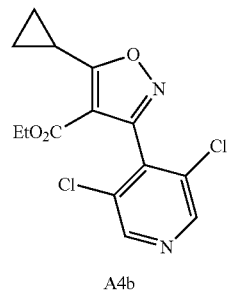

A stirred solution of ethyl 3-cyclopropyl-3-oxopropanoate (3.88 g, 24.5 mmol) in 40 mL of dry THF was treated with 15 mL of $Et_3N$ followed by a solution of compound A3b (5 g, 22.25 mmol) in 30 mL of dry THF. After stirring at room temperature for 18 h, the solvent was removed under reduced pressure. The resulting residue was partitioned with 100 mL of $Et_2O$ and 40 mL of water. The organic layer was washed with brine, dried over $Na_2SO_4$, filtered, concentrated and purified by chromatography on silica gel (eluent: PE/EtOAc=10/1) to give 3.25 g of compound A4b as a white solid (Yield: 45%).

Synthesis of Compound A5b

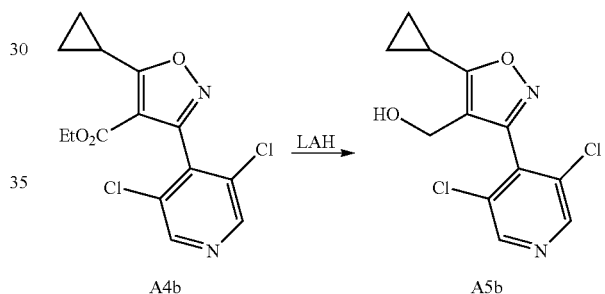

To a solution of compound A4b (2.0 g, 6.10 mmol) in 30 mL of anhydrous THF was added DIBAL-H (25.6 mL, 25.60 mmol) dropwise at −10° C. during 15 min under $N_2$ atmosphere. The resulting mixture was stirred at the same temperature for 3 h. Quenched with water and extracted with EA, the organic layer was washed with brine, dried over $Na_2SO_4$. Evaporation of the solvent to give the crude product which was further purified by flash chromatography on silica gel (eluent: PE/EtOAc=2/1) to afford 0.44 g of compound A5b as a white solid (Yield: 25%).

Synthesis of Compound A6b

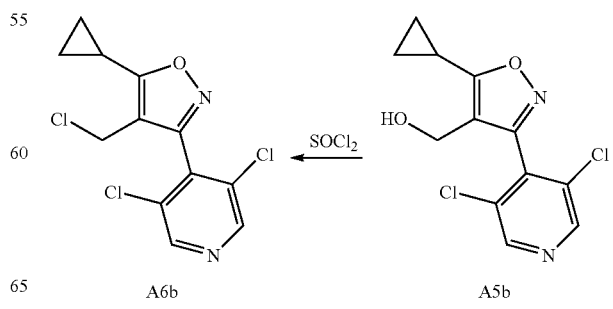

To the solution of benzotriazole (0.84 g, 9.1 mmol) in 20 mL of dry DCM was added SOCl$_2$ (1.08 mg, 9.1 mmol) at 0° C. dropwise. The resulting mixture was stirred for 30 min at room temperature under N$_2$ atmosphere. The resulting solution was transferred to an addition funnel and added dropwise during 10 min to a stirred solution of compound A5b (2.0 g, 7.0 mmol) in 20 mL of dry DCM. After stirring for 1 hour, the resulting suspension was filtered to remove the benzotriazole hydrochloride. The filtrate was washed with 30 mL water twice, 30 mL of 1 N NaOH solution and 30 mL of brine consecutively, dried over anhydrous Na$_2$SO$_4$, filtered, concentrated and purified by chromatography on silica gel (eluent: PE/EtOAc=10/1) to give 0.91 g of compound A6b as a white solid (Yield: 42.3%).

$^1$H NMR (400 MHz, CDCl$_3$): δ 1.21-1.35 (m, 4H), 2.14-2.18 (m, 1H), 4.38 (s, 2H), 8.67 (s, 2H).

Synthesis of Compound A6c

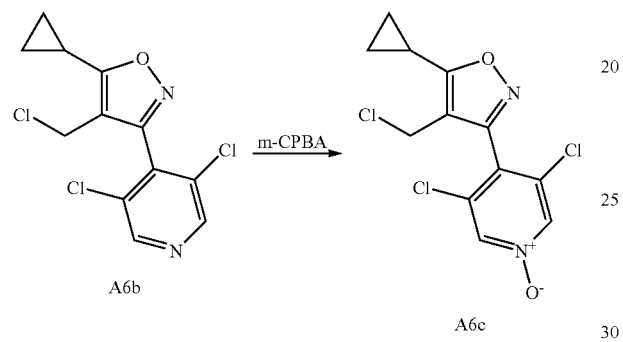

To a stirred solution of A6b (0.53 g, 1.75 mmol) in 10 mL of DCM was added m-CPBA (0.65 mg, 3.60 mmol) at room temperature. After stirring for 18 h at room temperature, the reaction mixture was quenched with sat. NaHCO$_3$ solution, extracted with DCM, washed with water and brine, dried over anhydrous Na$_2$SO$_4$, filtered, concentrated and purified by flash chromatography on silica gel (eluent: PE/EtOAc=5/1) to give 318 mg of compound A6c as a white solid (Yield: 57%).

$^1$H NMR (400 MHz, CDCl$_3$): δ 1.23-1.33 (m, 4H), 2.14 (m, 1H), 4.40 (s, 2H), 8.31 (s, 2H).

Scheme 1c

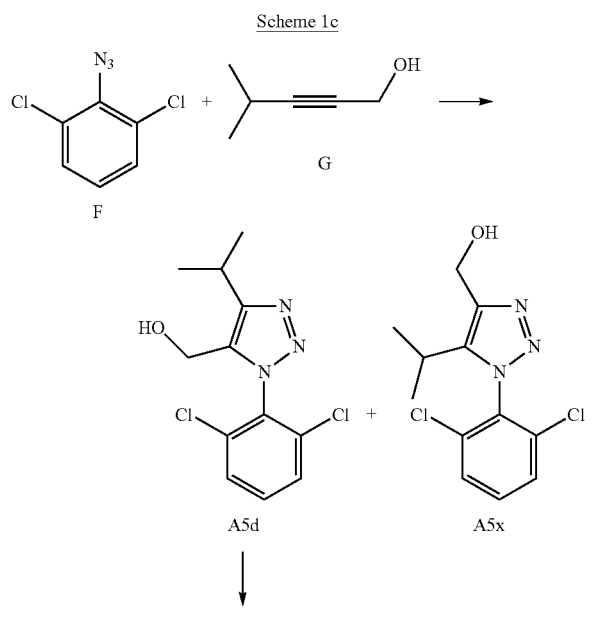

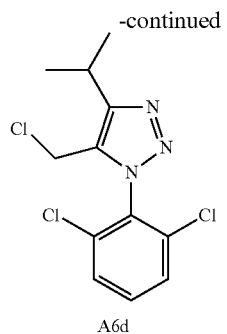

A6d

Preparation of Compound A5d

A solution of 2,6-dichlorophenyl azide (F, 25 g, 0.13 mol) in toluene (100 ml) and acetylenic alcohol (G, 52.1 g, 0.53 mol) was refluxed under argon for 35 h. Toluene was removed under vacuum and the resulting products were purified by careful column chromatography and isolated two triazole products as solids, Compound A5d (4.5 g, 23%) and Compound A5x (6.5 g, 34%).

Preparation of Compound A6d

To a solution of compound A5d (2.00 g, 7.0 mmol) in 20 mL of DCM and 2 mL of CCl$_4$ was added PPh$_3$ (3.67 g, 14.0 mmol). Then the solution was stirred at room temperature for 4 h, both of TLC and LCMS indicated that the reaction was over. Concentrated under reduced pressure and purified by flash chromatography on silica gel (eluent: PE/EtOAc=10/1) to give 2.02 g of compound Abd as a white solid (Yield: 95%).

$^1$H NMR (400 MHz, CDCl$_3$): δ 1.51-1.49 (d, 6H), 3.24-3.21 (m, 1H), 4.48 (s, 2H), 7.52-7.50 (t, 1H), 7.58-7.54 (d, 2H).

Scheme 1d

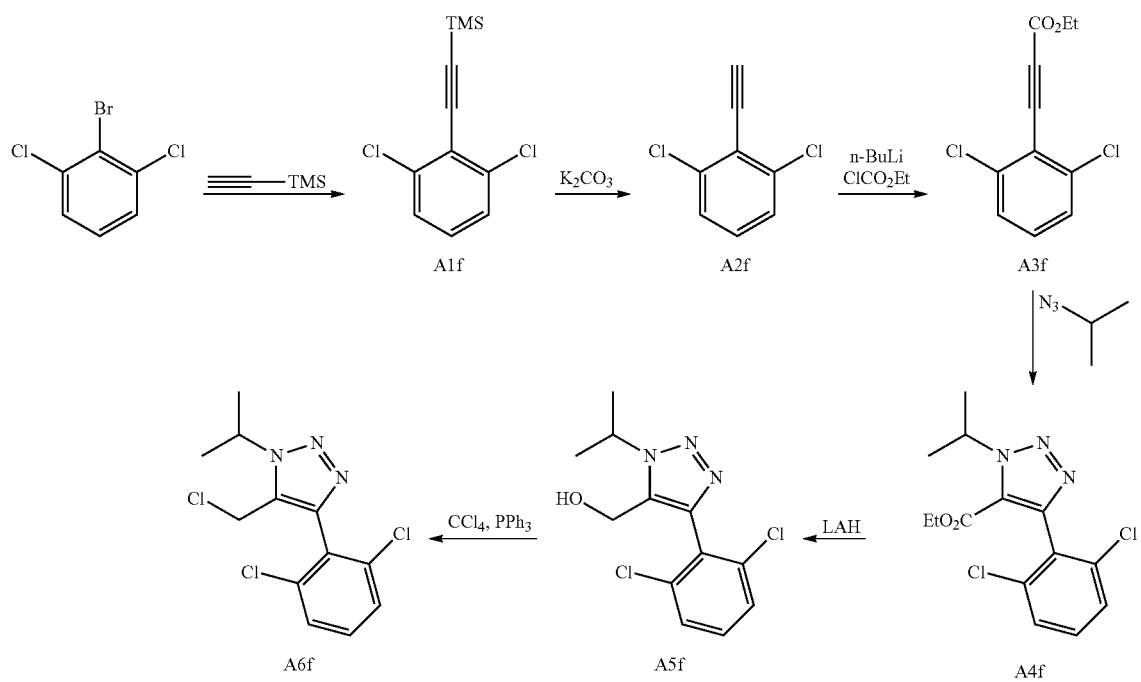

Synthesis of Compound A1f

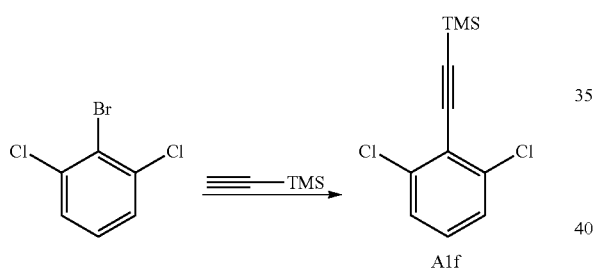

The solution of 2-bromo-1,3-dichlorobenzene (13 g, 58 mmol), 2,2-dimethyl-2-silabut-3-yne (90 mL, 64 mmol), CuI (100 mg, 5.5 mmol), PPh$_3$ (200 mg, 0.75 mmol) and Pd(PPh$_3$)$_2$Cl$_2$ (235 mg, 0.335 mmol) in 35 mL of NEt$_3$ was refluxed in a seal tube under N$_2$ atmosphere for 24 h. Both of TLC and LCMS indicated that the reaction was over. Concentrated and EtOAc was added. The solution was washed with water and brine, dried over Na$_2$SO$_4$, filtered, concentrated and purified by flash chromatography on silica gel (eluent: PE/EA=100/0) to give 13 g of crude compound A1f as an oil (yield 40%, purity 70%).

Synthesis of Compound A2f

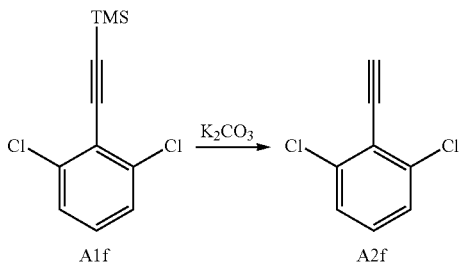

To the solution of crude compound A1f (13 g, 48.4 mmol) in 200 mL of MeOH was added K$_2$CO$_3$ (13 g, 94.3 mmol), and the mixture was stirred at room temperature overnight under N$_2$ atmosphere. Filtered and concentrated under reduced pressure to give 4.1 g of compound A2f as a white solid (Yield: 56.1%).

Synthesis of Compound A3f

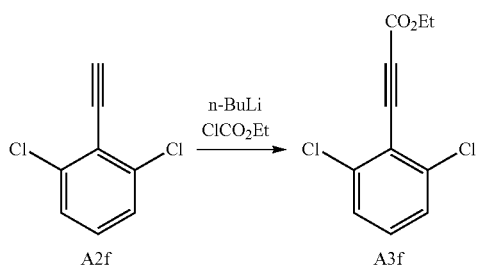

To the solution of compound A2f (2 g, 12 mmol) in 40 mL of dry THF was added n-BuLi (5.6 mL, 2.5 M in hexane, 14 mmol) at −78° C. under N$_2$ atmosphere, and the solution was stirred at this temperature for 30 min. Then the solution of ethyl chloroacetate (1.65 g, 15 mmol) in 10 mL of dry THF was added at −78° C. The mixture was stirred for 4 h. The resulting solution was poured into sat. NH$_4$Cl solution and EtOAc was added to extract twice. The combined organic layers were dried over Na$_2$SO$_4$, filtered, concentrated under reduced pressure and purified by flash chromatography on silica gel (eluent: PE/EA=50/1) to give 1.25 g of compound A3f as a yellow solid (Yield: 44.5%).

Synthesis of Compound A4f

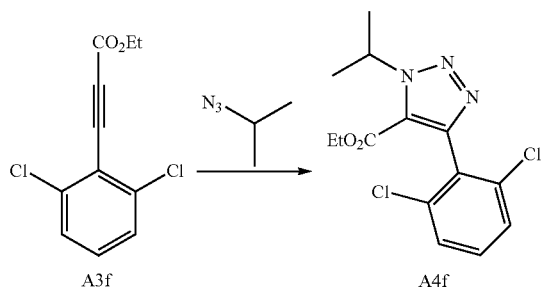

A3f → A4f

The solution of compound A3f (3 g, 12.4 mmol) and 2-azidopropane (20 mL) was heated at 110° C. for 24 h in the autoclave. Concentrated and purified by flash chromatography on silica gel (eluent: PE/EA=4/1) to give 1 g of compound A4f as a yellow solid (Yield: 34.8%).

Synthesis of Compound A5f

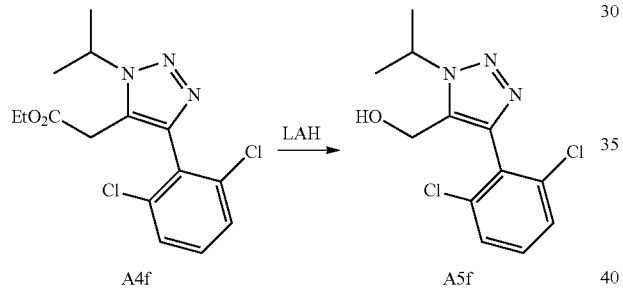

A4f → A5f

To an ice cold solution of compound A4f (1 g, 1.38 mmol) in 10 mL of anhydrous THF was added LAH (2M in THF, 2.76 mmol) dropwise. After addition, the reaction solution was stirred at this temperature for 2 h. TLC indicated that the reduction was over. 10 mL of MeOH was added slowly to quench followed by sat. $Na_2SO_4$ solution. The formed solid was filtered off, and the solution was concentrated under reduced pressure and purified by flash chromatography on silica gel (eluent: PE/EA=1/4) to give 180 mg of compound A5f as a yellow solid (Yield: 45.7%).

$^1$H NMR (400 MHz, $CDCl_3$) δ: 7.41-7.43 (m, 2H), 7.30-7.32 (m, 1H), 4.91-4.97 (m, 1H), 4.58-4.59 (d, J=5.6 Hz, 2H), 2.70-2.73 (br, 1H), 1.72 (s, 3H), 1.70 (s, 3H).

Synthesis of Compound A6f

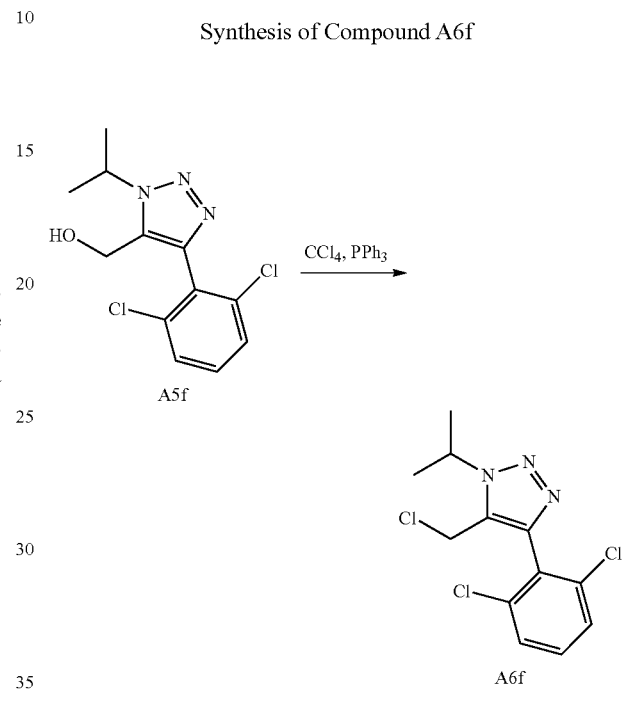

A5f → A6f

The solution of compound A5f (200 mg, 0.70 mmol), $CCl_4$ (1 mL, 10.4 mmol) and $PPh_3$ (368 mg, 1.40 mmol) in 5 mL of anhydrous DCM was stirred at room temperature for 2 h. Concentrated under reduced pressure and purified by flash chromatography on silica gel (eluent: PE/EA=3/1) to give 100 mg of compound A6f as a yellow oil (Yield: 47.1%).

$^1$H NMR (400 MHz, $CDCl_3$) δ: 7.45-7.47 (m, 2H), 7.36-7.39 (m, 1H), 4.81-4.85 (m, 1H), 4.51 (s, 1H), 1.78 (s, 3H), 1.74 (s, 3H).

Scheme 2:
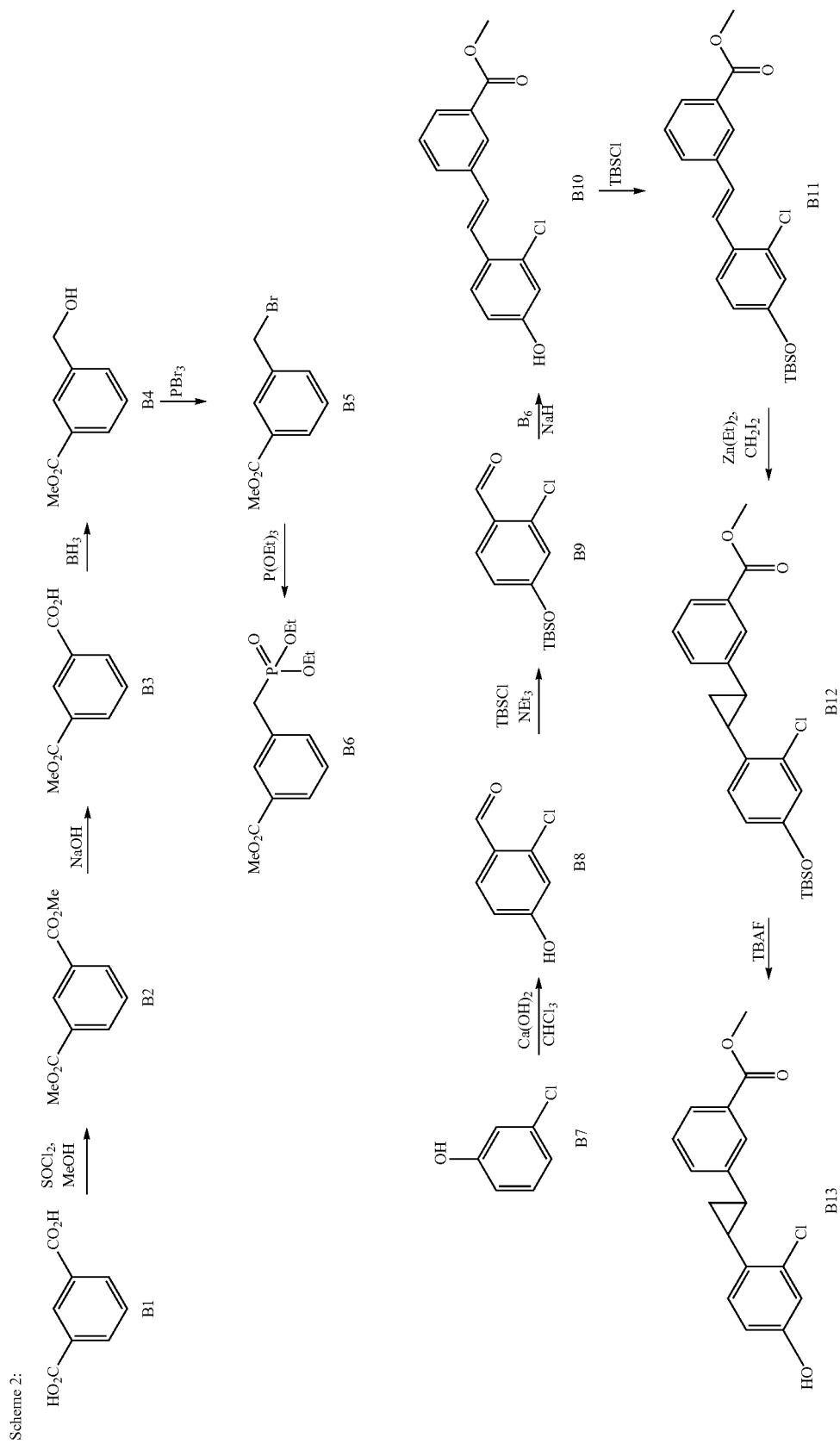

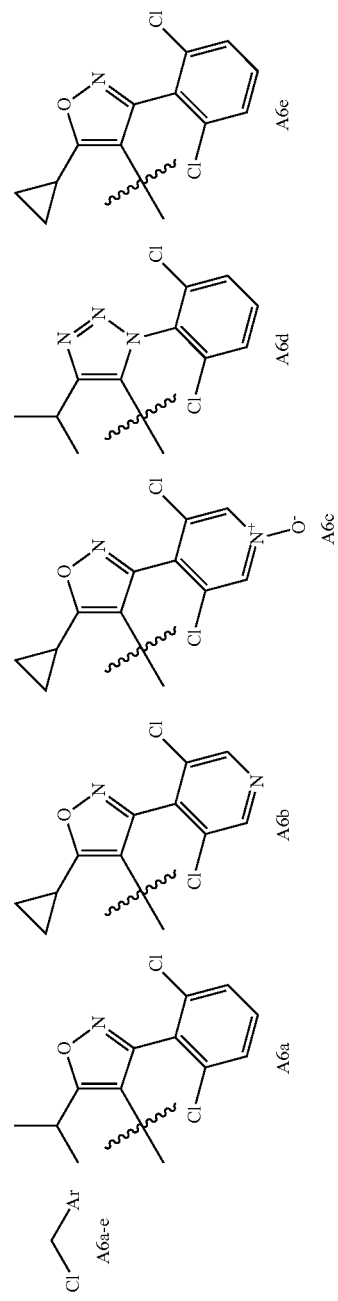
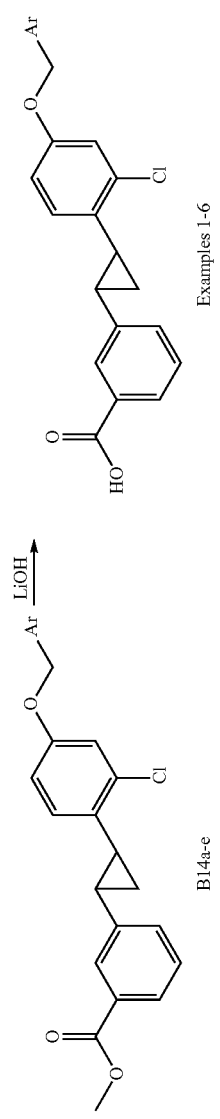

Synthesis of Compound B2

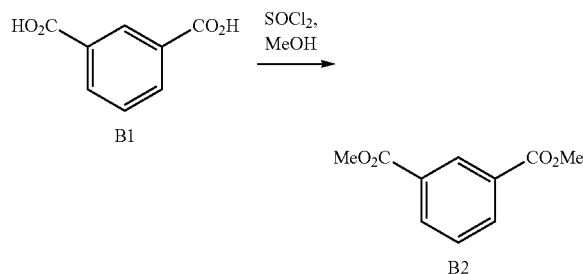

SOCl$_2$ (113.3 g, 0.96 mol) was added to 700 mL of dry methanol slowly at 0° C. After stirring for 1 hour at room temperature, compound B1 (80 g, 0.48 mol) was added and stirred for 1.5 h. The mixture was concentrated and aqueous NaHCO$_3$ solution was added for quench. The suspension was extracted with DCM twice. The combined organic layers was dried over Na$_2$SO$_4$, filtered and concentrated to give 85 g of compound B2 which was used into the next reaction without further purification.

Synthesis of Compound B3

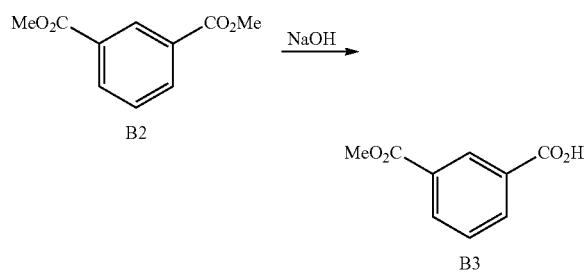

To a solution of compound B2 (60 g, 0.31 mol) in 500 mL of MeOH was added a solution of NaOH (12.4 g, 0.31 mol) in 200 mL of MeOH. The mixture was stirred overnight at room temperature. It was concentrated and the residue was dissolved in 500 mL of water and extracted with Et$_2$O. The aqueous solution was acidified with conc. HCl solution to pH=2, the formed white precipitate was collected and dried under vacuum to give 46 g of crude compound B3 as a white solid.

Synthesis of Compound B4

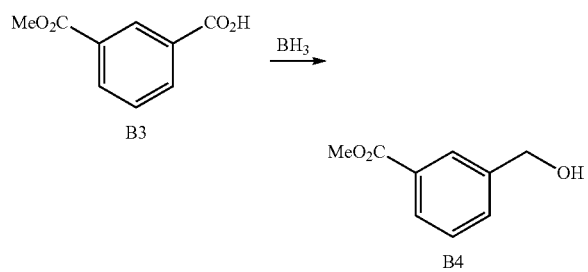

To a solution of compound B3 (46 g, 0.3 mol) in 700 mL of dry THF was added a solution of BH$_3$ in THF (1 M, 600 mL, 0.60 mol) at 0° C. under N$_2$ atmosphere over 20 min. Then the solution was stirred overnight at room temperature. To quench the reaction, 50% aqueous solution of acetic acid (400 mL) was added slowly. The reaction mixture was concentrated and then partitioned between EtOAc and water. The organic phase was washed with 10% aqueous Na$_2$CO$_3$ solution, H$_2$O, and brine consecutively. It was dried over Na$_2$SO$_4$, filtered, concentrated under reduced pressure and purified by chromatography on silica gel (eluent: PE/EtOAc=10/1) to give 28 g of compound B4 as a white solid (Yield in three steps: 54%).

Synthesis of Compound B5

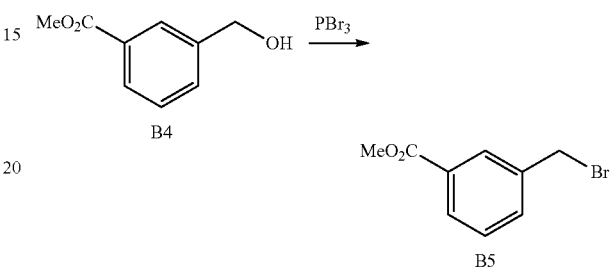

To the solution of compound B4 (28 g, 0.168 mol) in 700 mL of Et$_2$O was added PBr$_3$ (17.4 mL, 0.185 mol) dropwise. The solution was stirred for 2 h, and then the reaction was poured into 500 mL of ice-water. The aqueous layer was extracted with Et$_2$O. The combined organic layers were washed with sat. NaHCO$_3$, water, and brine consecutively. The organic phase was dried over Na$_2$SO$_4$, filtered and concentrated under reduced pressure to give 34 g of compound B5 as an oil (yield: 70%).

Synthesis of Compound B6

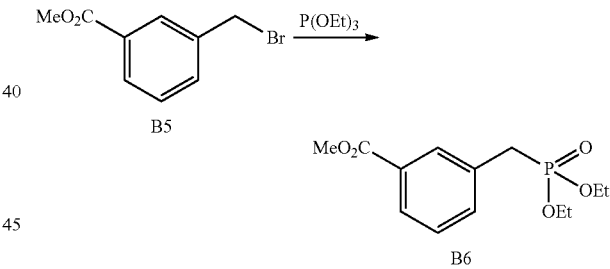

A mixture of compound B5 (34 g, 148 mmol) in 34 mL of triethoxyphosphine was heated at 175° C. for 4 h. The mixture was concentrated under reduced pressure to give 40 g of compound B6 used into the following reaction without further purification.

Synthesis of Compound B8

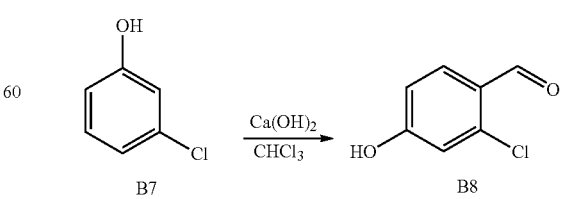

To a solution of compound B7 (150 g, 1.17 mol), calcium hydroxide (375 g, 5.07 mol), and sodium carbonate (420 g, 3.96 mol) in 1.5 L of water was added chloroform (270 g, 2.29 mol) for 80 min, and the mixture was refluxed under N₂ atmosphere for 3 h. The reaction mixture was cooled on an ice bath. 1 L of conc. aq. HCl and 1 L of chloroform were added. The mixture was shaken and after phase separation the aqueous layer was discarded. The organic one was dried with Na₂SO₄, concentrated and purified by chromatography on silica gel (eluent: PE/EtOAc=10/1) to give 28 g of compound B8 as a white solid (Yield: 15.3%).

Synthesis of Compound B9

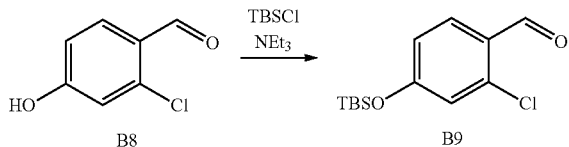

To a solution of compound B8 (11 g, 70.1 mmol) in 300 mL of dry DCM was added TBDMSCI (12.7 g, 84.2 mmol), TEA (19.6 mL, 140.2 mmol) and DMAP (100 mg, cat.). The reaction was stirred at room temperature for 1 hour. It was concentrated under reduced pressure to give 18.5 g of crude compound B9 used into the following reaction without further purification.

Synthesis of Compound B10

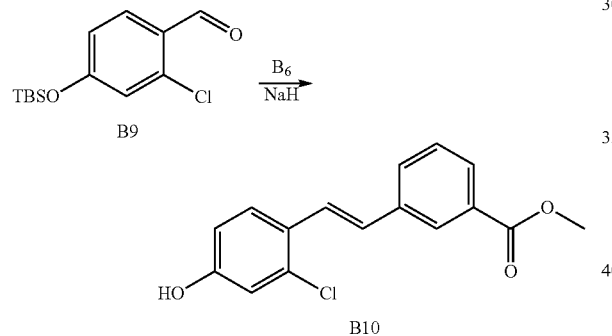

To a solution of compound B9 (23 g, 80.6 mmol) in 320 mL of dry THF was added sodium hydride (60% in mineral oil, 5 g, 123 mmol) at 0° C. for 30 min. To this resulting mixture was added a solution of compound B6 (18.5 g, 61.5 mmol) in 160 mL of dry THF at 0° C., and the solution was stirred at room temperature for 3 h. The mixture was quenched by sat. NH₄Cl solution and extracted with EtOAc. The organic layer was washed with brine, dried over Na₂SO₄, filtered, concentrated to give 23 g of compound B10 used in the following reaction without further purification.

Synthesis of Compound B11

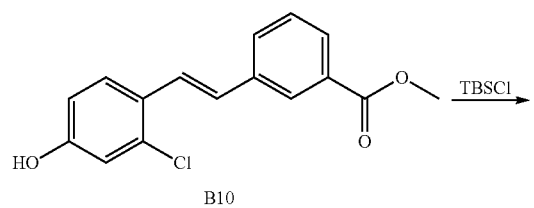

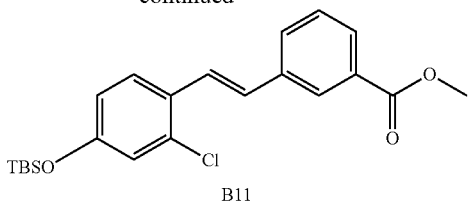

To a solution of compound B10 (23 g, 80.6 mmol) in 450 mL of dry DCM was added TBDMSCI (12.7 g, 84.2 mmol), TEA (19.6 mL, 161.2 mmol) and DMAP (0.5 g, cat.). The reaction was stirred at room temperature for 1 hour. It was concentrated under reduced pressure and purified by chromatography on silica gel (eluent: PE/EtOAc=30/1) to give 11.8 g of compound B11 as a white solid (Yield in three steps: 41.8%).

Synthesis of Compound B12

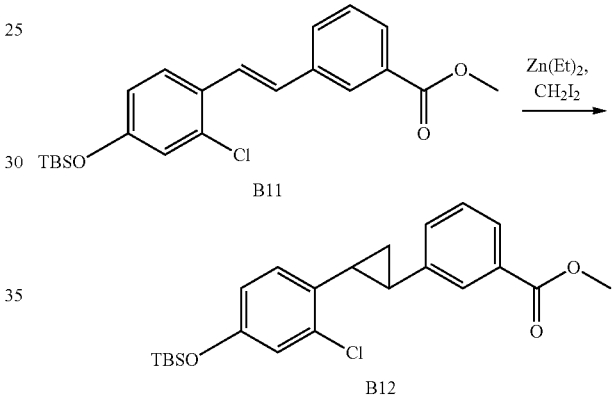

To a solution of diethyl zinc (290 mL, 1M in hexane, 290 mmol) in 600 mL of dry DCM was added diiodoethane (46 mL, 580 mmol) at −78° C. The solution was stirred for 30 min, and then the mixture was warmed to −30° C. TFA (38 g, 290 mmol) was added to the mixture, and stirred for 30 min. The solution of compound B11 (11.8 g, 29 mmol) in 200 mL of DCM was added to the mixture, and the mixture was stirred overnight at room temperature. The reaction mixture was quenched with 500 mL of 1 N aq. HCl. The organic layer was washed with brine, dried over Na₂SO₄, filtered, concentrated to dryness and purified by flash chromatography on silica gel (eluent: PE/EtOAc=20/1) to give 4.5 g of compound B12 as an oil (Yield: 36.9%).

Synthesis of Compound B13

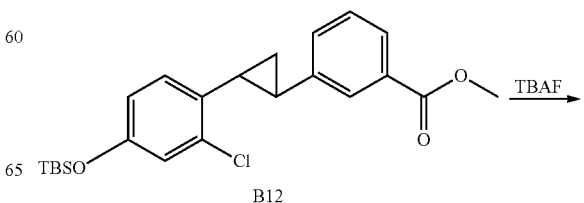

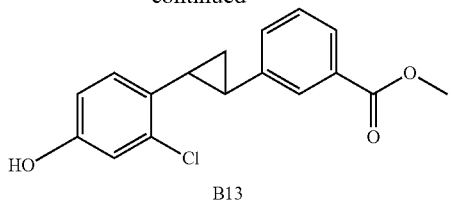
B13

A solution of compound B12 (4.5 g, 10.8 mmol) and TBAFH₂O (11 g, 42.1 mmol) in 300 mL of dry THF was stirred for 10 min at room temperature. Water (100 mL) was added and the mixture was extracted with 500 mL of EtOAc. The organic layer was washed with brine, dried over Na₂SO₄, concentrated under reduced pressure and purified by flash chromatography on silica gel (eluent: PE/EtOAc=10/1) to give 2.0 g of crude compound B13 with 80% purity (UV-HPLC) as a yellow oil.

Synthesis of Compound B14a

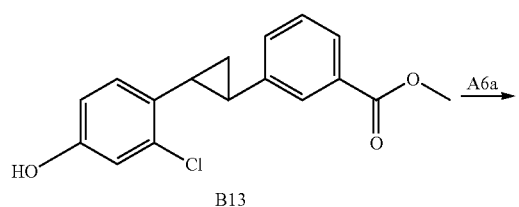

To a solution of the crude compound B13 (200 mg, 0.66 mmol) and compound A6a (200 mg, 0.66 mmol) in 5 mL of DMF was added K₂CO₃ (184 mg, 1.33 mmol). The mixture was heated overnight at 60° C., then cooled to room temperature, diluted with water (10 mL) and extracted with 30 mL of EtOAc. The organic layer was washed with brine twice, dried over Na₂SO₄, filtered, concentrated and purified by flash chromatography on silica gel (eluent: PE/EtOAc=20/1) to give 220 mg of compound B14a as a white solid (Yield: 59.8%).

Synthesis of Compound B14b

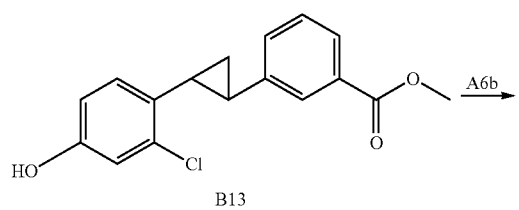

B14b

To a solution of crude compound B13 (200 mg, 0.66 mmol) and compound A6b (200 mg, 0.66 mmol) in 5 mL of DMF was added K₂CO₃ (184 mg, 1.33 mmol). The mixture was heated overnight at 60° C., then cooled to room temperature, diluted with water (10 mL) and extracted with 30 mL of EtOAc. The organic layer was washed with brine twice, dried over Na₂SO₄, filtered, concentrated and purified by chromatography on silica gel (eluent: PE/EtOAc=20/1) to give 100 mg of compound B14b as a white solid (Yield: 27.2%).

Synthesis of Compound B14c

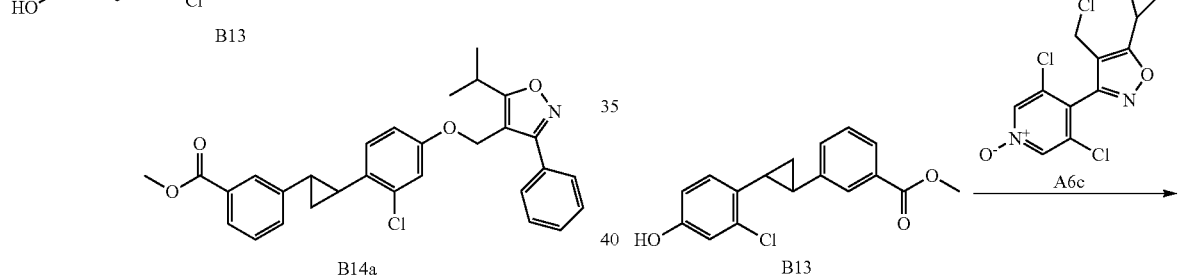

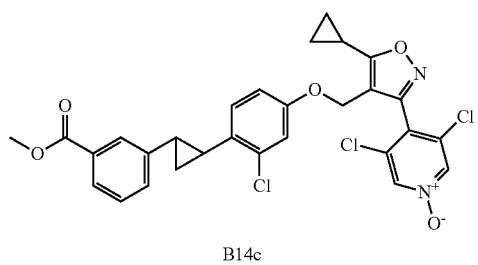
B14c

To a solution of crude compound 813 (200 mg, 0.66 mmol) and compound A6c (211 mg, 0.66 mmol) in 5 mL of DMF was added K₂CO₃ (184 mg, 1.33 mmol). The mixture was heated overnight at 60° C., then cooled to room temperature, diluted with water (10 mL) and extracted with 30 mL of EtOAc. The organic layer was washed with brine twice, dried over Na₂SO₄, filtered, concentrated and purified by flash chromatography on silica gel (eluent: PE/EA=8/1) to give 140 mg of compound B14c as a white solid (Yield: 38.1%).

Synthesis of Compound B14d

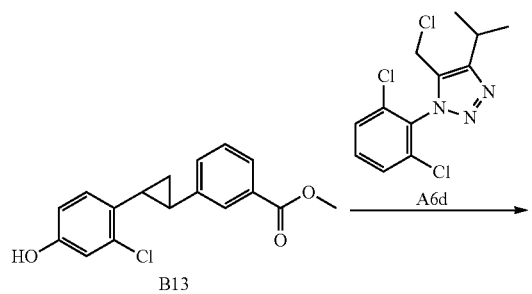

B13

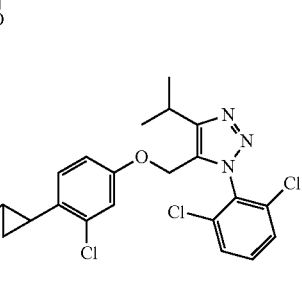

B14d

To a solution of crude compound B13 (200 mg, 0.66 mmol) and compound A6d (200 mg, 0.66 mmol) in 5 mL of DMF was added K$_2$CO$_3$ (184 mg, 1.33 mmol). The mixture was heated overnight at 60° C., then cooled to room temperature, diluted with water (10 mL) and extracted with 30 mL of EtOAc. The organic layer was washed with brine twice, dried over Na$_2$SO$_4$, filtered, concentrated and purified by flash chromatography on silica gel (eluent: PE/EA=10/1) to give 103 mg of compound B14d as a white solid (Yield: 28.0%).

Synthesis of Compound B14e

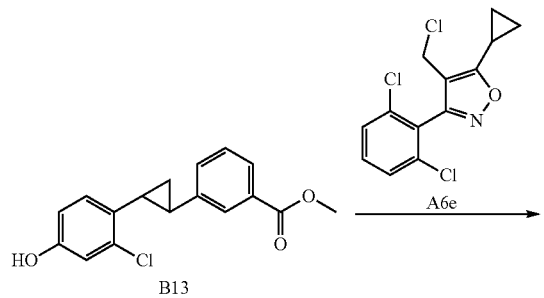

B13

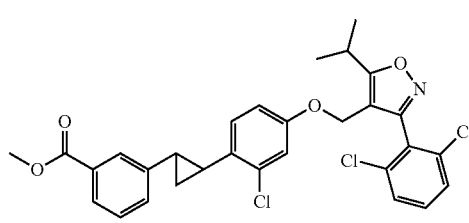

B14e

To a solution of crude compound B13 (1 g, 3.3 mmol, 1.00 eq) and Abe (1 g, 3.3 mmol, 1 eq) in 30 mL of DMF was added K$_2$CO$_3$ (1.4 g, 9.9 mmol, 3.00 eq). The mixture was heated overnight at 60° C., then cooled to room temperature, diluted with water (50 mL) and extracted with Et$_2$O (200 mL). The organic layer was washed with brine, dried over Na$_2$SO$_4$, filtered, concentrated and purified by flash chromatography on silica gel (eluent: PE/EtOAc=20/1) to give 1.2 g of B14e used in the following reaction without further purification.

Synthesis of Example 1

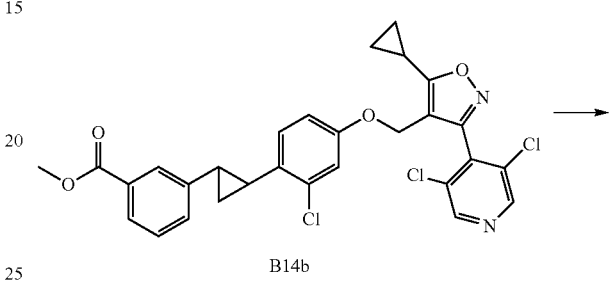

B14b

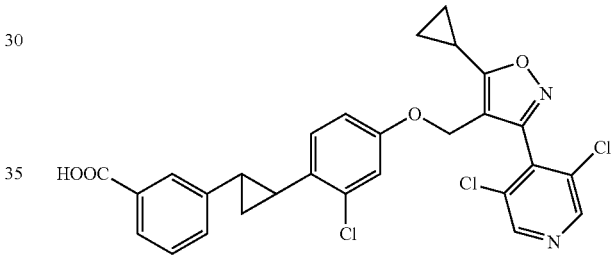

Example 1

To a solution of compound B14b (100 mg, 0.18 mmol) in 5 mL of THF and 2 mL of H$_2$O was added LiOH.H$_2$O (74 mg, 1.8 mmol), and then the mixture was stirred at room temperature for 24 h. The mixture was concentrated and diluted with 10 mL of H$_2$O, 1N aq. HCl was added to acidify the mixture to pH=5. The mixture was extracted with EtOAc and the organic layer was washed with brine, dried over Na$_2$SO$_4$, filtered, concentrated and the residue was purified by chromatography on silica gel (eluent: PE/EAtOAc=3/1) to give 30 mg of Example 1 (3-(2-(2-chloro-4-((5-cyclopropyl-3-(3,5-dichloropyridin-4-yl)isoxazol-4-yl)methoxy)phenyl)cyclopropyl)-benzoic acid) as a white solid (Yield: 30.8%).

$^1$H NMR (400 MHz, CDCl$_3$) δ: 1.23 (m, 2H), 1.31 (m, 2H), 1.47 (m, 2H), 2.09 (m, 1H), 2.17 (m, 1H), 2.39 (m, 1H), 4.84 (s, 2H), 6.65 (dd, J=1.6 Hz, 8.4 Hz, 1H), 6.84 (d, J=1.6 Hz, 1H), 6.99 (d, J=8.4 Hz, 1H), 7.43-7.48 (m, 2H), 7.97 (m, 2H), 8.64 (s, 2H);

LCMS (mobile phase: 60%-95% Acetonitrile-Water-0.01% TFA) purity>95%, Rt=3.304 min;

MS Calcd.: 554; MS Found: 555 (M+H)$^+$.

Synthesis of Example 2

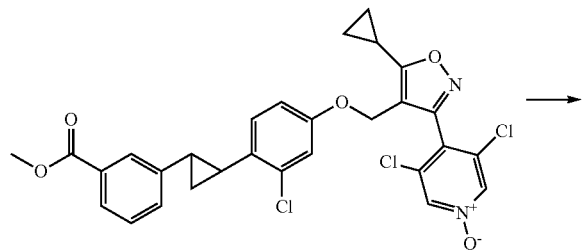

B14c

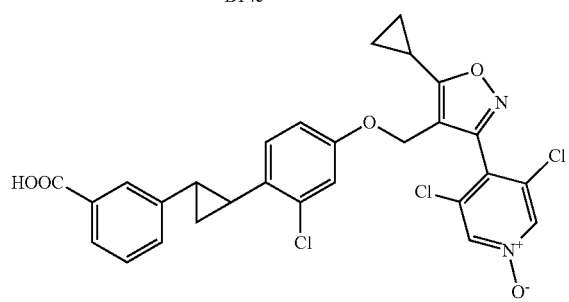

Example 2

To a solution of compound B14c (140 mg, 0.24 mmol) in 5 mL of THF and 2 mL of H₂O was added LiOH.H₂O (100 mg, 2.4 mmol), and then the mixture was stirred at room temperature for 24 h. The mixture was concentrated and diluted with 10 mL of H₂O, 1N aq. HCl was added to acidify the mixture to pH=5. The mixture was extracted with EtOAc and the organic layer was washed with brine, dried over Na₂SO₄, filtered, concentrated and purified by chromatography on silica gel (eluent: PE/EtOAc=1/1) to give 40 mg of Example 2 (4-(4-((4-(2-(3-carboxyphenyl)cyclopropyl)-3-chlorophenoxy)methyl)-5-cyclopropylisoxazol-3-yl)-3,5-dichloropyridine 1-oxide) as a white solid (Yield: 29.3%).

¹H NMR (400 MHz, CDCl₃) δ: 1.21-1.33 (m, 4H), 1.44-1.50 (m, 2H), 2.10-2.19 (m, 2H), 2.39 (m, 1H), 4.85 (s, 2H), 6.67 (dd, J=2.4 Hz, 8.4 Hz, 1H), 6.88 (d, J=2.4 Hz, 1H), 7.02 (d, J=8.4 Hz, 1H), 7.40-7.48 (m, 2H), 7.95 (m, 2H), 8.31 (s, 2H);

LCMS (mobile phase: 40%-95% Acetonitrile-Water-0.01% TFA) purity>95%, Rt=3.421 min;

MS Calcd.: 570; MS Found: 571 (M+H)⁺.

Synthesis of Example 3

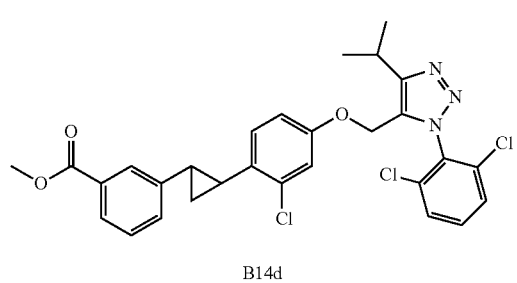

B14d

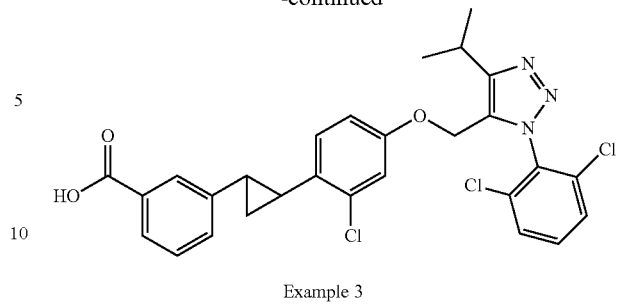

Example 3

To a solution of compound B14d (103 mg, 0.18 mmol) in 10 mL of THF and 5 mL of H₂O was added LiOH.H₂O (76 mg, 1.8 mmol), and then the mixture was stirred at room temperature for 24 h. The mixture was concentrated and diluted with 10 mL of H₂O, 1N aq. HCl was added to acidify the mixture to pH=5. The mixture was extracted with EtOAc and the organic layer was washed with brine, dried over Na₂SO₄, filtered, concentrated and purified by chromatography on silica gel (eluent: PE/EtOAc=2/1) to give 80 mg of Example 3 (3-(2-(2-chloro-4-((1-(2,6-dichlorophenyl)-4-isopropyl-1H-1,2,3-triazol-5-yl)methoxy)phenyl)cyclopropyl)benzoic acid) as a white solid (Yield: 79.6%).

¹H NMR (400 MHz, CDCl₃) δ: 1.45 (m, 8H), 2.08 (m, 1H), 2.38 (m, 1H), 3.24 (m, 1H), 4.92 (s, 2H), 6.67 (d, J=8.0 Hz, 1H), 6.82 (s, 1H), 7.00 (d, J=8.8 Hz, 1H), 7.41-7.52 (m, 5H), 7.94-7.98 (m, 2H);

LCMS (mobile phase: 60%-95% Acetonitrile-Water-0.01% TFA) purity>95%, Rt=3.082 min;

MS Calcd.: 555; MS Found: 556 (M+H)⁺.

Synthesis of Example 4

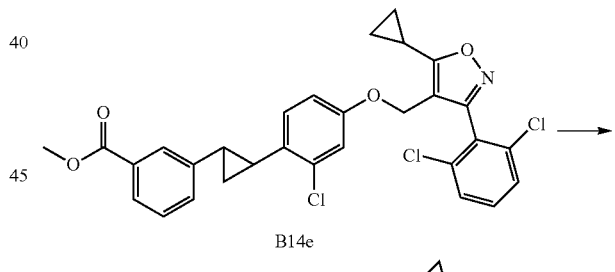

B14e

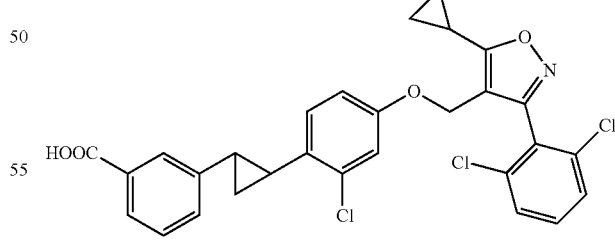

Example 4

To a solution of compound B14e in 30 mL of THF and 15 mL of H₂O was added LiOH.H₂O (3 g), and then the mixture was stirred at room temperature for 24 h. It was concentrated and diluted with 30 mL of H₂O, 1N aq. HCl was added to acidify the mixture. The mixture was extracted with EtOAc. The organic layer was washed with brine, dried over Na₂SO₄, filtered, concentrated and purified by chromatography on silica gel (eluent: PE/EtOAc=20/1) to give 320 mg of Example 4 (racemic 3-(2-(2-chloro-4-((5-cyclopropyl-3-(2,6-dichlorophenyl)isoxazol-4-yl)methoxy)phenyl)-cyclopropyl)benzoic acid) as a white solid (Yield: 17.5%%).

¹HNMR (CDCl₃, 400 MHz) δ: 1.14-1.18 (m, 2H), 1.24-1.31 (m, 2H), 1.41-1.46 (m, 2H), 2.07-2.08 (m, 1H), 2.15-2.17 (m, 1H), 2.35-2.37 (m, 1H), 4.78 (s, 2H), 6.67 (dd, J=2.4 Hz, 8.8 Hz, 1H), 6.84 (d, J=2.4 Hz, 1H), 6.96 (d, J=8.4 Hz, 1H), 7.30-7.34 (m, 1H), 7.38-7.45 (m, 4H), 7.92-7.95 (m, 2H).

LCMS (mobile phase: 60%-95% Acetonitrile-Water-0.01% TFA) purity>97%, Rt=3.699 min;

MS Calcd.: 553; MS Found: 554 (M+H)⁺.

Resolution of racemic 3-(2-(2-chloro-4-((5-cyclopropyl-3-(2,6-dichlorophenyl)isoxazol-4-yl)methoxy)phenyl)-cyclopropyl)benzoic acid into enantiomers:

290 mg of racemic 3-(2-(2-chloro-4-((5-cyclopropyl-3-(2,6-dichlorophenyl)isoxazol-4-yl)methoxy)phenyl)-cyclopropyl)benzoic acid was separated by prep. chiral HPLC with chiral column (column: CHIRALPAK AD-H; Column size: 0.46 cm I.D.×15 cm L; Mobile phase: Hexane/EtOH/HOAc=50/50/0.1 (v/v/v); Flow rate: 0.5 ml/min; Wave length: UV 220 nm; HPLC equipment: Shimadzu LC 20 with UV detector SPD-20A) to give 137 mg of (−)-3-(2-(2-chloro-4-((5-cyclopropyl-3-(2,6-dichlorophenyl)isoxazol-4-yl)methoxy)phenyl)cyclopropyl)benzoic acid (Rt=7.250 min, ee %: >98%) and 132 mg of (+)-3-(2-(2-chloro-4-((5-cyclopropyl-3-(2,6-dichlorophenyl)isoxazol-4-yl)-methoxy)phenyl)cyclopropyl)benzoic acid (Rt=8.930 min, ee %: >98%).

−)-3-(2-(2-chloro-4-((5-cyclopropyl-3-(2,6-dichlorophenyl)isoxazol-4-yl)methoxy)phenyl)cyclopropyl)benzoic acid (Example 5a)

¹HNMR (CDCl₃, 400 MHz) δ: 1.14-1.18 (m, 2H), 1.24-1.31 (m, 2H), 1.41-1.46 (m, 2H), 2.07-2.08 (m, 1H), 2.15-2.17 (m, 1H), 2.35-2.37 (m, 1H), 4.78 (s, 2H), 6.67 (dd, J=2.4 Hz, 8.8 Hz, 1H), 6.84 (d, J=2.4 Hz, 1H), 6.96 (d, J=8.4 Hz, 1H), 7.30-7.34 (m, 1H), 7.38-7.45 (m, 4H), 7.92-7.95 (m, 2H).

LCMS (mobile phase: 60%-95% Acetonitrile-Water-0.01% TFA) purity>97%, Rt=3.692 min;

MS Calcd.: 553; MS Found: 554 (M+H)⁺.

Optical rotation: $[\alpha]_D^{25}$=−92° (MeOH, c=0.3)

For absolute configuration of the chiral centers see scheme 14.

+)-3-(2-(2-chloro-4-((5-cyclopropyl-3-(2,6-dichlorophenyl)isoxazol-4-yl)methoxy)phenyl)cyclopropyl)benzoic acid (Example 5b)

¹HNMR (CDCl₃, 400 MHz) δ: 1.14-1.18 (m, 2H), 1.24-1.31 (m, 2H), 1.41-1.46 (m, 2H), 2.07-2.08 (m, 1H), 2.15-2.17 (m, 1H), 2.35-2.37 (m, 1H), 4.78 (s, 2H), 6.67 (dd, J=2.4 Hz, 8.8 Hz, 1H), 6.84 (d, J=2.4 Hz, 1H), 6.96 (d, J=8.4 Hz, 1H), 7.30-7.34 (m, 1H), 7.38-7.45 (m, 4H), 7.92-7.95 (m, 2H).

LCMS (mobile phase: 60%-95% Acetonitrile-Water-0.01% TFA) purity>97%, Rt=3.690 min;

MS Calcd.: 553; MS Found: 554 (M+H)⁺.

Optical rotation: $[\alpha]_D^{25}$=+91° (MeOH, c=0.3)

For absolute configuration of the chiral centers see scheme 14.

Synthesis of Example 6

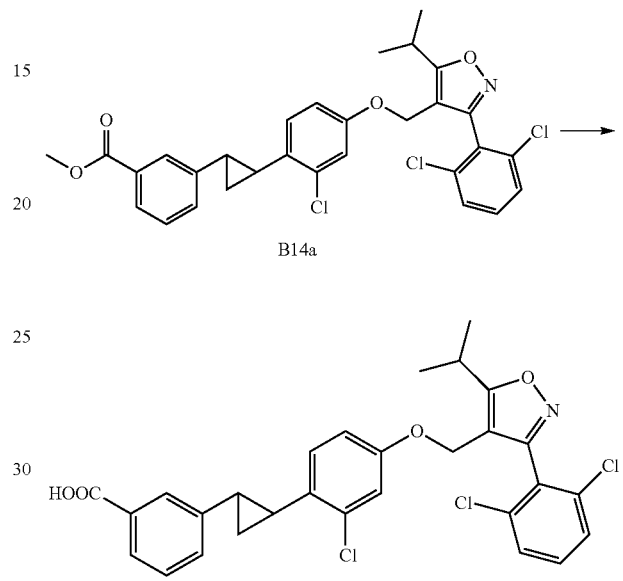

To a solution of compound B14a (220 mg, 0.39 mmol) in 6 mL of THF and 3 mL of H₂O was added LiOH.H₂O (162 mg, 3.9 mmol), and then the mixture was stirred at room temperature for 24 h. It was concentrated and diluted with 10 mL of H₂O. 1N aq. HCl was added to acidify the mixture to pH=4 and the mixture was extracted with EtOAc. The organic layer was washed with brine, dried over Na₂SO₄, filtered, concentrated and purified by chromatography on silica gel (eluent: PE/EtOAc=3/1) to give 80 mg of Example 6 (3-(2-(2-chloro-4-((3-(2,6-dichlorophenyl)-5-isopropyl isoxazol-4-yl)methoxy)phenyl)cyclopropyl)benzoic acid) as a white solid (Yield: 37.3%).

¹HNMR (400 MHz, CDCl₃) δ: 1.45 (m, 8H), 2.09 (m, 1H), 2.38 (m, 1H), 3.35 (m, 1H), 4.73 (s, 2H), 6.67 (dd, J=2.4 Hz, 8.4 Hz, 1H), 6.83 (d, J=2.4 Hz, 1H), 6.99 (d, J=8.8 Hz, 1H), 7.34-7.48 (m, 5H), 7.95 (m, 2H);

LCMS (mobile phase: 80%-95% Acetonitrile-Water-0.01% TFA) purity>95%, Rt=3.983 min;

MS Calcd.: 555; MS Found: 556 (M+H)⁺.

Scheme 3

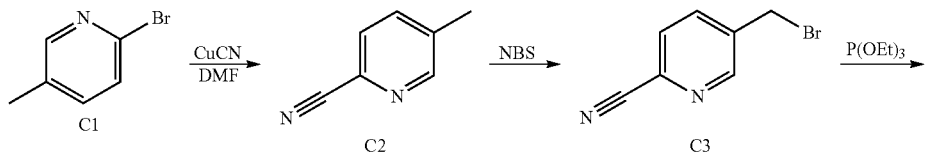

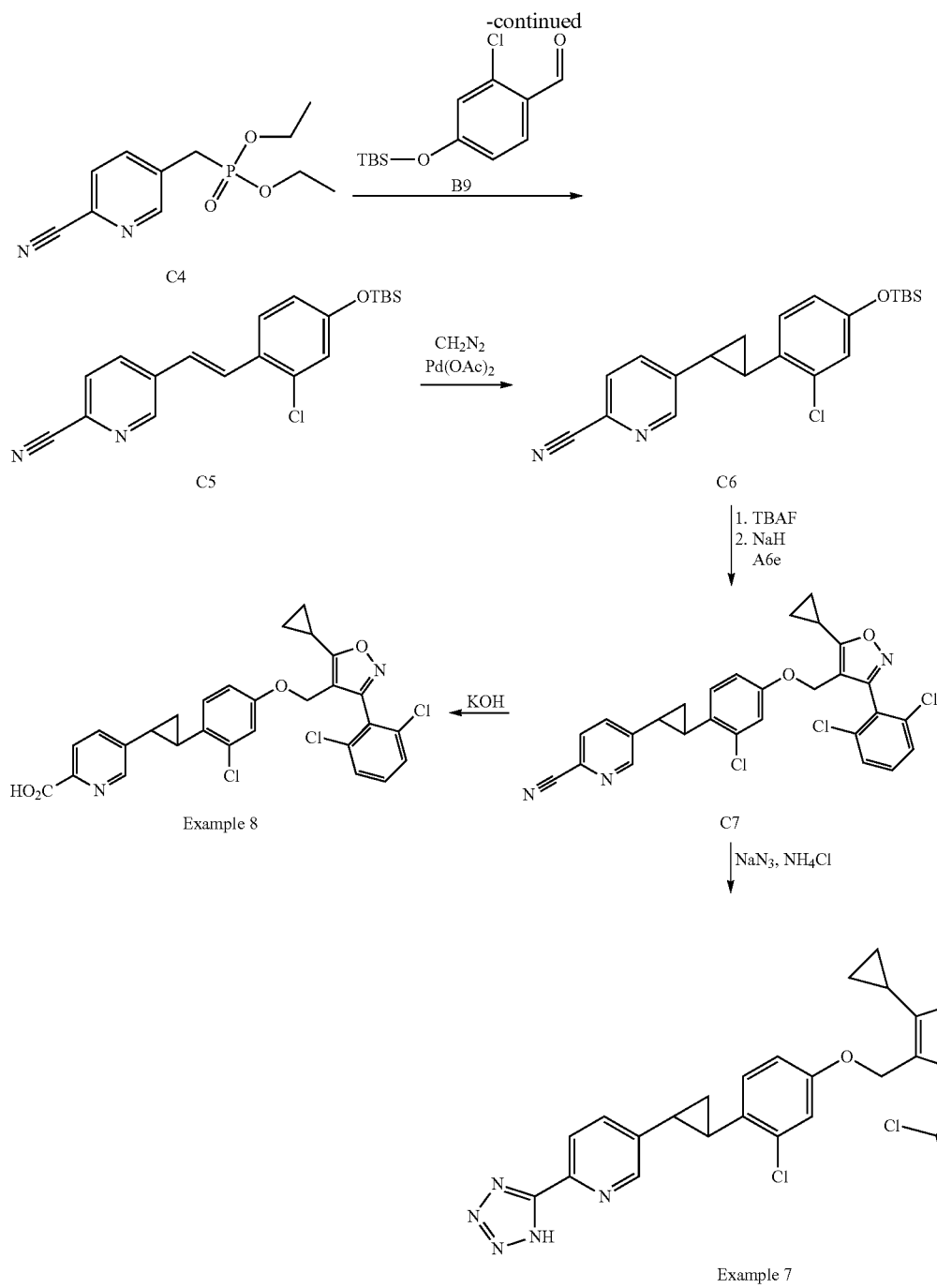
Synthesis of Compound C2
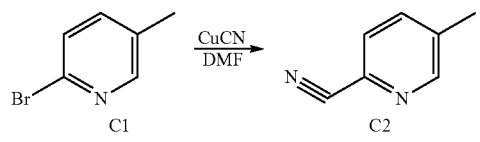
A solution of compound C1 (78.0 g, 456 mmol) and CuCN (45.2 g, 502 mmol) in 400 mL of DMF was refluxed for 3 h. The mixture was concentrated under vacuum and the residue purified by chromatography on silica gel (eluent: PE/EtOAc=10/1) to give 7.7 g of compound C2 as a white solid (Yield: 14.3%).
Synthesis of Compound C3
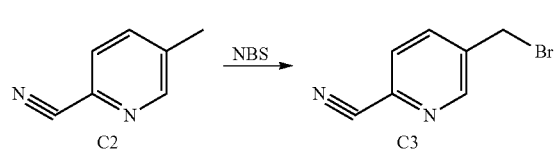

A solution of compound C2 (7.5 g, 63.6 mmol), benzoylperoxide (0.54 g, 2.24 mmol), and N-bromosuccinimide (12.5 g, 70.2 mmol) in 100 mL of CCl₄ was refluxed for 2 h. The resulting suspension was filtered and the filtrate diluted with 400 mL of DCM, washed with a saturated sodium bicarbonate solution, dried over MgSO₄, filtered, and concentrated under reduced pressure. The residue was purified by flash chromatography on silica gel (eluent: PE/EtOAc=10/1) to give 3.3 g of crude compound C3 as a yellow solid used in the following reaction without further purification.

Synthesis of Compound C4

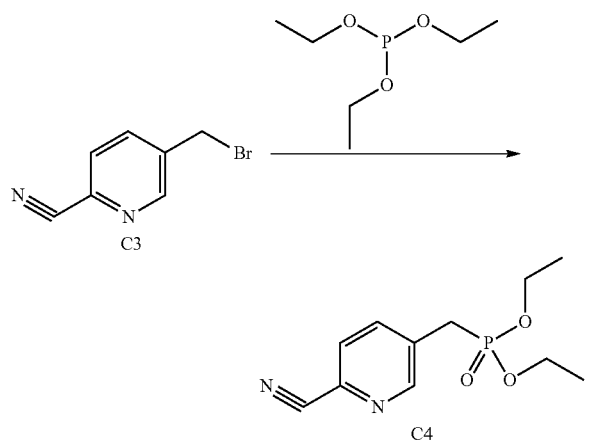

A solution of compound C3 (3.3 g, 16.8 mmol) in 30 mL of triethoxyphosphine was heated at 175° C. for 4 h. The mixture was concentrated under reduced pressure to give 3.99 g of compound C4 which was used in the following step without further purification.

Synthesis of Compound C5

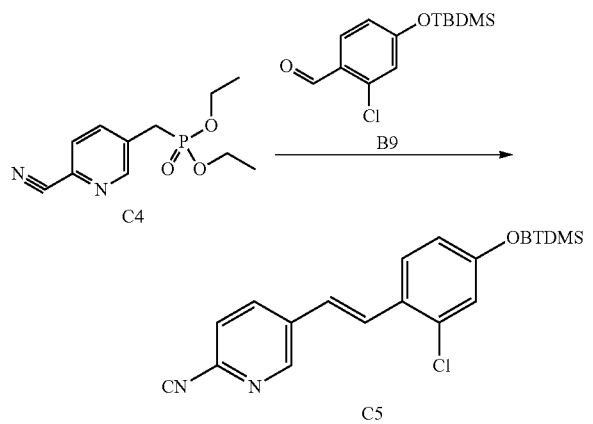

To a solution of compound C4 (3.90 g, 15.4 mmol) in 40 mL of dry THF was added sodium hydride (1.23 g, 60% in mineral oil, 30.8 mmol) at 0° C. for 30 min. To this resulting mixture was added a solution of compound B9 (4.15 g, 15.4 mmol) in 40 mL of dry THF at 0° C., and the solution was stirred at room temperature for 3 h. The mixture was quenched with sat. NH₄Cl solution and extracted with EtOAc. The organic layer was washed with brine, dried over Na₂SO₄, filtered, concentrated and purified by chromatography on silica gel (eluent: PE/EtOAc=10/1) to give 2.11 g of compound C5 as a white solid (Yield: 37.1%).

Synthesis of Compound C6

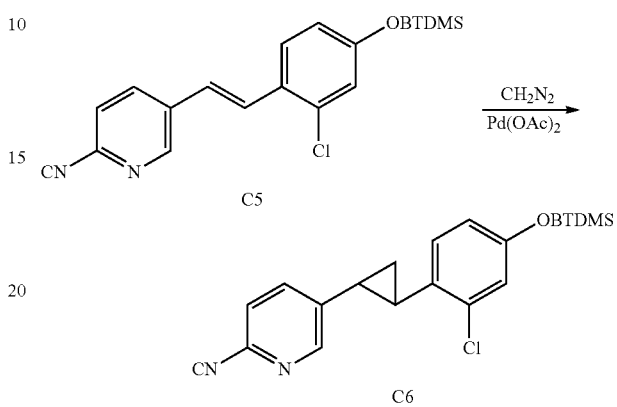

To a solution of compound C5 (2.10 g, 5.68 mmol) and Pd(OAc)₂ (0.3 g) in 30 mL of Et₂O was added a solution of CH₂N₂ in Et₂O (70 mL, 280 mmol) at −50° C. under N₂ atmosphere. Then the solution was warmed to room temperature slowly, and stirred for another 4 h. The reaction mixture was filtered, concentrated and the residue was purified by flash chromatography on silica gel (eluent: PE/EtOAc=10/1) to give 1.68 g of compound C6 as a white solid (Yield: 77.1%).

Synthesis of Compound C7

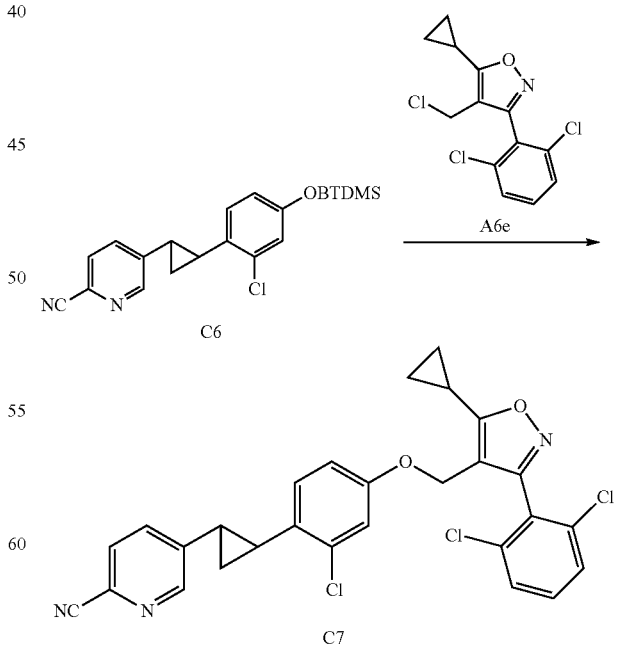

To a solution of compound C6 (600 mg, 1.56 mmol) in 10 mL of DMF was added NaH (188 mg, 60% in mineral oil, 4.68 mmol) at 0° C., and stirred for one hour at room temperature. Then compound A6e (472 mg, 1.56 mmol) was added under stirring, followed by stirring overnight at room temperature. The solution was poured into 10 mL of ice-water and extracted with 20 mL of DCM. The organic layer was washed by water twice and brine twice consecutively and dried over Na$_2$SO$_4$. The solvent was removed under reduced pressure and the residue was purified by chromatography on silica gel (eluent: PE/EtOAc=10/1) to give 370 mg of compound C7 as a white solid (yield: 44.2%).

Hz, 1H), 7.56 (m, 1H), 7.64 (m, 2H), 7.83 (d, J=7.6 Hz, 1H), 8.13 (d, J=8.0 Hz, 1H), 8.72 (s, 1H);

LCMS (mobile phase: 60-95% Acetonitrile-Water-0.1% TFA) purity>95%, Rt=2.886 min; MS Calcd.: 578; MS Found: 579 (M+1).

Synthesis of Example 7

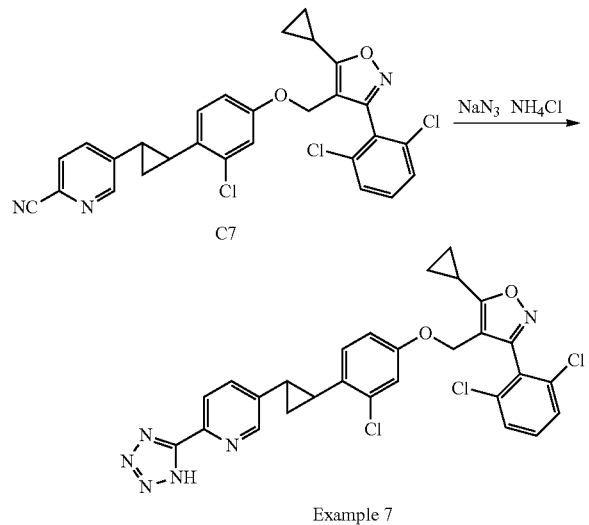

Example 7

Synthesis of Example 8

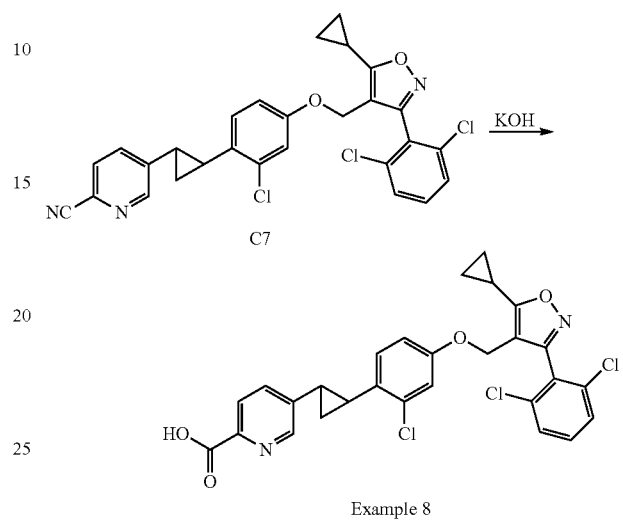

Example 8

To a solution of compound C7 (220 mg, 0.41 mmol) in 5 mL of DMF was added NaN$_3$ (66 mg, 1.02 mmol), NH$_4$Cl (54 mg, 1.02 mmol), and then the mixture was stirred at 100t overnight. After cooling to room temperature DMF was removed, and then water (10 mL) was added and the mixture was acidified with 1 N aq. HCl to pH=4. The formed solid was collected by filtration and washed with EtOAc and Et$_2$O to give mg of Example 7 (4-((4-(2-(6-(1H-tetrazol-5-yl)pyridin-3-yl)cyclopropyl)-3-chlorophenoxy)methyl)-5-cyclopropyl-3-(2,6-dichlorophenyl)isoxazole) as a yellow solid (yield: 12.2%).

$^1$H-NMR (400 MHz, DMSO-d$_6$) δ 1.12-1.22 (m, 4H), 1.63 (s, 2H), 2.19 (m, 1H), 2.38 (m, 1H), 2.43 (m, 1H), 4.91 (s, 2H), 6.76 (d, J=8.4 Hz, 1H), 6.94 (d, J=1.2 Hz, 1H), 7.14 (d, J=8.4

A solution of compound C7 (150 mg, 0.28 mmol), KOH (1.57 g, 28 mmol) in 15 mL of ethanol and 6 mL of water were stirred at 100° C. for 4 h. The mixture was cooled to room temperature and concentrated. The residue was dissolved in 30 mL of water, acidified with 1 N aq. HCl to pH=4 and the formed solid was collected by filtration. The solid was washed by EtOAc and dried under vacuum to give 45 mg of Example 8 (5-(2-(2-chloro-4-((5-cyclopropyl-3-(2,6-dichlorophenyl)isoxazol-4-yl)methoxy)-phenyl)cyclopropyl)picolinic acid) as a white solid (yield: 29%).

$^1$H NMR (400 MHz, DMSO-d6) δ 8.52 (s, 1H), 7.88 (d, J=7.2 Hz, 1H), 7.54-7.65 (m, 4H), 7.11 (d, J=8.8 Hz, 1H), 6.93 (d, J=2.8 Hz, 1H), 6.74 (dd, J=2.4 Hz, 8.4 Hz, 1H), 4.91 (s, 2H), 2.45 (m, 1H), 2.33 (m, 1H), 2.11 (m, 1H), 1.52-1.59 (m, 2H), 1.11-1.20 (m, 4H);

LCMS (mobile phase: 50-95% Acetonitrile-Water-0.1% TFA) purity is >95%, Rt=3.023 min;

MS Calcd.: 554; MS Found: 555 (M+1).

Scheme 3a

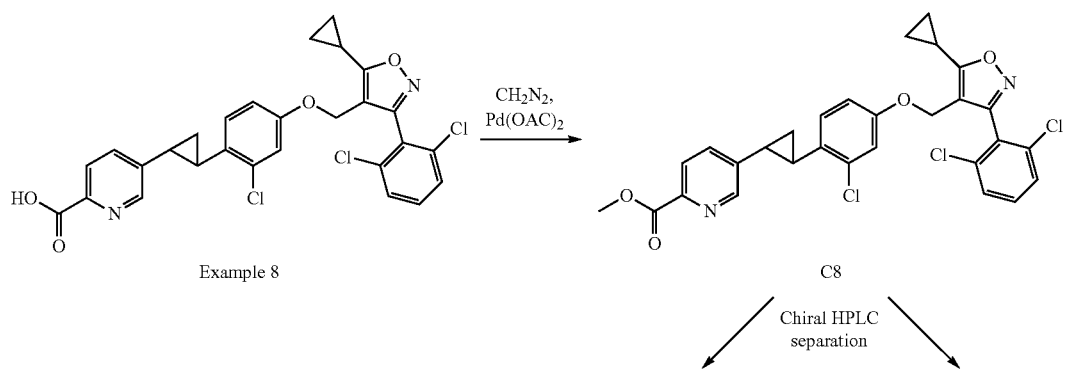

Chiral HPLC separation

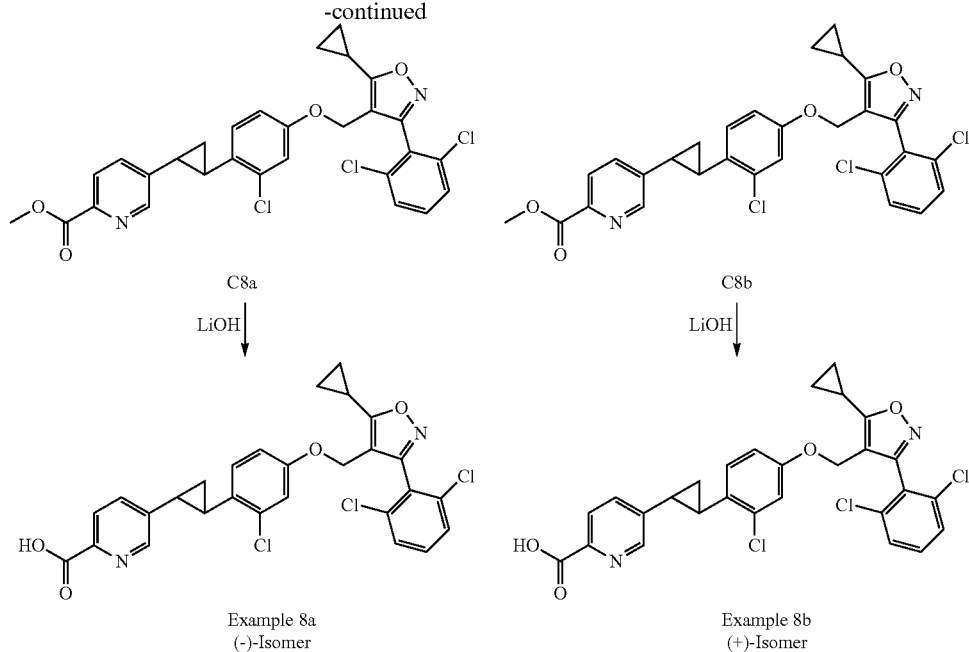

Example 8a
(−)-Isomer

Example 8b
(+)-Isomer

Synthesis of Compound C8

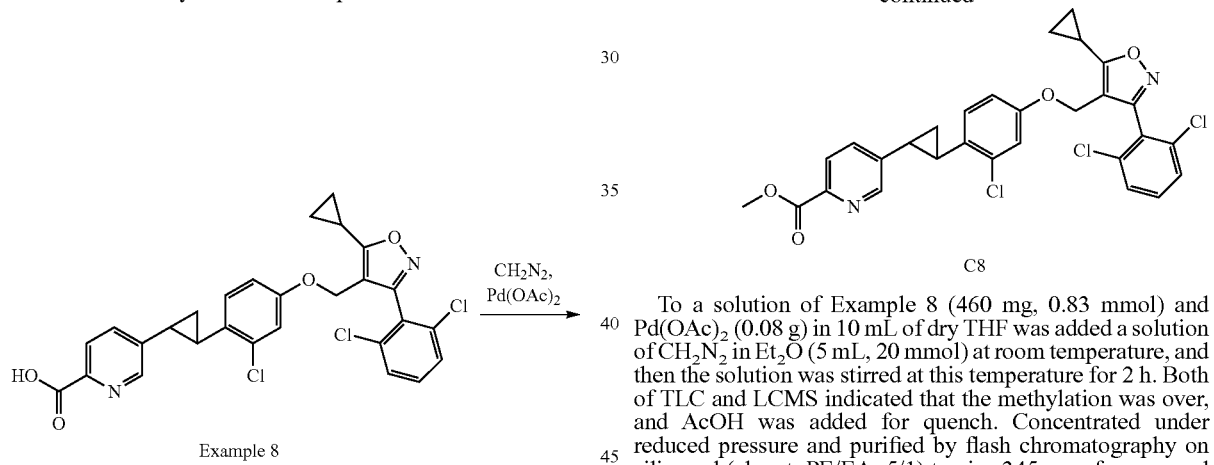

To a solution of Example 8 (460 mg, 0.83 mmol) and Pd(OAc)$_2$ (0.08 g) in 10 mL of dry THF was added a solution of CH$_2$N$_2$ in Et$_2$O (5 mL, 20 mmol) at room temperature, and then the solution was stirred at this temperature for 2 h. Both of TLC and LCMS indicated that the methylation was over, and AcOH was added for quench. Concentrated under reduced pressure and purified by flash chromatography on silica gel (eluent: PE/EA=5/1) to give 345 mg of compound C8 as a yellow oil (Yield: 73.1%).

Chiral HPLC Separation

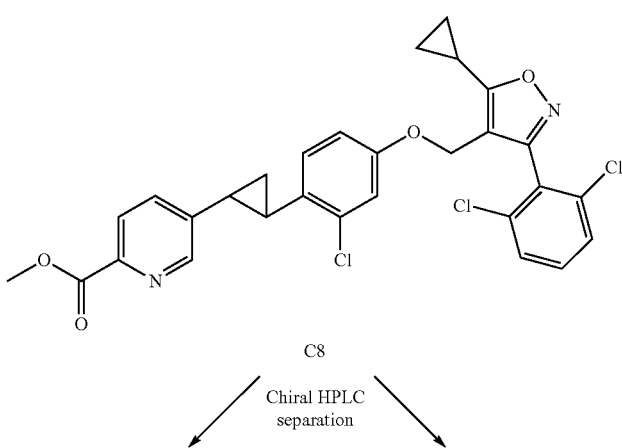

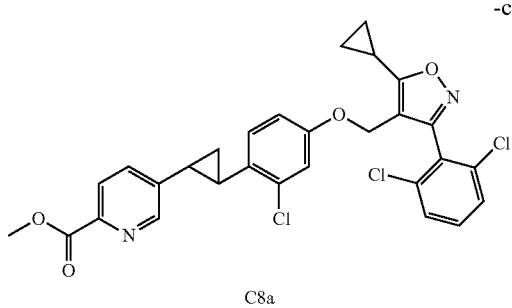

C8a

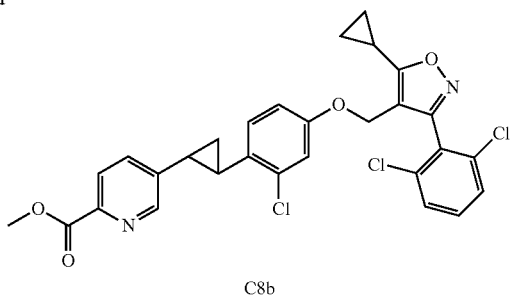

C8b 340 mg of compound C8 was separated by preparative chiral HPLC with a chiral column (column: CHIRALPAK AD-H; Column size: 0.46 cm I.D.×15 cm L; Mobile phase: Hexane/EtOH/HOAc=60/40/0.1 (v/v/v); Flow rate: 1.0 mL/min; Wave length: UV 220 nm; HPLC equipment: Shimadzu LC 20 with UV detector SPD-20A) to give 106 mg of C8a (Rt=6.923 min, ee %: >98%) and 119 mg of C8b (Rt=8.907 min, ee %: >97%).

Synthesis of Example 8a $^1$HNMR (DMSO-d6, 400 MHz) δ: 1.12-1.22 (m, 4H), 1.57-1.64 (m, 2H), 2.16 (m, 1H), 2.37 (m, 1H), 2.48 (m, 1H), 4.91 (s, 2H), 6.75 (dd, J=2.4 Hz, 8.4 Hz, 1H), 6.93 (d, J=2.4 Hz, 1H), 7.13 (d, J=8.4 Hz, 1H), 7.56 (m, 1H), 7.64 (m, 2H), 7.73 (dd, J=2.4 Hz, 8.4 Hz, 1H), 7.97 (d, J=8.0 Hz, 1H), 8.63 (d, J=1.6 Hz, 1H);

LCMS (mobile phase: 50%-95% Acetonitrile-Water-0.05% TFA) purity is >97%, Rt=3.124 min;

MS Calcd.: 554; MS Found: 555 (M+1).

Optical rotation: $[\alpha]_D^{25}$=−127° (CHCl3, c=0.3).

Synthesis of Example 8b

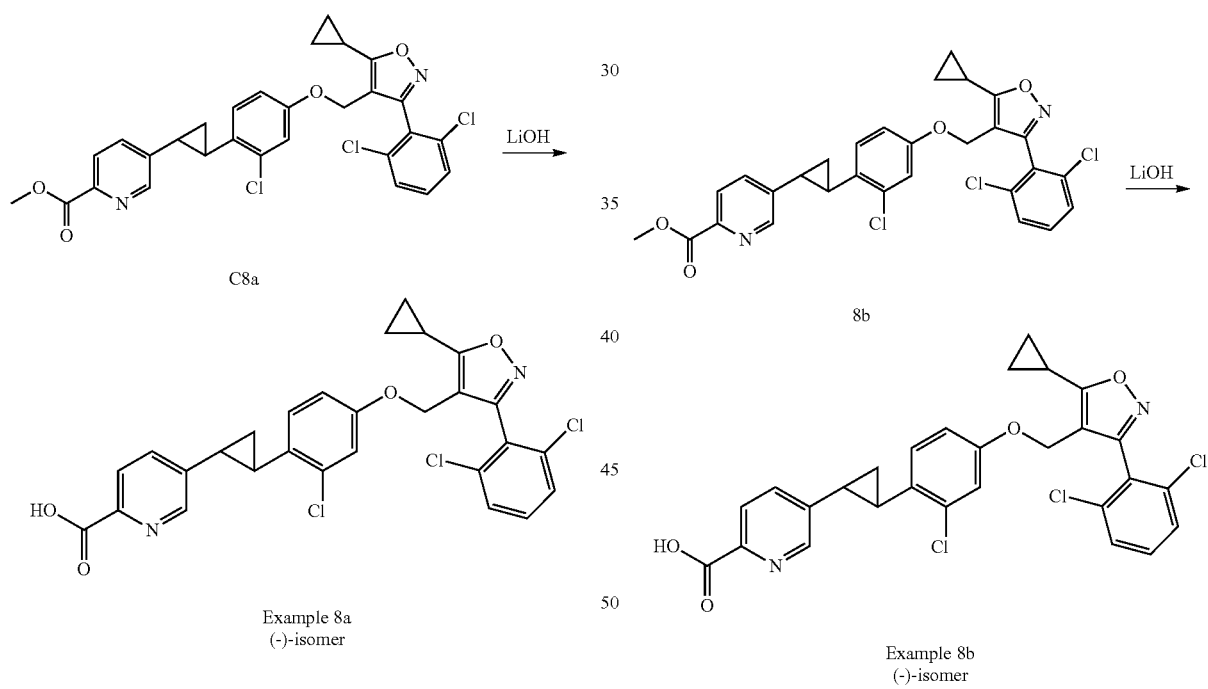

To the solution of compound C8a (106 mg, 0.19 mmol) in 5 mL of THF and 2 mL of H$_2$O was added LiORH$_2$O (8 mg, 1.9 mmol), and then the mixture was stirred at room temperature for 4 h. Concentrated, diluted with 5 mL of H$_2$O, and 1N aq. HCl solution was added to acidify the mixture to pH=5. The formed solid was collected, and the filter cake was washed by 3 mL of water. The solid was added to 2 mL of water, and the suspension was stirred for 2 h. The solid was filtered again, and the filter cake was washed by 2 mL of water. Filtered, EtOAc was added, dried over Na$_2$SO$_4$, filtered, and concentrated under reduced pressure to give 98 mg of Example 8a ((−)-5-(2-(2-chloro-4-((5-cyclopropyl-3-(2,6-dichlorophenyl)isoxazol-4-yl)methoxy)phenyl)cyclopropyl)picolinic acid) as a yellow solid (Yield: 93.6%).

In a similar manner as that described for Example 8a 112 mg of Example 8b ((+)-5-(2-(2-chloro-4-((5-cyclopropyl-3-(2,6-dichlorophenyl)isoxazol-4-yl)methoxy)phenyl)cyclopropyl)picolinic acid) was obtained.

$^1$HNMR (DMSO-d6, 400 MHz) δ: 1.12-1.22 (m, 4H), 1.57-1.64 (m, 2H), 2.16 (m, 1H), 2.37 (m, 1H), 2.48 (m, 1H), 4.91 (s, 2H), 6.75 (dd, J=2.4 Hz, 8.4 Hz, 1H), 6.93 (d, J=2.4 Hz, 1H), 7.13 (d, J=8.4 Hz, 1H), 7.56 (m, 1H), 7.64 (m, 2H), 7.73 (dd, J=2.4 Hz, 8.4 Hz, 1H), 7.97 (d, J=8.0 Hz, 1H), 8.63 (d, J=1.6 Hz, 1H);

LCMS (mobile phase: 40%-95% Acetonitrile-Water-0.05% TFA) purity is >97%, Rt=3.551 min;

MS Calcd.: 554; MS Found: 555 (M+1).

Optical rotation: $[\alpha]_D^{25}$=+128° (CHCl$_3$, c=0.29).

Scheme 4:
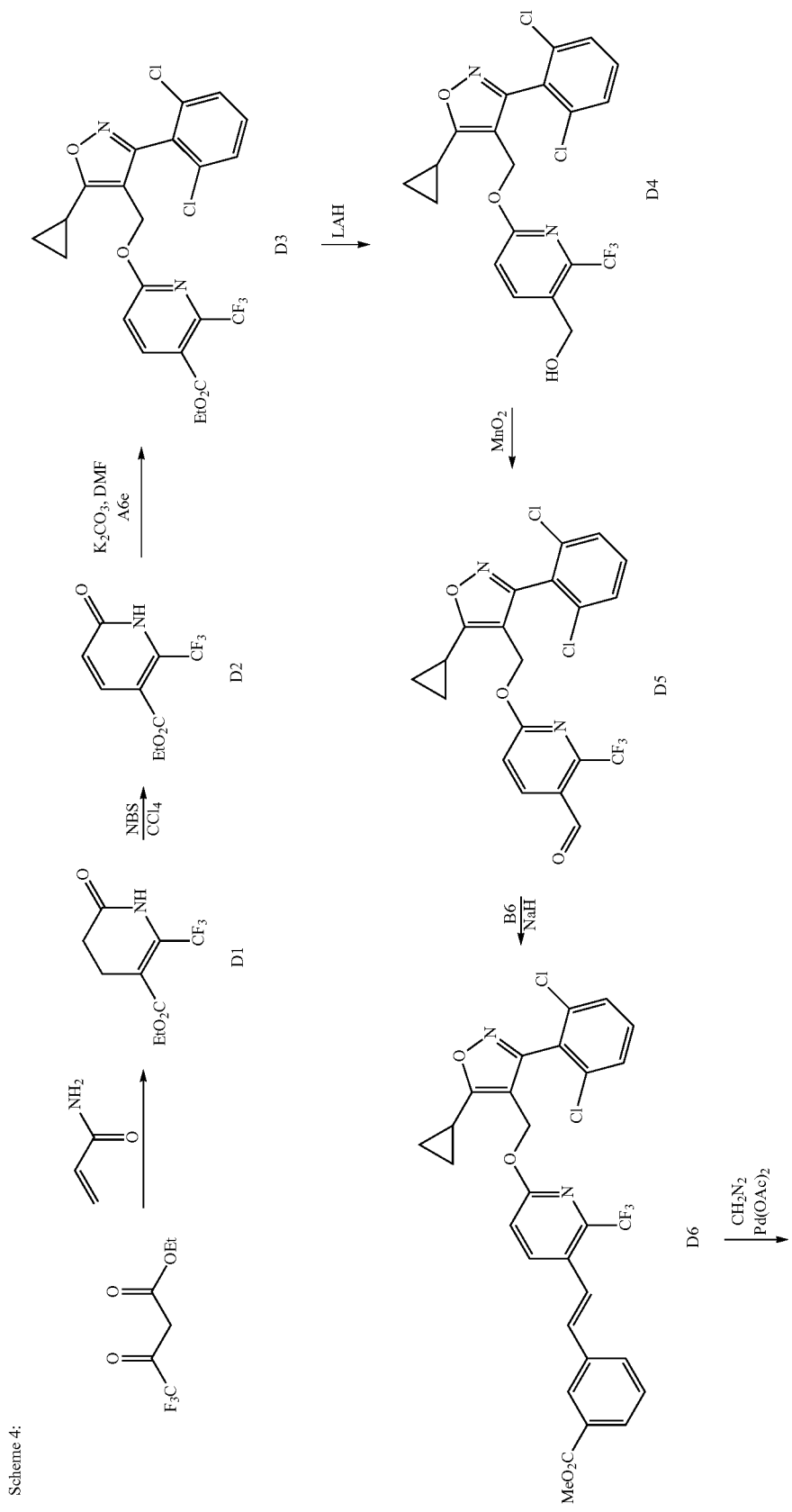

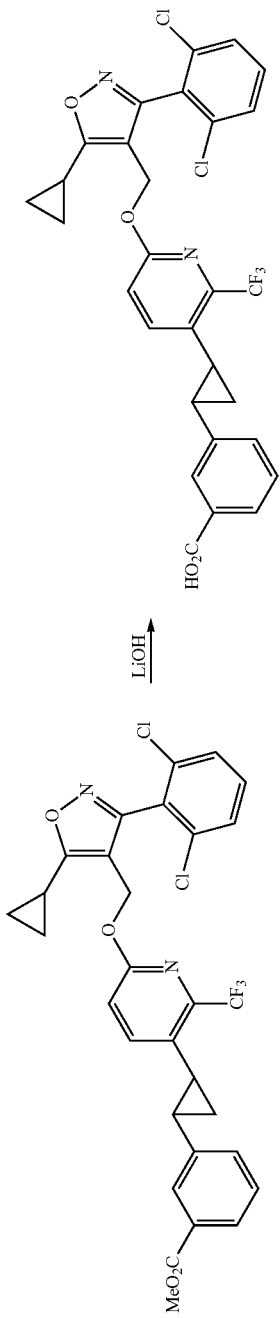

Synthesis of Compound D2

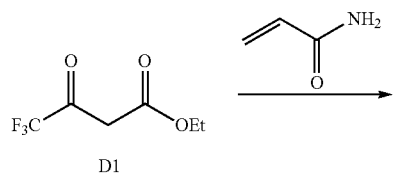

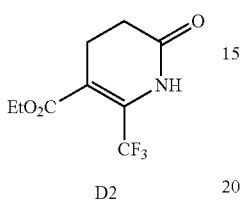

A mixture of acrylamide (210 g, 1.14 mol), compound D1 (700 ml, 4.73 mol) and p-toluene sulphonic acid (7 g, 38.29 mmol) in 3500 mL of dry toluene was refluxed for 48 h with azeotropic removal of water. The reaction mixture was concentrated in vacuo and the residue was purified by flash chromatography on silica gel (eluent: PE/EA=10/1) to give 25 g of compound D2 as a white solid (yield: 9.3%).

Synthesis of Compound D3

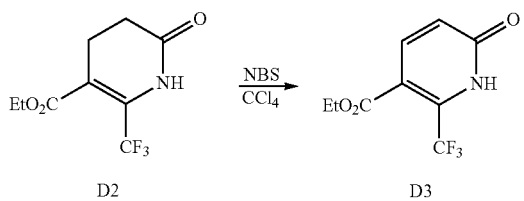

A solution of compound D2 (25 g, 105.48 mmol) and NBS (22.53 g, 126.58 mol) in 250 mL of CCl$_4$ was heated under reflux for 18 h. The resulting precipitate was filtered off and the filtrate was concentrated under reduced pressure to afford a solid that was purified by flash chromatography on silica gel (eluent: PE/EA=10:1) to give 17.35 g of compound D3 as a white solid (yield: 70%).

Synthesis of Compound D4

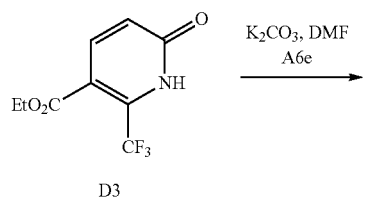

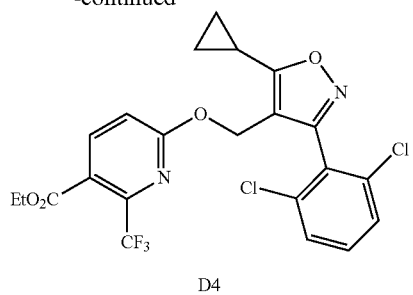

To the solution of compound D3 (4.34 g, 18.46 mmol) in 20 mL of DMF was added compound A6e (5.56 g, 18.46 mmol) and K$_2$CO$_3$ (2.55 g, 18.46 mmol). The mixture was heated overnight at 60° C. Both of TLC and LCMS indicated that the reaction was over. The mixture was concentrated under reduced pressure and purified by chromatography on silica gel (eluent: PE/EA=6/1) to give 6.33 g of compound D4 as a white solid (Yield: 68%).

Synthesis of Compound D5

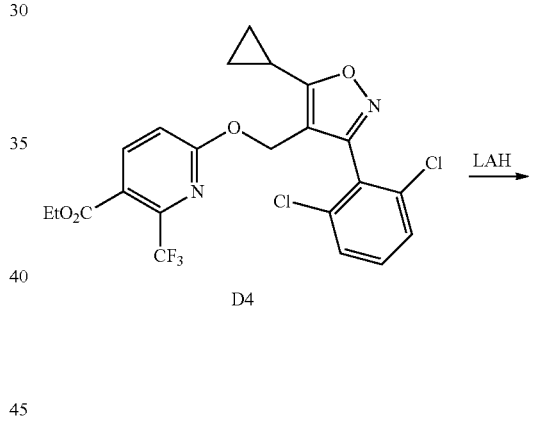

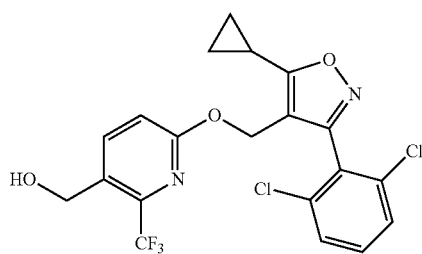

To a suspension of LAH (0.46 g, 12.6 mmol) in 50 mL of dry THF, a solution of compound D4 (6.33 g, 12.6 mmol) in 50 mL of dry THF was added at 0° C. and the mixture was stirred at room temperature for 2 h. MeOH was added to the resulting solution for quench followed by sat. Na$_2$SO$_4$ solution. The formed solid was filtered off and the filtrate was concentrated, and purified by chromatography on silica gel (eluent: PE/EA=4/1) to give 4.17 g of compound D5 as a light green solid (yield: 72.0%).

Synthesis of Compound D6

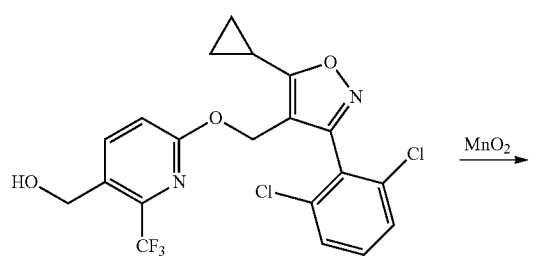

D5

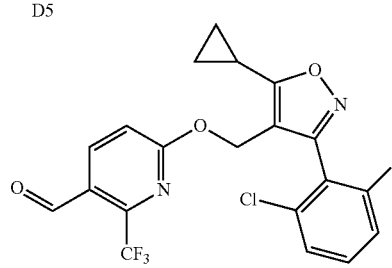

D6

To the solution of compound D5 (3 g, 6.55 mmol) in 30 mL of CHCl₃ was added active MnO₂ (2.28 g, 26.2 mmol), and then the suspension was refluxed for 3. The reaction mixture was filtered and the filter cake was washed with hot CHCl₃, then the filtrate was concentrated to give 2.81 g of compound D6 as a yellow solid used into the following reaction without further purification.

Synthesis of Compound D7

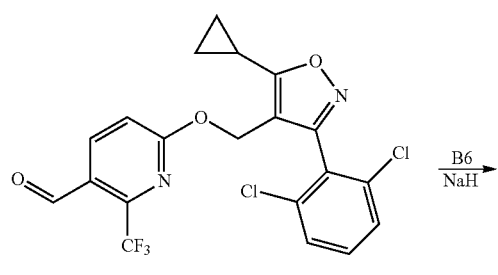

D6

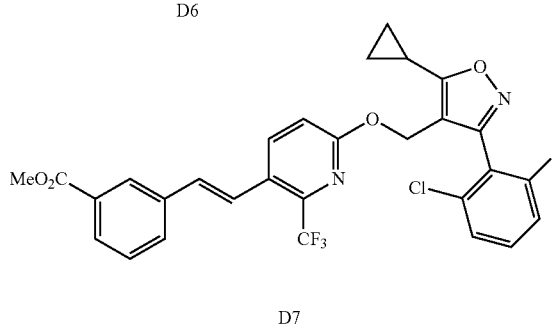

D7

To the solution of compound B6 (2.3 g, 8.06 mmol) in 30 mL of dry THF was added sodium hydride (0.5 g, 12.3 mmol) at 0° C. for 30 min. To this resulting mixture was added the solution of compound D6 (2.81 g, 6.16 mmol) in 20 mL of dry THF at 0° C., and the solution was stirred at room temperature for 3 h. The mixture was quenched by sat. NH₄Cl solution and extracted with EtOAc. The organic layer was washed with brine, dried over Na₂SO₄, filtered, concentrated and purified by chromatography on silica gel (eluent: PE/EA=10/1) to give 0.98 g of compound D7 as a white solid (Yield: 27.3%).

Synthesis of Compound D8

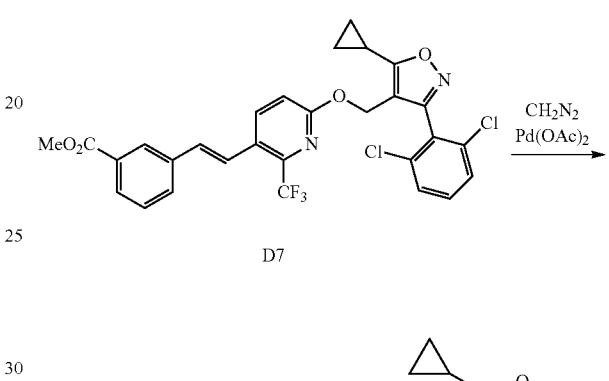

D7

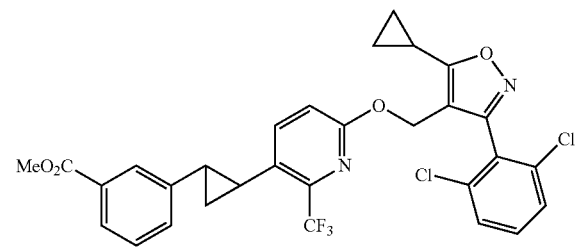

D8

To the solution of compound D7 (970 g, 1.65 mmol) and Pd(OAc)₂ (150 mg) in 20 mL of Et₂O was added a solution of CH₂N₂ in Et₂O (20 mL, 80 mmol) at −50° C. under N₂ atmosphere. Then the solution was warmed to room temperature slowly, and stirred for another 4 h. Both of TLC and LCMS indicated that the reaction was ok. Filtered, concentrated and purified by flash chromatography on silica gel (eluent: PE/EA=10/1) to give 378 mg of crude compound D8 as a white solid (Yield: 38.6%).

Synthesis of Example 9

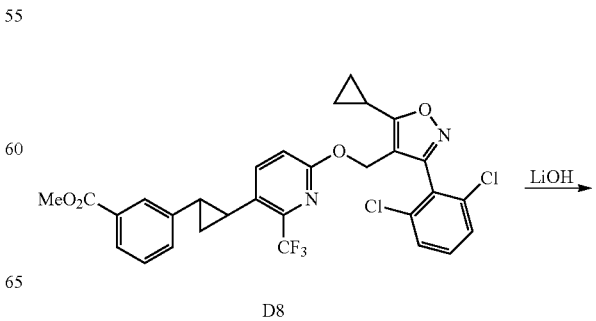

D8

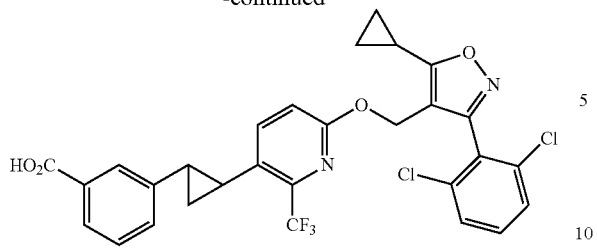

Example 9

To the solution of compound D8 (367 mg, 0.61 mmol) in 10 mL of THF and 4 mL of H$_2$O was added LiOH.H$_2$O (200 mg, 4.76 mmol), and then the mixture was stirred at room temperature for 24 h. The reaction mixture was concentrated and diluted with 10 mL of H$_2$O, 1N aq. HCl solution was added to acidify the mixture to pH=5, which was extracted with EtOAc later. The organic layer was washed with brine, dried over Na$_2$SO$_4$, filtered, concentrated and purified by chromatography on silica gel (eluent: PE/EA=1/3) to give 140 mg of Example 9 (3-(2-(6-((5-cyclopropyl-3-(2,6-dichlorophenyl)isoxazol-4-yl)methoxy)-2-(trifluoromethyl)pyridin-3-yl)cyclopropyl)benzoic acid) as a white solid (Yield: 39.1%).

$^1$H NMR (400 MHz, DMSO-d6) δ: 1.16 (m, 4H), 1.60 (m, 2H), 2.30 (m, 3H), 5.28 (s, 2H), 6.87 (d, J=8.4 Hz, 1H), 7.44 (s, 2H), 7.50 (m, 1H), 7.55 (m, 2H), 7.70 (m, 1H), 7.76 (m, 2H);

LCMS (mobile phase: 70%-95% Acetonitrile-Water-0.01% TFA) purity is >97%, Rt=3.033 min;

MS Calcd.: 588; MS Found: 589 (M+1).

Scheme 5:
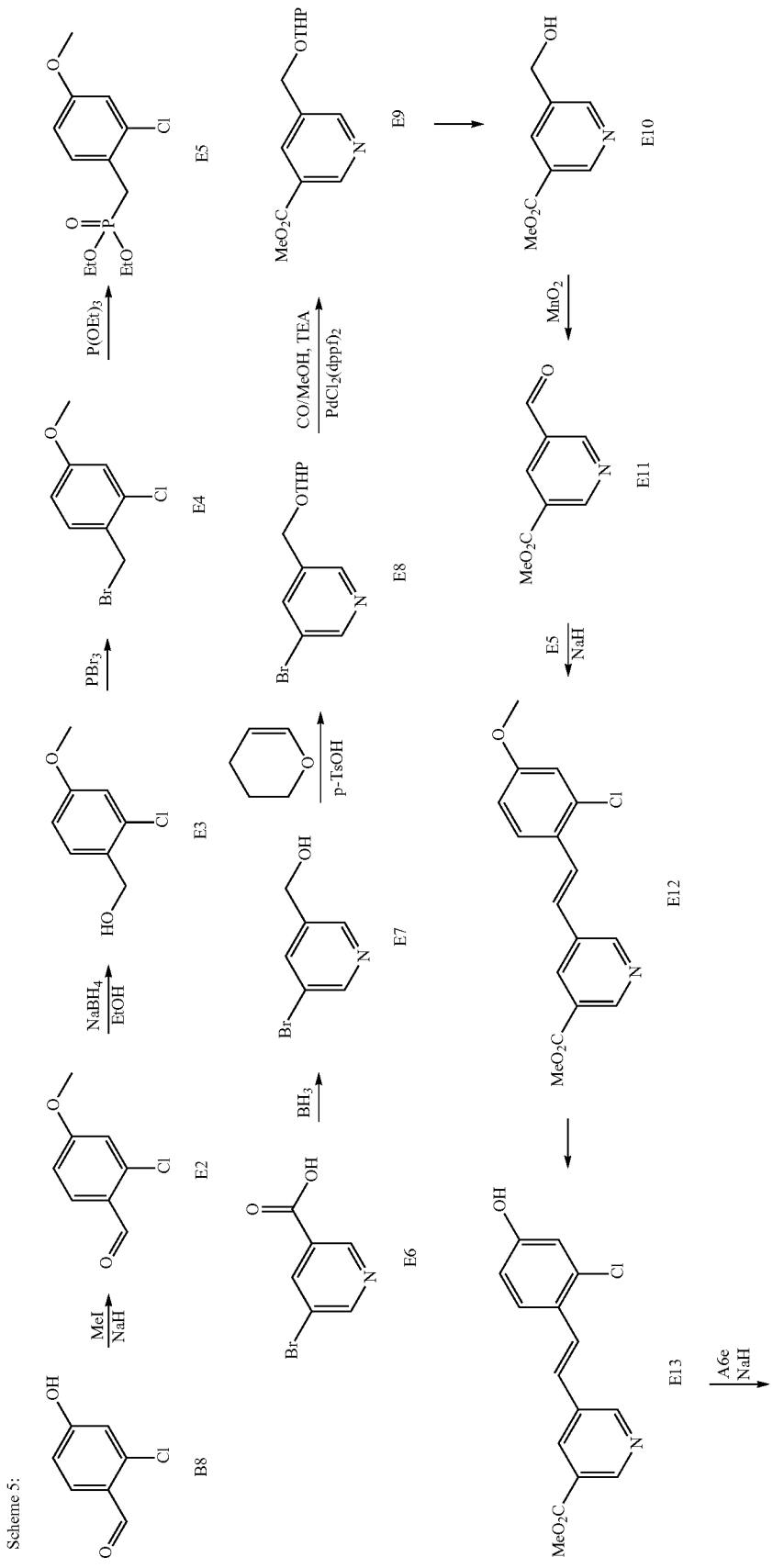

-continued
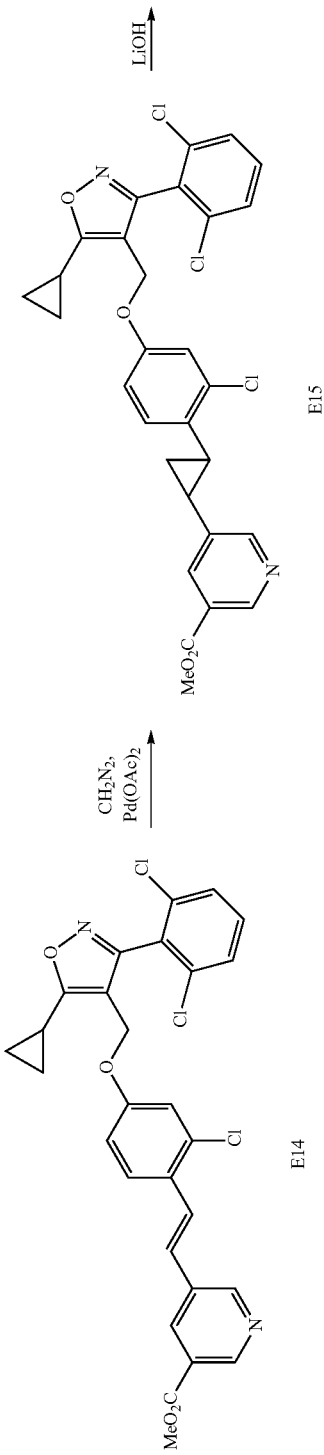
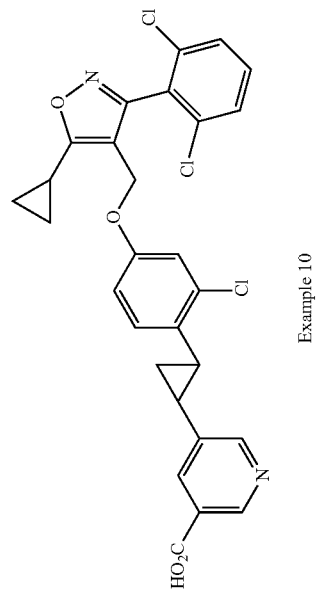

Synthesis of Compound E2

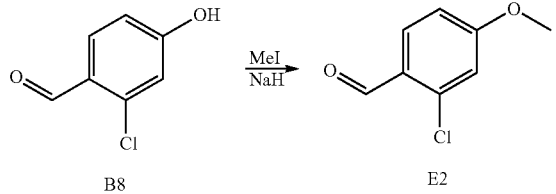

To the solution of compound B8 (10 g, 64.1 mmol) in 100 mL of CH$_3$CN was added K$_2$CO$_3$ (18.0 g, 130.4 mmol) and MeI (20 mL, 321.0 mmol). The reaction was stirred at room temperature overnight. The reaction mixture was concentrated under reduced pressure to give 11 g of crude compound E2 used into the following reduction without the further purification.

Synthesis of Compound E3

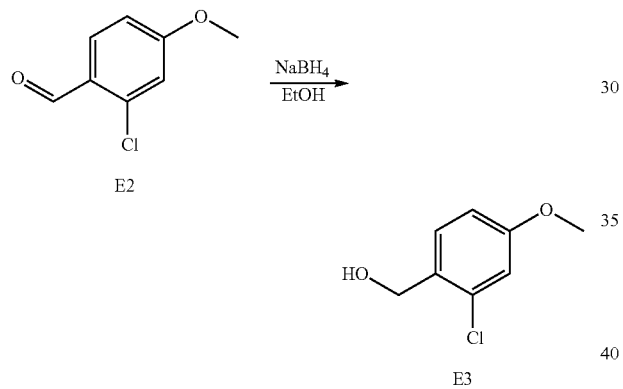

To the solution of compound E2 (10 g, 81.8 mmol) in 100 mL of EtOH was added NaBH$_4$ (5.0 g, 123.6 mmol), and the mixture was stirred at room temperature for 2 h under N$_2$ atmosphere. 1 N HCl solution was added for quench. The reaction mixture was concentrated under reduced pressure and EtOAc was added to extract twice. The combined organic layers were washed with water and brine consecutively, dried over Na$_2$SO$_4$, filtered, concentrated and purified by chromatography on silica gel (eluent: PE/EA=2/1) to give 10 g of compound E3 as an oil (Yield: 94.2%).

Synthesis of Compound E4

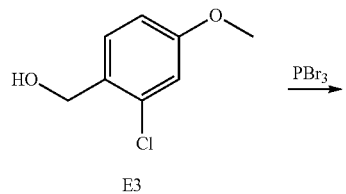

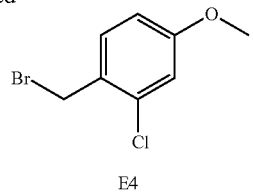

To the solution of compound E3 (10 g, 58.1 mmol) in 100 mL of dry DCM was added PBr$_3$ (31.2 g, 116.2 mmol) under N$_2$ atmosphere at room temperature, and the solution was stirred at this temperature for 2 h. The resulting solution was poured into ice-water, and the organic layer was dried over Na$_2$SO$_4$, filtered and concentrated under reduced pressure to give 13.5 g of compound E4 as a brown oil used into the following reaction without the further purification.

Synthesis of Compound E5

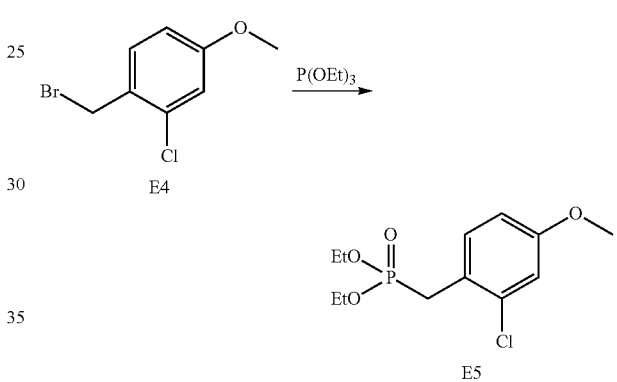

The solution of compound E4 (13.5 g, 57.7 mmol) in 50 mL of triethoxyphosphine was heated at 175° C. for 4 h. The reaction mixture was concentrated under reduced pressure to give 17 g of compound E5 used into the following reaction without further purification.

Synthesis of Compound E7

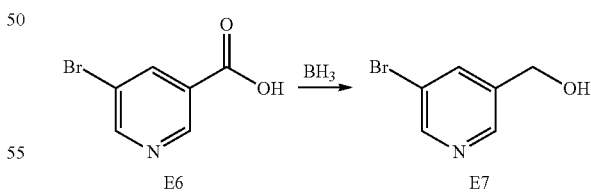

To a solution of compound E6 (50 g, 0.25 mol) in 400 mL of anhydrous THF was added a solution of BH$_3$ in THF (1M, 500 mL, 0.50 mol) dropwise at cooling with an ice-bath. After addition, the reaction solution was stirred at room temperature overnight. TLC indicated that the reduction was over. 400 mL of MeOH was added slowly to quench. The mixture was concentrated under reduced pressure and purified by flash chromatography on silica gel (eluent: PE/EA=1/1) to give 15 g of compound E7 as a white solid (Yield: 32.2%).

Synthesis of Compound E8

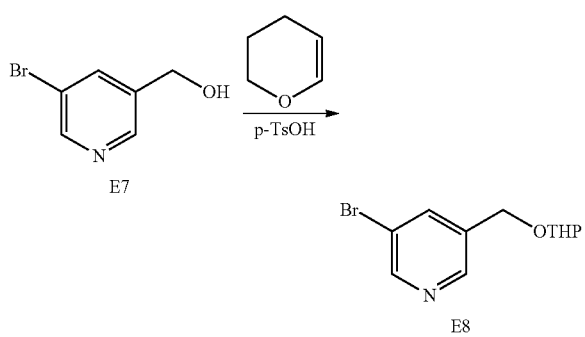

The solution of compound E7 (15 g, 80.2 mmol), 2H-3,4-dihydropyran (26.9 g, 160.4 mmol) and p-TsOH (1.5 g, 8.7 mmol) in 200 mL of anhydrous DCM was stirred at room temperature for 2 h. Water was added, and the organic phase was washed by brine, dried over Na$_2$SO$_4$, filtered and concentrated under reduced pressure to give 23 g of crude compound E8 as an oil used into the following reaction without further purification.

Synthesis of Compound E9

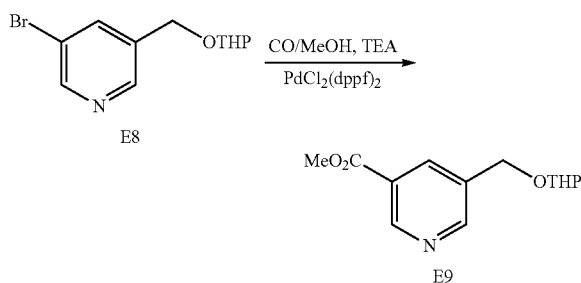

An autoclave vessel was charged with crude compound E8 (23 g, 80.2 mmol), PdCl$_2$(dppf)$_2$ (1.15 g, 2 mol %), and triethylamine (16.2 g, 160.4 mmol) in 200 mL of methanol. The vessel was purged with nitrogen three times and carbon monoxide three times. The vessel was pressurized to 2 MPa with carbon monoxide and heated to 100° C. The reaction was thus stirred overnight, then allowed to cool to room temperature. The resulting solution was filtered through a pad of silica, and the filter cake was washed by 50 mL of MeOH. The filtrate was concentrated and purified by flash chromatography on silica gel (eluent: PE/EA=8/1) to afford 18 g of compound E9 as a yellow solid (Yield in two steps: 89.4%).

Synthesis of Compound E10

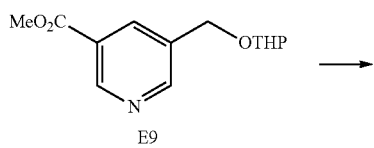

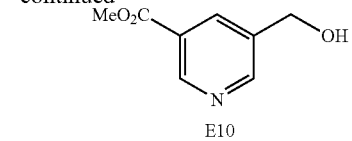

To a solution of compound E9 (18 g, 71.7 mmol) in 200 mL of MeOH was added p-TsOH (22.8 g, 120.0 mmol). Then the solution was stirred at room temperature for 2 h. The mixture was concentrated and water and EtOAc were added consecutively. The organic phase was washed with brine, dried over Na$_2$SO$_4$, filtered and concentrated to afford 40.8 g of crude compound E10 as a colorless liquid used in the following reaction without further purification.

Synthesis of Compound E11

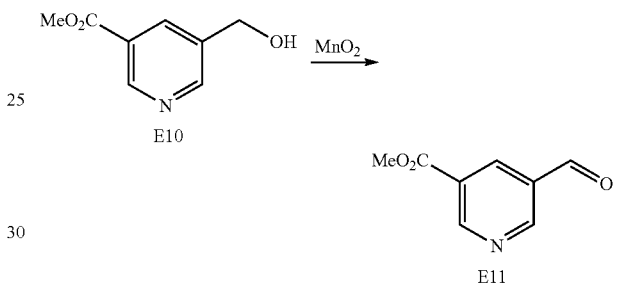

To the solution of crude compound E10 (40.8 g, 71.7 mmol) in 300 mL of CHCl$_3$ was added active MnO$_2$ (31.2 g, 358.5 mmol), and then the suspension was refluxed for 7 h. TLC indicated that the oxidation was ok. The reaction mixture was filtered and the cake was washed with hot CHCl$_3$, then the filtrate was concentrated to give 10.3 g of compound E11 as a white solid (Yield in two steps: 87.1%).

Synthesis of Compound E12

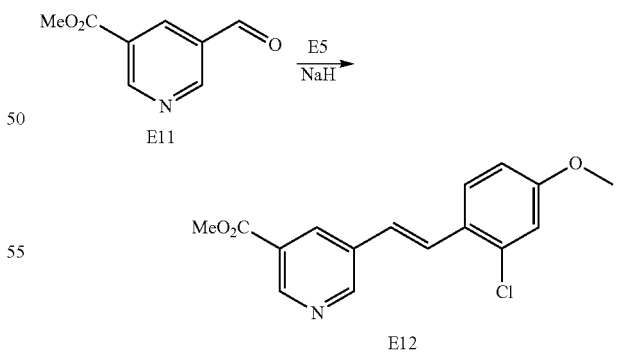

To the solution of compound E5 (17 g, 58.2 mmol) in 200 mL of dry THF was added sodium hydride (4.66 g, 116.4 mmol) at 0° C. for 30 min. To the resulting mixture was added the solution of compound E11 (9.6 g, 58.2 mmol) in 80 mL of dry THF at 0° C., and the solution was stirred at room temperature for 1 h. The mixture was quenched by water, and extracted with EtOAc. The organic layer was washed with brine, dried over Na$_2$SO$_4$, filtered, concentrated and purified by chromatography on silica gel (eluent: PE/EA=5/1) to give 9.55 g of compound E12 as a yellow solid (Yield: 54.2%).

Synthesis of Compound E13

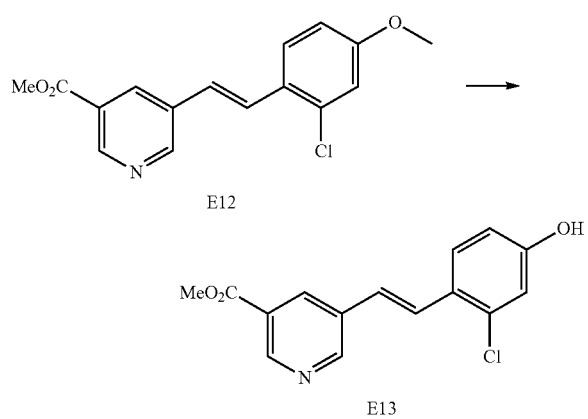

To the solution of compound E12 (9.55 g, 31.5 mmol) in 100 mL of dry DCM was added BBr$_3$ (29.8 mL, 315 mmol) at −70° C. under N$_2$ atmosphere, and then the solution was stirred at room temperature for 1 h. Both TLC and LCMS indicated that the de-methylation was over. The solution was cooled to −30° C. again and 50 mL of MeOH were added to quench. The mixture was concentrated under reduced pressure and water and DCM was added to the residue. The organic layer was dried over Na$_2$SO$_4$, filtered and concentrated to give 10.1 g of crude compound E13 as a brown solid used in the following coupling without further purification.

Synthesis of Compound E14

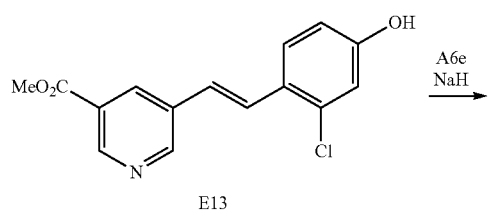

To the solution of the crude compound E13 (10.1 g, 31.5 mmol) and compound Aha (9.51 g, 31.5 mmol) in 50 mL of DMF was added K$_2$CO$_3$ (43.47 g, 315 mmol). The mixture was heated overnight at 60° C. Filtered, concentrated under reduced pressure, diluted with 100 mL of H$_2$O and extracted with 300 mL of EtOAc. The organic layer was washed with water and brine twice consecutively, dried over Na$_2$SO$_4$, filtered, concentrated and purified by chromatography on silica gel (eluent: PE/EA=5/1) to give 4.75 g of compound E14 as a yellow solid (Yield: 27.2%).

Synthesis of Compound E15

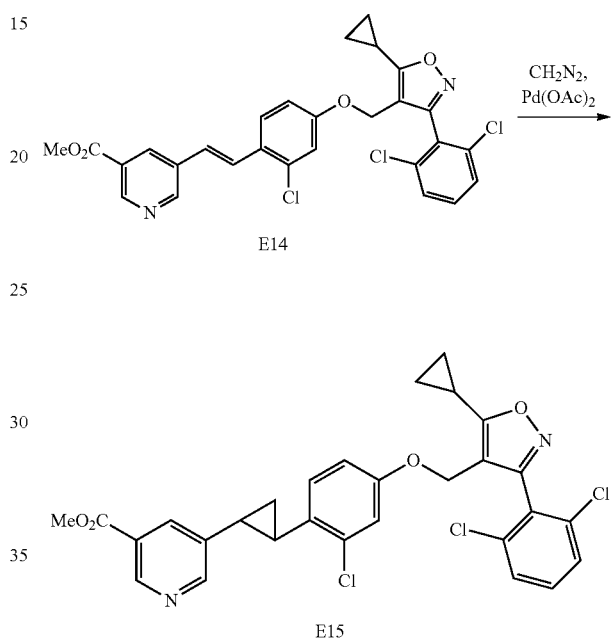

To the solution of compound E14 (4.0 g, 7.22 mmol) and Pd(OAc)$_2$ (0.4 g) in 60 mL of Et$_2$O was added the solution of CH$_2$N$_2$ in Et$_2$O (70 mL, 280 mmol) at −50° C. under N$_2$ atmosphere. Then the solution was warmed to room temperature slowly, and stirred for another 4 h. Both of TLC and LCMS indicated that the reaction was ok. Filtered, concentrated and purified by flash chromatography on silica gel (eluent: PE/EA=4/1) to give 1.53 g of compound E15 as a yellow solid (Yield: 37.3%).

Synthesis of Example 10

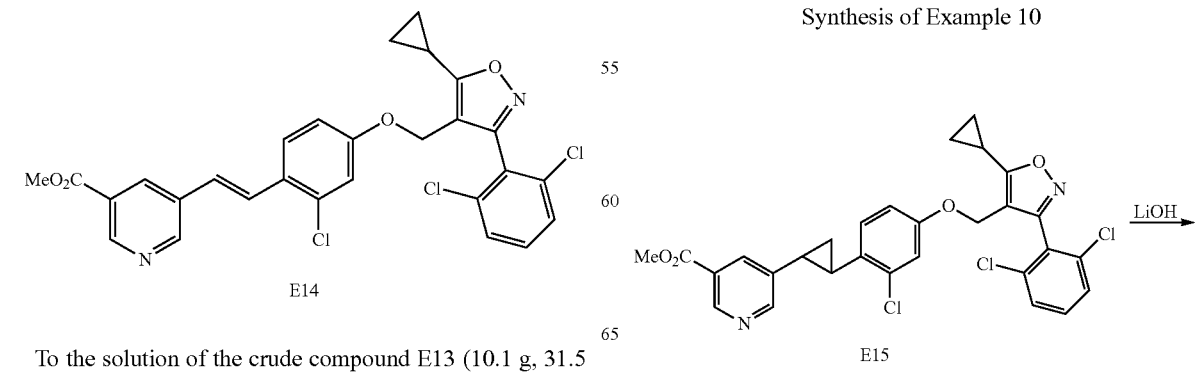

-continued

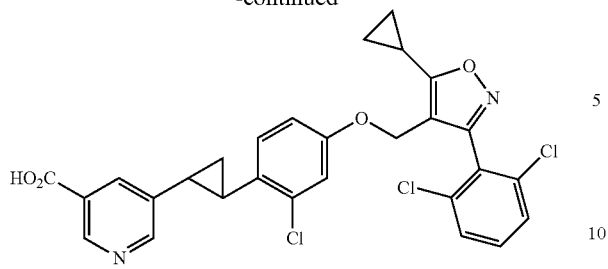

Example 10

To the solution of compound E15 (1.53 g, 2.69 mmol) in 40 mL of THF and 10 mL of H₂O was added LiOH.H₂O (1.51 g, 36 mmol), and then the mixture was stirred at room temperature for 24 h. Concentrated, diluted with 50 mL of H₂O, and 1N aq. HCl solution was added to acidify the mixture to pH=5. The formed solid was collected, and the cake was washed by 20 mL of water. The solid was added to 50 mL of water, and the suspension was stirred for 2 h. The solid was filtered again, and the cake was washed by 20 mL of water. Then the solid was purified by prep. HPLC to give 705 mg of Example 10 (5-(2-(2-chloro-4-((5-cyclopropyl-3-(2,6-dichlorophenyl)isoxazol-4-yl)methoxy)phenyl)cyclopropyl)nicotinic acid) as a yellow solid (Yield: 47.3%).

$^1$H NMR (400 MHz, CD3OD) δ: 1.23 (m, 4H), 1.58-1.69 (m, 2H), 2.20 (m, 1H), 2.35 (m, 1H), 2.45 (m, 1H), 4.91 (s, 2H), 6.74 (dd, J=2.8 Hz, 8.8 Hz, 1H), 6.86 (d, J=2.8 Hz, 1H), 7.11 (d, J=8.4 Hz, 1H), 7.45-7.54 (m, 3H), 8.37 (s, 1H), 8.77 (s, 1H), 9.02 (s, 1H);

LCMS (mobile phase: 50%-95% Acetonitrile-Water-0.01% TFA) purity is >97%, Rt=3.007 min; MS Calcd.: 554; MS Found: 555 (M+1).

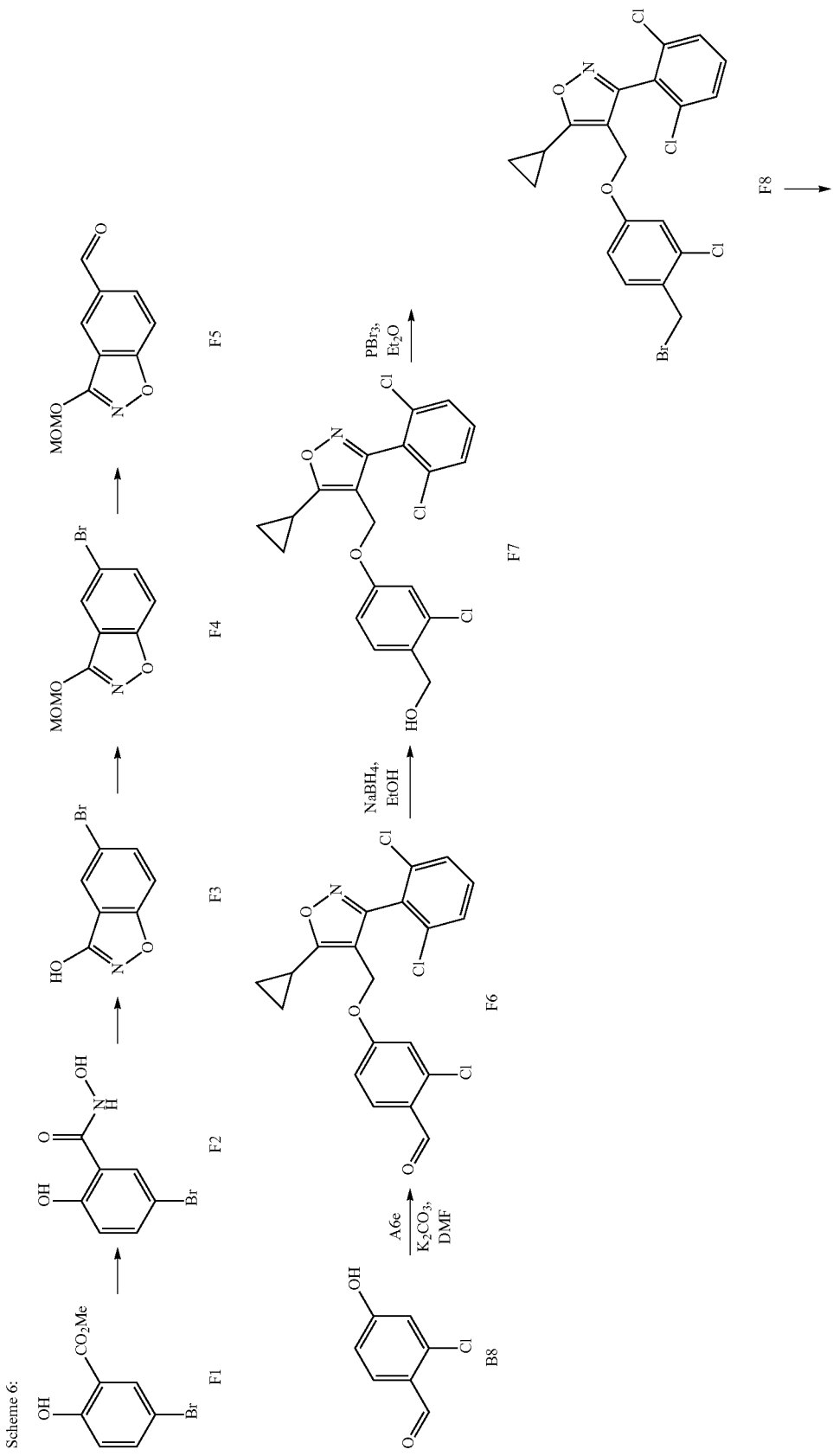

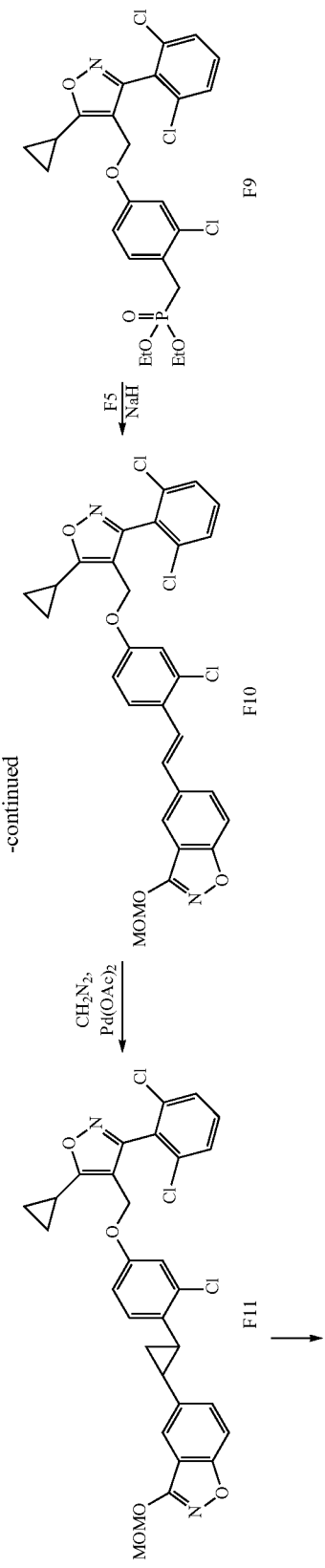

Synthesis of Compound F3

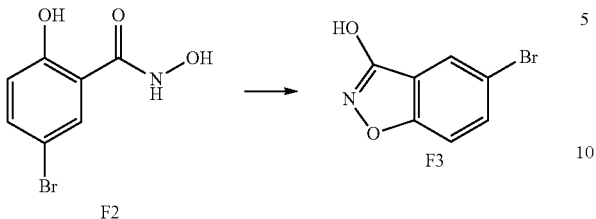

To a solution of 5-bromosalicylcarbohydroxamic acid F2 (21.6 g) in tetrahydrofuran (60 ml) was added thionyl chloride (10 ml) dropwise with stirring at 10-20° C. After being stirred for 2 h at the same temperature, the reaction mixture was evaporated under reduced pressure and the residue was dissolved in dioxane (60 ml) and cooled to 0-5° C. Triethylamine (38 ml) was added to the reaction mixture and stirred at room temperature for 1 hour. The solvent was evaporated under reduced pressure and ice water (300 mL) was added to the residue. The mixture was adjusted to pH 2 with concentrated hydrochloric acid and the crystals precipitated were filtered and washed with water. Compound F3 (17.5 g, 88%) was obtained as colorless needle crystals by recrystallization from ethyl acetate.

Synthesis of Compound F4

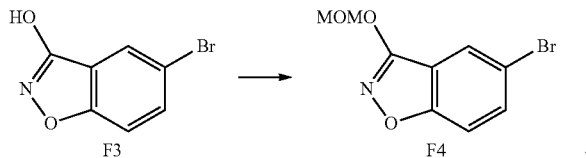

To a suspension of compound F3 (1 g, 4.67 mmol) in DMF (10 mL) was added NaH (0.23 g, 9.35 mmol). The resulting mixture was stirred at room temperature for 1 h. Then the mixture was cooled to 5° C. and chloromethyl methyl ether (0.45 g, 80.5 mol) was added, followed by stirring at the same temperature for 1 h. The mixture was poured into ice-water and extracted with ether. The organic layer was washed with brine, dried over MgSO$_4$, concentrated and purified by flash column chromatography on silica gel to give compound F4 (1.1 g, yield 92%).

$^1$HNMR (300 MHz, DMSO-d$_6$): δ8.01-8.02 (d, 1H), 7.79-7.82 (dd, 1H), 7.64-7.67 (d, 1H), 5.52 (s, 2H), 3.51 (s, 3H).

Synthesis of Compound F5

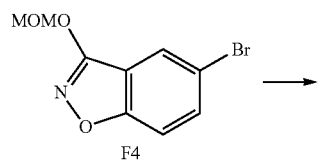

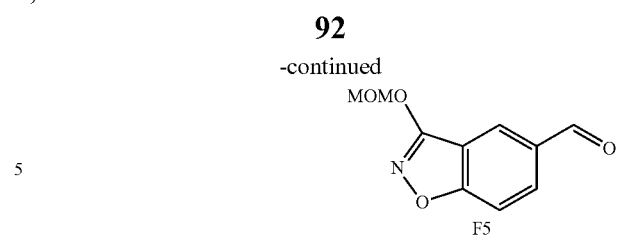

To a solution of compound F4 (2 g, 7.7 mmol) in anhydrous THF (20 mL), n-BuLi (2.5 M in hexane, 4.6 mL) was added dropwise at −78° C. under N$_2$ protection, and the mixture was stirred at −78° C. for 1 h. Then anhydrous DMF (11.6 mmol, 0.9 mL) was added dropwise at −78° C., and the mixture was stirred at −78° C. for another 1 h. Saturated aq. NH$_4$Cl was added to quench the reaction and the mixture was extracted with ethyl acetate. The organic layer was washed with brine, dried over MgSO$_4$ and concentrated. The residue was purified by flash column chromatography on silica gel to give compound F5 (800 mg, yield 50%).

$^1$HNMR (300 MHz, DMSO-d6): δ10.07 (s, 1H), 8.38 (d, 1H), 8.11-8.15 (dd, 1H), 7.80-7.82 (d, 1H), 5.55 (s, 2H), 3.53 (s, 3H).

Synthesis of Compound F7

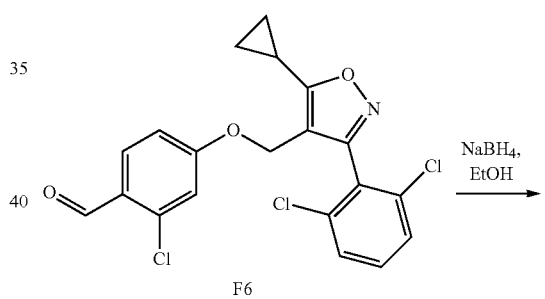

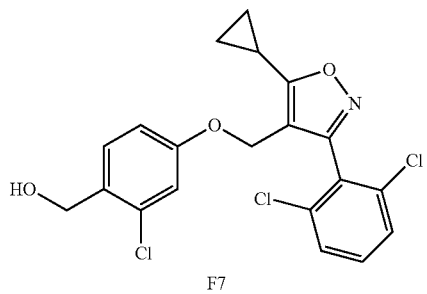

To the solution of compound F6 (5.1 g, 12.1 mmol) in 10 mL of EtOH was added NaBH$_4$ (0.92 g, 24.2 mmol). Then the solution was stirred for 1 hour at room temperature. Concentrated and EtOAc was added. The solution was washed with water and brine, dried over Na$_2$SO$_4$, filtered and concentrated

Synthesis of Compound F8

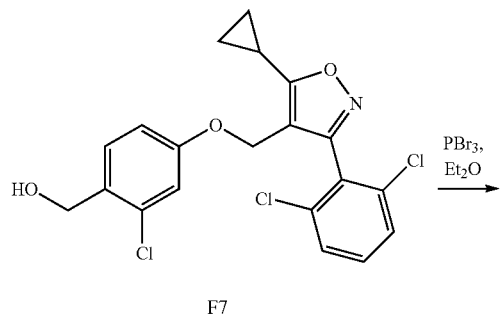

F7

To the solution of compound F7 (4 g, 9.46 mmol) in 30 mL of dry Et$_2$O was added PBr$_3$ (2.56 g, 9.46 mmol) under N$_2$ atmosphere at 0° C. After stirring for 0.5 hour, both of TLC and LCMS indicated that the reaction was over. The resulting solution was poured into the sat. NaHCO$_3$ solution and the organic layer was washed with water and brine. Dried over Na$_2$SO$_4$, filtered and concentrated to give 3.99 g of crude F8 as a yellow solid used into the following reaction without the further purification.

Synthesis of Compound F9

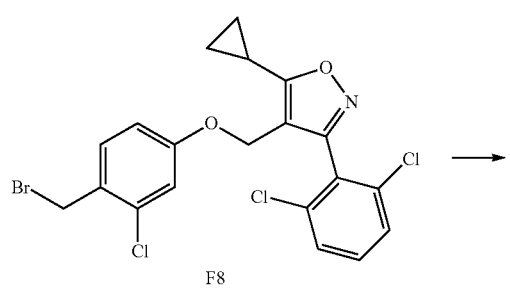

F8

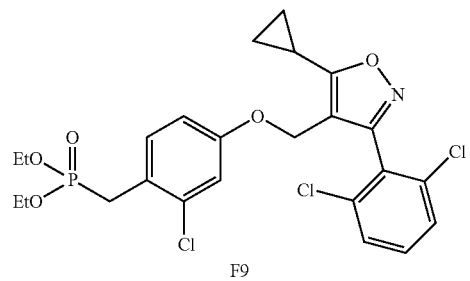

F9

The solution of compound F8 (2 g, 4.12 mmol) in 15 mL of triethoxyphosphine was heated at 175° C. for 2 h. Concentrated under reduced pressure to give 2.3 g of compound F9 as an oil used into the following reaction without the further purification.

Synthesis of Compound F10

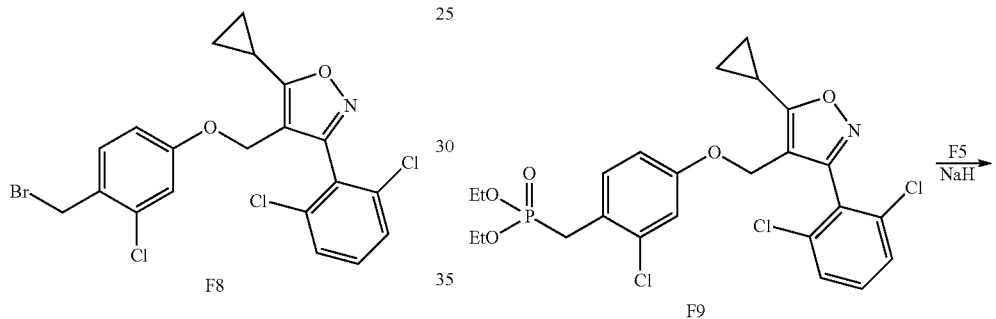

F9

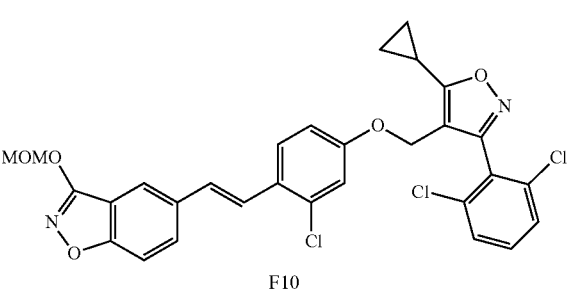

F10

To the solution of compound F9 (2.3 g, 4.12 mmol) in 20 mL of dry THF was added sodium hydride (247 mg, 6.18 mmol) at 0° C. for 30 mins. To this resulting mixture was added the solution of compound F5 (0.85 g, 4.12 mmol) in 160 mL of dry THF at 0° C., and the solution was stirred at room temperature for 3 h. The mixture was quenched by sat. NH$_4$Cl solution and extracted with EtOAc. The organic layer was washed with brine, dried over Na$_2$SO$_4$, filtered, concentrated to give 311 mg of compound F10 as a brown solid (Yield: 12.7%).

Synthesis of Compound F11

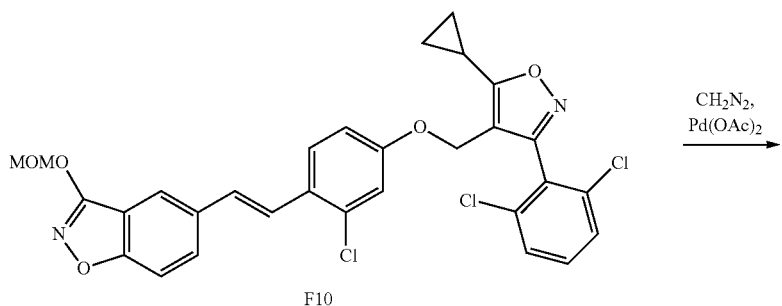

F10

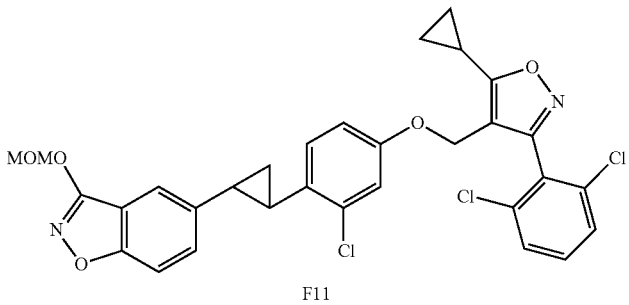

F11

To the solution of compound F10 (311 mg, 0.52 mmol) and Pd(OAc)$_2$ (0.1 g) in 10 mL of dry THF was added the solution of CH$_2$N$_2$ in Et$_2$O (10 mL, 40 mmol) at −50° C. under N$_2$ atmosphere. Then the solution was warmed to room temperature slowly, and stirred for another 4 h. Both of TLC and LCMS indicated that the reaction was ok. Filtered, concentrated and purified by flash chromatography on silica gel (eluent: PE/EA=4/1) to give 214 mg of compound F11 as a yellow solid (Yield: 67.5%).

Synthesis of Example 11

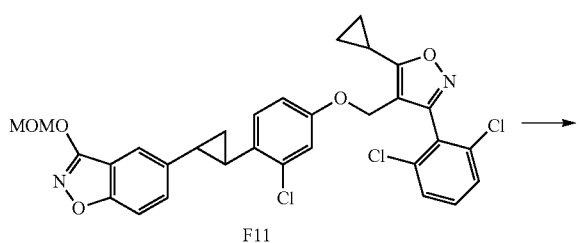

F11

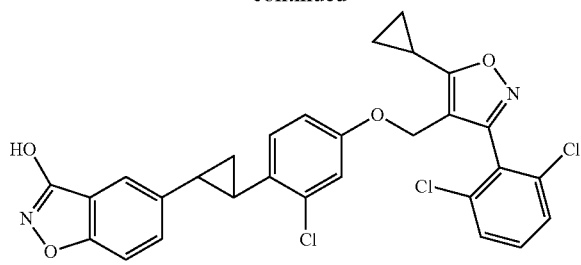

Example 11

To a solution of compound F11 (214 mg, 0.35 mmol) in 5 mL of 1,4-dioxane, 3M hydrochloric acid (1 mL) was added, and this mixture was stirred overnight at room temperature. Then water and ethyl acetate was added to the reaction mixture. The organic layer was washed with brine, dried over MgSO$_4$ and concentrated. The residue was purified by preparative TLC to give 22 mg of Example 11 as a yellow solid (Yield: 11.1%).

$^1$H NMR (400 MHz, CDCl3) δ: 1.18 (m, 2H), 1.30 (m, 2H), 1.45 (m, 2H), 2.13-2.19 (m, 2H), 2.35 (m, 1H), 4.81 (s, 2H), 6.70 (d, J=6.4 Hz, 1H), 6.87 (s, 1H), 6.99 (d, J=8.4 Hz, 1H), 7.36 (m, 2H), 7.43 (m, 2H), 7.50 (d, J=8.8 Hz, 1H), 7.59 (s, 1H);

LCMS (mobile phase: 40%-95% Acetonitrile-Water) purity is 90%, Rt=2.966 min;

MS Calcd.: 566; MS Found: 567 (M+1).

Scheme 7:

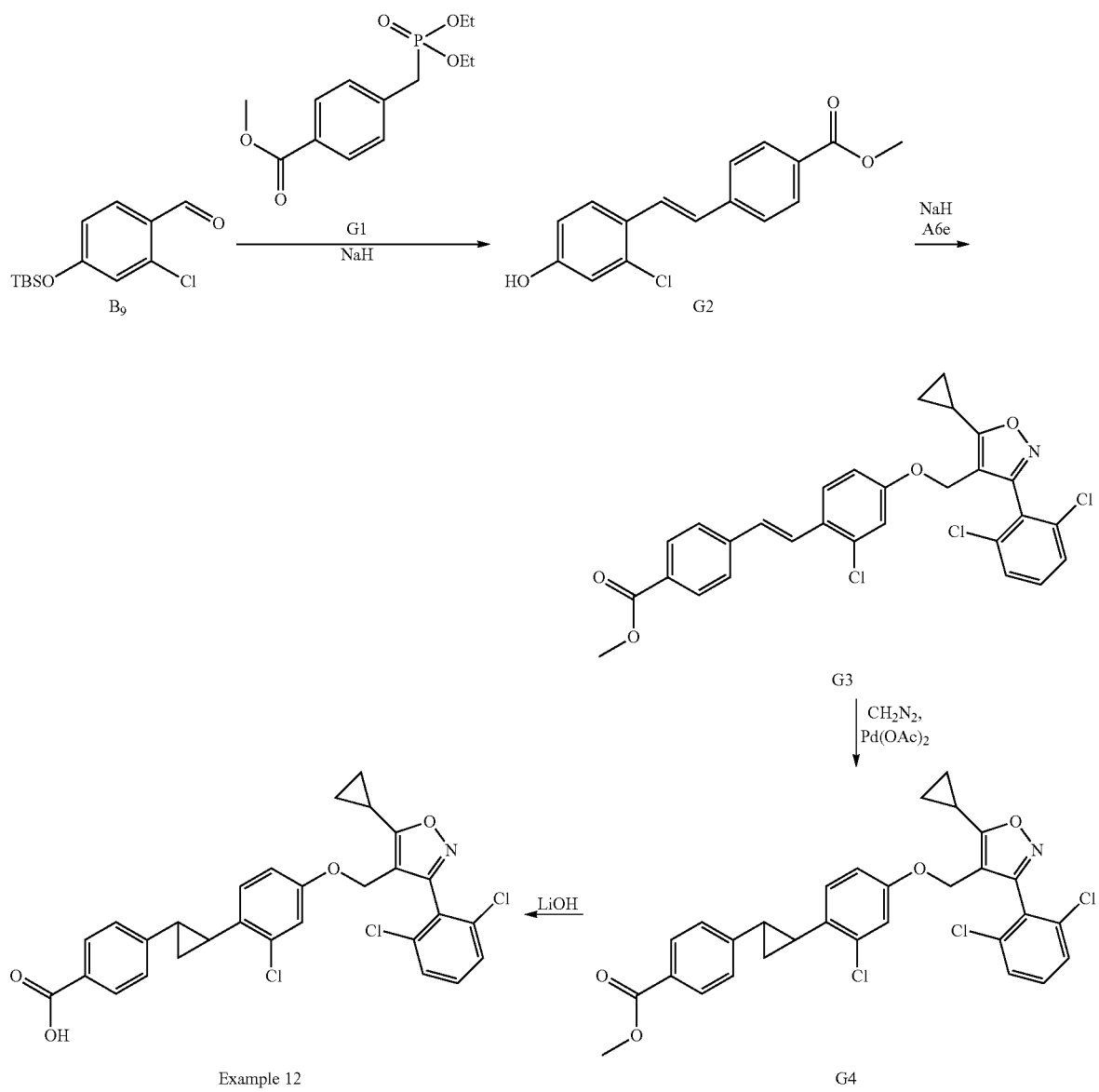

Example 12

Synthesis of Compound G2

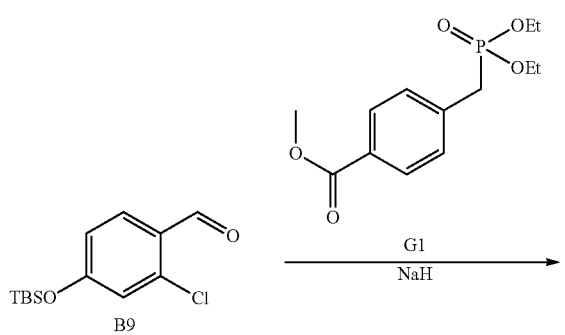

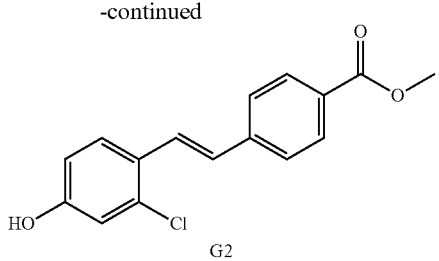

To the solution of compound B9 (31 g, 110 mmol) in 300 mL of dry THF was added sodium hydride (8.8 g, 220 mmol) at 0° C. for 30 min. To this resulting mixture was added the solution of compound G1 (20.1 g, 130 mmol) in 160 mL of dry THF at 0° C., and the solution was stirred at room temperature for 3 h. The mixture was quenched by sat. NH$_4$Cl solution and extracted with EtOAc. The organic layer was washed with brine, dried over Na₂SO₄, filtered, concentrated and purified by flash chromatography on silica gel (eluent: PE/EA=10/1) to give 25 g of compound 3 as a yellow solid (Yield: 78.9%).

Synthesis of Compound G3

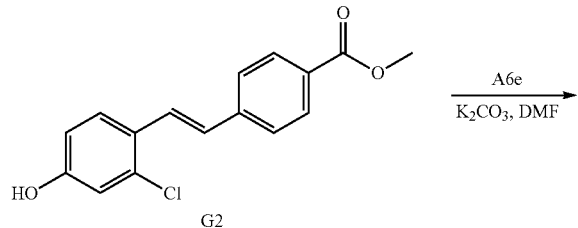

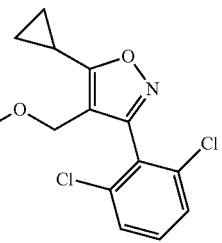

To the solution of the crude compound G2 (25 g, 86.8 mmol) and compound A6e (26.2 g, 86.8 mmol) in 100 mL of DMF was added K₂CO₃ (56.9 g, 173.6 mmol). The mixture was heated overnight at 60° C. Cooled to room temperature, diluted with 10 mL of H₂O and extracted with 300 mL of EtOAc. The organic layer was washed with brine twice, dried over Na₂SO₄, filtered, concentrated and purified by flash chromatography on silica gel (eluent: PE/EA=20/1) to give 30 g of compound 4 as a white solid (Yield: 62.5%).

Synthesis of Compound G4

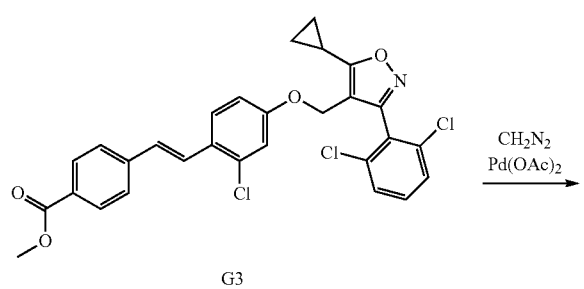

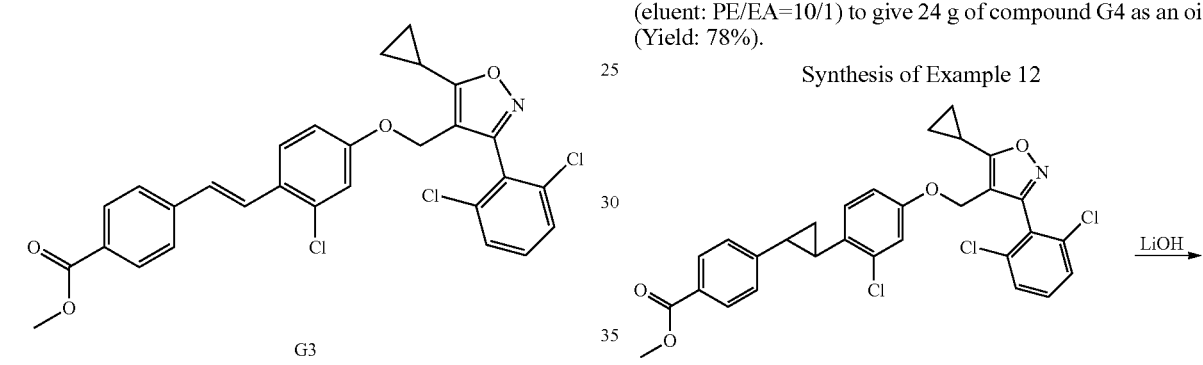

To the solution of compound G3 (30 g, 54.2 mmol) and Pd(OAc)₂ (3 g) in 300 mL of Et₂O was added the solution of CH₂N₂ in Et₂O (700 mL, 2.80 mol) at −50° C. under N₂ atmosphere. Then the solution was warmed to room temperature slowly, and stirred for another 4 h. Both of TLC and LCMS indicated that the reaction was ok. Filtered, concentrated and purified by flash chromatography on silica gel (eluent: PE/EA=10/1) to give 24 g of compound G4 as an oil (Yield: 78%).

Synthesis of Example 12

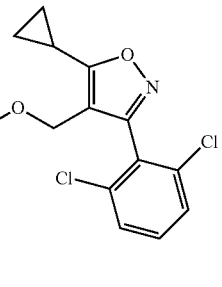

To the solution of compound G4 (24 g, 42.3 mmol) in 200 mL of THF and 50 mL of H₂O was added LiOH.H₂O (17.77 g, 423 mmol), and then the mixture was stirred at room temperature for 24 h. Concentrated and diluted with 200 mL of H₂O, 1N aq. HCl solution was added to acidify the mixture to pH=4, which was extracted with EtOAc later. The organic layer was washed with brine, dried over Na₂SO₄, filtered, concentrated and purified by chromatography on silica gel (eluent: PE/EA=3/1) to give 16.35 g of Example 12 as a white solid (Yield: 37.3%).

¹HNMR (400 MHz, CDCl₃) δ: 1.13 (m, 2H), 1.18 (m, 2H), 1.53 (m, 2H), 2.10 (m, 1H), 2.31 (m, 1H), 2.46 (m, 1H), 4.89 (s, 2H), 6.73 (dd, J=2.4 Hz, 8.4 Hz, 1H), 6.91 (d, J=2.4 Hz, 1H), 7.08 (d, J=8.8 Hz, 1H), 7.30 (d, J=8.4 Hz, 2H), 7.55 (m, 1H), 7.63 (m, 2H), 7.85 (d, J=8.4 Hz, 2H);

LCMS (mobile phase: 30%-95% Acetonitrile-Water) purity is >95%, Rt=2.875 min;

MS Calcd.: 553; MS Found: 554 (M+1).

Example 12a

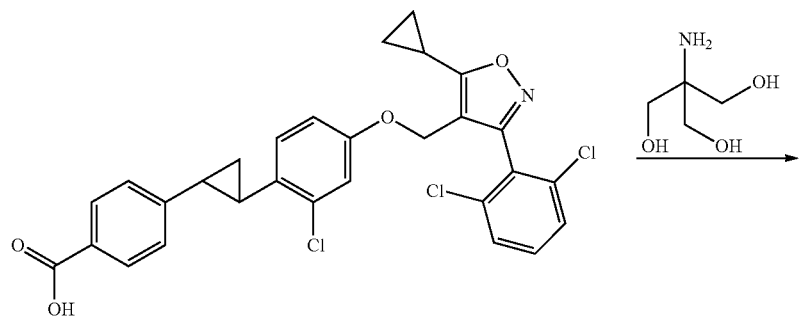

Example 12

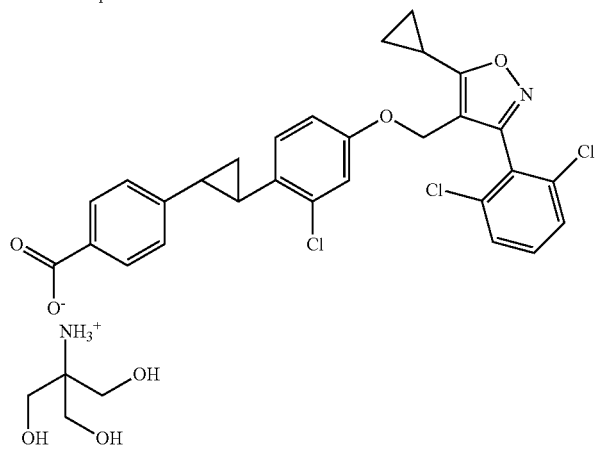

Example 12a

The appropriate quantity of tromethamine is added to 1 g of Example 12 (free acid) so that the parent compound and its counter ion are in an equimolar ratio. Ethanol (30 mL) is added. The mixture is stirred at 55° C. until complete solubilization (ca. 1 h) and the solvent is then removed under vacuum. Isopropanol is slowly added until the film is completely solubilized while the medium is stirred at 75° C. The sample is then slowly cooled down from 75° C. to room temperature by decreasing the temperature by 2 degrees every 15 minutes. The supernatant is removed from the flask. The powder is dried under dynamic vacuum over 2 h at 70° C. The powder is then further dried at 40° C. for 4 h.

$^1$HNMR (400 MHz, CDCl$_3$) δ: 1.09-1.18 (m, 4H); 1.39-1.46 (m, 2H); 1.98-2.06 (m, 1H); 2.21-2.28 (m, 1H); 2.40-2.45 (m, 1H); 3.44 (s, 6H); 4.87 (s, 2H); 6.15 (bs, 6H); 6.70 (dd, J1=18.8 Hz, J2=2.5 Hz, 1H); 6.87 (d, J=2.5 Hz, 1); 7.01 (d, J=8.8 Hz, 1H); 7.14 (d, J=8.2 Hz, 2H); 7.49-7.54 (m, 1H); 7.57-7.61 (m, 2H); 7.79 (d, J=8.2 Hz, 2H); T$_m$=143° C.

Scheme 7a

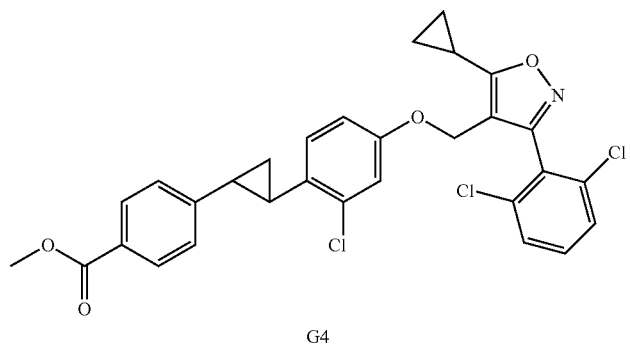

G4

Chiral HPLC separation

103                                              104
-continued
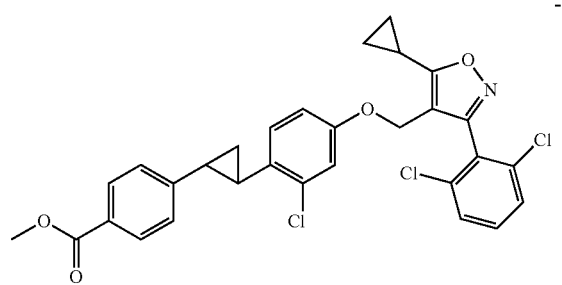
G4a
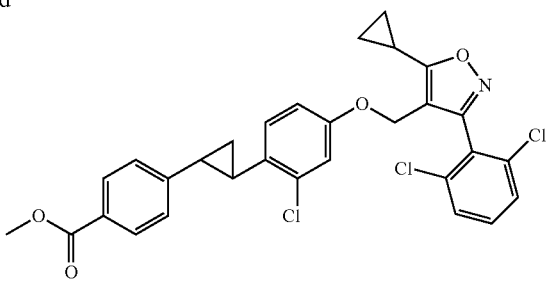
G4b
LiOH ↓                                              LiOH ↓
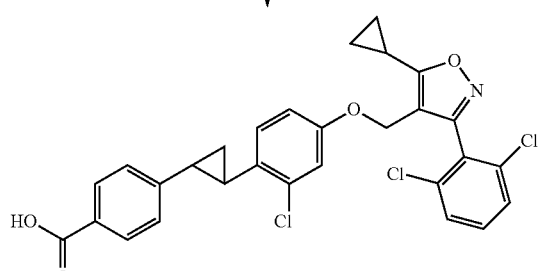
Example 12b
(+)-Isomer
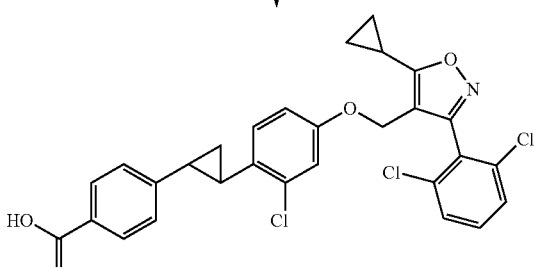
Example 12c
(−)-Isomer
Chiral HPLC Separation
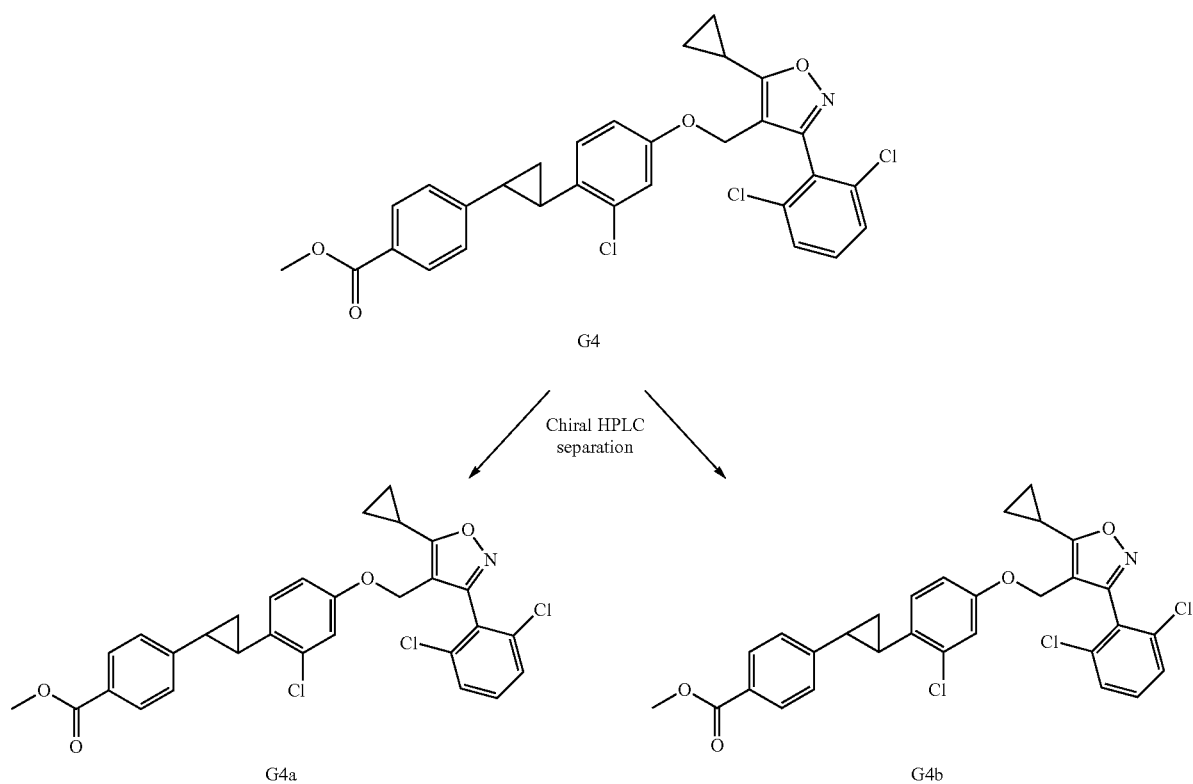
3.5 g of G4 (racemic) was separated by preparative chiral HPLC with a chiral column (column: CHIRALPAK IA; Column size: 0.46 cm I.D.×15 cm L; Mobile phase: Hexane/Isopropyl alcohol=70/30 (v/v); Flow rate: 1 mL/min; Wave

Synthesis of Example 12b

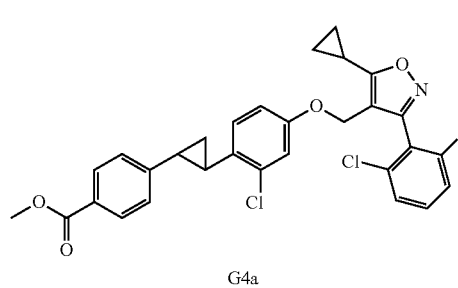

G4a

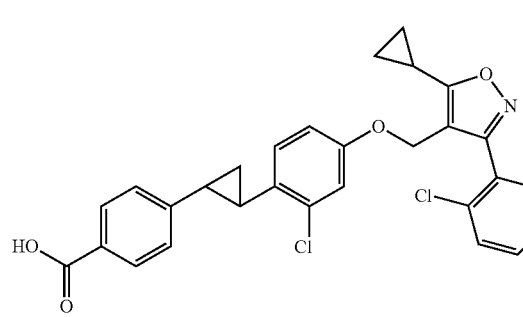

Example 12b
(+)-Isomer

To a solution of G4a (1.5 g, 2.65 mmol) in 20 mL of THF and 15 mL of H₂O was added LiOH.H₂O (800 mg, 19 mmol), and then the mixture was stirred at 50° C. overnight. Concentrated under reduced pressure, diluted with 5 mL of H₂O, and 1N aq. HCl solution was added to acidify the mixture to pH=4. The formed solid was filtered and dried in vacuum to give 1.1 g of Example 12b ((+)-4-(2-(2-chloro-4-((5-cyclopropyl-3-(2,6-dichlorophenyl)isoxazol-4-yl)methoxy)phenyl)cyclopropyl)benzoic acid) as a white solid (Yield: 75.2%).

¹HNMR (400 MHz, CDCl₃) δ: 1.13 (m, 2H), 1.18 (m, 2H), 1.53 (m, 2H), 2.10 (m, 1H), 2.31 (m, 1H), 2.46 (m, 1H), 4.89 (s, 2H), 6.73 (dd, J=2.4 Hz, 8.4 Hz, 1H), 6.91 (d, J=2.4 Hz, 1H), 7.08 (d, J=8.8 Hz, 1H), 7.30 (d, J=8.4 Hz, 2H), 7.55 (m, 1H), 7.63 (m, 2H), 7.85 (d, J=8.4 Hz, 2H);

LCMS (mobile phase: 60%-95% Acetonitrile-Water-0.05% TFA) purity is >98%, Rt=3.632 min;

MS Calcd.: 553; MS Found: 554 (M+1)

Chiral HPLC (Column: Chiral pak AD-H 250*4.6; Mobile phase: 93/7 Hexane/EtOH): ee % is 100%, Rt=16.408;

Optical rotation: $[\alpha]_D^{25}$=+132° (MeOH, c=0.295).

Synthesis of Example 12c

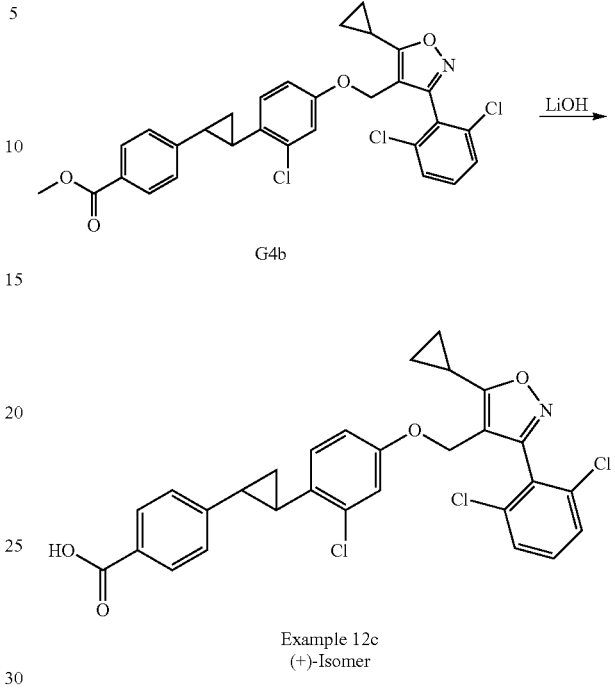

G4b

Example 12c
(+)-Isomer

To a solution of G4b (1.5 g, 2.65 mmol) in 20 mL of THF and 15 mL of H₂O was added LiOH.H₂O (800 mg, 19 mmol), and then the mixture was stirred at 50° C. overnight. Concentrated under reduced pressure, diluted with 5 mL of H₂O, and 1N aq. HCl solution was added to acidify the mixture to pH=4. The formed solid was filtered and dried in vacuum to give 1.1 g of Example 12c ((−)-4-(2-(2-chloro-4-((5-cyclopropyl-3-(2,6-dichlorophenyl)isoxazol-4-yl)methoxy)phenyl)cyclopropyl)benzoic acid) as a white solid (Yield: 75.2%).

¹HNMR (400 MHz, CDCl₃) δ: 1.13 (m, 2H), 1.18 (m, 2H), 1.53 (m, 2H), 2.10 (m, 1H), 2.31 (m, 1H), 2.46 (m, 1H), 4.89 (s, 2H), 6.73 (dd, J=2.4 Hz, 8.4 Hz, 1H), 6.91 (d, J=2.4 Hz, 1H), 7.08 (d, J=8.8 Hz, 1H), 7.30 (d, J=8.4 Hz, 2H), 7.55 (m, 1H), 7.63 (m, 2H), 7.85 (d, J=8.4 Hz, 2H);

LCMS (mobile phase: 60%-95% Acetonitrile-Water-0.05% TFA) purity >98%, Rt=3.632 min; MS Calcd.: 553; MS Found: 554 (M+1);

Chiral HPLC (Column: Chiral pak AD-H 250*4.6; Mobile phase: 93/7 Hexane/EtOH): ee % is 100%, Rt=24.411;

Optical rotation: $[\alpha]_D^{25}$=−140.6° (MeOH, c=0.31).

Scheme 8:

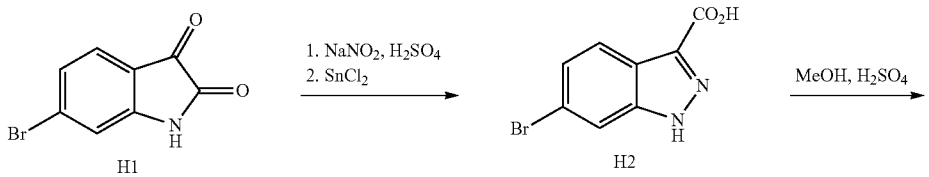

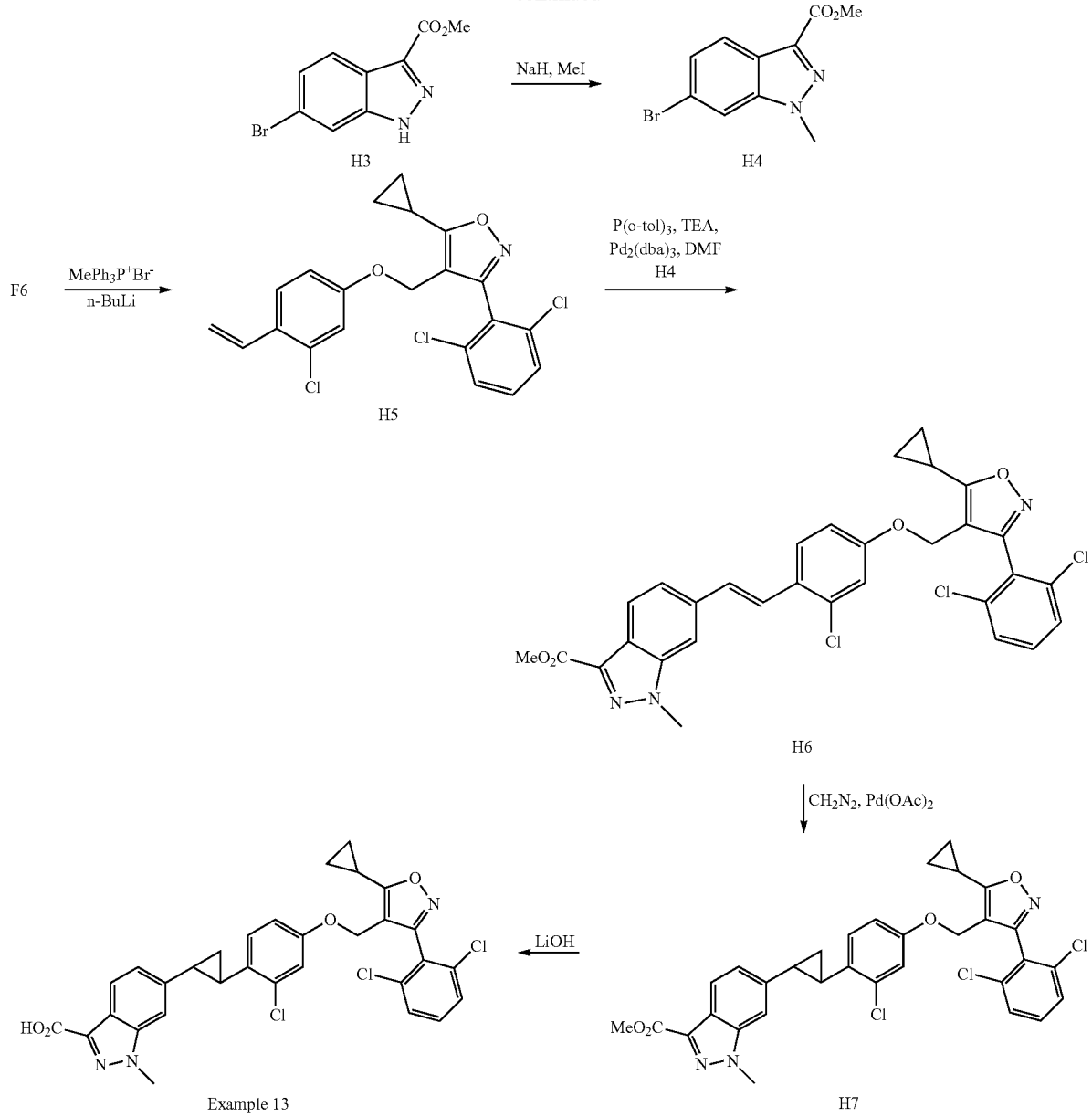

Synthesis of Compound H2

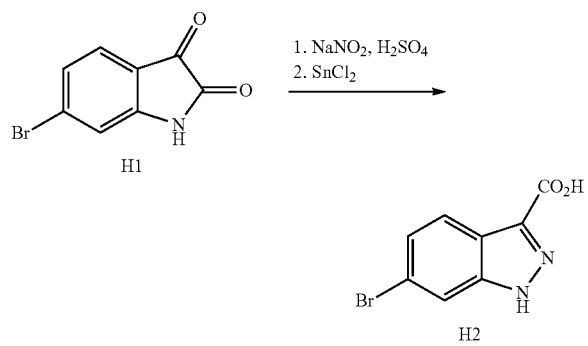

A chilled (0° C.) aqueous solution of NaNO$_2$ (6.1 g, 88.5 mmol, 27 mL of water) was added to a chilled (0° C.) solution of commercially available compound H1 (20 g, 88.5 mmol) in aqueous NaOH (96 mL, 96 mmol, 1 N). The combined solutions were added slowly to chilled aqueous H$_2$SO$_4$ (9.2 mL of conc. H$_2$SO$_4$, 80 mL of water) by means of an addition funnel with the tip below the surface of the acid solution. Ice was added to the reaction to maintain 0° C. and ether was added to control foaming, as needed. After stirring an additional 10 min, the diazonium solution was added slowly to a chilled mixture of SnCl$_2$.2H$_2$O (50 g, 221 mmol) in concentrated HCl (80 mL) by means of an addition funnel with the tip below the surface of the acid solution. Ice was added to the reaction to maintain 0° C. and ether was added to control foaming, as needed. After stirring an additional hour at 0° C., the reaction mixture was stirred at room temperature overnight. Filtered, the golden yellow powder was dissolved in aqueous NaOH, washed with ether, precipitated with aqueous HCl, filtered, and dried to give 20 g of crude compound H2 as yellow powder used into the following reaction without the further purification.

Synthesis of Compound H3

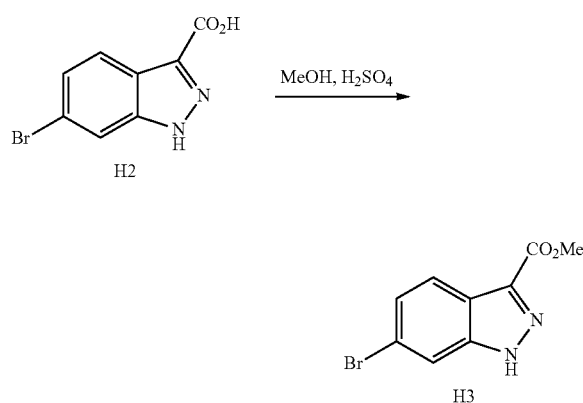

To a solution of compound H2 (20 g, 84 mmol) in 200 mL of dry MeOH was added dropwise conc. $H_2SO_4$ (15.4 g, 168 mmol) at 0-5° C. The resulting mixture was refluxed overnight. The reaction mixture was filtrated, evaporated, and poured into water (50 mL). The solution was adjusted to pH=7 with a saturated $NaHCO_3$ aqueous solution, extracted with ether (50*3 ml), dried over $MgSO_4$, concentrated and purified by flash chromatography on silica gel (eluent: PE/EA=1/1) to give 7.1 g of compound H3 as a yellow solid (yield: 35%).

Synthesis of Compound H4

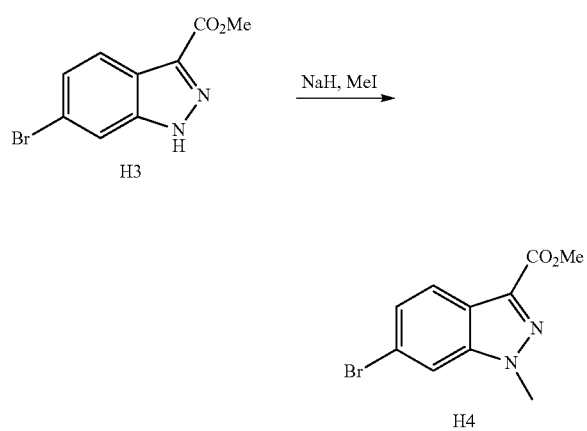

To a mixture of compound H3 (7 g, 27.45 mmol) and potassium carbonate (45 g, 137.25 mmol) in 200 mL of $CH_3CN$ was added $CH_3I$ (19.60 g, 138 mmol) at room temperature. The reaction mixture was stirred at room temperature for 15 h. Concentrated under reduced pressure, diluted with water, and extracted with EtOAc (10 mL*3). The combined organics were dried over $Na_2SO_4$ and concentrated under reduced pressure. The crude residue is purified by flash chromatography (eluent: PE/EA=4:1) to give 4.9 g of compound H4 as a yellow solid (Yield: 70%).

Synthesis of Compound H5

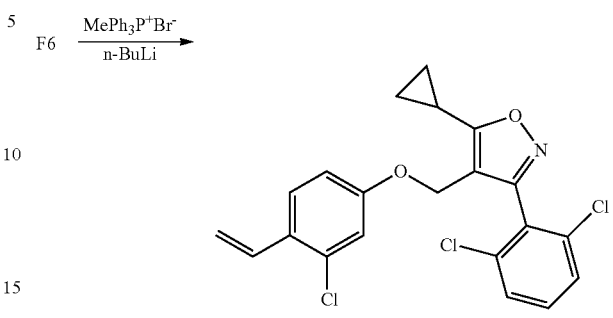

To a stirred solution of n-BuLi (4 mL, 2.5 M solution in Hexane, 10 mmol) in 30 mL of dry THF was added methyltriphenylphosphonium bromide (3.57 g, 10 mmol) over a period of 5 min at −60° C. The reaction mixture was stirred for 4 h at this temperature. To the resulting orange solution was added the solution of compound F6 (4.21 g, 10 mmol) in 5 mL of dry THF dropwise at −60° C. The solution became colorless, and was allowed to cool to room temperature. 20 mL of water was added for quench, and extracted with EtOAc twice. The combined organic layers were washed by brine, and then dried over anhydrous $MgSO_4$. The solvent was removed to give 4.53 g of crude compound H5 used into the following Heck reaction without the further purification.

Synthesis of Compound H6

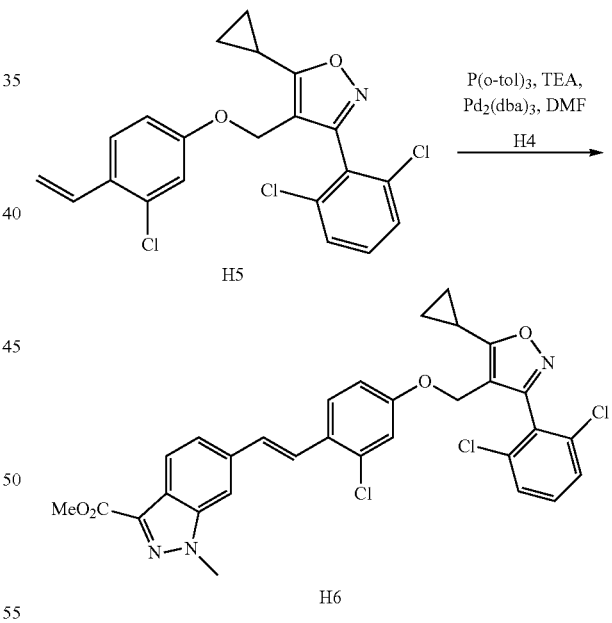

A mixture of compound H5 (3.57 g, 10 mmol), compound H6 (3.57 g, 10 mmol), tri(orthotolyl)phosphine (3.57 g, 10 mmol) and TEA (3.57 g, 10 mmol) in 5 mL of DMF was placed in a preheated bath at 100° C. $Pd_2(dba)_3$ (3.57 g, 10 mmol) was added and the mixture was maintained at 100° C. for 16 h. After cooling to room temperature, the mixture was partitioned in EtOAc/water/$NaHSO_4$ (pH<4). The organic layers were washed with water, brine, and then dried over $MgSO_4$. After evaporation of solvent, the crude material was purified by flash chromatography on silica gel (eluent: PE/EA=5/1) to give 1.40 g of compound H6 as a white solid (Yield: 23%).

Synthesis of Compound H7

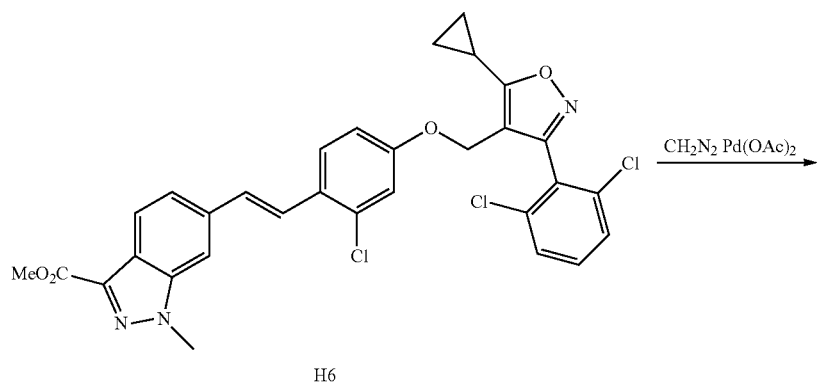

H6

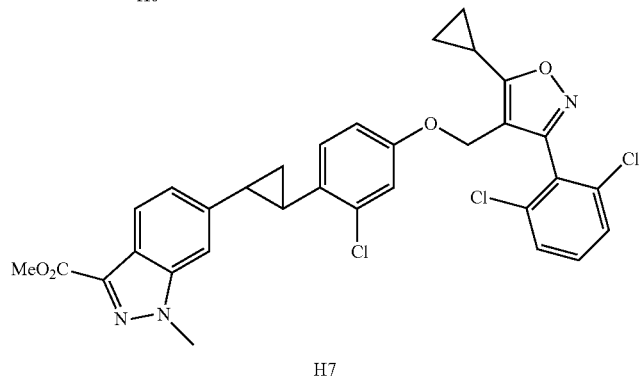

H7

To the solution of compound H6 (400 mg, 0.66 mmol) and Pd(OAc)₂ (200 mg) in 20 mL of Et₂O was added the solution of CH₂N₂ in Et₂O (20 mL, 80 mmol) at −50° C. under N₂ atmosphere. Then the solution was warmed to room temperature slowly, and stirred for another 4 h. Both of TLC and LCMS indicated that the reaction was ok. Filtered, concentrated and purified by flash chromatography on silica gel (eluent: PE/EA=10/1) to give 278 mg of crude compound H7 as a white solid (Yield: 68%).

Example 13

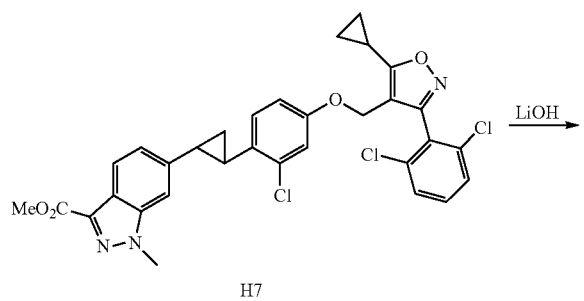

H7

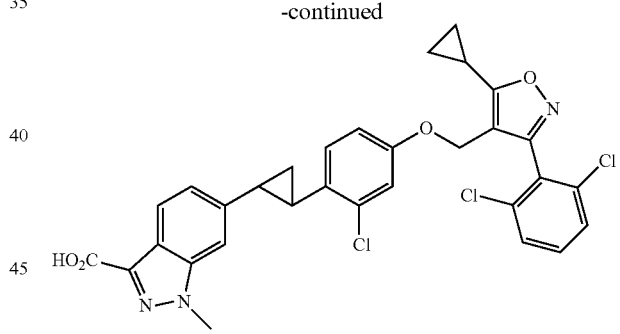

Example 13

To the solution of compound H7 (278 mg, 0.45 mmol) in 10 mL of THF and 4 mL of H₂O was added LiOH.H₂O (188 mg, 4.48 mmol), and then the mixture was stirred at room temperature for 24 h. Concentrated and diluted with 10 mL of H₂O, 1N aq. HCl solution was added to acidify the mixture to pH=5, which was extracted with EtOAc later. The organic layer was washed with brine, dried over Na₂SO₄, filtered, concentrated and purified by chromatography on silica gel (eluent: PE/EA=1/1) to give 130 mg of Example 13 as a white solid (Yield: 48%).

¹H NMR (400 MHz, DMSO-d6) δ: 1.16 (m, 4H), 1.59 (m, 2H), 2.23 (m, 1H), 2.39 (m, 1H), 2.48 (m, 1H), 4.09 (s, 3H), 4.91 (s, 2H), 6.75 (dd, J=2.4 Hz, 8.8 Hz, 1H), 6.92 (d, J=2.4 Hz, 1H), 7.12 (d, J=8.8 Hz, 1H), 7.20 (d, J=8.4 Hz, 1H), 7.56 (m, 2H), 7.64 (m, 2H), 7.96 (d, J=8.4 Hz, 1H), 12.88 (s, 1H);

LCMS (mobile phase: 30%-95% Acetonitrile-Water) purity is >95%, Rt=3.258 min;

MS Calcd.: 607; MS Found: 608 (M+1).

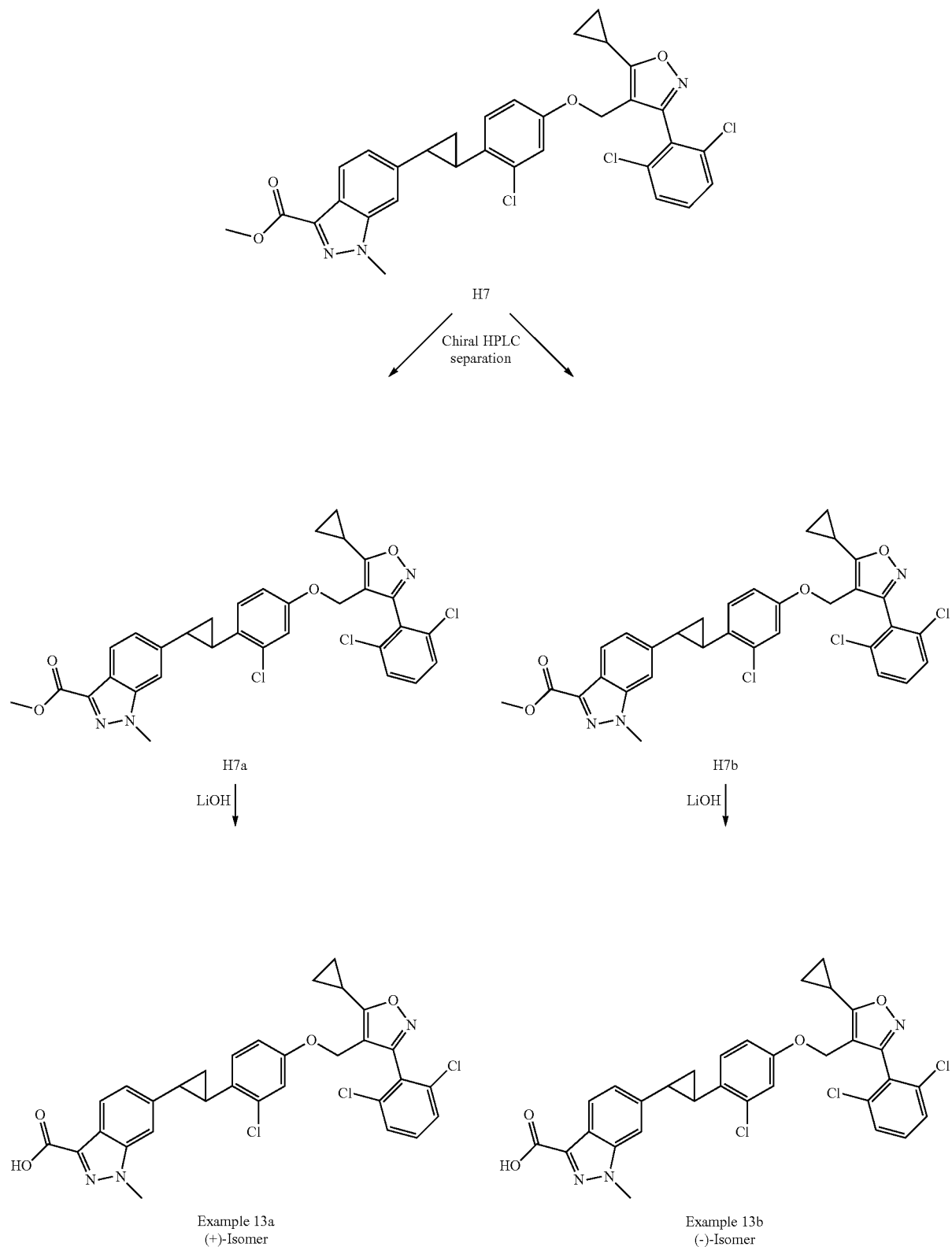
Scheme 8a

Chiral HPLC Separation

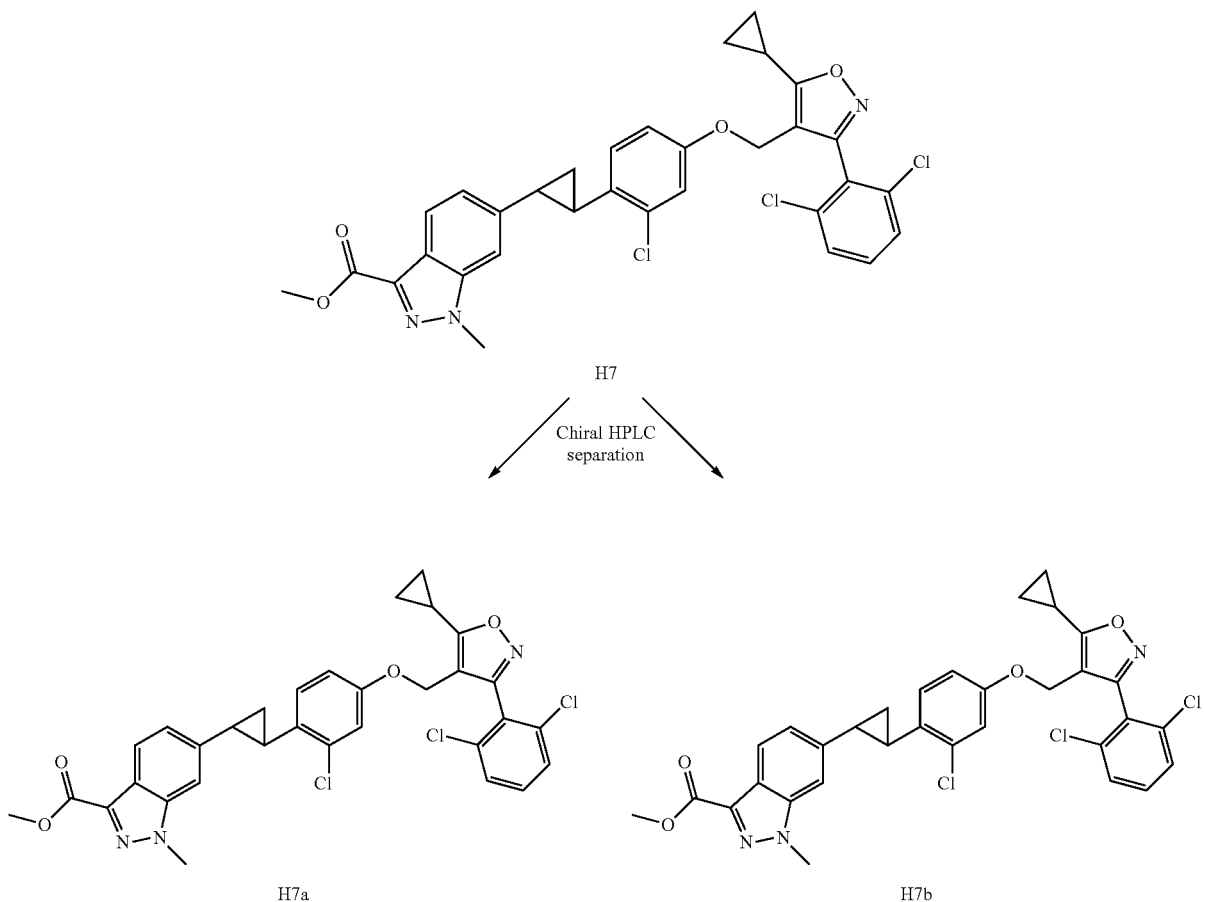 [SMILES: COC(=O)c1nn(C)c2cc(C3CC3c3ccc(OCc4c(-c5c(Cl)cccc5Cl)noc4C4CC4)cc3Cl)ccc12 ; "H7" ; COC(=O)c1nn(C)c2cc(C3CC3c3ccc(OCc4c(-c5c(Cl)cccc5Cl)noc4C4CC4)cc3Cl)ccc12 ; COC(=O)c1nn(C)c2cc(C3CC3c3ccc(OCc4c(-c5c(Cl)cccc5Cl)noc4C4CC4)cc3Cl)ccc12]

H7

Chiral HPLC separation

H7a

H7b 600 mg of H7 (racemic) was separated by preparative chiral HPLC with a chiral column (column: CHIRALPAK IA; Column size: 0.46 cm I.D.×15 cm L; Mobile phase: Hexane/Ethyl alcohol/DEA=50/50/0.1 (v/v/v); Flow rate: 1.0 mL/min; Wave length: UV 254 nm; HPLC equipment: Shimadzu LC 20 with UV detector SPD-20A) to give 210 mg of H7a (Rt=5.325 min, ee %: >99%) and 186 mg of H7b (Rt=6.804 min, ee %: >99%).

Synthesis of Example 13a

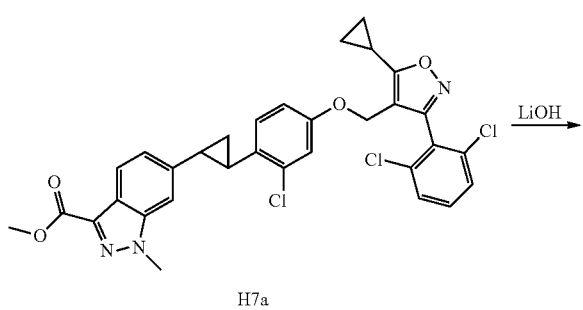

H7a

-continued

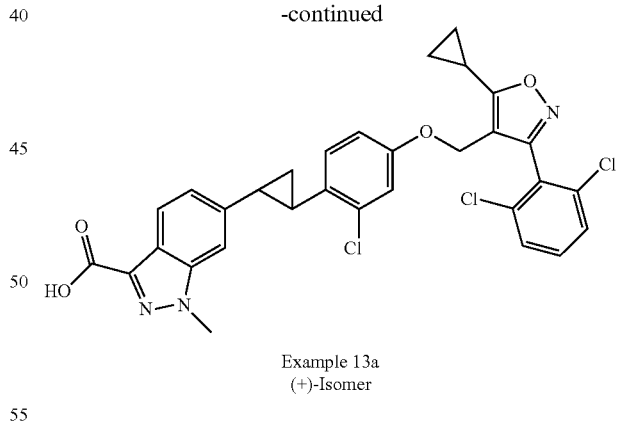

Example 13a
(+)-Isomer

To the solution of H7a (210 mg, 0.35 mmol) in 5 mL THF and 2 mL $H_2O$ was added $LiOH \cdot H_2O$ (8 mg, 1.9 mmol), and then the mixture was stirred at room temperature for 4 h. It was concentrated, diluted with 5 mL of $H_2O$, and 1N aq. HCl solution was added to acidify the mixture to pH=5. EtOAc was added to extract twice, and the combined organic phases were dried over $Na_2SO_4$, filtered, concentrated under reduced pressure and purified by flash chromatography on silica gel (eluent: PE/EA=1/2) to give 108 mg of Example 13a ((+)-6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid) as a yellow solid (Yield: 50.8%).

$^1$HNMR (400 MHz, CDCl$_3$) δ: 1.18 (m, 2H), 1.32 (m, 2H), 1.51 (m, 2H), 2.19 (m, 1H), 2.45 (m, 1H), 4.18 (s, 3H), 4.82 (s, 2H), 6.71 (dd, J=2.4 Hz, 8.4 Hz, 1H), 6.87 (d, J=1.6 Hz, 1H), 7.01 (d, J=8.4 Hz, 1H), 7.23 (m, 2H), 7.36 (m, 1H), 7.43 (m, 2H), 8.17 (d, J=8.4 Hz, 1H);

LCMS (mobile phase: 60%-95% Acetonitrile-Water-0.05% TFA) purity is >98%, Rt=3.144 min;

MS Calcd.: 607; MS Found: 608 (M+1);

Chiral HPLC (Column: Chiral pak AD-H 250*4.6; Mobile phase: 65/35 Hexane/EtOH): ee % is 100%, Rt=13.101;

Optical rotation: $[α]_D^{25}$=+159° (MeOH, c=0.300).

Synthesis of Example 13b

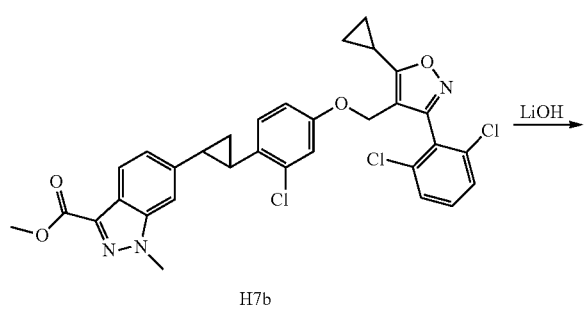

H7b

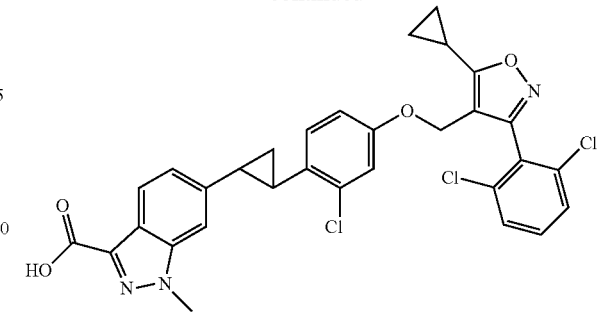

Example 13b
(−)-Isomer

In a similar manner as that described for Example 13a, Example 13b ((−)-6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid) was obtained (120 mg; Yield: 59.2%):

$^1$HNMR (400 MHz, CDCl$_3$) δ: 1.10-1.21 (m, 6H), 1.56 (m, 2H), 2.20 (m, 1H), 2.35 (m, 1H), 2.45 (m, 1H), 4.09 (s, 3H), 4.89 (s, 2H), 6.74 (dd, J=2.4 Hz, 8.8 Hz, 1H), 6.91 (d, J=2.0 Hz, 1H), 7.12 (m, 2H), 7.53 (m, 2H), 7.62 (m, 2H), 7.99 (d, J=8.4 Hz, 1H);

LCMS (mobile phase: 60%-95% Acetonitrile-Water-0.05% TFA) purity is >98%, Rt=3.180 min;

MS Calcd.: 607; MS Found: 608 (M+1);

Chiral HPLC (Column: Chiral pak AD-H 250*4.6; Mobile phase: 65/35 Hexane/EtOH): ee % is 99.7%, Rt=30.037;

Optical rotation: $[α]_D^{25}$=−161° (MeOH, c=0.300).

Example 14

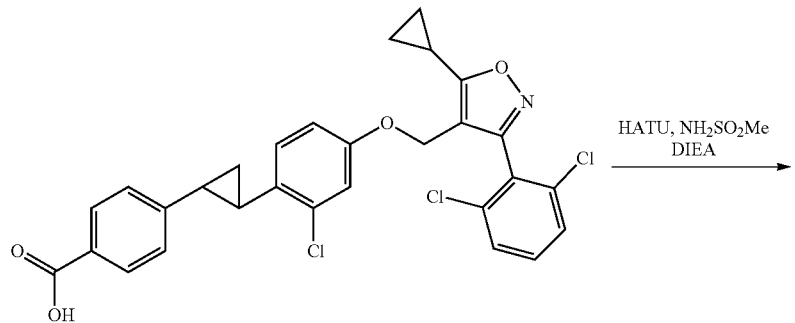

Example 12

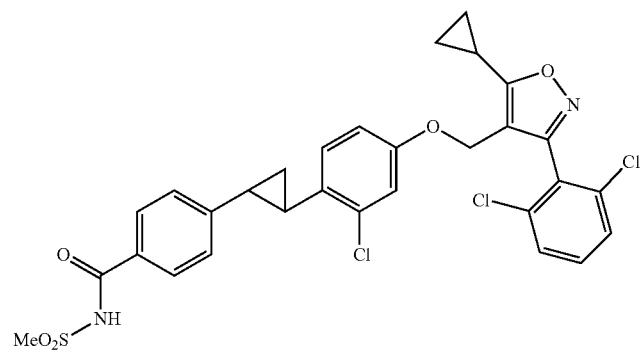

Example 14

To the solution of compound Example 12 (400 mg, 0.72 mmol) and one drop of DMF in 10 mL of anhydrous DCM was added a 2 M solution of oxalyl chloride (0.75 mL, 1.5 mmol) in anhydrous DCM at 0° C., and then the solution was stirred at room temperature for 2 h. Concentrated under reduced pressure, and the residue was diluted with 10 mL of anhydrous THF. The solution was added DIEA (0.25 mL, 1.5 mmol), methanesulfonamide (14.3 mg, 1.5 mmol) and DMAP (10 mg). The solution was stirred overnight. Concentrated under reduced pressure, and purified by prep. HPLC to give 40 mg of Example 14 as a white solid (Yield: 8.8%).

$^1$H NMR (400 MHz, CDCl3) δ 1.16~1.21 (m, 2H), 1.24-1.34 (m, 2H), 1.52 (m, 2H), 2.04 (m, 1H), 2.18 (m, 1H), 2.44 (m, 1H), 3.47 (s, 3H), 4.81 (s, 2H), 6.69 (dd, J=2.8 Hz, 8.4 Hz, 1H), 6.86 (d, J=2.4 Hz, 1H), 6.98 (d, J=8.4 Hz, 1H), 7.31 (m, 2H), 7.35 (m, 1H), 7.44 (m, 2H), 7.80 (d, J=8.4 Hz, 2H), 8.57 (s, 1H);

LCMS (mobile phase: 60%-95% Acetonitrile-Water-0.05% TFA) purity is >95%, Rt=3.255 min; MS Calcd.: 630; MS Found: 631 (M+1).

Example 15

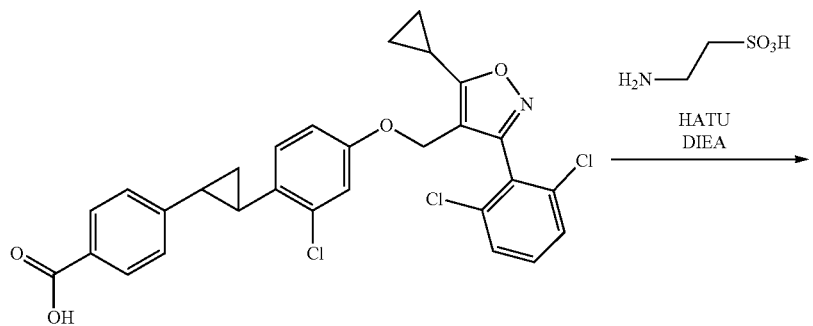

Example12

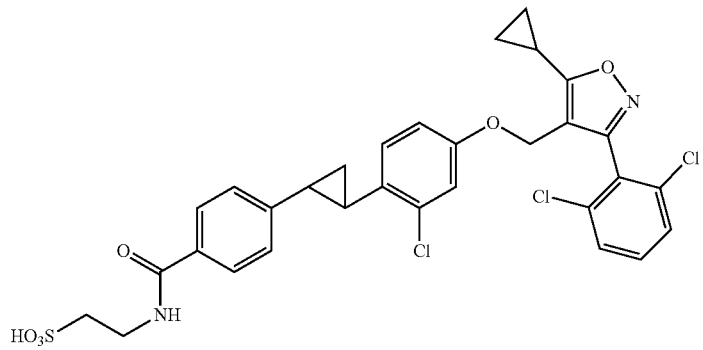

Example15

The solution of compound Example 12 (500 mg, 0.90 mmol) and HATU (500 mg, 1.32 mmol) in 20 mL of dry DMF was stirred at 0° C. for 30 min, then 2-aminoethanesulfonic acid (150 mg, 1.2 mmol) was added, followed by DIEA (0.4 mL). After stirring at room temperature for 18 h, the reaction mixture was concentrated under reduce pressure, and purified by prep. HPLC to give 250 mg of Example 15 as a white solid (Yield: 42%).

$^1$H NMR (400 MHz, CD3OD) δ 1.17~1.24 (m, 4H), 1.41-1.54 (m, 2H), 2.04 (m, 1H), 2.346 (m, 2H), 3.09 (m, 2H), 3.82 (m, 2H), 4.90 (s, 2H), 6.72 (dd, J=2.8 Hz, 8.8 Hz, 1H), 6.82 (d, J=2.4 Hz, 1H), 7.05 (d, J=8.4 Hz, 1H), 7.28 (d, J=8.8 Hz, 2H), 7.46~7.55 (m, 3H), 7.77 (d, J=8.0 Hz, 2H), 7.94 (s, 1H);

LCMS (mobile phase: 20%-95% Acetonitrile-Water) purity is >95%, Rt=4.099 min;
MS Calcd.: 660; MS Found: 659 (M−1).

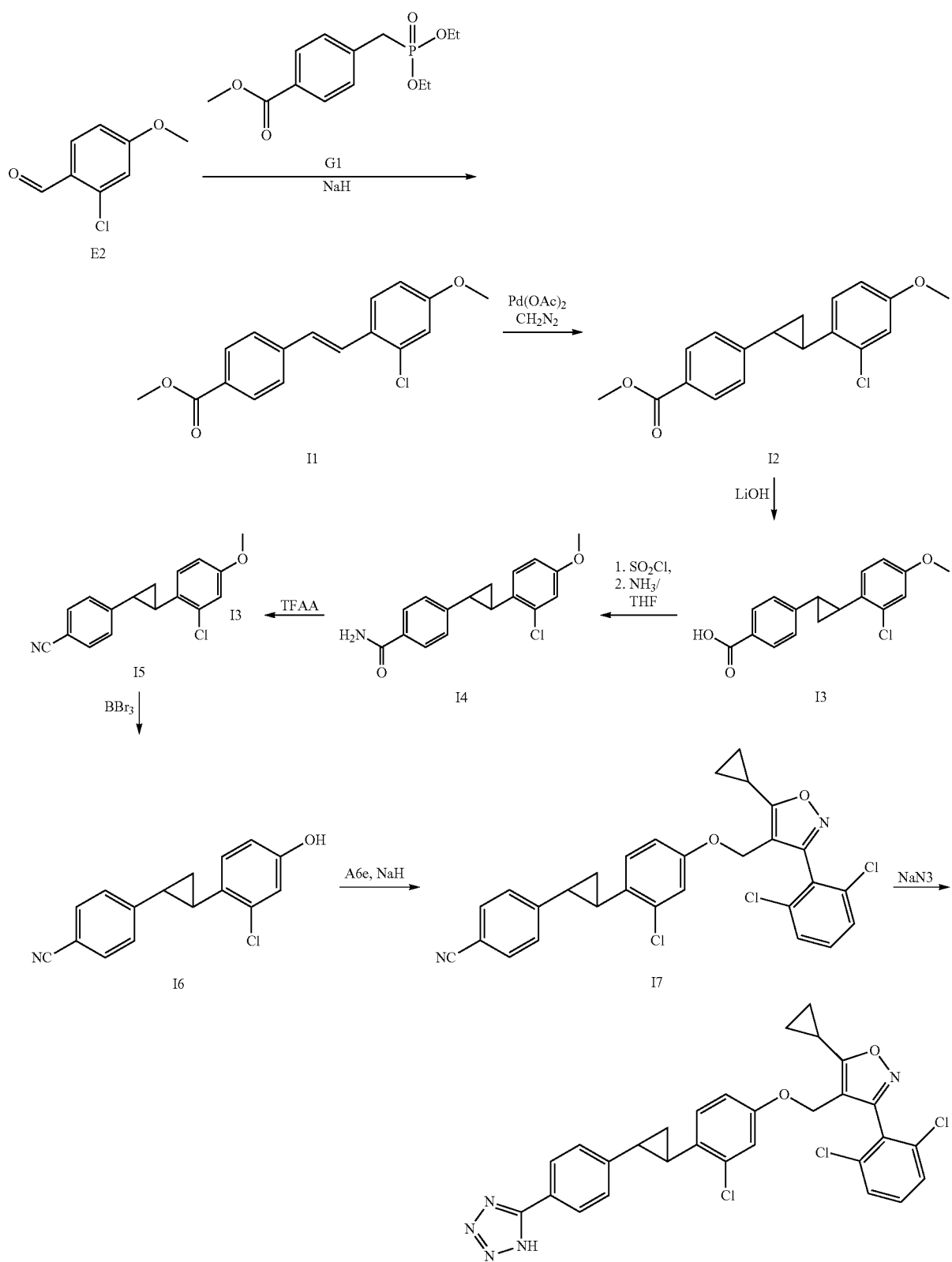
Scheme 9

Synthesis of Compound I1

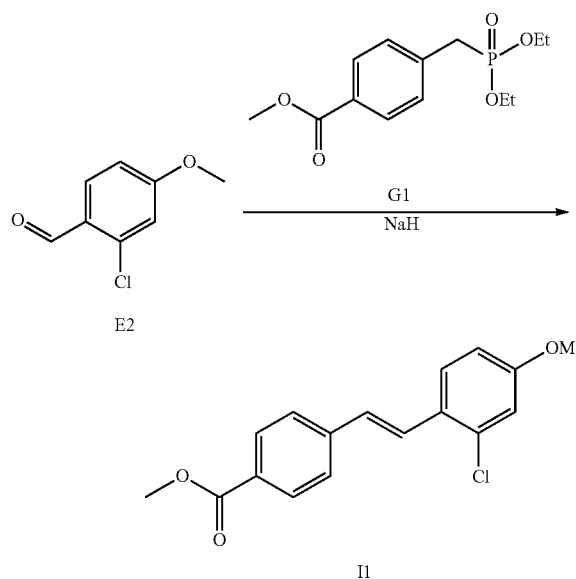

To a solution of compound G1 (65 g, 240 mmol) in 500 mL of dry THF was added sodium hydride (12 g, 288 mmol) at 0° C. for 30 min. To this resulting mixture was added the solution of compound E2 (41 g, 240 mmol) in 300 mL of dry THF at 0° C., and the solution was stirred at room temperature for 3 h. The mixture was quenched by sat. $NH_4Cl$ solution, and extracted with EtOAc. The organic layer was washed with brine, dried over $Na_2SO_4$, filtered, concentrated and purified twice by flash chromatography on silica gel (eluent: PE/EA=10/1) to give 72.5 g of compound I1 as a white solid (Yield: 100%).

Synthesis of Compound I2

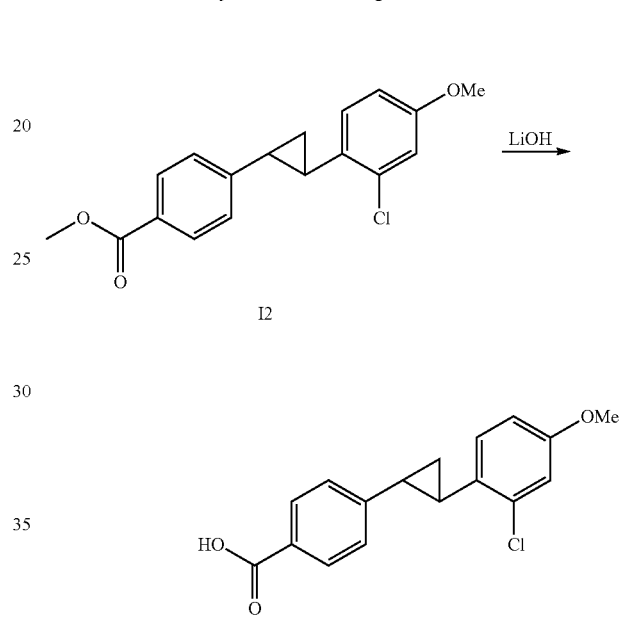

To a solution of compound I1 (20 g, 66.2 mmol) and $Pd(OAc)_2$ (3.5 g) in 200 mL of $Et_2O$ was added the solution of $CH_2N_2$ in $Et_2O$ (250 mL, 1 mol) at −50° C. under $N_2$ atmosphere. Then the solution was warmed to room temperature slowly, and stirred for another 4 h. LCMS indicated that the reaction was not over. Filtered and concentrated. 200 mL of dry $Et_2O$ was added to the residue followed by $Pd(OAc)_2$ (2 g). Then the solution of $CH_2N_2$ in $Et_2O$ (150 mL, 0.6 mol) was added at −50° C. under $N_2$ atmosphere. Then the solution was warmed to room temperature slowly, and stirred for another 4 h. LCMS indicated that the reaction was over and purified by flash chromatography on silica gel (eluent: PE/EA=50/1) to give 9 g of compound I2 as a off-white solid (Yield: 43%).

This reaction was re-conducted using the same quality with the same conditions three times, and 26 g of compound I2 was obtained (Yield: 43.2%).

Synthesis of Compound I3

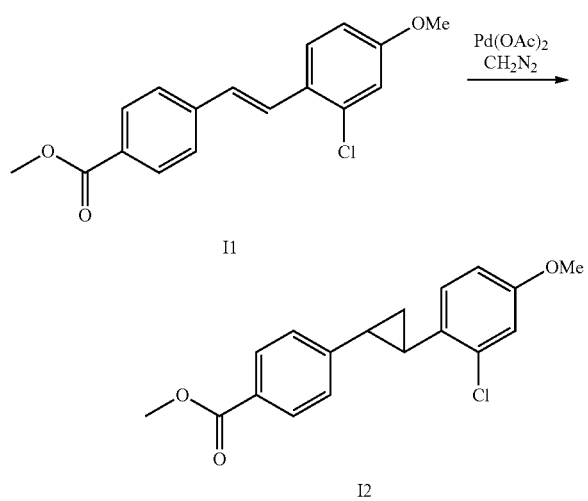

A stirred mixture of compound I2 (10.5 g, 33.23 mmol) and $LiOH \cdot H_2O$ (6.98 g, 166.1 mmol) dissolved in 20 mL of water and 100 mL of THF was stirred overnight at 55° C. The mixture was concentrated under reduced pressure, treated with a 6 N aq. HCl solution for adjusting pH to 1 and stirred for additional 30 min. The resulting precipitate was collected by filtering, washed with water and dried in vacuo to give 9.1 g of compound I3 as a white solid (Yield: 90.7%).

Synthesis of Compound I4

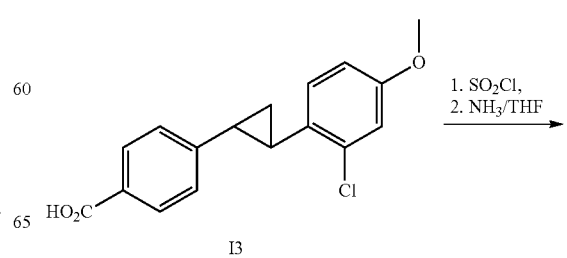

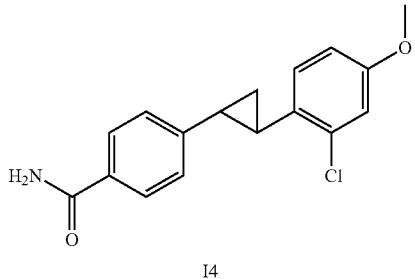

I4

To a solution of compound I3 (4.5 g, 15.0 mmol) in 30 mL of anhydrous DCM was added SOCl₂ (2 mL, 28.2 mmol), and then this solution was stirred at room temperature for 1.5 h. Concentrated under reduced pressure and the residue was diluted with THF. This solution was added to the solution of 6 N NH₃ in THF at 0° C., and then this solution was stirred at room temperature for 2 h. Concentrated under reduced pressure and 100 mL of water was added. The formed solid was collected and dried in vacuo to give 4.0 g of compound I4 as a white solid (Yield: 88.6%).

Synthesis of Compound I5

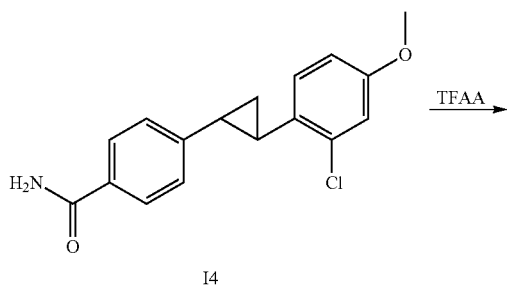

I4

I5

To a solution of compound I4 (4.0 g, 13 mmol) in 60 mL of anhydrous THF was added DIEA (4.0 g, 31 mmol) and TFAA (5.5 g, 26 mmol), and then this mixture was stirred for 4 h at room temperature. Concentrated under reduced pressure and the residue was diluted with 100 mL of EtOAc. The solution was washed with aq. NaHCO₃ solution and brine consecutively. Dried over Na₂SO₄, filter, concentrated under reduced pressure and purified by flash chromatography on silica gel (eluent: PE/EA=10/1) to give 3.5 g of compound I5 as a white solid (Yield: 95.1%).

Synthesis of Compound I6

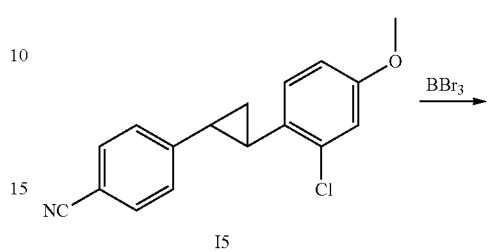

I5

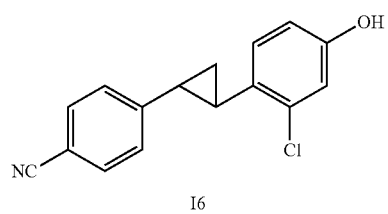

I6

To a solution of compound I5 (3.5 g, 12 mmol) in 70 mL of anhydrous DCM was added BBr₃ (5 mL, 52.9 mmol) at −78° C., and then this solution was stirred at −78° C. for 1 hour. MeOH was added to this mixture for quench, and then this solution was poured into 200 mL of sat. NaHCO₃ solution. Concentrated under reduce pressure, and Et₂O was added to extract twice. The combined organic layers were dried over Na₂SO₄, filter, concentrated under reduced pressure and purified by flash chromatography on silica gel (eluent: PE/EA=8/1) to give 2.2 g of compound I6 as a white solid (Yield: 68.2%).

Synthesis of Compound I7

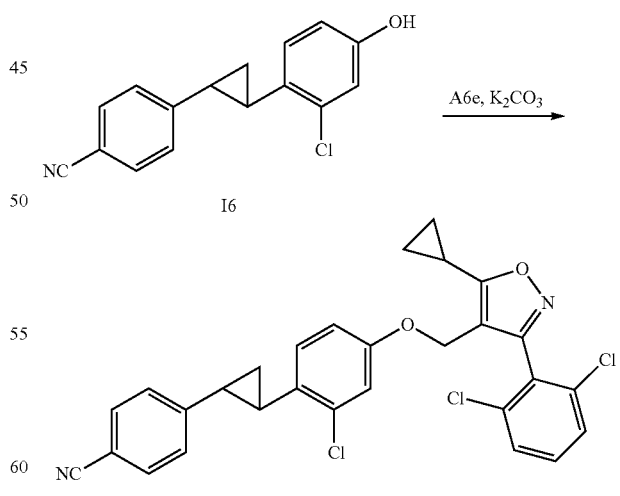

I6

I7

To a solution of compound I6 (2.1 g, 8.0 mmol) in 15 mL of DMF was added compound A6e (2.5 g, 8.3 mmol) and K₂CO₃ (2.2 g, 16 mmol), and then this solution was stirred overnight at 50° C. Cooled to room temperature, and diluted with EtOAc. The solution was washed with water and brine, dried over Na₂SO₄, filtered, concentrated under reduced pressure and purified by flash chromatography on silica gel (eluent: PE/EA=1/10) to give 2.1 g of compound I7 as a white solid (Yield: 49.2%).

Synthesis of Example 16

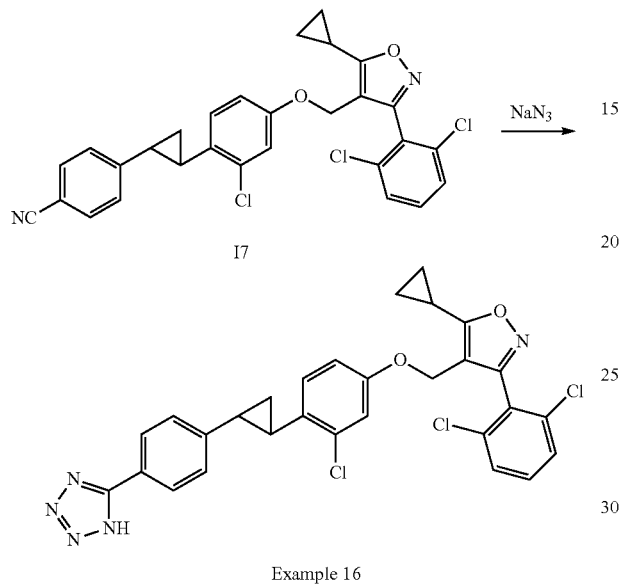

Example 16

To a solution of compound I7 (400 mg, 0.8 mmol) in 5 mL of DMF was added NH₄Cl (140 mg, 2.64 mmol) and NaN₃ (140 mg, 2.15 mmol), and then this solution was heated overnight at 100° C. Cooled to room temperature, and concentrated under reduced pressure. The residue was diluted with EtOAc, and washed with water three times, the organic layer was dried over Na₂SO₄, filter, concentrated under reduced pressure, and purify by prep. HPLC to give 130 mg of Example 16 as a white solid (Yield: 28.2%).

¹H NMR (400 MHz, DMSO-d6) δ 1.12-1.22 (m, 4H), 1.51-1.58 (m, 2H), 2.10-2.14 (m, 1H), 2.32-2.36 (m, 1H), 2.45-2.49 (m, 1H), 3.18 (s, 1H), 4.91 (s, 2H), 6.73-6.76 (dd, J=2.4 Hz, 8.8 Hz, 1H), 6.93 (d, J=2.0 Hz, 1H), 7.11 (d, J=8.8 Hz, 1H), 7.44 (d, J=8.4 Hz, 2H), 7.56 (m, 1H), 7.64 (d, J=7.6 Hz, 2H), 7.96 (d, J=7.6 Hz, 2H);

LCMS (mobile phase: 50%-95% Acetonitrile-Water-0.05% TFA) purity is >95%, Rt=3.962 min; MS Calcd.: 577; MS Found: 578 (M+1).

Scheme 10

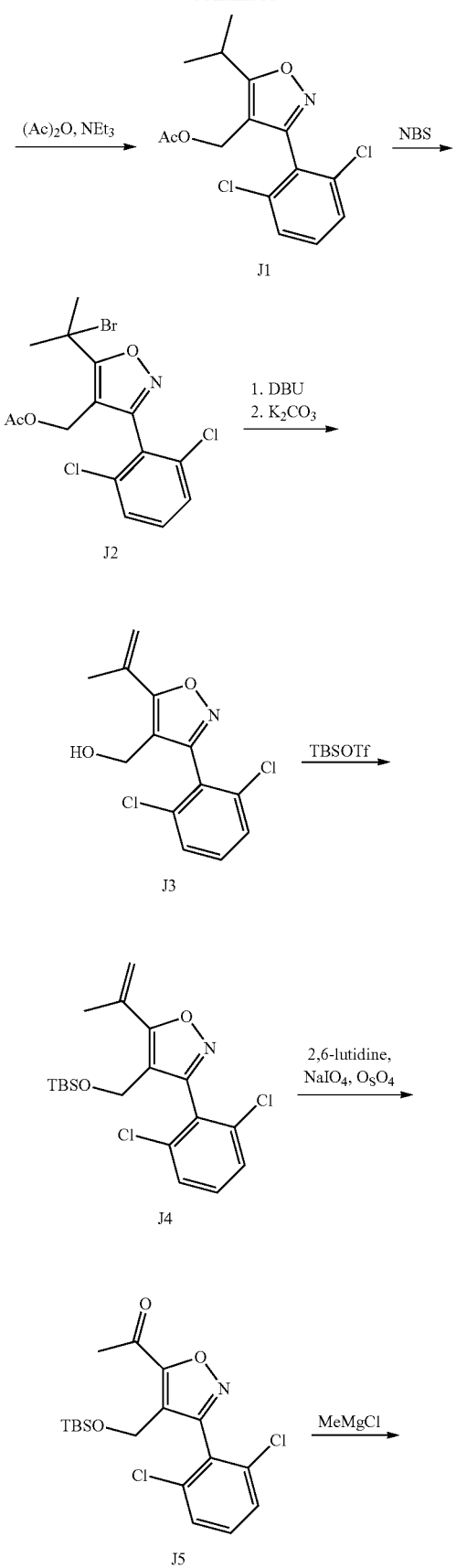

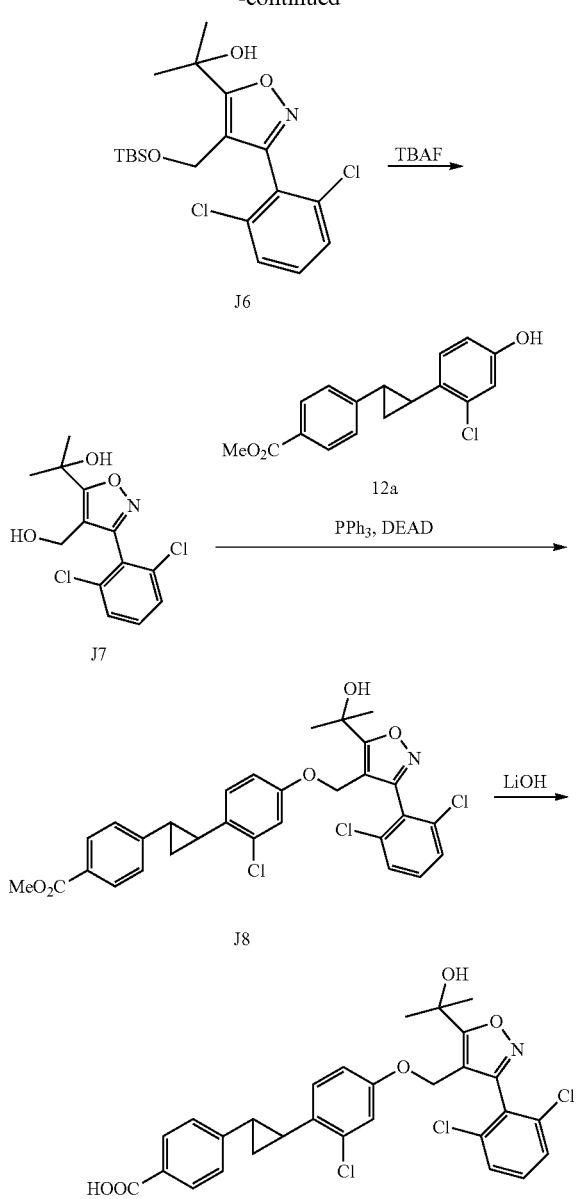

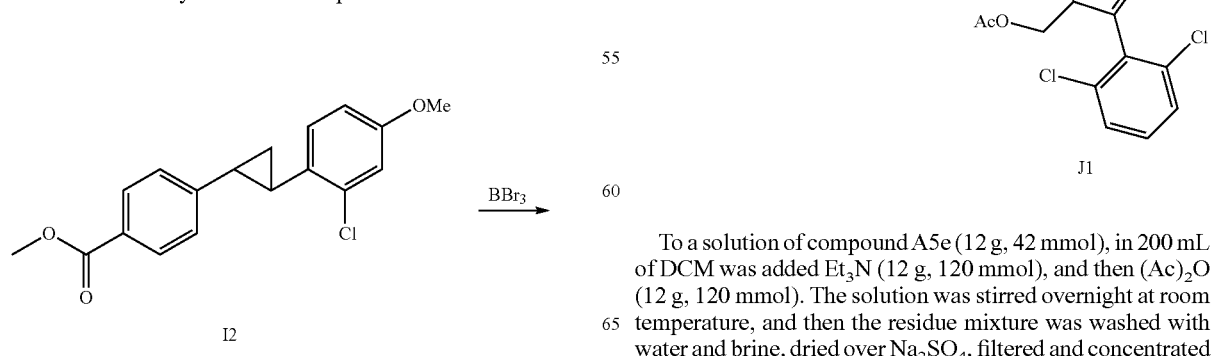

To the solution of compound I2 (5 g, 15.8 mmol) in 40 mL of dry DCM was added BBr₃ (14.8 mL, 158 mmol) at −70° C. under N₂ atmosphere, and then the solution was stirred at room temperature for 1 hour. Both of TLC and LCMS indicated that the de-methylation was over. The solution was cooled to −30° C. again and 50 mL of MeOH was added to quench. Concentrated under reduced pressure, and water and DCM was added to the residue. The organic layer was dried over Na₂SO₄, filtered, concentrated under reduced pressure and purified by flash chromatography on silica gel (eluent: PE/EA=10/1) to give 3.9 g of I2a as a yellow solid (Yield: 81.7%).

¹HNMR (400 MHz, CDCl₃) δ: 1.49 (m, 2H), 2.08 (m, 1H), 2.41 (m, 1H), 3.94 (s, 3H), 6.74 (dd, J=2.4 Hz, 8.4 Hz, 1H), 6.92 (d, J=2.4 Hz, 1H), 7.01 (d, J=8.4 Hz, 1H), 7.25 (d, J=8.0 Hz, 2H), 8.00 (d, J=8.4 Hz, 2H).

Synthesis of Compound J1

To a solution of compound A5e (12 g, 42 mmol), in 200 mL of DCM was added Et₃N (12 g, 120 mmol), and then (Ac)₂O (12 g, 120 mmol). The solution was stirred overnight at room temperature, and then the residue mixture was washed with water and brine, dried over Na₂SO₄, filtered and concentrated under reduced pressure and purified by flash chromatography

Synthesis of Compound J2

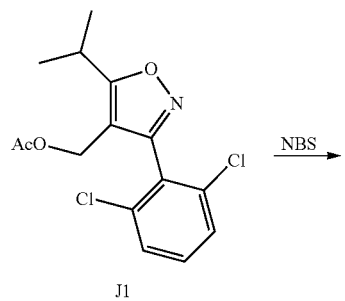

To a solution of compound J1 (13 g, 40 mmol) in 300 mL of CCl₄ was added NBS (7.8 g, 45 mmol), and this solution was stirred at reflux for 1 hour. The resulting solution was concentrated under reduced pressure and purified by flash chromatography on silica gel (eluent: PE/EtOAc=15/1) to give 12.5 g of compound J2 as an oil (Yield: 77%).

Synthesis of Compound J3

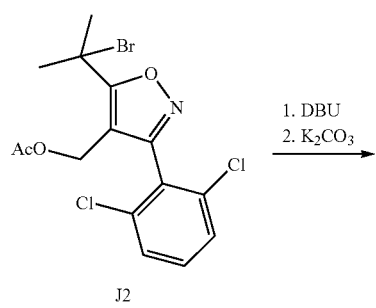

To a solvent of compound J2 (12.5 g, 30.8 mmol) in 200 mL of THF was added DBU (10 g), and this solution was stirred overnight at room temperature. This solution was concentrated under reduced pressure to give a residue. To this residue mixture which was dissolved in 80 mL of MeOH and 40 mL of H₂O was added K₂CO₃ (6 g, 43.5 mmol), and this solution was stirred at room temperature for 30 min. The resulting solution was quenched with water and concentrated under reduced pressure. The suspension was extracted with EtOAc three times, and the combined organic phases were dried over Na₂SO₄, filtered, concentrated under reduced pressure and purified by flash chromatography on silica gel (eluent: PE/EtOAc=5/1) to give 8 g of compound J3 as an oil (Yield: 90%).

Synthesis of Compound J4

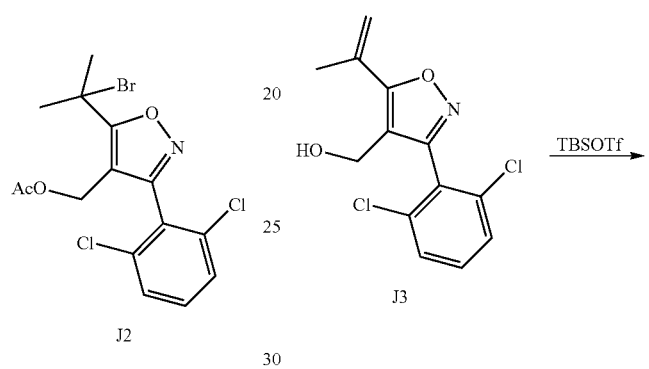

To a solution of compound J3 (8 g, 28 mmol) and DIEA (24 mL) in 150 mL of anhydrous THF was added TBSOTf (8.2 g, 31 mmol) at 0° C., and then the solution was stirred overnight at room temperature. The resulting solution was quenched with water at 0° C., and extracted with EtOAc three times. The combined organic phases were dried over MgSO₄, filtered, concentrated in vacuo and purified by flash chromatography on silica gel (eluent: PE/EtOAc=15/1) to give 9 g of compound J4 as a colorless oil (Yield: 90%).

Synthesis of Compound J5

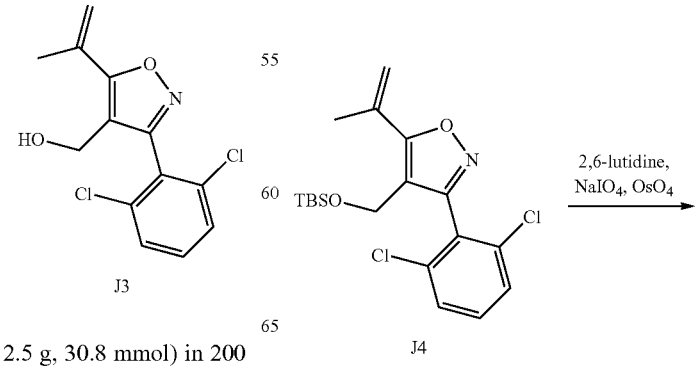

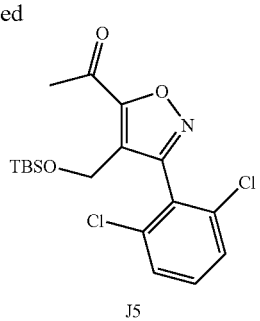

J5

The solution of compound J4 (2 g, 5 mmol), 2,6-lutidine (1 g, 10 mmol), NaOI₄ (4.27 g, 20 mmol) and OsO₄ (300 mg) in 40 mL of 1,4-dioxane and 15 mL of water was stirred at room temperature for 2 h. The resulting solution was diluted with water and extracted with EtOAc three times. The combined organic phases were washed with aq. NaHCO₃ solution twice, dried over Na₂SO₄, filtered, concentrated under reduced pressure and purified by flash chromatography on silica gel (eluent: PE/EtOAc=15/1) to give 1.8 g of compound J5 as an oil (Yield 94%).

Synthesis of Compound J6

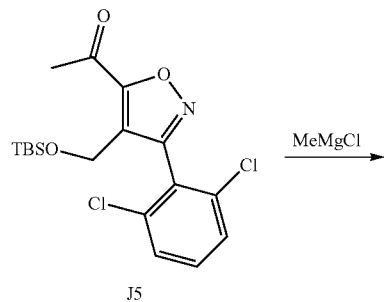

J5

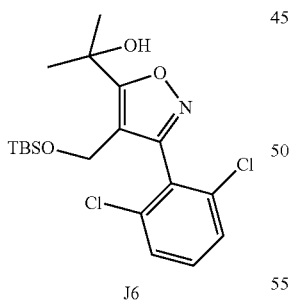

J6

To the solution of compound J5 (1.6 g, 4 mmol) in 40 mL of anhydrous THF was added MeMgCl (3 M, 3.2 mL, 9.6 mmol) for 30 min at −30° C. under N₂ atmosphere. The solution was stirred at −30° C.~−20° C. for 3 h. 30 mL of aq. NH₄Cl solution was added for quench. The water layer was extracted with DCM twice. The combined organic phases were dried over Na₂SO₄, filtered, concentrated reduced pressure and purified by flash chromatography on silica gel (eluent: PE/EA=30/1) to give 1.2 g of compound J6 as a colorless oil (Yield: 72.2%).

Synthesis of Compound J7

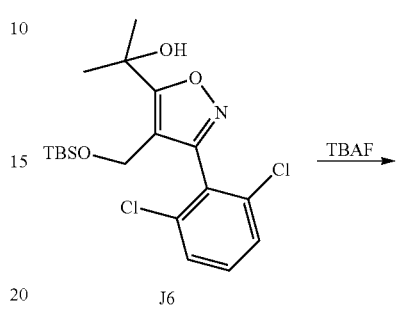

J6

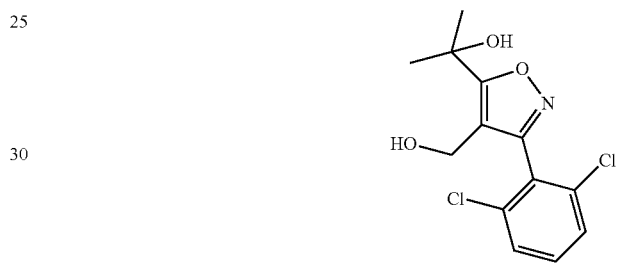

J7

To the solution of J6 (1.2 g, 2.9 mmol) in 40 mL of anhydrous THF was added TBAF (1 M, 2.9 ml, 2.9 mmol) for 30 min at 0° C. under N₂ atmosphere. The reaction mixture was stirred at −5° C.~0° C. for 3 h. TLC indicated the reaction was completed. 30 mL of aq. NH₄Cl solution was added for quench. The water layer was extracted with DCM twice. The combined organic layers were dried over Na₂SO₄, filtered, concentrated and purified by flash chromatography on silica gel (eluent: PE/EA=10/1) to give 500 mg of compound J7 (Yield: 57%).

Synthesis of Compound J8

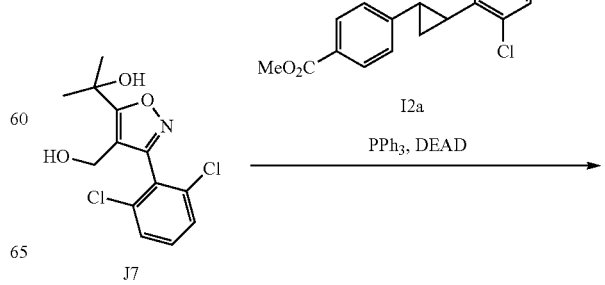

J7

135

-continued

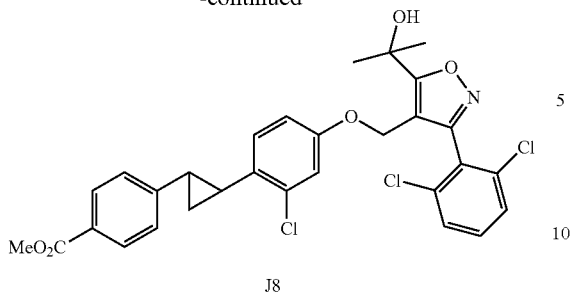

J8

To the mixture of compound J7 (500 mg, 1.65 mmol), compound I2a (500 mg, 1.65 mmol) and Ph₃P (875 mg, 3.7 mmol) in dry 50 ml THF was added dropwise DEAD (675 mg, 3.7 mmol) at 0° C. under N₂ atmosphere, and the solution was stirred overnight at room temperature. Then 10 ml MeOH was added slowly. The solution was evaporated out, and the residue was purified by flash column chromatography on silica gel (eluent: PE/EA=5/1) to give 600 mg of compound J8 as a solid (Yield: 62%).

Synthesis of Example 17

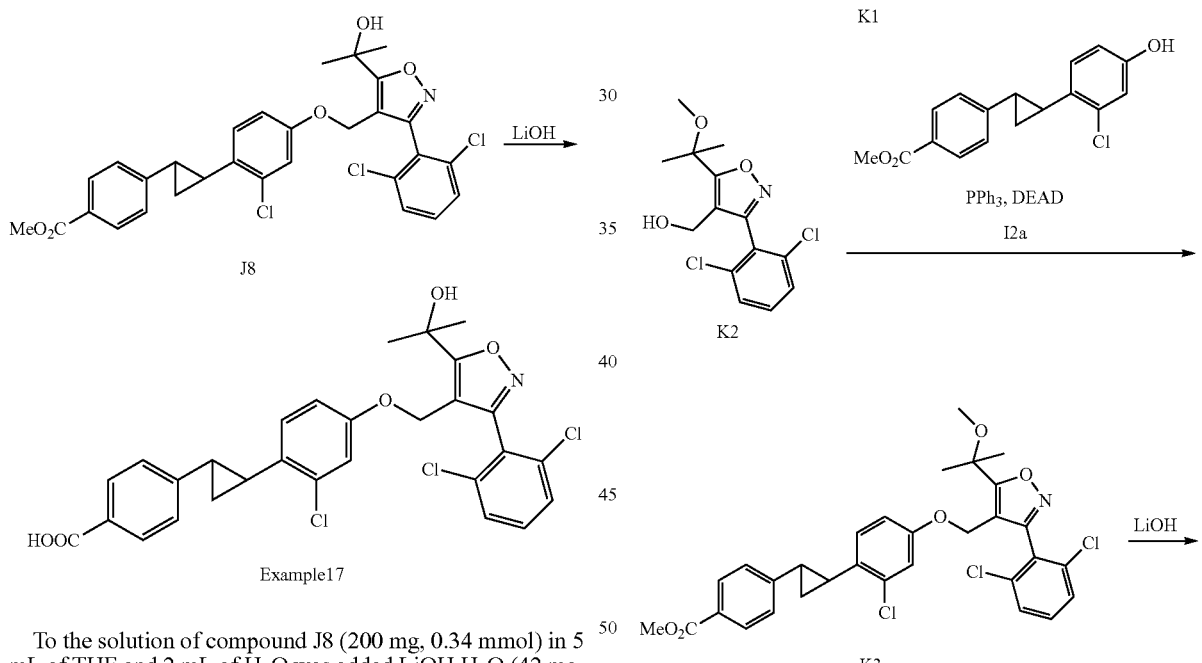

J8

Example 17

To the solution of compound J8 (200 mg, 0.34 mmol) in 5 mL of THF and 2 mL of H₂O was added LiOH.H₂O (42 mg, 1.0 mmol), and then the mixture was stirred overnight at room temperature. Concentrated and diluted with H₂O. 1N aq. HCl solution was added to adjust pH to 5, which was extracted with DCM. The organic layer was washed with brine, dried over Na₂SO₄, filtered, concentrated and purified by flash chromatography on silica gel (eluent: PE/EA=2/1) to give 50 mg of Example 17 (4-(2-(2-chloro-4-((3-(2,6-dichlorophenyl)-5-(2-hydroxypropan-2-yl)isoxazol-4-yl)methoxy)phenyl)cyclopropyl)benzoic acid) as a white solid (Yield: 24%).

$^1$H NMR (DMSO, 400 MHz) δ: 1.47-1.61 (m, 8H), 2.09-2.12 (m, 1H), 2.29-2.34 (m, 1H), 5.04 (s, 2H), 5.98 (s, 1H), 6.64-6.66 (m, 1H), 6.81-6.82 (m, 1H), 7.06-7.08 (m, 1H) 7.29-7.32 (m, 2H), 7.53-7.57 (m, 1H), 7.61-7.63 (m, 2H), 7.84-7.86 (m, 2H), 12.80 (s, 1H). LCMS (mobile phase: 30%-95% Acetonitrile-Water) purity is >95%, Rt=3.11 min; MS Calcd.: 571; MS Found: 572 (M+1).

136

Scheme 11

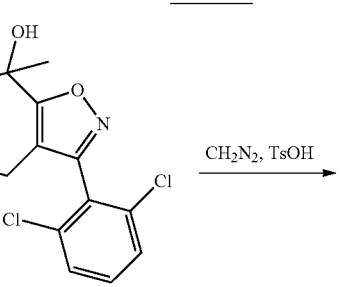

J6

K1

K2

K3

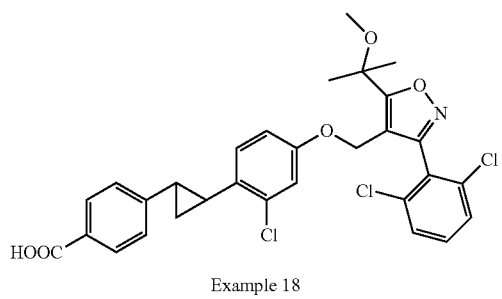

Example 18

Synthesis of Compound K1

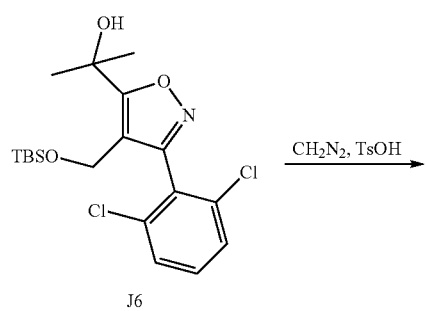

To the solution of compound J6 (600 mg, 1.45 mmol) and TsOH.H$_2$O (6 mg, 0.034 mmol) in 20 mL of THF was added CH$_2$N$_2$ (5M, 14.5 mmol in Et$_2$O) at 0° C., and then the mixture was stirred overnight at room temperature. The organic layer was washed with brine, dried over Na$_2$SO$_4$, filtered, concentrated and purified by flash chromatography on silica gel (eluent: PE/EA=10/1) to give 300 mg of compound K1 as a yellow oil (Yield: 50%).

Synthesis of Compound K2

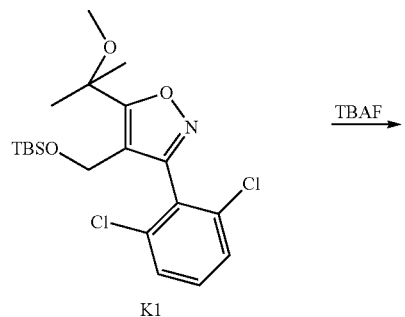

To the solution of compound K1 (300 mg, 0.7 mmol) in 40 mL of anhydrous THF was added TBAF (1 M, 0.7 ml, 0.7 mmol) for 30 min at 0° C. under N$_2$ atmosphere. The reaction mixture was stirred at −5° C.~0° C. for 3 h. TLC indicated the reaction was completed. 30 mL of aq. NH$_4$Cl solution was added for quench. The water layer was extracted with DCM twice. The combined organic layers were dried over Na$_2$SO$_4$, filtered, concentrated under reduced pressure and purified by flash chromatography on silica gel (eluent: PE/EA=2/1) to give 150 mg of compound K2 as a colorless oil (Yield: 68%).

Synthesis of Compound K3

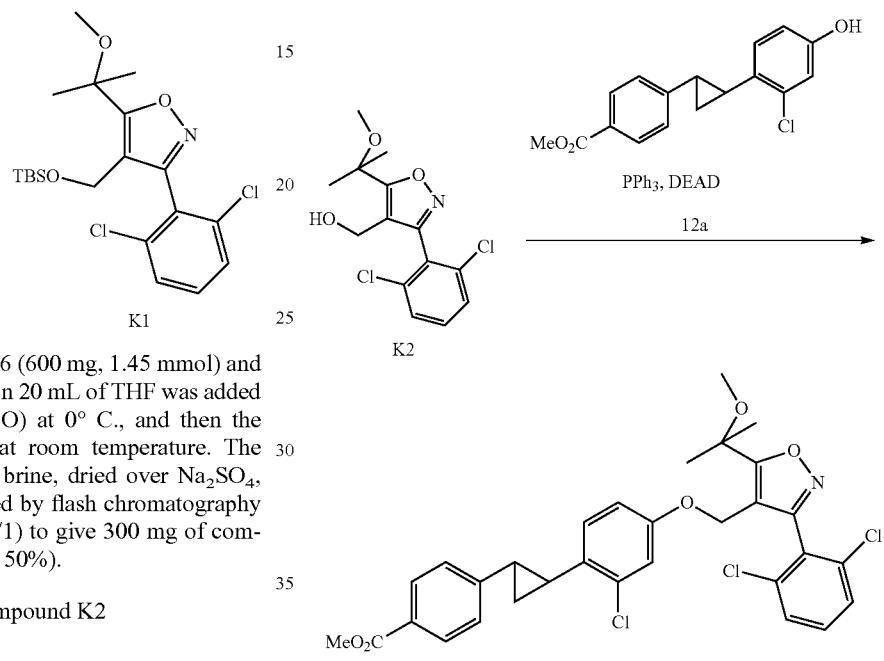

To the mixture of compound K2 (150 mg, 0.47 mmol), I2a (142 mg, 0.47 mmol) and Ph$_3$P (247 mg, 0.94 mmol) in dry 30 mL of anhydrous THF was added dropwise DEAD (172 mg, 0.94 mmol) at 0° C. under N$_2$ atmosphere, and the solution was stirred overnight at room temperature. Then 5 mL of MeOH was added slowly. The solution was concentrated, and the residue was purified by flash column chromatography on silica gel (eluent: PE/EA=5/1) to give 150 mg of compound K3 as a solid (Yield: 53%).

Synthesis of Example 18

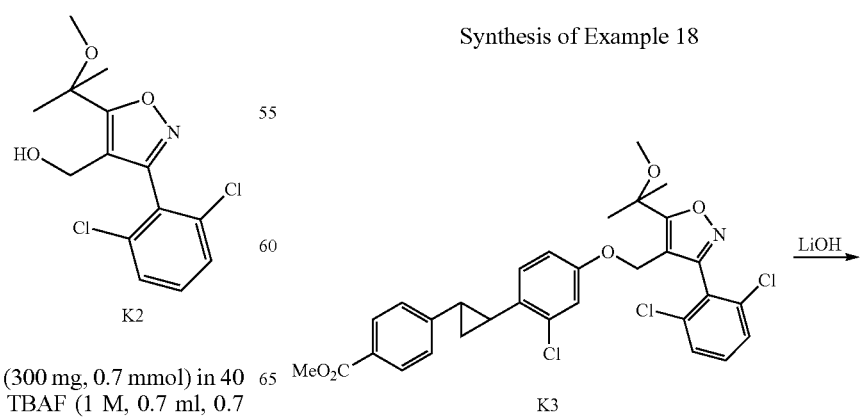

-continued

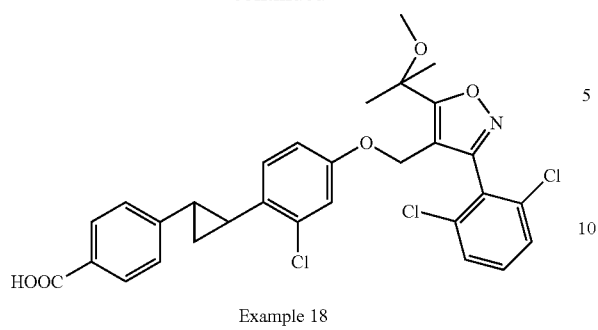

Example 18

To the solution of compound K3 (150 mg, 0.25 mmol) in 5 mL of THF and 2 mL of H$_2$O was added LiOH.H$_2$O (42 mg, 1.0 mmol), and then the mixture was stirred overnight at room temperature. Concentrated and diluted with H$_2$O. 1N aq. HCl solution was added to adjust PH to 5, which was extracted with DCM. The organic layer was washed with brine, dried over Na$_2$SO$_4$, filtered, concentrated and purified by flash chromatography on silica gel (eluent: PE/EA=2/1) to give 45 mg of Example 18 4-(2-(2-chloro-4-((3-(2,6-dichlorophenyl)-5-(2-methoxypropan-2-yl)isoxazol-4-yl)methoxy)phenyl)cyclopropyl)benzoic acid (Yield: 30%).

$^1$HNMR (CD3OD, 400 MHz) δ: 1.48-1.54 (m, 2H), 1.67 (s, 6H), 2.06-2.08 (m, 1H), 2.37-2.39 (m, 1H), 3.29 (s, 3H), 4.97 (s, 2H), 6.65-6.67 (m, 1H), 6.75-6.76 (m, 1H), 7.03-7.05 (m, 1H) 7.28-7.30 (m, 2H), 7.47-7.54 (m, 3H), 7.95-7.97 (m, 2H);

LCMS (mobile phase: 40%-95% Acetonitrile-Water) purity is >95%, Rt=3.27 min;

MS Calcd.: 587; MS Found: 586 (M−1).

Scheme 12

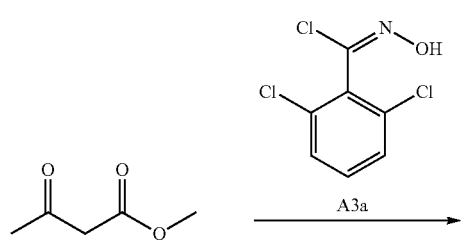

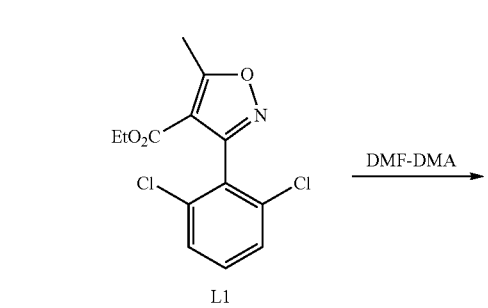

-continued

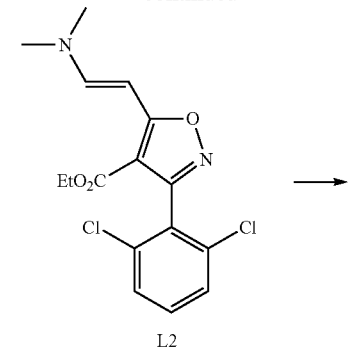

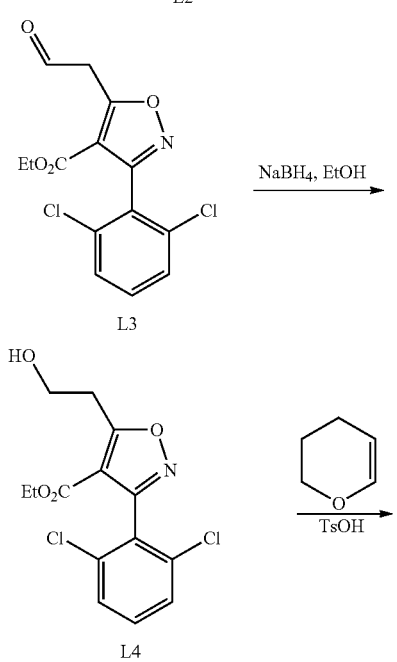

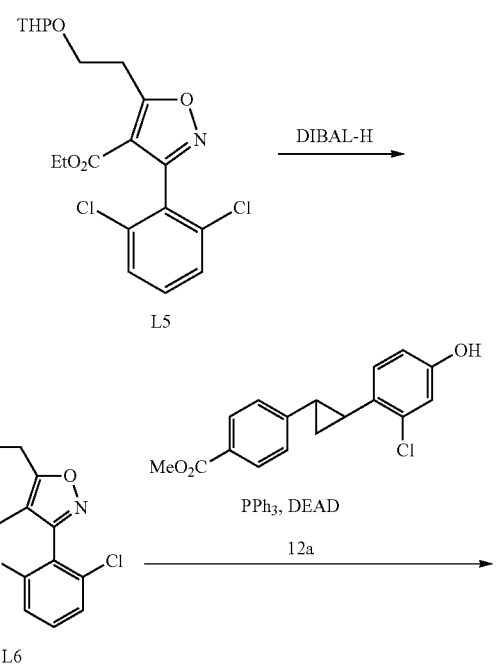

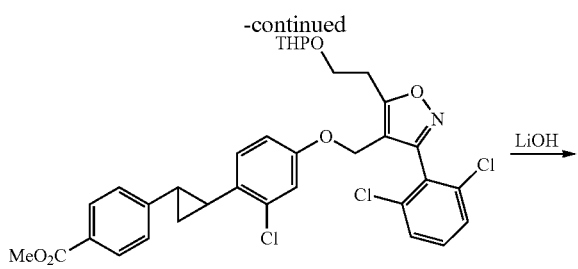

L7

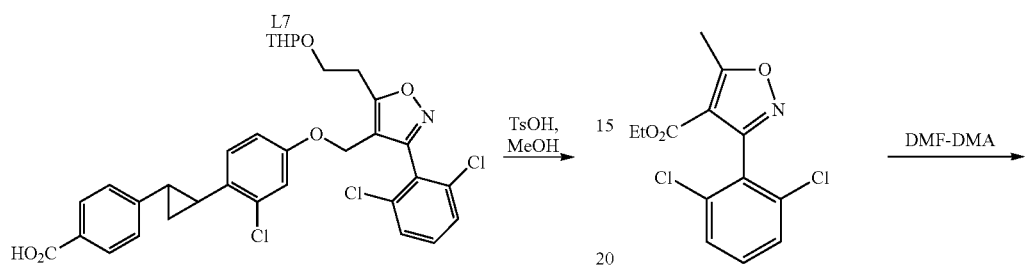

Example 19

Synthesis of Compound L1

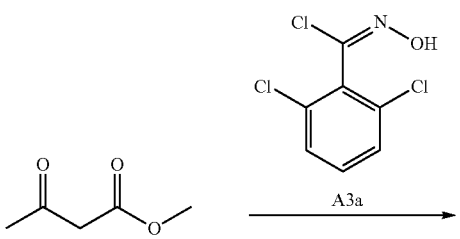

To the solution of methyl 3-oxobutanoate (8.9 g, 40 mmol, 1.0 eq) and compound A3a (4.64 g, 40 mmol, 1.0 eq) in 70 mL of THF was added MeONa (2.16 g, 40 mmol, 1.0 eq), and then the mixture was stirred at room temperature for 16 h. The reaction was washed with 1N HCl solution, extracted with EtOAc, dried over Na$_2$SO$_4$, concentrated under reduced pressure and purified by flash chromatography on silica gel (eluent: PE/EA=10/1) to give 4.3 g of compound L1 as a yellow solid (Yield: 38%).

Synthesis of Compound L2

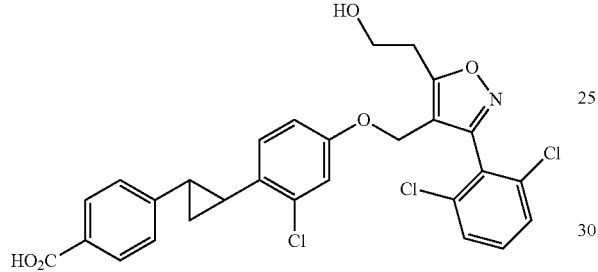

The solution of compound L1 (4.3 g, 15 mmol, 1 eq) in 60 mL of DMF and 60 mL of DMF-DMA was heated at 110° C. for 3 h. The reaction was concentrated under reduced pressure and purified by flash chromatography on silica gel (PE/EA=10/1) to give 3.86 g of compound L2 as a yellow solid (Yield: 76%).

Synthesis of Compound L3

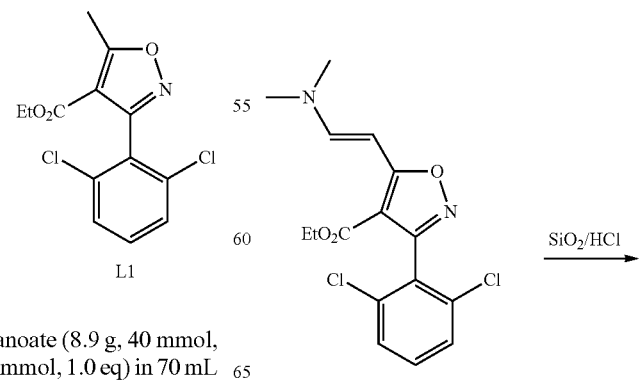

-continued

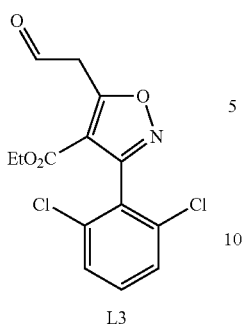

L3

To the solution of compound L2 (2.16 g, 6.3 mmol, 1.0 eq) and SiO$_2$ (in 22 mL of water) in 54 mL of THF, then the 44 mL of conc. HCl solution was added dropwise at 40° C. for 1 hour. The reaction was filtered, extracted with EtOAc, washed with water, dried over Na$_2$SO$_4$, concentrated under reduced pressure to give 1.99 g of compound L3 as a yellow oil (Yield: 99%).

Synthesis of Compound L4

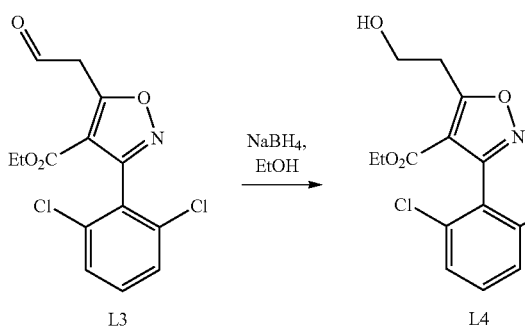

To the solution of compound L3 (1.99 g, 6.4 mmol, 1.0 eq) in 20 mL of EtOH was added NaBH$_4$ (266 mg, 7 mmol, 1.1 eq) at 0° C. for 20 min. Then aq. HCl solution (1 mol/L) was added until the color of reaction disappeared. The reaction was washed with water, extracted with EtOAc, dried over Na$_2$SO$_4$, concentrated under reduced pressure to give 2.01 g of compound L4 as a yellow solid (Yield: 99%).

Synthesis of Compound L5

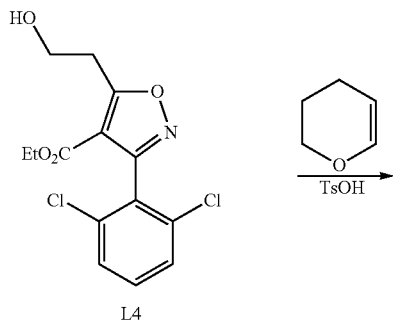

-continued

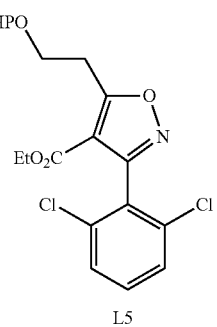

L5

To the solution of compound L4 (2.0 g, 6.3 mmol, 1.0 eq) and p-toluene sulfonic acid (16 mg, 0.06 mmol, 0.01 eq) in 80 mL of anhydrous DCM was added 3,4-dihydro-2H-pyran (800 mg, 9.5 mmol, 1.5 eq) dropwise under N$_2$ atmosphere, and the solution was stirred overnight at room temperature. The reaction mixture was washed with 40 mL of aq. NaHCO$_3$ solution twice, and the aqueous layer was extracted three times with 100 mL of DCM. The combined organic layers were dried over Na$_2$SO$_4$, filtered, concentrated and purified by flash column chromatography on silica gel (eluent: PE/EA=10/1) to give 1.0 g of compound L5 as an oil (Yield: 40%).

Synthesis of Compound L6

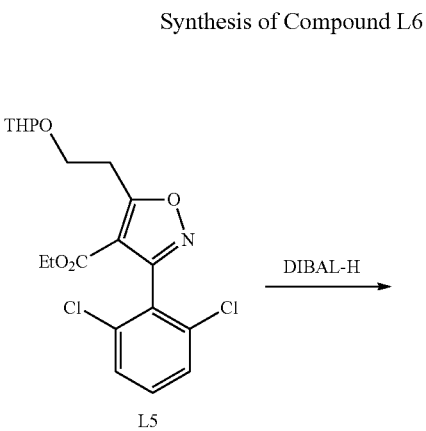

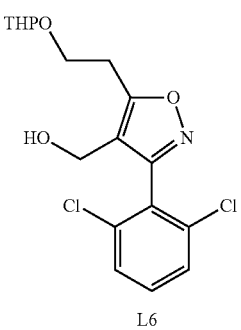

L6

To the solution of L5 (1.0 g, 2.5 mmol, 1.00 eq) in 40 mL of anhydrous THF was added DIBAL-H (1 M, 10 mL, 3.75 eq) for 30 min at −30° C. under N$_2$ atmosphere. The reaction mixture was stirred at −5° C.~0° C. for 3 h. TLC indicated the reaction was completed. 30 mL of aq. NH$_4$Cl solution was added for quench. The water layer was extracted with DCM twice. The combined organic layers were dried over Na$_2$SO$_4$, filtered, concentrated and purified by flash chromatography on silica gel (eluent: PE/EA=5/1) to give 800 mg of compound L6 as a pale-yellow oil (Yield: 86%).

Synthesis of Compound L7

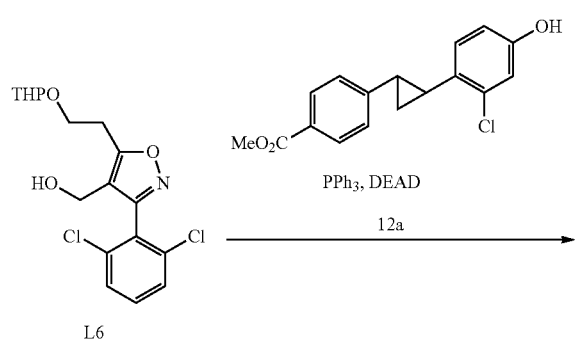

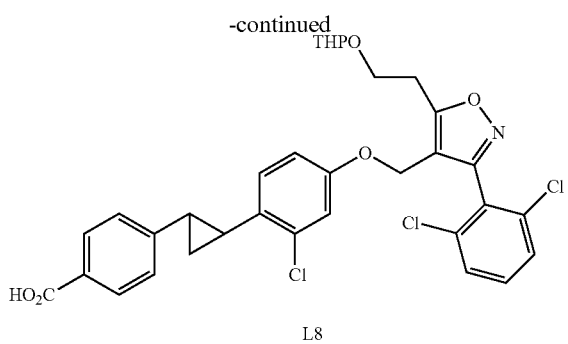

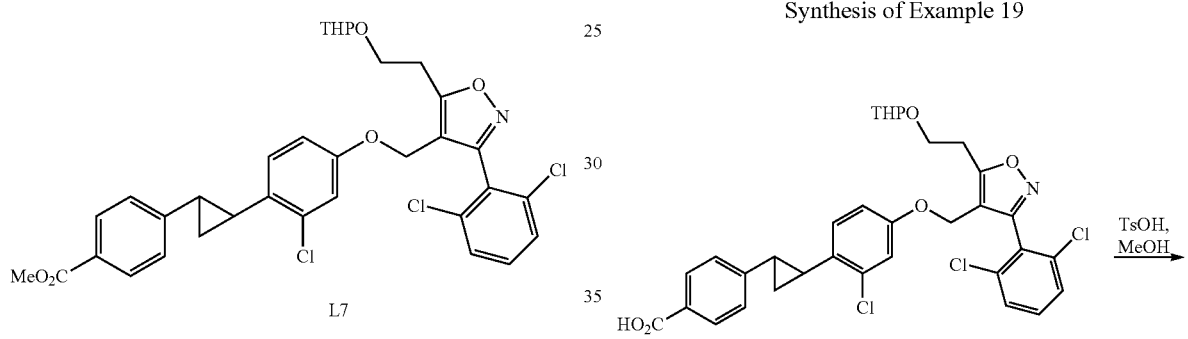

To the mixture of compound L6 (372 mg, 1 mmol, 1.0 eq), I2a (302 mg, 1 mmol, 1.0 eq, prepared according procedure for B13) and Ph₃P (524 mg, 2 mmol, 2.0 eq) in dry 20 mL of anhydrous THF was added dropwise DEAD (348 mg, 2 mmol, 2.0 eq) at 0° C. under N₂ atmosphere, and the solution was stirred overnight at room temperature. Then 10 mL of MeOH was added slowly. The solution was evaporated out, and the residue was purified by flash column chromatography on silica gel (eluent: PE/EA=10/1) to give 170 mg of compound L7 as a solid (Yield: 26%).

Synthesis of Compound L8

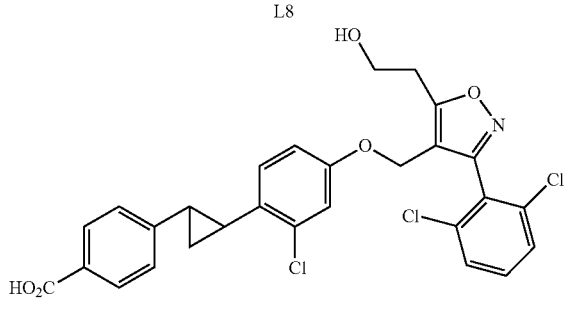

To the solution of compound L7 (170 mg, 026 mmol, 1.00 eq) in 5 mL of THF and 1 mL of H₂O was added LiOH.H₂O (110 mg, 2.6 mmol, 10 eq), and then the mixture was stirred overnight at room temperature. Concentrated and diluted with H₂O. 1N aq. HCl solution was added to adjust pH to 5, which was extracted with DCM. The organic layer was washed with brine, dried over Na₂SO₄, filtered, concentrated to give 150 mg of compound L8 as a white solid (Yield: 90%).

Synthesis of Example 19

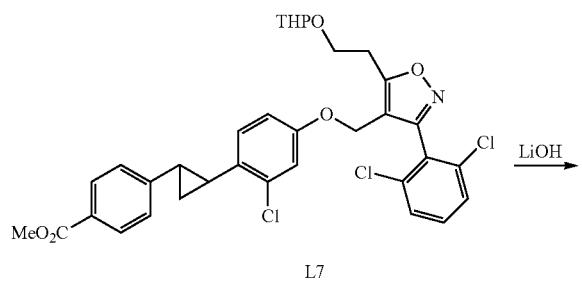

To the solution of compound L8 (150 mg, 0.23 mmol, 1.00 eq) in 5 mL of MeOH was added TsOH.H₂O (65 mg, 0.34 mmol, 1.5 eq), and then the mixture was stirred overnight at room temperature. Concentrated and diluted with H₂O, which was extracted with DCM. The organic layer was washed with brine, dried over Na₂SO₄, filtered, concentrated and purified by flash chromatography on silica gel (eluent: PE/EA=2/1) to give 50 mg of Example 19 (4-(2-(2-chloro-4-((3-(2,6-dichlorophenyl)-5-(2-hydroxyethyl)isoxazol-4-yl) methoxy)phenyl)-cyclopropyl)benzoic acid) as a white solid (Yield: 34%).
$^1$HNMR (DMSO, 400 MHz) δ: 1.48-1.55 (m, 2H), 2.01-2.11 (m, 1H), 2.31-2.32 (m, 1H), 3.09-3.12 (m, 2H), 3.74-3.78 (m, 2H), 4.87 (s, 2H), 4.99-5.01 (m, 1H), 6.67-6.70 (m, 1H), 6.84-6.85 (m, 1H), 7.07-7.09 (m, 1H) 7.30-7.32 (m, 2H), 7.55-7.64 (m, 3H), 7.85-7.87 (m, 2H);

LCMS (mobile phase: 10%-95% Acetonitrile-Water) purity is >95%, Rt=3.19 min;
MS Calcd.: 557; MS Found: 556 (M−1).

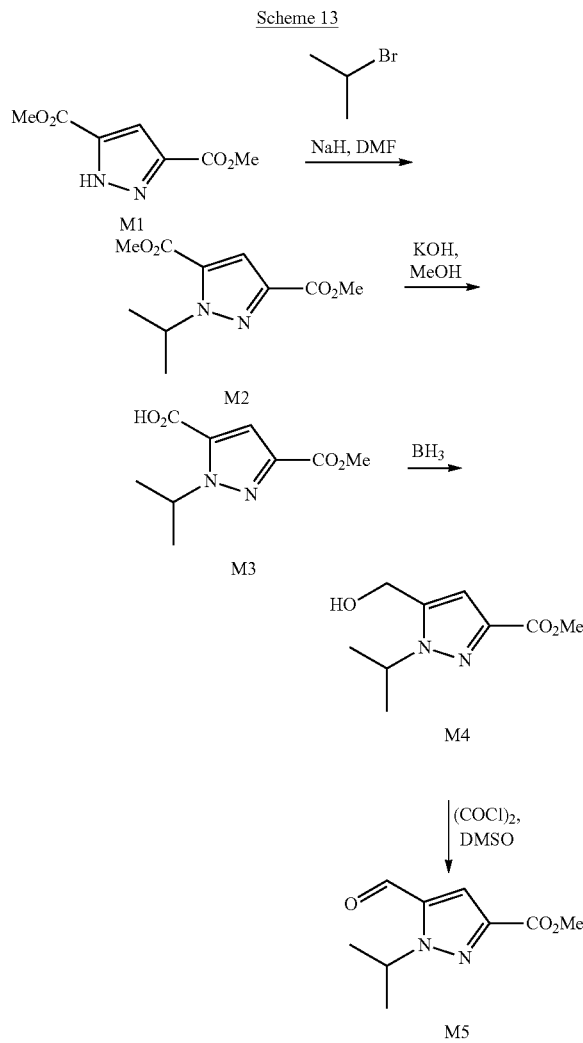

Scheme 13

M1, M2, M3, M4, M5

Synthesis of Compound M2

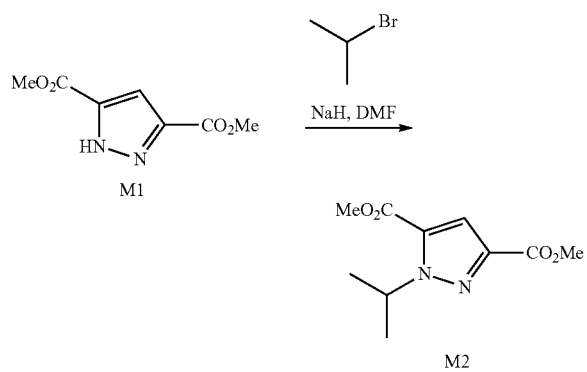

To the solution of compound M1 (5 g, 27.2 mmol) in 30 mL of DMF was added 60% NaH (1.20 g, 30 mmol) at 0° C., and the solution was stirring for 0.5 hour. Then a solution of 2-iodopropane (5.1 g, 30 mmol) in 10 mL of DMF was added dropwise at 0° C., and the mixture was stirred for 2.5 h at room temperature. Water was added to quench the reaction, and the solution was extracted with EtOAc three times. The combined organic layers were washed with water three times and brine twice consecutively, dried over $Na_2SO_4$, filtered, concentrated under reduced pressure and purified by flash chromatography on silica gel (eluent: PE/EA=5/1) to give 2 g of compound M2 (Yield: 18%).

Synthesis of Compound M3

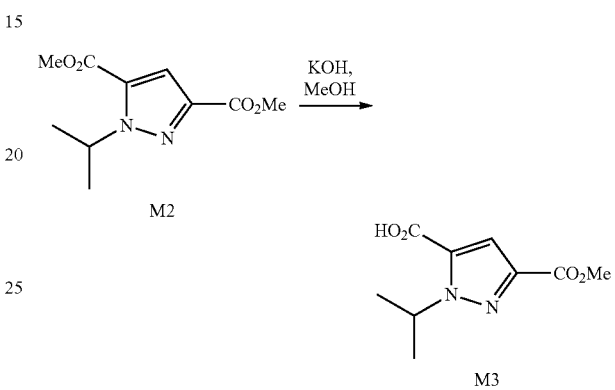

To the solution of compound M2 (2 g, 8.85 mmol) in 20 mL of MeOH was added a solution of KOH in MeOH (10 mL of a 2.2 M solution), and the solution was stirred at 20° C. for 24 h. After removal of the solvent under vacuum at low temperature, the residue was dissolved in 20 mL of water and the solution was neutralized with 1 N aqueous HCl (10 mL, 10 mmol). After being stirred for 20 h at 0° C., the formed solid was filtered, and the cake was washed with water to give 1.16 g of compound M3 as a white solid (Yield: 62%).

Synthesis of Compound M4

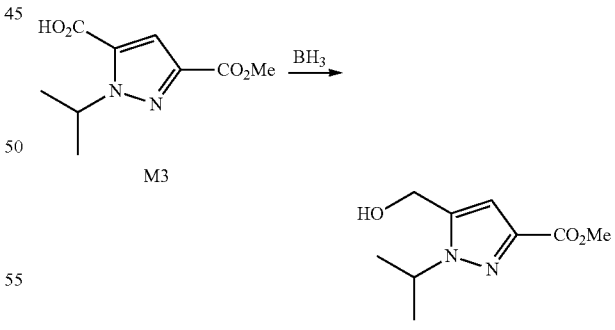

To a stirred solution of compound M3 (1 g, 4.8 mmol) in 10 mL of anhydrous THF was added $BH_3 \cdot Me_2S$ (1 mL, 2M in THF) at 0° C. under $N_2$ atmosphere, and this solution was stirred at room temperature overnight, water was added to quench the reaction, and the resulting solution was extracted with EtOAc twice. The combined organic layers were washed with brine, dried over $Na_2SO_4$, filtered, concentrated under reduced pressure and purified by flash chromatography on silica gel (eluent: PE/EA=3/1) to give 578 mg of compound M4 as a colorless oil (Yield: 70%).

Synthesis of Intermediate M5

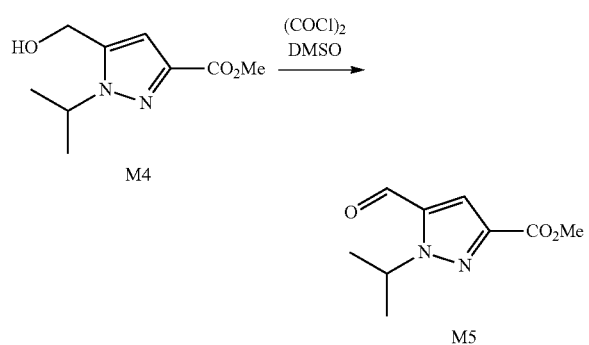

To a stirred solution of oxalyl chloride (0.4 mL, 5.28 mmol) in 5 mL of anhydrous DCM was added a solution of DMSO (0.38 mL, 5.28 mmol) in 1 mL of anhydrous DCM at −30° C. After being stirred for 20 min, the solution of compound M4 (578 mg, 2.92 mmol) in 2 mL of anhydrous DCM was added in portions at −30° C. The solution was stirred for another 1 hour, and then $Et_3N$ (1.4 mL, 10.2 mmol) was added at −30° C. After stirring overnight at room temperature, 20 mL of DCM was added to dilute the reaction mixture, washed with citric acid and then brine. The solution was dried over $Na_2SO_4$, filtered, concentrated under reduced pressure and purified by flash chromatography on silica gel (eluent: PE/EA=5/1) to give 400 mg of M5 as a white solid (Yield: 69.4%).

Further Examples

| Preparative Example | Structure | Prepared according preparative Example | MW (g/mol) | Measured m/z of [M + H]+ |
|---|---|---|---|---|
| 20 | 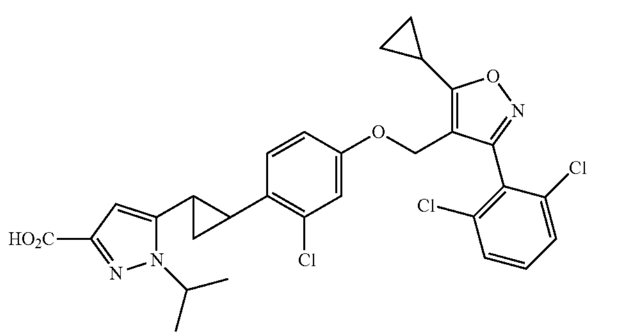 [SMILES: CC(C)n1nc(C(=O)O)cc1C1CC1c1ccc(OCc2c(-c3c(Cl)cccc3Cl)noc2C2CC2)cc1Cl] | Prepared from M5, according Ex. 11 with final ester hydolysis | 586.89 | 586 |
| 21 | 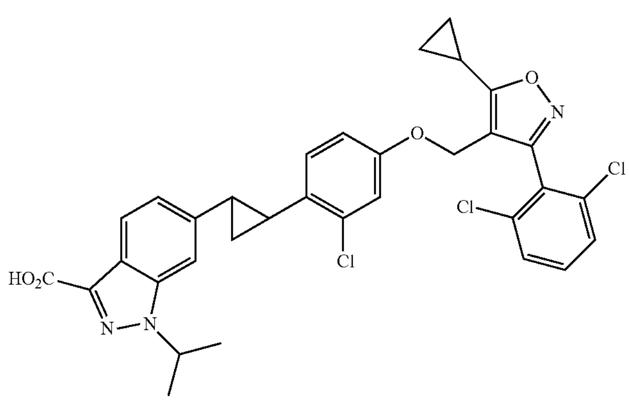 [SMILES: CC(C)n1nc(C(=O)O)c2ccc(C3CC3c3ccc(OCc4c(-c5c(Cl)cccc5Cl)noc4C4CC4)cc3Cl)cc21] | 13 | 636.95 | 636 |

-continued
| Preparative Example | Structure | Prepared according preparative Example | MW (g/mol) | Measured m/z of [M + H]+ |
|---|---|---|---|---|
| 22 | 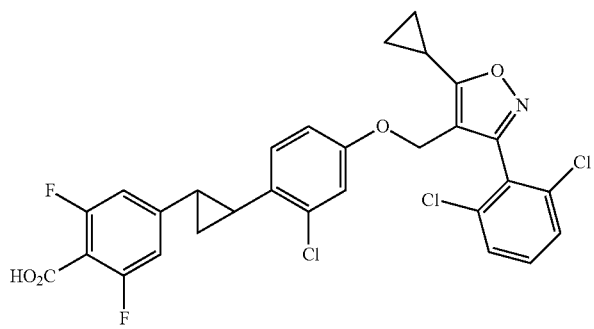 [SMILES: O=C(O)c1c(F)cc(C2CC2c2ccc(OCc3c(-c4c(Cl)cccc4Cl)noc3C3CC3)cc2Cl)cc1F] | 12 | 590.83 | 590 |
| 23 | 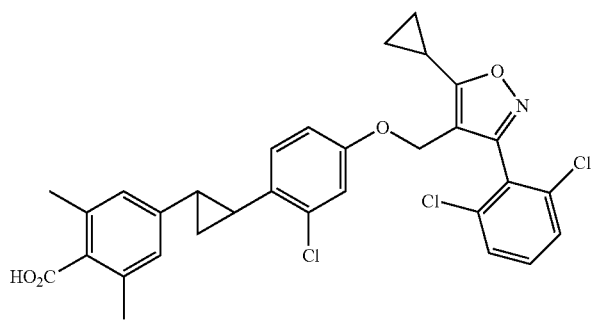 [SMILES: Cc1cc(C2CC2c2ccc(OCc3c(-c4c(Cl)cccc4Cl)noc3C3CC3)cc2Cl)cc(C)c1C(=O)O] | 12 | 582.90 | 582 |
| 24 | 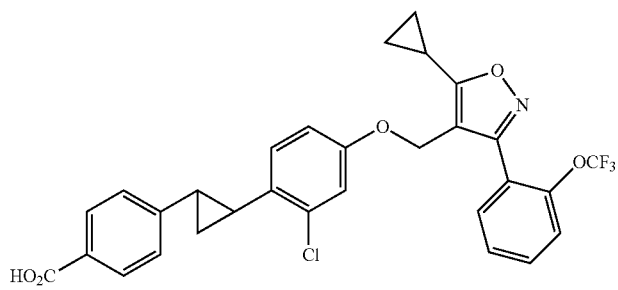 [SMILES: O=C(O)c1ccc(C2CC2c2ccc(OCc3c(-c4ccccc4OC(F)(F)F)noc3C3CC3)cc2Cl)cc1] | 12 | 569.99 | 570 |
| 25 | 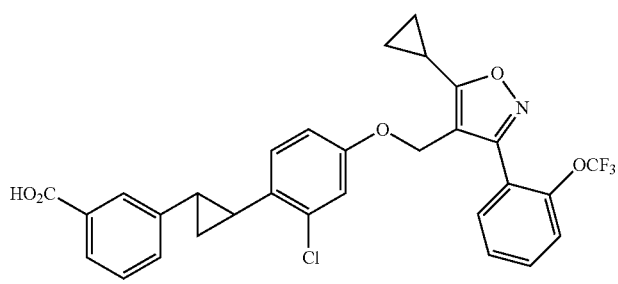 [SMILES: O=C(O)c1cccc(C2CC2c2ccc(OCc3c(-c4ccccc4OC(F)(F)F)noc3C3CC3)cc2Cl)c1] | 12 | 569.96 | 570 |

-continued

| Preparative Example | Structure | Prepared according preparative Example | MW (g/mol) | Measured m/z of [M + H]+ |
|---|---|---|---|---|
| 26 | (+)-enantiomer | 15, from 12b | 661.98 | 659, [M − H]− |
| 27 | (−)-enantiomer | 15, from 12c | 661.98 | 659, [M − H]− |
| 28 | 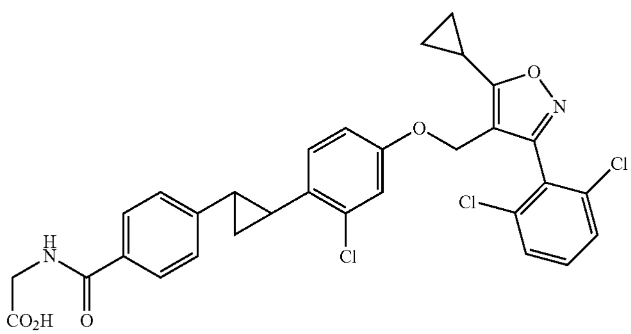 [SMILES: O=C(O)CNC(=O)c1ccc(C2CC2c2ccc(OCc3c(-c4c(Cl)cccc4Cl)noc3C3CC3)cc2Cl)cc1] | 15 | 611.90 | 611 |
| 29 | 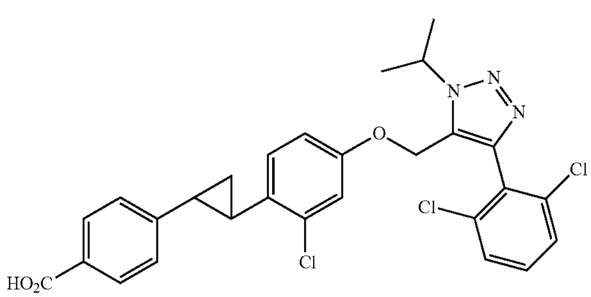 [SMILES: CC(C)n1nnc(-c2c(Cl)cccc2Cl)c1COc1ccc(C2CC2c2ccc(C(=O)O)cc2)c(Cl)c1] | From A6f and I2a according Ex. 1 | 556.87 | 556 |

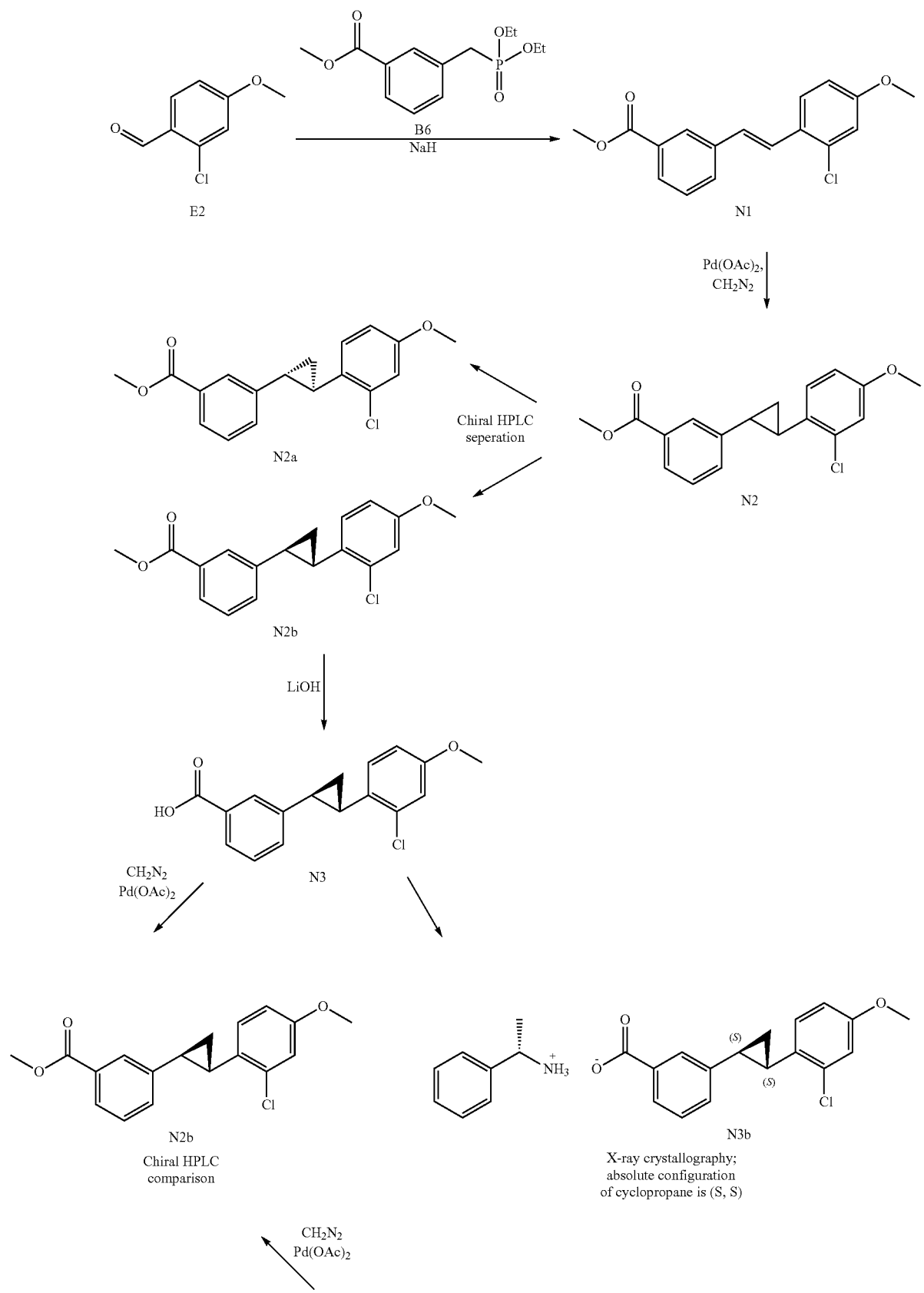
Scheme 14, Elucidation of absolute configuration of example

-continued

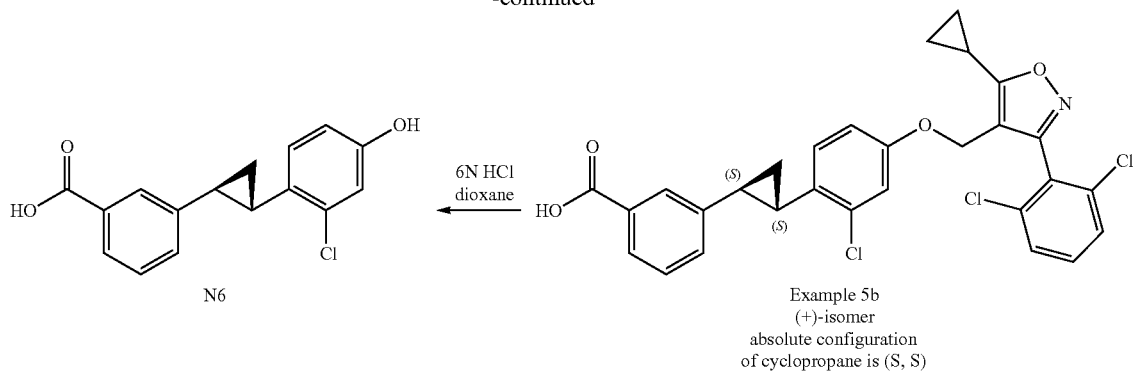

Example 5b
(+)-isomer
absolute configuration
of cyclopropane is (S, S)

Synthesis of Compound N1

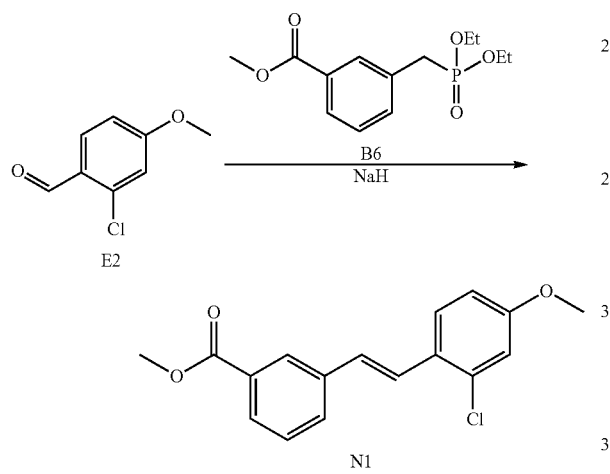

To a solution of compound B6 (14.3 g, 50 mmol) in 70 mL of dry THF was added sodium hydride (2.4 g, 60 mmol) at 0° C. for 30 mins. To this resulting mixture was added the solution of compound E2 (8.5 g, 50 mmol) in 50 mL of dry THF at 0° C., and the solution was stirred at room temperature for 3 h. The mixture was quenched by sat. NH$_4$Cl solution and extracted with EtOAc. The organic layer was washed with brine, dried over Na$_2$SO$_4$, filtered, concentrated and purified by flash chromatography on silica gel (eluent: PE/EA=50/1) to give 7.7 g of compound N1 as a white solid (Yield: 51%).

Synthesis of Compound N2

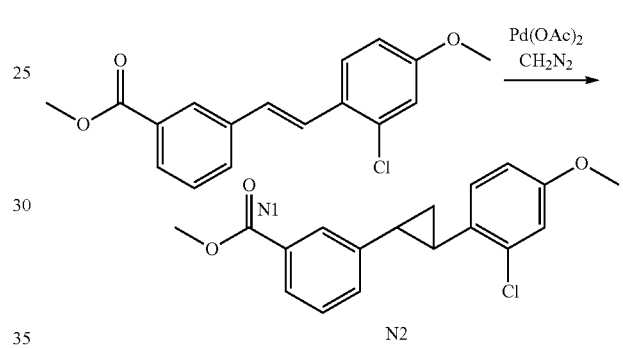

To a solution of compound N1 (7.7 g, 25.5 mmol) and Pd(OAc)$_2$ (1 g) in 50 mL of anhydrous THF was added a solution of CH$_2$N$_2$ in Et$_2$O (25 mL, ~100 mmol) at −50° C. under N$_2$ atmosphere. Then the solution was warmed to room temperature slowly, and stirred for another 4 h. Both of TLC and LCMS indicated that the reaction was ok. Concentrated and purified by flash chromatography on silica gel (eluent: PE/EA=50/1) to give 5.1 g of compound N2 as an oil (Yield: 63.3%).

Chiral HPLC Separation

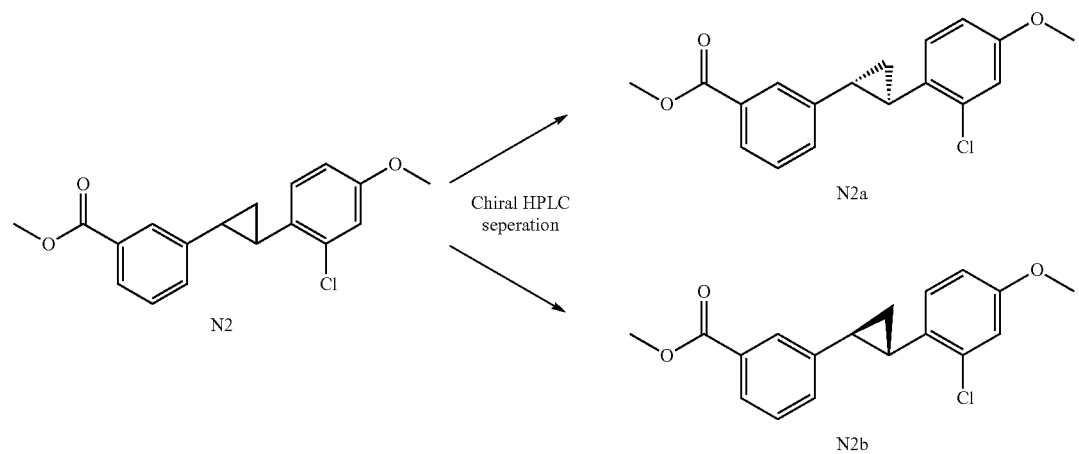

1.7 g of compound N2 (racemic) was separated by preparative chiral HPLC with a chiral column (column: CHIRALPAK IA; Column size: 0.46 cm I.D.×15 cm L; Mobile phase: Hexane/Isopropyl alcohol=80/20 (v/v); Flow rate: 1.0 mL/min; Wave length: UV 254 nm; HPLC equipment: Shimadzu LC 20 with UV detector SPD-20A) to give 534 mg of compound N2a (Rt=5.143 min, ee %: >99%) and 577 mg of compound N2b (Rt=6.325 min, ee %: >99%).

Synthesis of Compound N3

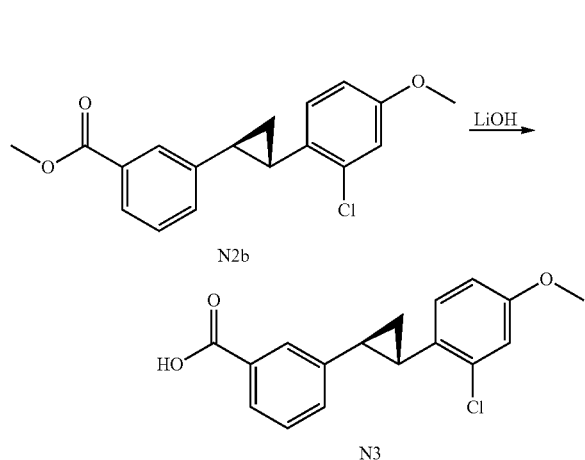

To a solution of compound N2b (500 mg, 1.58 mmol) in 10 mL of THF and 3 mL of H$_2$O was added LiOH.H$_2$O (664 mg, 15.8 mmol), and then the mixture was stirred at 40° C. for 4 h. Concentrated, diluted with 5 mL of H$_2$O, and 1N aq. HCl solution was added to acidify the mixture to pH=4. EtOAc was added to extract twice, and the combined organic phases were dried over Na$_2$SO$_4$, filtered, concentrated under reduced pressure and purified by flash chromatography on silica gel (eluent: PE/EA=1/3) to give 430 mg of compound N3 as a white solid (Yield: 90.1%).

Synthesis of Salt N3b

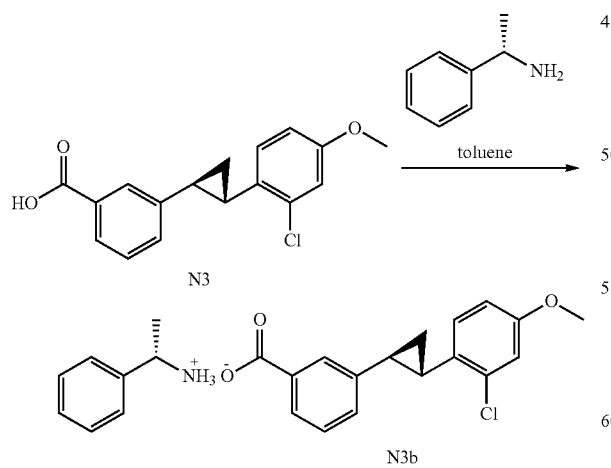

The solution of compound N3 (200 mg, 0.66 mmol) and (S)-1-phenylethylamine (80 mg, 0.66 mmol) in 5 mL of dry toluene was refluxed overnight. Cooled to room temperature and the formed solid was collected. The solid was washed by 1 mL of cooled toluene, dried in vacuo to give 137 mg of salt N3b with >99% HPLC and NMR purity.

$^1$HNMR (400 MHz, DMSO-d6) δ: 1.37 (d, J=6.4 Hz, 3H), 1.47 (m, 2H), 2.15 (m, 1H), 2.30 (m, 1H), 3.77 (s, 3H), 4.17 (m, 1H), 6.90 (dd, J=2.4 Hz, 8.8 Hz, 1H), 7.04 (d, J=2.4 Hz, 1H), 7.16 (d, J=8.8 Hz, 1H), 7.26 (t, J=7.2 Hz, 1H), 7.33 (m, 4H), 7.44 (d, J=7.2 Hz, 2H), 7.73 (m, 2H).

Crystal Growth and Absolute Configuration Determination of N3b

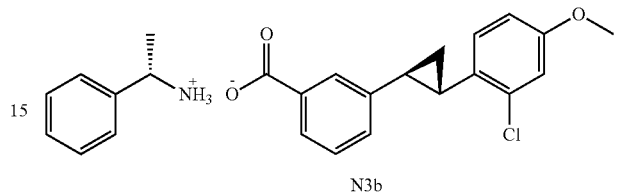

Salt N3b (100 mg) was dissolved in 30 mL of anhydrous EtOH followed by 1.8 mL of n-hexane (hexane was added until solution became slightly cloudy). Solution was filtered and put aside on the shelf in the dry box (~20° C.). After 3 days, colorless crystals formed.

According to the examination under low power (10×) magnification, a crystal was chosen.

| | |
|---|---|
| Crystal size | 0.35 × 0.15 × 0.14 mm |
| Unit cell parameters with standard deviation | a = 11.898(5) Å α = 90° |
| | b = 6.801(3) Å β = 92.725(5)° |
| | c = 13.836(5) Å γ = 90° |
| Unit cell volume | 1118.3(7) Å$^3$ |
| Space group symbol | P21 |
| Z value | 2 |
| Calculated density | 1.259 g/cm$^3$ |
| Temperature in study (in K) | 293(2) K |
| R-factor | R$_1$ = 0.0992 wR$_2$ = 0.1918 |

Based on the X-ray crystallographic data from salt N3a, its absolute configuration is (S,S).

Synthesis of Compound N2b from N4

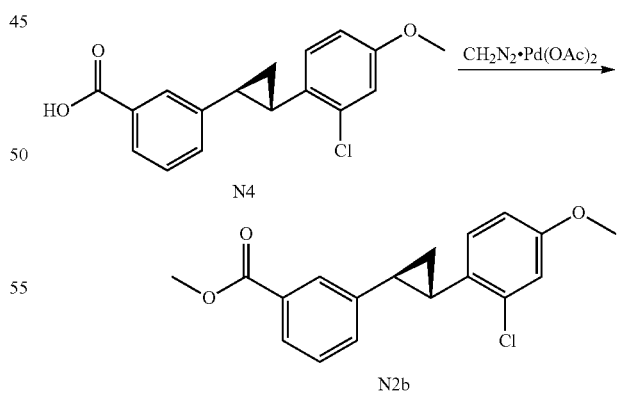

To a solution of crude acid N4 (120 mg, 0.21 mmol) in 5 mL of THF was added a solution of CH$_2$N$_2$ in Et$_2$O (0.7 mL, 2.80 mmol) at −50° C. under N$_2$ atmosphere. Then the solution was warmed to room temperature slowly, and stirred for another 4 h. TLC indicated that the reaction was ok. Concentrated and purified by preparative TLC to give 21 mg of N2b as a white solid (Yield in two steps: 32.3%).

¹HNMR (400 MHz, CDCl₃) δ: 1.47 (m, 2H), 2.12 (m, 1H), 2.40 (m, 1H), 3.82 (s, 3H), 3.95 (s, 3H), 6.80 (dd, J=2.4 Hz, 8.4 Hz, 1H), 6.97 (d, J=2.4 Hz, 1H), 7.06 (d, J=8.4 Hz, 1H), 7.41 (m, 2H), 7.89 (dd, J=2.4 Hz, 6.4 Hz, 2H).

Chiral HPLC analysis (chiral column: CHIRALCEL OD; Column size: 4.6*250 mm; Mobile phase: Hexane/EtOH/AcOH=60/40/0.1 (v/v/v)); Flow rate: 0.8 ml/min): Rt=9.312 min (first eluting enantiomer, compared with racemate).

Synthesis of Compound N5

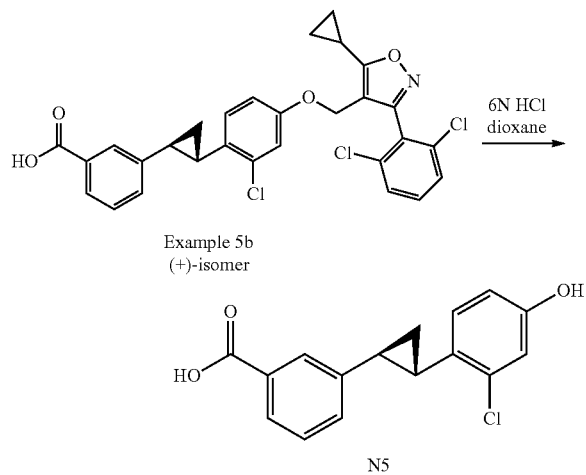

Example 5b
(+)-isomer

N5

A solution of Example 5b ((+)-Isomer) (50 mg, 0.09 mmol) and 6 N HCl solution (5 mL) in 5 mL of dioxane was heated at 85° C. for 4 h, and EtOAc was added to extract. The organic layer was washed by brine, dried over Na₂SO₄, filtered and concentrated under reduced pressure to give 51 mg of crude acid N5 used into the following reaction without further purification.

Synthesis of Compound N2b from N5

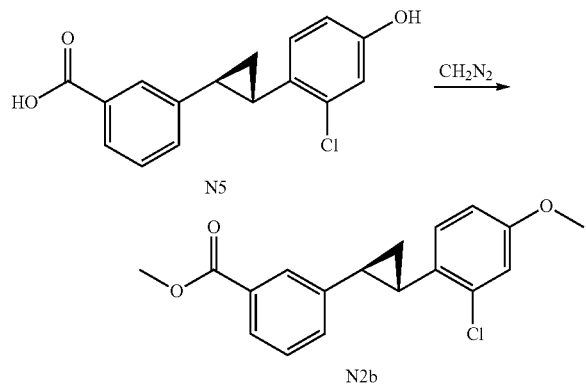

N5

N2b

To a solution of crude acid N5 (51 mg, 0.09 mmol) in 5 mL of THF was added a solution of CH₂N₂ in Et₂O (1 mL, 4.00 mmol) at −50° C. under N₂ atmosphere. Then the solution was warmed to room temperature slowly, and stirred overnight. LCMS indicated that the reaction was ok. Concentrated and purified by prep. TLC to give 23 mg of N2b as a white solid (Yield in two steps: 80.9%).

¹HNMR (400 MHz, CDCl₃) δ: 1.47 (m, 2H), 2.12 (m, 1H), 2.40 (m, 1H), 3.82 (s, 3H), 3.95 (s, 3H), 6.80 (dd, J=2.4 Hz, 8.4 Hz, 1H), 6.97 (d, J=2.4 Hz, 1H), 7.06 (d, J=8.4 Hz, 1H), 7.41 (m, 2H), 7.89 (dd, J=2.4 Hz, 6.4 Hz, 2H).

Chiral HPLC analysis (chiral column: CHIRALCEL OD; Column size: 4.6*250 mm; Mobile phase: Hexane/EtOH/AcOH=60/40/0.1 (v/v/v)); Flow rate: 0.8 ml/min): Rt=9.466 min (first eluting enantiomer, compared with racemate).

Assays

FRET Activity Assay

Determination of a ligand mediated cofactor peptide interaction to quantify ligand binding to the nuclear receptor FXR was performed as follows: Preparation of human FXR alpha ligand binding domain: The human FXRalpha LBD was expressed in *E. coli* strain BL21(DE3) as an N-terminally GST tagged fusion protein. The DNA encoding the FXR ligand binding domain was cloned into vector pDEST15 (Invitrogen). Expression was under control of an IPTG inducible T7 promoter. The amino acid boundaries of the ligand binding domain were amino acids 187-472 of Database entry NM_005123 (RefSeq). Expression and purification of the FXR-LBD: An overnight preculture of a transformed *E. coli* strain was diluted 1:20 in LB-Ampicillin medium and grown at 30° C. to an optical density of OD₆₀₀=0.4-0.6. Gene expression was then induced by addition of 0.5 mM IPTG. Cells were incubated an additional 6 h at 30° C., 180 rpm. Cells were collected by centrifugation (7000×g, 7 min, room temperature). Per liter of original cell culture, cells were resuspended in 10 mL lysis buffer (50 mM Glucose, 50 mM Tris pH 7.9, 1 mM EDTA and 4 mg/mL lysozyme) and left on ice for 30 min. Cells were then subjected to sonication and cell debris removed via centrifugation (22000×g, 30 min, 4° C.). Per 10 mL of supernatant 0.5 mL prewashed Glutathione 4B sepharose slurry (Qiagen) was added and the suspension kept slowly rotating for 1 h at 4° C. Glutathione 4B sepharose beads were pelleted by centrifugation (2000×g, 15 sec, 4° C.) and washed twice in wash buffer (25 mM Tris, 50 mM KCl, 4 mM MgCl₂ and 1M NaCl). The pellet was resuspended in 3 mL elution buffer per liter of original culture (elution buffer: 20 mM Tris, 60 mM KCl, 5 mM MgCl₂ and 80 mM glutathione added immediately prior to use as powder). The suspension was left rotating for 15 min at 4° C., the beads pelleted and eluted again with half the volume of elution buffer than the first time. The eluates were pooled and dialysed overnight in 20 mM Hepes buffer (pH 7.5) containing 60 mM KCl, 5 mM MgCl₂ as well as 1 mM dithiothreitol and 10% (v/v) glycerol. The protein was analysed by SDS-Page.

The method measures the ability of putative ligands to modulate the interaction between the purified bacterial expressed FXR ligand binding domain (LBD) and a synthetic biotinylated peptide based on residues 676-700 of SRC-1 (LCD2, 676-700). The sequence of the peptide used was B-CPSSHSSLTERHKILHRLLQEGSPS-COOH where the N-terminus was biotinylated (B). The ligand binding domain (LBD) of FXR was expressed as fusion protein with GST in BL-21 cells using the vector pDEST15. Cells were lysed by sonication, and the fusion proteins purified over glutathione sepharose (Pharmacia) according to the manufacturers instructions. For screening of compounds for their influence on the FXR-peptide interaction, the Perkin Elmer LANCE technology was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection Assays were done in a final volume of 25 μL in a 384 well plate, in a Tris-based buffer (20 mM Tris-HCl pH 7.5; 60 mM KCl, 5 mM $MgCl_2$; 35 ng/μL BSA), containing 20-60 ng/well recombinantly expressed FXR-LBD fused to GST, 200-600 nM N-terminally biotinylated peptide, representing SRC1 aminoacids 676-700, 200 ng/well Streptavidin-xlAPC conjugate (Prozyme) and 6-10 ng/well Eu W1024—antiGST (Perkin Elmer). DMSO content of the samples was kept at 1%. After generation of the assay mix and diluting the potentially FXR modulating ligands, the assay was equilibrated for one hour in the dark at room temperature in FIA-plates black 384 well (Greiner). The LANCE signal was detected by a Perkin Elmer VICTOR2V™ Multilabel Counter. The results were visualized by plotting the ratio between the emitted light at 665 and 615 nm. A basal level of FXR-peptide formation is observed in the absence of added ligand. Ligands that promote the complex formation induce a concentration-dependent increase in time-resolved fluorescent signal. Compounds which bind equally well to both monomeric FXR and to the FXR-peptide complex would be expected to give no change in signal, whereas ligands which bind preferentially to the monomeric receptor would be expected to induce a concentration-dependent decrease in the observed signal.

To assess the inhibitory potential of the compounds, $EC_{50}$-values were determined for example compounds as well as for comparative compounds as listed below in Table 1.

Mammalian One Hybrid (M1H) Assay

Determination of a ligand mediated Gal4 promoter driven transactivation to quantify ligand binding mediated activation of FXR was performed as follows: The cDNA part encoding the FXR ligand binding domain was cloned into vector pCMV-BD (Stratagene) as a fusion to the yeast GAL4 DNA binding domain under the control of the CMV promoter. The amino acid boundaries of the ligand binding domain were amino acids 187-472 of Database entry NM_005123 (RefSeq). The plasmid pFR-Luc (Stratagene) was used as the reporter plasmid, containing a synthetic promoter with five tandem repeats of the yeast GAL4 binding sites, driving the expression of the *Photinus pyralis* (American firefly) luciferase gene as the reporter gene. In order to improve experimental accuracy the plasmid pRL-CMV (Promega) was cotransfected. pRL-CMV contains the constitutive CMV promoter, controlling the expression of the *Renilla reniformis* luciferase. All Gal4 reporter gene assays were done in HEK293 cells (obtained from DSMZ, Braunschweig, Germany) grown in MEM with L-Glutamine and Earle's BSS supplemented with 10% fetal bovine serum, 0.1 mM nonessential amino acids, 1 mM sodium pyruvate, and 100 units Penicillin/Streptavidin per mL at 37° C. in 5% $CO_2$. Medium and supplements were obtained from Invitrogen. For the assay, $5 \times 10^5$ cells were plated per well in 96 well plates in 100 μL per well MEM without Phenol Red and L-Glutamine and with Earle's BSS supplemented with 10% charcoal/dextran treated FBS (HyClone, South Logan, Utah), 0.1 mM nonessential amino acids, 2 mM glutamine, 1 mM sodium pyruvate, and 100 units Penicillin/Streptavidin per mL, incubated at 37° C. in 5% $CO_2$. The following day the cells were >90% confluence. Medium was removed and cells were transiently transfected using 20 μL per well of a OptiMEM—polyethylene-imine-based transfection-reagent (OptiMEM, Invitrogen; Polyethyleneimine, Aldrich Cat No. 40, 827-7) including the three plasmids described above. MEM with the same composition as used for plating cells was added 2-4 h after addition of transfection mixture. Then compound stocks, prediluted in MEM were added (final vehicle concentration not exceeding 0.1%). Cells were incubated for additional 16 h before firefly and *renilla luciferase* activities were measured sequentially in the same cell extract using a Dual-Light-Luciferase-Assay system (Dyer et al., Anal. Biochem. 2000, 282, 158-161). All experiments were done in triplicates.

To assess the FXR agonistic potency of the example compounds as well as for reference compounds from WO 2000/037077, potency ranges were determined in the FRET and M1H assays as listed below in Table 1.

TABLE 1

| Compound | FRET | Gal4 (M1H) |
|---|---|---|
| GW4064 | B | B |
| Px20535 | B | B |
| Example 1 | B | B |
| Example 2 | B | B |
| Example 3 | B | B |
| Example 4 | B | B |
| Example 5a | A | B |
| Example 5b | C | C |
| Example 6 | B | B |
| Example 7 | B | B |
| Example 8 | B | B |
| Example 12 | C | B |
| Example 12b | C | C |
| Example 12c | B | B |
| Example 13 | B | B |
| Example 13a | B | B |
| Example 13b | A | A |
| Example 14 | C | B |
| Example 15 | B | C |
| Example 16 | C | B |
| Example 17 | C | C |
| Example 20 | A | A |
| Example 21 | A | A |
| Example 23 | B | A |
| Example 24 | C | C |
| Example 28 | C | C |

(A = $EC_{50}$ < 10 nM; B = 10 < $EC_{50}$ < 100 nM; C = $EC_{50}$ > 100 nM)

Determination of Pharmacokinetics in Rat, Mouse and Monkey

Compounds were applied perorally by gavage at 5 mg/kg each and by i.v. Injection at 1 mg/kg each to male 12 weeks old C57Bl/6J or Sprague Dawley rats and plasma concentrations of the test items were determined by LC-MS/MS after time points as indicated. In the case of Cynomolgus monkeys (*Macacca mulatta*), the dose was adjusted to 12 mg/kg p.o., no i.v. injection was given (FIG. 1a, 1b and Table 2).

TABLE 2

The non-compartment pharmacokinetic parameters of Example 4 and Example 12 in monkeys after oral administration at a dose level of 12 mg/kg.

| Parameter | Example 4 (Avg) | Example 4 % RSD | Example 12 (Avg) | Example 12 % RSD |
|---|---|---|---|---|
| $t_{1/2}$ (min) | 175.04 | 51.3 | 272.29 | 51.8 |
| $T_{max}$ (min) | 85.0 | 71.3 | 175.0 | 64.3 |
| $C_{max}$ (ng/mL) | 7336.54 | 56.2 | 2218.77 | 64.3 |
| $MRT_{0-t}$ (min) | 258.34 | 16.2 | 366.50 | 28.5 |
| Vz/F (L/kg) | 1.926 | 81.5 | 5.187 | 53.2 |
| CLz/F (L/min/kg) | 0.007 | 31.2 | 0.013 | 8.7 |
| $AUC_{(0-t)}$ (ng · min/mL) | 1828898.50 | 30.3 | 868263.37 | 12.1 |
| $AUC_{(0-inf)}$ (ng · min/mL) | 1844978.86 | 28.7 | 905286.64 | 12.3 |

A solution of 2.5 mg/mL of each test item was produced by diluting them in the vehicle, 0.5% Hydroxypropyl-Methylcellulose (w/v) in 20 mM phosphate buffered saline pH 7.4. The solutions were stirred overnight at room temperature and heated to 40° C. for 10 minutes, resulting in fully homogenous suspension. The application was performed by administrating the solution perorally to the mice, with an application volume of 5 mL/kg. For each time point three mice or rats were used. In case of the Cynomolgus monkeys blood samples were obtained by repeated vein puncture. Blood samples were treated with L1-heparin during collection procedure and stored on ice until centrifugation at 645 g (5 min, 4° C.). Plasma was harvested and kept at −20° C. until being assayed. To 50 μL of plasma sample 6 μL acetonitrile containing an internal standard was added. Samples were vigorously shaken and centrifuged for 10 minutes at 6000 g and 20° C. An aliquot of the particle-free supernatant was transferred to 200 μL sampler vials and subsequently subjected to LC MS/MS for quantification. Plasma concentrations at various time points were determined and are plotted against sampling times as shown in FIG. 2.

Unexpectedly, it was found that FXR agonists described herein exhibit increased plasma levels after oral administration in vivo as compared to known FXR agonists described in the prior art.

TABLE 3

Plasma concentration versus time profile of GW4064, Example 4 and Example 12 in Male Sprague Dawley Rat after intravenous administration at a dose level of 1 mg/kg GW4064 (1 mg/kg i.v.)

| Time (hr) | Mean Concentration (ng/mL) | SD | % CV |
|---|---|---|---|
| 0.083 | 405.13 | 44.9 | 11.09 |
| 0.25 | 207.52 | 17.9 | 8.62 |
| 0.50 | 123.94 | 20.3 | 16.41 |
| 1.00 | 68.33 | 15.6 | 22.82 |
| 2.00 | 24.98 | 4.7 | 18.71 |
| 4.00 | 15.00 | 7.4 | 49.50 |

Example 4

1 mg/kg i.v.

| Time (hr) | Mean Concentration (ng/mL) | SD | % CV |
|---|---|---|---|
| 0.083 | 1188.90 | 149.9 | 12.60 |
| 0.25 | 748.71 | 197.6 | 26.39 |
| 0.50 | 450.93 | 49.8 | 11.04 |
| 1.00 | 201.63 | 39.3 | 19.51 |
| 2.00 | 78.93 | 16.1 | 20.41 |
| 4.00 | 44.48 | 3.2 | 7.21 |

Example 12

1 mg/kg i.v.

| Time (hr) | Mean Concentration (ng/mL) | SD | % CV |
|---|---|---|---|
| 0.083 | 660.89 | 60.6 | 9.17 |
| 0.25 | 358.74 | 21.5 | 5.99 |
| 0.50 | 174.34 | 20.8 | 11.92 |
| 1.00 | 84.63 | 12.3 | 14.49 |
| 2.00 | 37.69 | 6.3 | 16.67 |
| 4.00 | 19.24 | 2.3 | 11.95 |

As an example, Example 4 and Example 12 showed substantially higher plasma levels in C57/bl6 and Male Sprague Dawley Rat as compared to GW4064 as depicted in FIG. 1c and Table 3.

TABLE 4

Mean Pharmacokinetic Parameters of GW4064, Example 4 and Example 12 in Male Sprague Dawley Rat after Intravenous Administration of 1 mg/kg of compounds.

| Parameter | GW4064 | Example 4 | Example 12 |
|---|---|---|---|
| Rsq | 0.9793 | 0.9537 | 0.9420 |
| *$C_{max}$ (ng/mL) | 564.93 | 1496.10 | 895.38 |
| $T_{max}$ (hr) | 0.083 | 0.083 | 0.083 |
| $t_{1/2}$ (hr) | 1.22 | 1.14 | 1.47 |
| #$AUC_{(0-8)}$ (hr * ng/mL) | 267.55 | 850.00 | 399.19 |
| $AUC_{(0-\infty)}$ (hr * ng/mL) | 293.90 | 923.32 | 440.02 |
| AUC Extrapolated (%) | 9.0 | 7.94 | 9.28 |
| $MRT_{last}$ (hr) | 0.84 | 0.83 | 0.78 |
| Vd(ml/kg) | 5977.72 | 1785.2 | 4822.49 |
| Cl(ml/hr/kg) | 3402.50 | 1083.05 | 2272.63 |

*Co for Intravenous;
AUC (0-4) (hr * ng/mL) for i.v.

TABLE 5

Mean Pharmacokinetic Parameters of Example 4 and Example 12 in Male Sprague Dawley Rat after Oral Administration of 5 mg/kg of compounds.

| Parameter | GW4064 | Example 4 | Example 12 |
|---|---|---|---|
| Rsq | n.d. | 0.9720 | 0.9036 |
| Dose (mg/kg) | n.d. | 5 | 5 |
| $C_{max}$ (ng/mL) | n.d. | 93.09 | 210.12 |
| $T_{max}$ (hr) | n.d. | 0.50 | 0.50 |
| $t_{1/2}$ (hr) | n.d. | 4.08 | 2.78 |
| $AUC_{(0-8)}$ (hr * ng/mL) | n.d. | 286.55 | 569.74 |
| $AUC_{(0-\infty)}$ (hr * ng/mL) | n.d. | 406.44 | 680.88 |
| AUC Extrapolated (%) | n.d. | 33.93 | 16.32 |
| $MRT_{last}$ (hr) | n.d. | 2.97 | 2.42 |
| Vd(ml/kg) | n.d. | 72491.39 | 29444.42 |
| Cl(ml/hr/kg) | n.d. | 12302.06 | 7343.42 |
| Absolute Bioavailability (%) | n.d. | 8.8 | 30.95 |

The absolute oral bioavailability for Example 4 is found to be 8.8% and for Example 12 30.95%.

Determination of Lipid Lowering Effects in db/db Mice

Compounds were applied perorally by gavage at 2×5 mg/kg each to C57BLKS lepr$^{-/-}$ db/db mice starting at the age of 12 weeks. Animals have been set on a High-Fat Diet (ssniff EF R/M 12330 with 59% (kcal) fat from Ssniff, Soest, Germany) for two weeks prior to start of gavage. Baseline blood was taken by retroorbital bleeding. Blood samples were treated with L1-heparin during collection procedure and stored on ice until centrifugation at 645 g (5 min, 4° C.). Plasma was harvested and kept at −20° C. until being assayed. Total triglycerides and total cholesterol were measured in a 3 μL aliquot of plasma using commercial kits LabAssay™ Triglyceride (Code No 290-63701) and LabAssay™ Cholesterol (Code No 294-65801) from Wako Diagnostics (Neuss, Germany). To assess the pharmacological effect of the compounds, mean plasma triglycerides and cholesterol values per dosing group were compared between baseline and after 8 weeks of treatment.

Whereas GW4064 treatment resulted in a non-significant reduction of −6% against vehicle in fasting blood glucose after 3 days of dosing at 2×5 mg/kg/day, treatment with Example 5 resulted in a lowering of −16% against vehicle in this setting. Moreover, Example 5 showed a significant reduction in plasma lipids after 3 days of dosing at 2×5 mg/kg/day with a −24.0% reduction in total cholesterol and a −24.2% reduction in total triglycerides as compared to vehicle control.

In Vivo Activity of Selected Compounds in Animal Experiments

Figure 4:
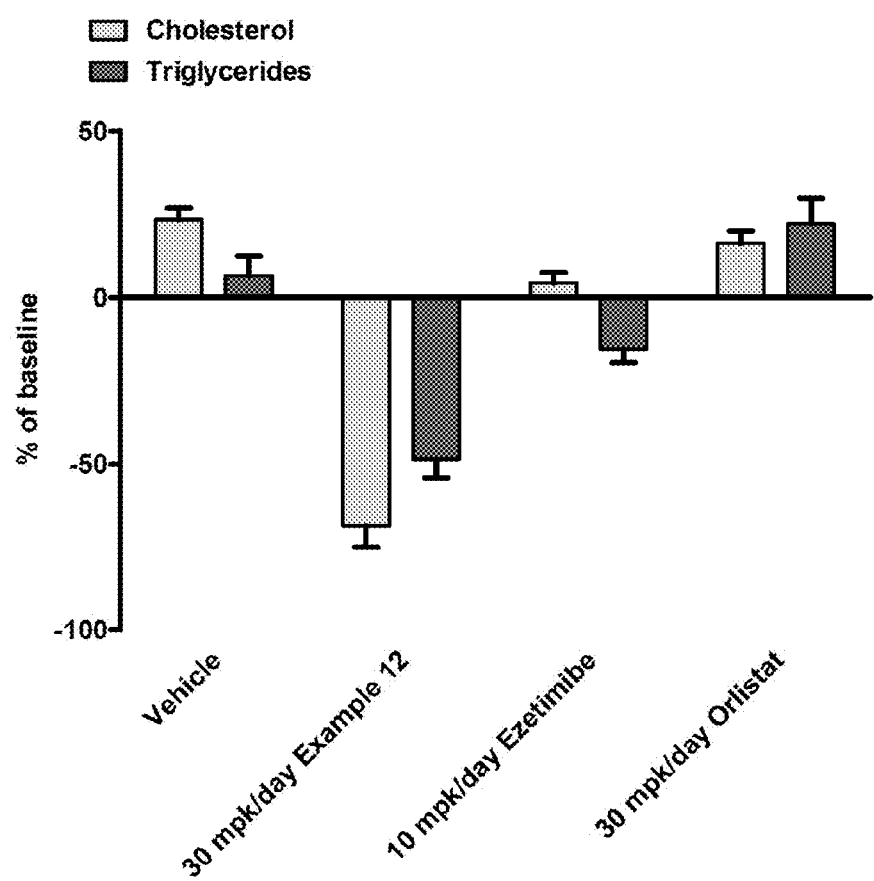
FIG. 4 shows the effects on plasma cholesterol and triglycerides after 8 weeks of high-fat diet (HFD) in the presence or absence of compounds.
Figure 5:
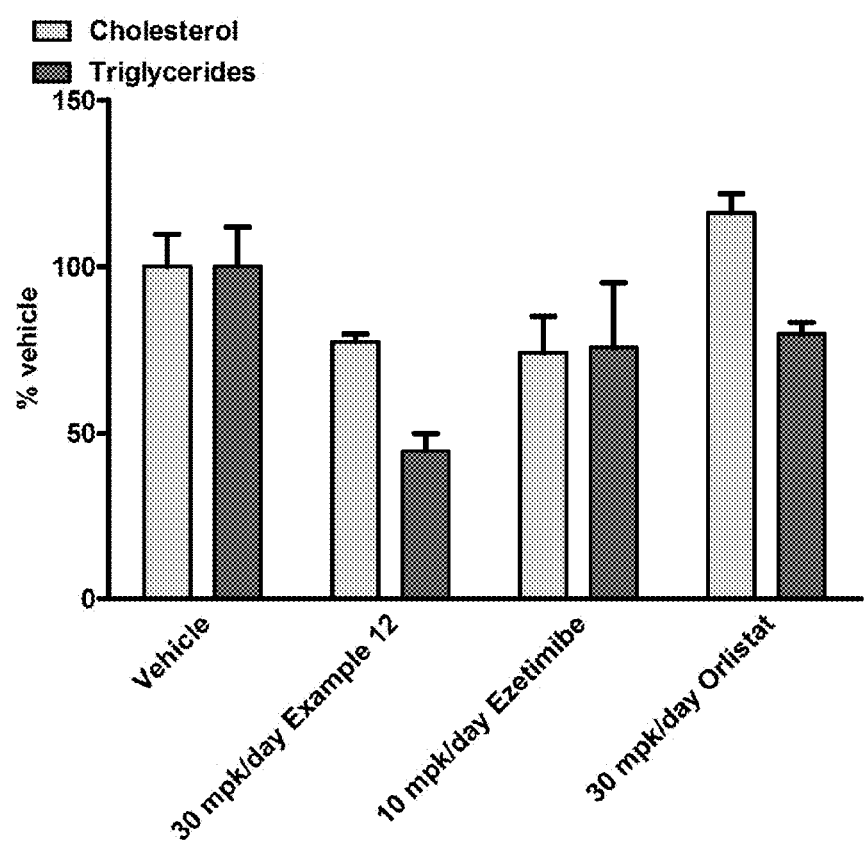
FIG. 5 shows liver cholesterol and triglyceride content after 8 weeks of high-fat diet (HFD in the presence or absence of compounds.

C57/bI6 mice (Elevage Janvier, France) at the age of 8 weeks were put on a high fat diet (60% kcal from fat, Sniff, Soest, Germany, Cat. No. E15771-30 (Mod. Surwit)+0.5 cholesterol (Sigma-Aldrich, Germany) added) for 4 weeks. Baseline blood samples were taken after overnight starvation and fasting plasma glucose was determined using a Roche Accucheck device. In parallel L1-heparin plasma was generated for the determination of baseline total triglyceride (TG) and total cholesterol (TC) levels. Animals were maintained on the HFD+0.5% cholesterol diet for 8 weeks and weekly blood samples were taken for the monitoring of plasma TG and TC levels using routine enzymatic analysis kits (WAKO Diagnostics, Neuss, Germany). The test compounds were dissolved in 100% palm fat and then mixed into molten food for an estimated daily uptake of 30 mg/kg based on averaged food consumption in the 4 weeks HFD adaptation period. FIGS. 4 and 5 show the development of TG and TC values.

After sacrification of the mice, liver triglycerides and cholesterol was determined using the method of Folch (J. Folch et al. "A simple method for the isolation and purification of total lipides from animal tissues." J. Biol. Chem. 1957, 226, 497-509) with modifications. In brief, frozen liver tissues were homogenized and extracted twice with Hexane/2-Propanol (3:2) (30 mg tissue/1 mL organic solvent). The organic layer was removed and dried. The resulting pellet was dissolved in 0.5 mL phosphate buffered saline containing 0.1% (w/v) SDS. Triglyceride and cholesterol content were measured by specific enzymatic reagents (Wako Diagnostics, Neuss, Germany).

Figure 6:
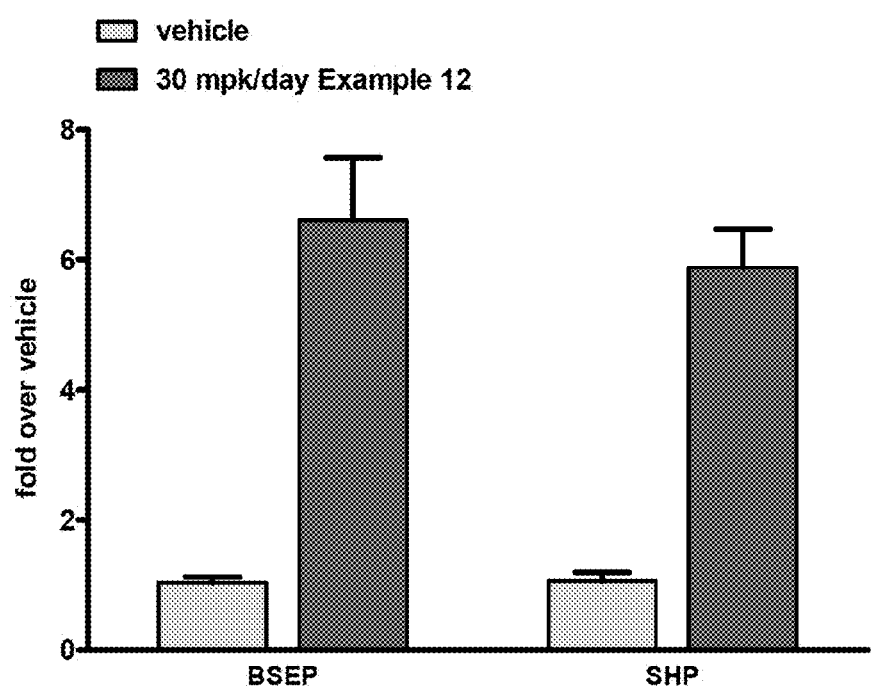
FIG. 6 shows the FXR target gene induction in mouse liver.

RNA was isolated using RNAzol RT Reagent (Fermentas) and mRNA levels determined by quantitative reverse-transcription polymerase chain reaction (qRT-PCR) using Absolute QPCR Rox Mix (Invitrogen) and a real-time PCR machine from Applied Biosystems (CA). Primer and probe sequences (5' to 3') used were: SHP, Fwd CACCAGACTC-CATTCCACG; Rev CTACCCTCAAGAACATTCCAGG; probe 56-FAM/CAGTGATGTCAACGTCTCCCATGATAG and BSEP, Fwd CTGACTGTTGAT AGGCGATGG; Rev CCTCATACGGAAACCCAAGATC; probe 56-FAM/ATG-GCT ACCTCAGCACTGGACAAT. All samples were run in duplicate. Gene expression (FIG. 6) was expressed in arbitrary units and normalized relative to the housekeeping gene TATA box binding protein (TBP, Fwd AAGAAAGGGAGA ATCATGGACC; Rev GAGTAAGTCCTGTGCCGTAAG; probe:56-FAM/CCTGAGCAT/Zen/AAGGTGGAAGGCT GTT). The gene expression of BSEP and SHP was 6-fold higher in mice treated with Example 12.

Determination of UV Photostability

The compounds of interest were dissolved using ethanol and their UV spectrum was analyzed to determine their $\lambda_{max}$ to establish an irradiation wavelength to be used in the study (see FIG. 2). The best wavelength for testing the UV stability of the —CH═CH— double bond was determined to be 254 nm. Further material of the compounds was then dissolved in deuterated ethanol and the $^1$H NMRs (400 MHz) analyzed (T=0). Each sample was then recovered from the NMR tube and subjected to UV irradiation (254 nm) for 4 h, 15 h and 70 h. At the respective timepoints the individual samples were re-analyzed by $^1$H NMR and the signal for the —CH═CH— protons evaluated to assess the percent of remaining intact double bond. Other changes in the chemical shift signals were also analyzed for further changes on the overall structure of the molecules.

Unlike Example 4 (racemic 3-(2-(2-chloro-4-((5-cyclopropyl-3-(2,6-dichlorophenyl)isoxazol-4-yl)methoxy)phenyl)cyclopropyl)benzoic acid), compounds GW4064 and PX20535 underwent major changes in the $^1$H NMR spectrum after prolonged UP irradiation. Based on the relative integration of the $^1$H NMR signals, less than 30% of the GW4064 and 45% of the PX20535 are still present in the mixture which suggests in turn, that 70% of the GW4064 was decayed after 70 h. Example 4 seemed to be inert to the 70 h of UV irradiation at lambda=254 nm (see FIG. 3a-l).

Figure 3A:
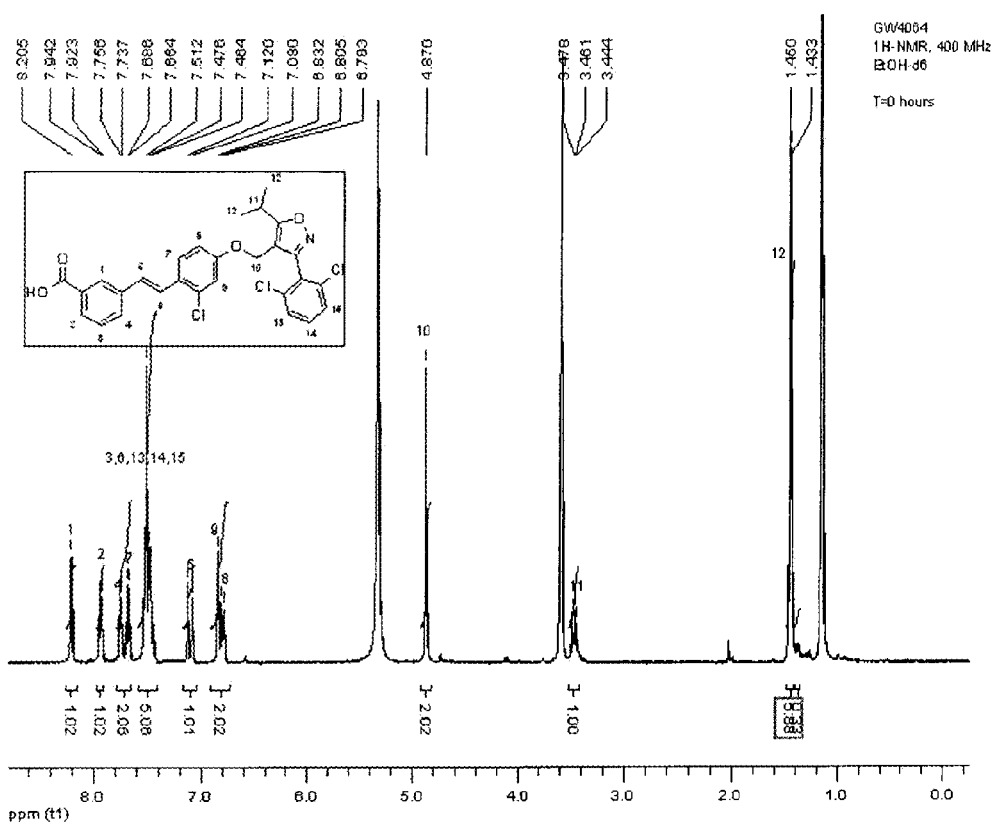
FIG. 3a shows the $^1$H-NMR spectra of GW4064 at t=0 h prior to UV irradiation at 254 nm.
Figure 3B:
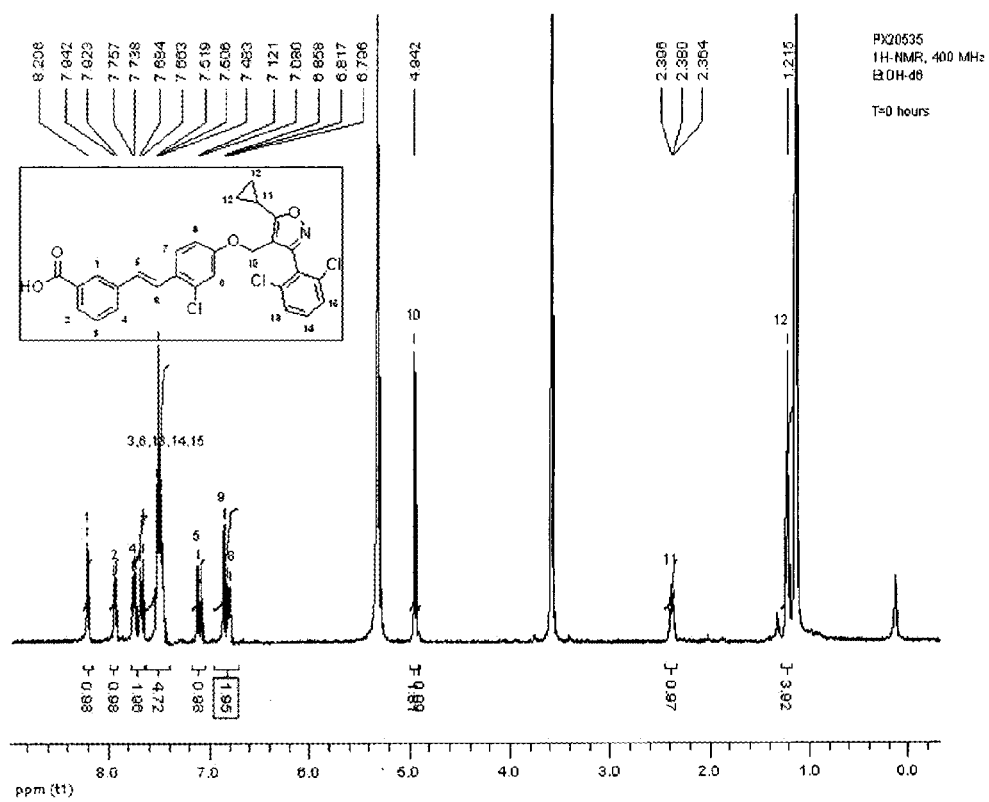
FIG. 3b shows the $^1$H-NMR spectra of Px20535 at t=0 h prior to UV irradiation at 254 nm.
Figure 3C:
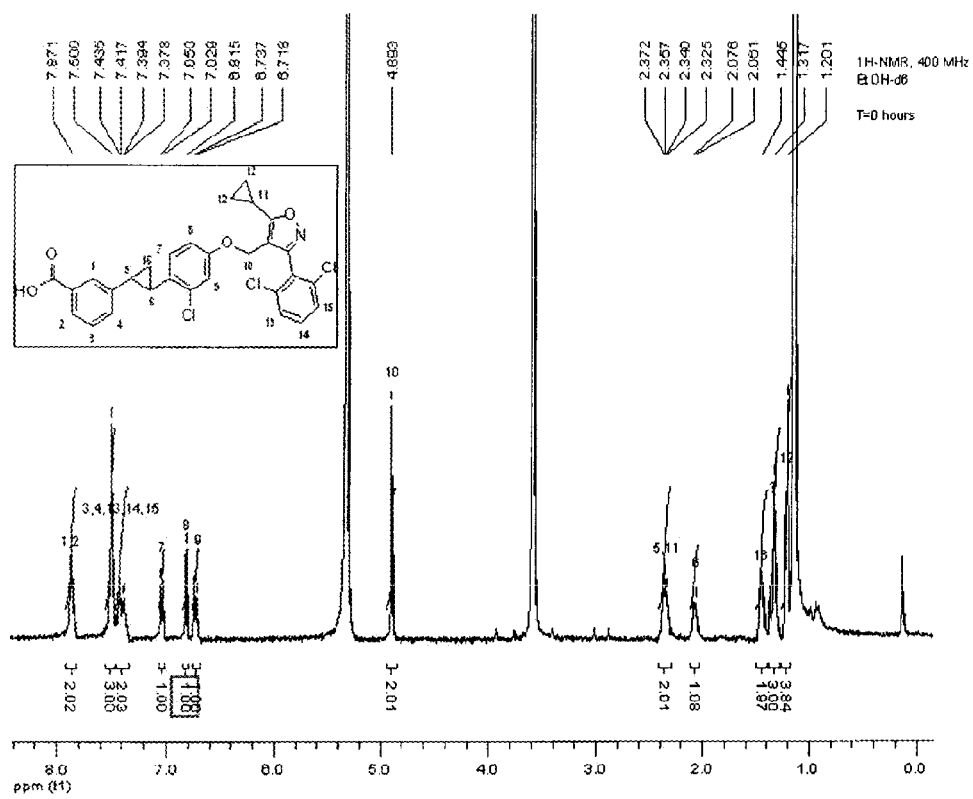
FIG. 3c shows the $^1$H-NMR spectra of Example 4 at t=0 h prior to UV irradiation at 254 nm.
Figure 3D:
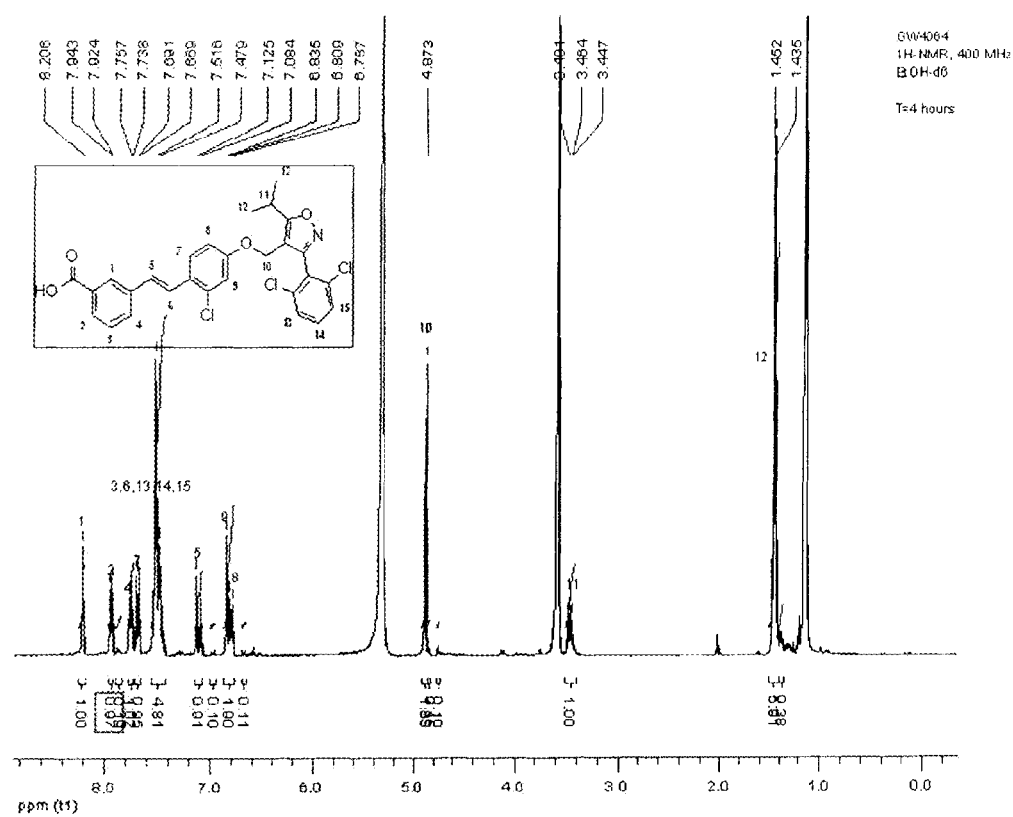
FIG. 3d shows the $^1$H-NMR spectra of GW4064 at t=4 h of UV irradiation at 254 nm.
Figure 3E:
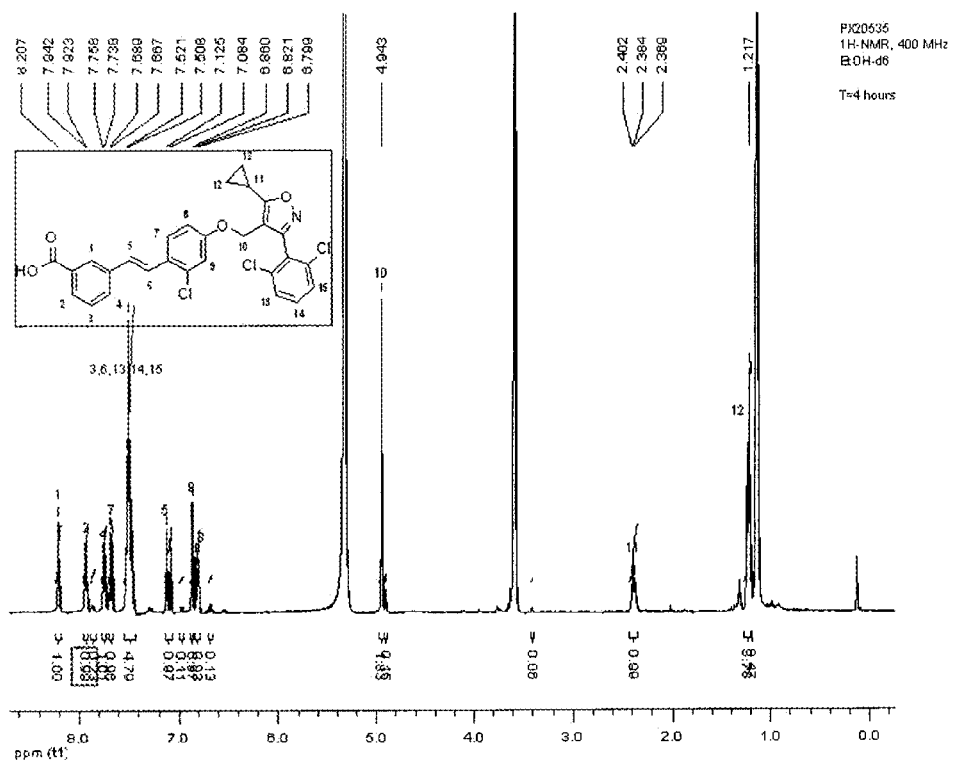
FIG. 3e shows the $^1$H-NMR spectra of Px20535 at t=4 h of UV irradiation at 254 nm.
Figure 3F:
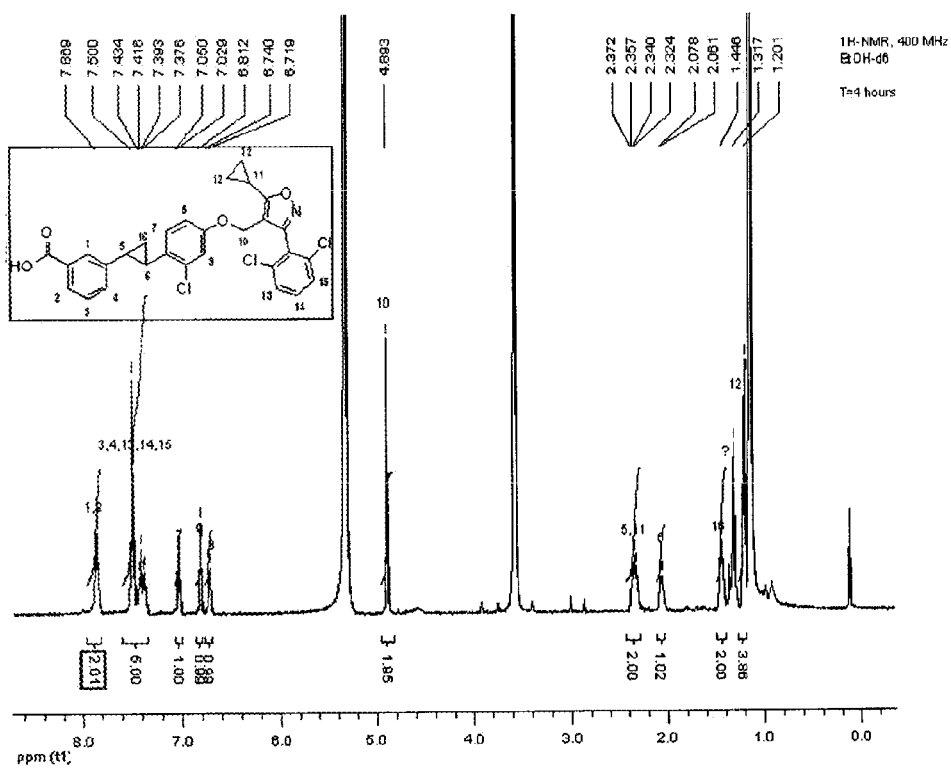
FIG. 3f shows the $^1$H-NMR spectra of Example 4 at t=4 h of UV irradiation at 254 nm.
Figure 3G:
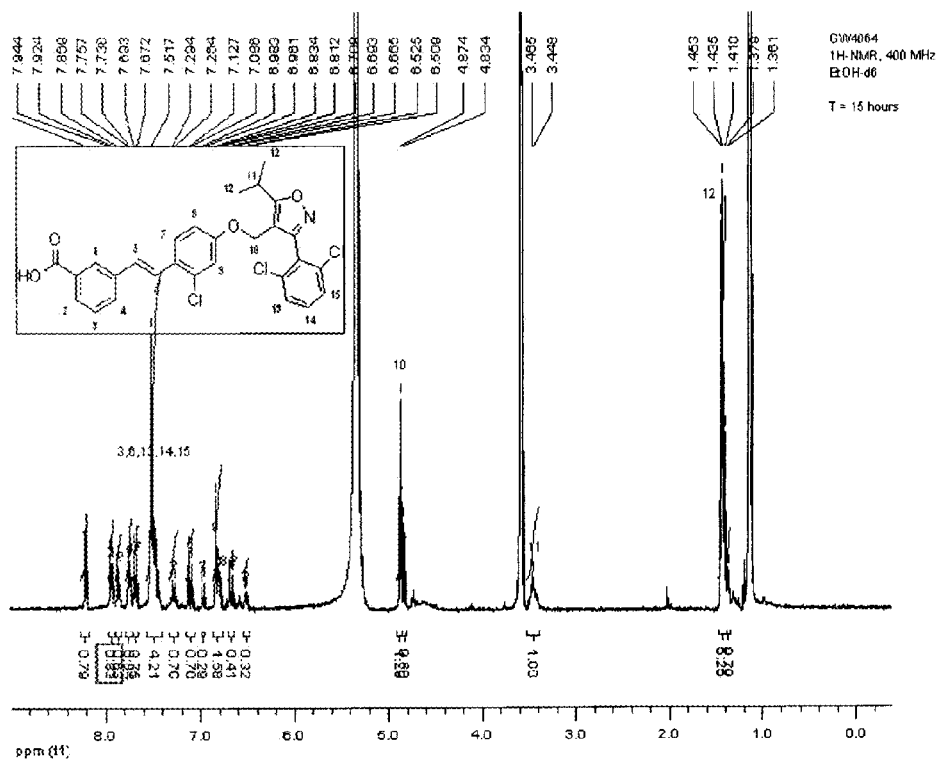
FIG. 3g shows the $^1$H-NMR spectra of GW4064 at t=15 h of UV irradiation at 254 nm.
Figure 3H:
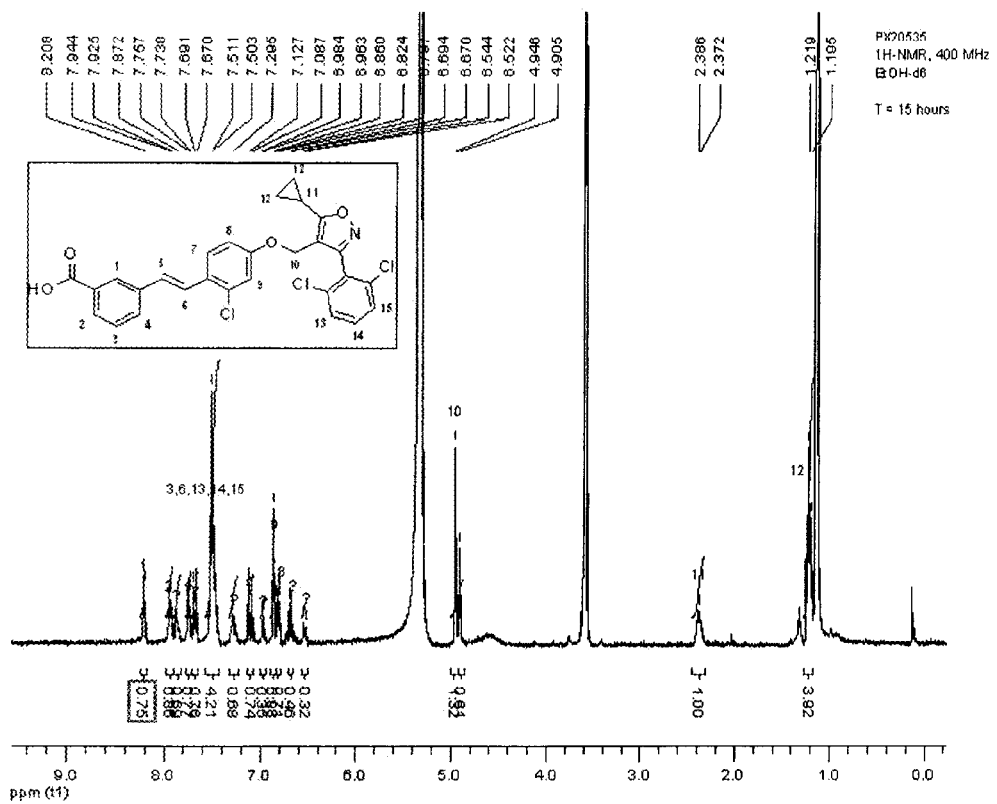
FIG. 3h shows the $^1$H-NMR spectra of Px20535 at t=15 h of UV irradiation at 254 nm.
Figure 3I:
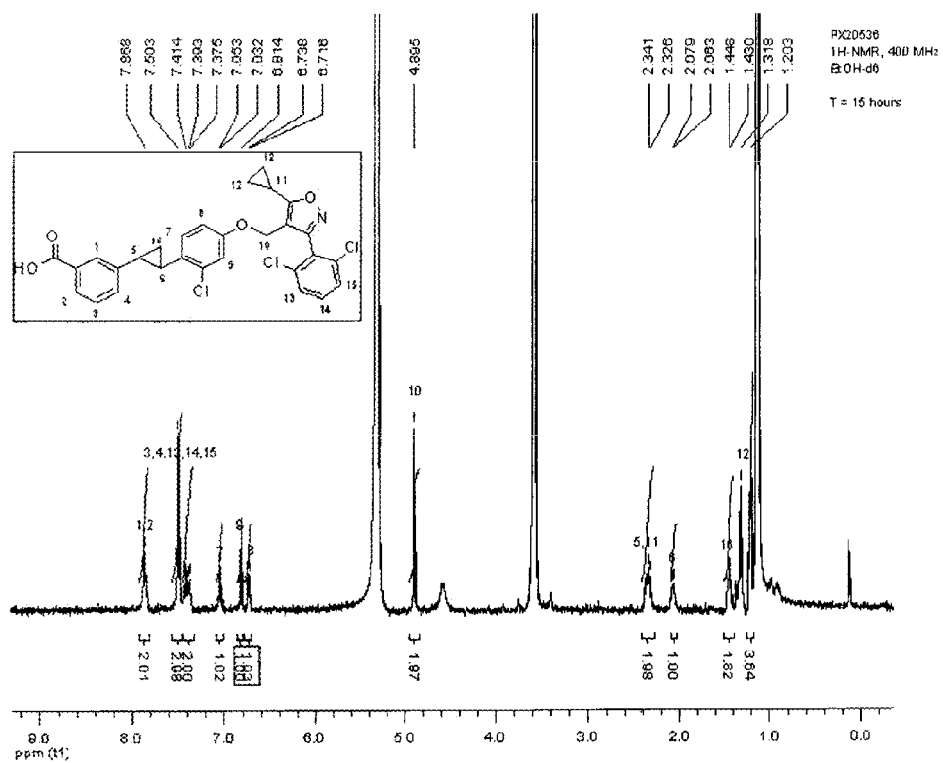
FIG. 3i shows the $^1$H-NMR spectra of Example 4 at t=15 h of UV irradiation at 254 nm.
Figure 3J:
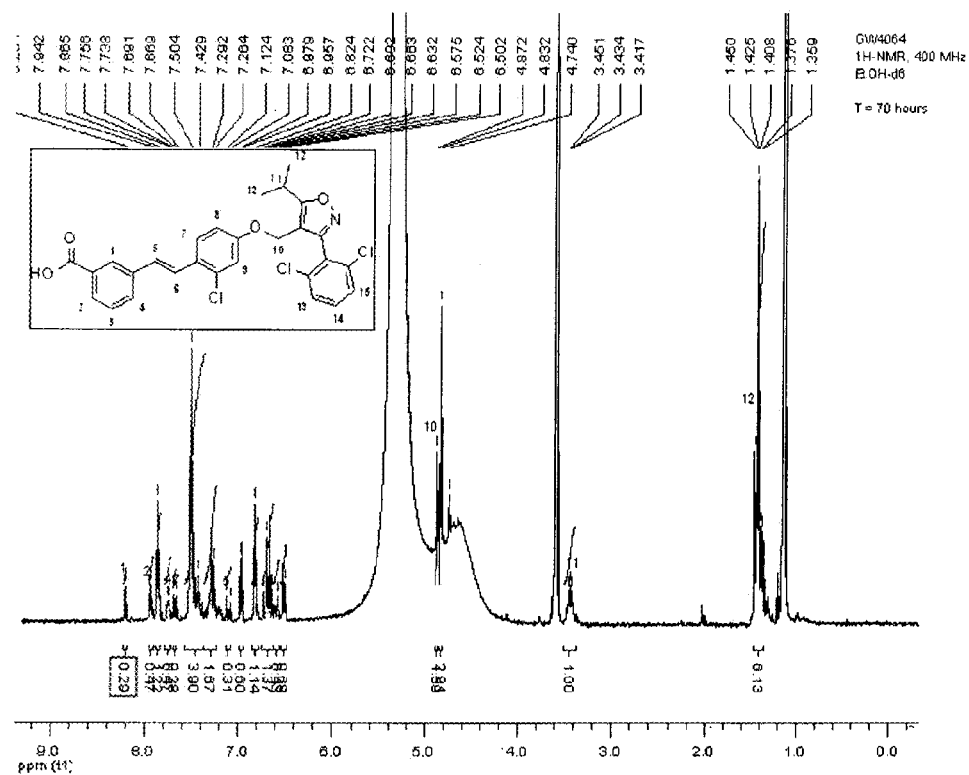
FIG. 3j shows the $^1$H-NMR spectra of GW4064 at t=70 h of UV irradiation at 254 nm.
Figure 3K:
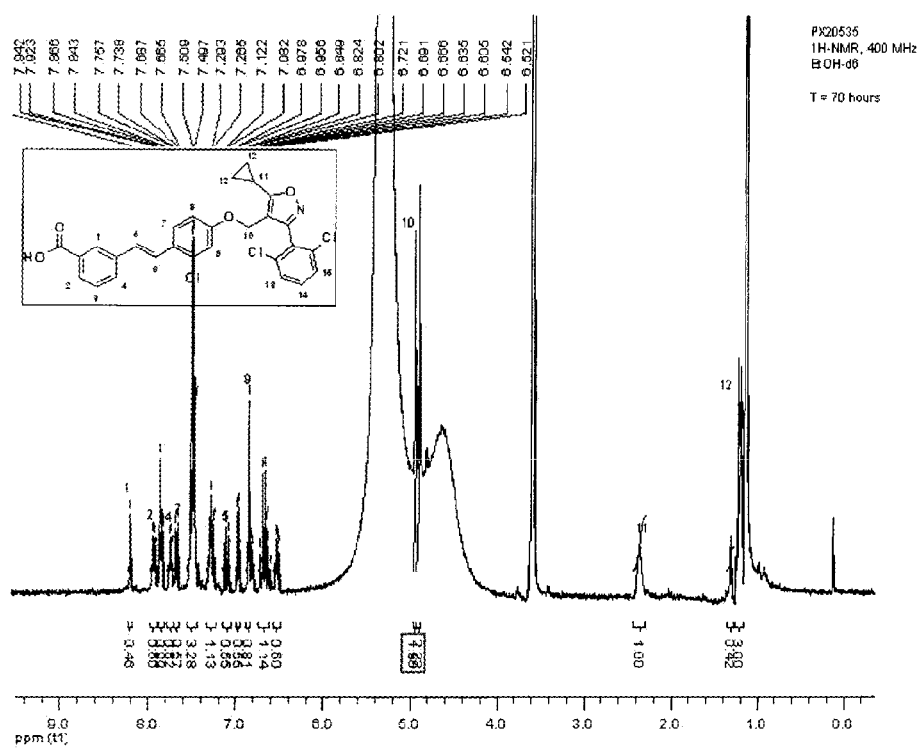
FIG. 3k shows the $^1$H-NMR spectra of Px20535 at t=70 h of UV irradiation at 254 nm.
Figure 3I:
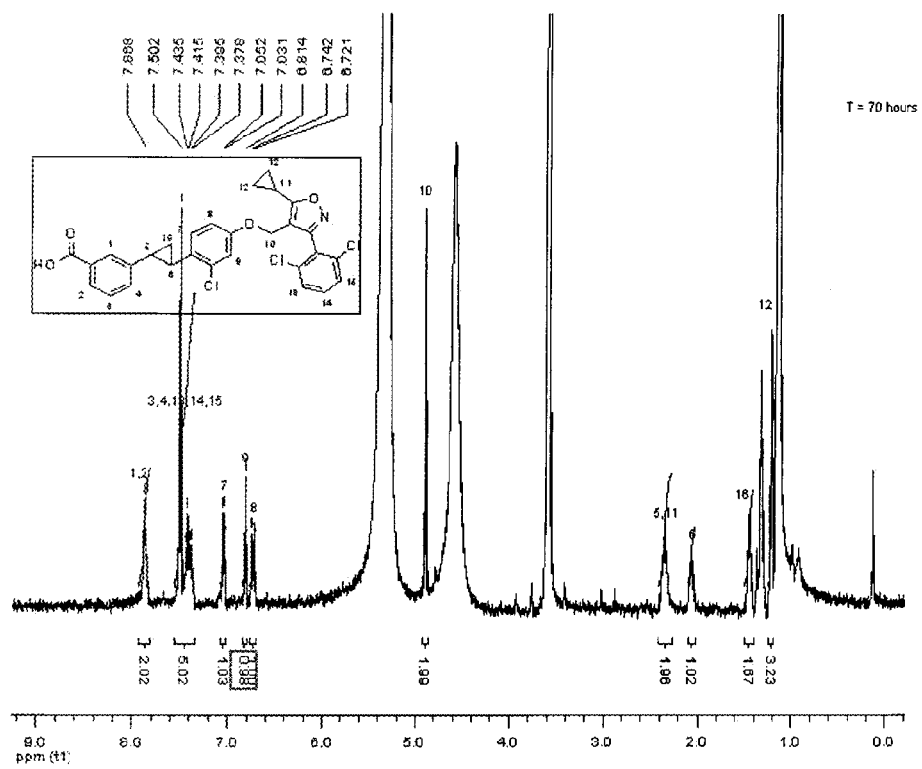
Figure 3M:
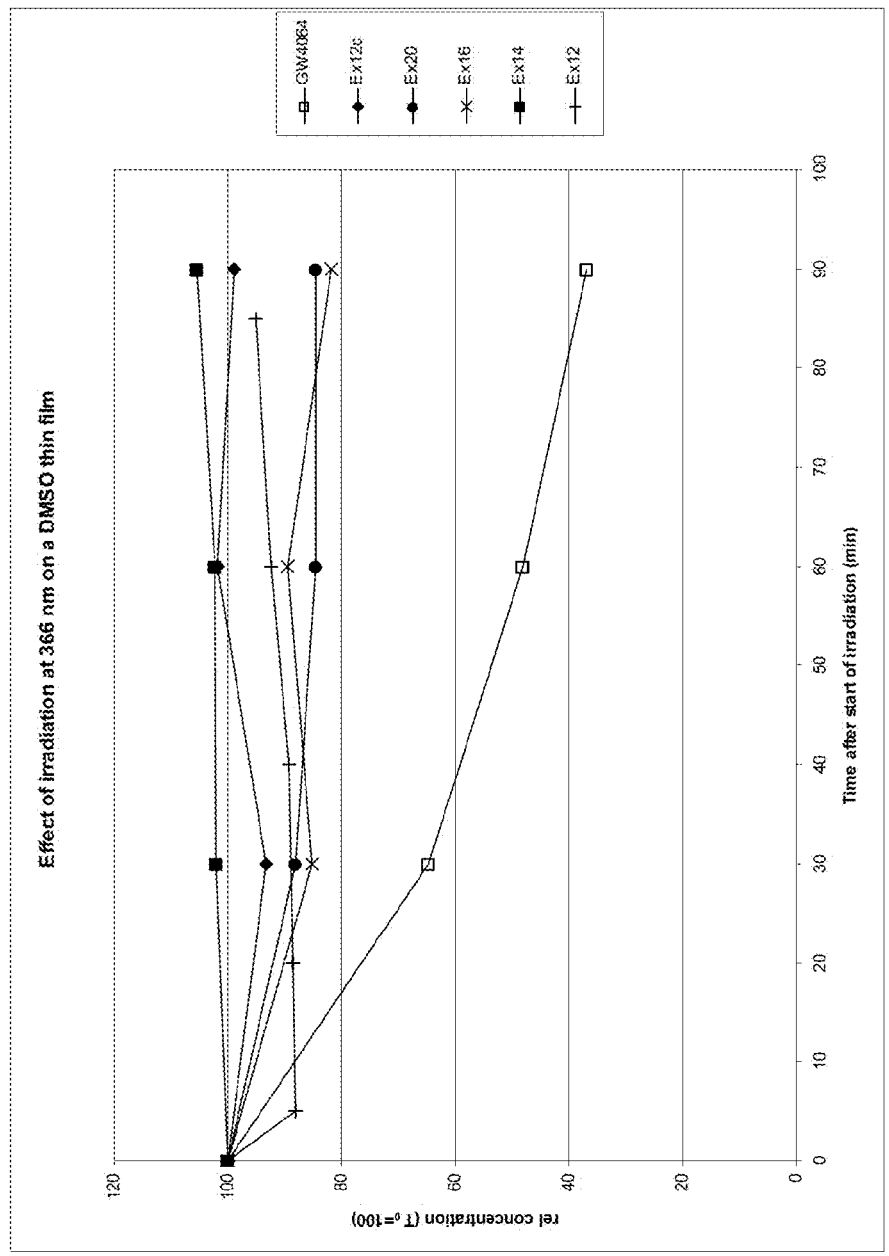
FIG. 3m shows the comparative UV-stabilities, effect of irradiation at λ=366 nm on a DMSO thin film.

A different, more rapid experimental setup was used to investigate a broader set of compounds in comparison to GW4064. The substances were dissolved in reagent grade DMSO (99.5%, Karl Roth) at a concentration of 250 μM. DMSO solution was spread over a silica glass slide to a depth of approximately 2 mm and irradiated using a UV lamp set to 366 nM emission (Benda Instruments, Wiesloch Germany) using an 8 W tube set approximately 2.5 cm from the target materials. The solution was sampled prior to irradiation (T=0 min) and at various intervals thereafter. Stocks and samples were maintained in foil wrapped tubes out of direct light. Samples were injected (2 μL) directly onto a LCMS System for analysis without any further preparation. The results are depicted in FIG. 3m and show the higher photostability of compounds of the present invention (Examples 12, 12c, 20, 16, 14) compared to the stilbene moiety containing GW4064.

The invention claimed is:

1. A compound according to the following formula (1), or an enantiomer, diastereomer, tautomer, solvate, prodrug or pharmaceutical acceptable salt thereof:

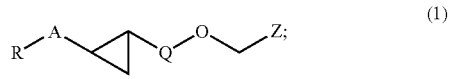

(1)

wherein:
R is selected from the group consisting of COOR$_6$, CONR$_7$R$_8$, tetrazolyl and H, with R$_6$ independently selected from the group consisting of H and lower alkyl, and R$_7$ and R$_8$ independently from each other selected from the group consisting of H, lower alkyl, C$_{1-6}$ haloalkyl, C$_{1-6}$ alkylene-R$_9$, and SO$_2$—C$_{1-6}$alkyl wherein R$_9$ is selected from the group consisting of COOH, OH, and SO$_3$H;

A is selected from the group consisting of phenyl, pyridyl, pyrazolyl, indolyl, thienyl, benzothienyl, indazolyl, benzisoxazolyl, benzofuranyl, benzotriazolyl, furanyl, benzothiazolyl, and thiazolyl, each optionally substituted with one or two groups independently selected from the group consisting of OH, lower alkyl, lower cycloalkyl, and halogen;

Q is selected from the group consisting of phenyl, pyridyl, thiazolyl, thiophenyl, and pyrimidyl, each optionally substituted with one or two groups independently selected from the group consisting of lower alkyl, halogen and $CF_3$; and

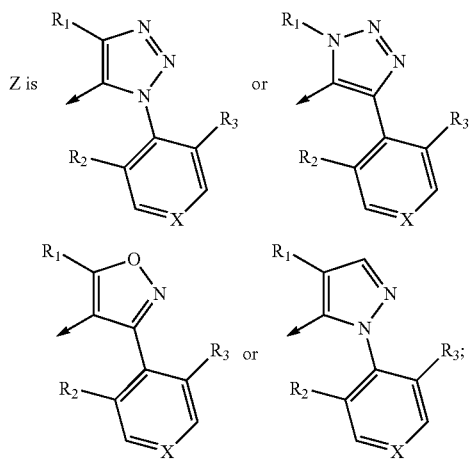

wherein:

X is CH, N or NO;

$R_1$ is selected from the group consisting of hydrogen, $C_1$-$C_3$ alkyl, $C_3$-$C_6$ cycloalkyl, and $C_4$-$C_5$ alkylcycloalkyl, wherein $C_{1-3}$ alkyl is optionally substituted with 1 to 3 substituents independently selected from halogen, hydroxy or $C_{1-6}$ alkoxy; and $R_2$ and $R_3$ are independently selected from the group consisting of hydrogen, $C_1$-$C_3$ alkyl, $C_1$-$C_3$ haloalkyl, $C_1$-$C_3$ alkoxy, $C_1$-$C_3$ haloalkoxy and halogen.

2. The compound of claim 1 wherein:

R is selected from the group consisting of $COOR_6$, $CONR_7R_8$, tetrazolyl and H, with $R_6$, $R_7$ and $R_8$ independently selected from the group consisting of H and lower alkyl;

A is selected from the group consisting of phenyl, pyridyl, indolyl, thienyl, benzothienyl, indazolyl, benzisoxazolyl, benzofuranyl, benzotriazolyl, furanyl, benzothiazolyl, and thiazolyl, each optionally substituted with one or two groups independently selected from the group consisting of OH, lower alkyl and lower cycloalkyl;

Q is selected from the group consisting of phenyl, pyridyl, thiazolyl, thiophenyl, and pyrimidyl, each optionally substituted with one or two groups independently selected from the group consisting of lower alkyl, halogen and $CF_3$;

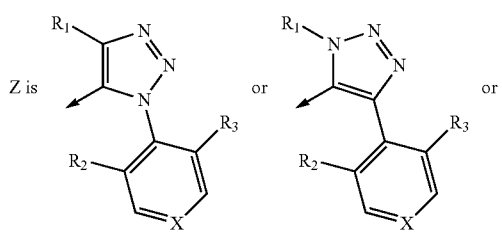

wherein

X is CH, N or NO;

$R_1$ is selected from the group consisting of hydrogen, $C_1$-$C_3$ alkyl, $C_1$-$C_3$ alkyl substituted with 1 to 3 halogens, $C_3$-$C_6$ cycloalkyl, and $C_4$-$C_5$ alkylcycloalkyl;

$R_2$ and $R_3$ are independently selected from the group consisting of hydrogen, $C_1$-$C_3$ alkyl, $C_1$-$C_3$ haloalkyl, $C_1$-$C_3$ alkoxy, $C_1$-$C_3$ haloalkoxy and halogen.

3. The compound of claim 1, having the following structure:

wherein $X_1$ is CH or N;

$R_4$ and $R_5$ are independently selected from the group consisting of H, lower alkyl, halogen and $CF_3$;

R-A is selected from:

$R_1$ is selected from the group consisting of isopropyl and cyclopropyl;

$R_2$ and $R_3$ are independently selected from the group consisting of halogen, $C_1$-$C_3$ alkyl, methoxy and trifluoromethoxy.

4. The compound of claim 1, wherein

A is phenyl;

Q is phenyl optionally substituted as defined in claim 1;

X is CH;

$R_1$ is cycloalkyl; and $R_2$ and $R_3$ each are halogen.

5. The compound of claim 1 selected from:

3-(2-(2-chloro-4-((5-cyclopropyl-3-(2,6-dichlorophenyl)isoxazol-4-yl)methoxy)phenyl)cyclopropyl)benzoic acid;

(−)-3-(2-(2-chloro-4-((5-cyclopropyl-3-(2,6-dichlorophenyl)isoxazol-4-yl)methoxy)phenyl)cyclopropyl)benzoic acid;

(+)-3-(2-(2-chloro-4-((5-cyclopropyl-3-(2,6-dichlorophenyl)isoxazol-4-yl)methoxy)phenyl)cyclopropyl)benzoic acid;

3-(2-(2-chloro-4-((3-(2,6-dichlorophenyl)-5-isopropyl-isoxazol-4-yl)methoxy)phenyl)cyclopropyl)benzoic acid;

3-(2-(2-chloro-4-((5-cyclopropyl-3-(3,5-dichloropyridin-4-yl)isoxazol-4-yl)methoxy)phenyl)cyclopropyl)benzoic acid;

4-(4-((4-(2-(3-carboxyphenyl)cyclopropyl)-3-chlorophenoxy)methyl)-5-cyclopropylisoxazol-3-yl)-3,5-dichloropyridine 1-oxide;

3-(2-(2-chloro-4-((1-(2,6-dichlorophenyl)-4-isopropyl-1H-1,2,3-triazol-5-yl)methoxy)phenyl)cyclopropyl)benzoic acid;

4-((4-(2-(6-(1H-tetrazol-5-yl)pyridin-3-yl)cyclopropyl)-3-chlorophenoxy)methyl)-5-cyclopropyl-3-(2,6-dichlorophenyl)isoxazole; or 5-(2-(2-chloro-4-((5-cyclopropyl-3-(2,6-dichlorophenyl)isoxazol-4-yl)methoxy)phenyl)cyclopropyl)picolinic acid.

6. The compound of claim 1 selected from:

3-(2-(6-((5-cyclopropyl-3-(2,6-dichlorophenyl)isoxazol-4-yl)methoxy)-2-(trifluoromethyl)pyridin-3-yl)cyclopropyl)benzoic acid;

4-(2-(2-chloro-4-((5-cyclopropyl-3-(2,6-dichlorophenyl)isoxazol-4-yl)methoxy)phenyl)cyclopropyl)benzoic acid;

1,3-dihydroxy-2-(hydroxymethyl)propan-2-aminium 4-(2-(2-chloro-4-((5-cyclopropyl-3-(2,6-dichlorophenyl)isoxazol-4-yl)methoxy)phenyl)cyclopropyl)benzoate;

(+)-4-(2-(2-chloro-4-((5-cyclopropyl-3-(2,6-dichlorophenyl)isoxazol-4-yl)methoxy)phenyl)cyclopropyl)benzoic acid;

(−)-4-(2-(2-chloro-4-((5-cyclopropyl-3-(2,6-dichlorophenyl)isoxazol-4-yl)methoxy)phenyl)cyclopropyl)benzoic acid;

6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid;

(+)-6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid;

(−)-6-(2-(2-chloro-4-((5-cyclopropyl-3-(2,6-dichlorophenyl)isoxazol-4-yl)methoxy)phenyl)cyclopropyl)-1-methyl-1H-indazole-3-carboxylic acid;

4-(2-(2-chloro-4-((5-cyclopropyl-3-(2,6-dichlorophenyl)isoxazol-4-yl)methoxy)phenyl)cyclopropyl)-N-(methylsulfonyl)benzamide;

2-(4-(2-(2-chloro-4-((5-cyclopropyl-3-(2,6-dichlorophenyl)isoxazol-4-yl)methoxy)phenyl)cyclopropyl)benzamido)ethanesulfonic acid;

4-((4-(2-(4-(1H-tetrazol-5-yl)phenyl)cyclopropyl)-3-chlorophenoxy)methyl)-5-cyclopropyl-3-(2,6-dichlorophenyl)isoxazole;

4-(2-(2-chloro-4-((3-(2,6-dichlorophenyl)-5-(2-hydroxypropan-2-yl)isoxazol-4-yl)methoxy)phenyl)cyclopropyl)benzoic acid;

5-(2-(2-chloro-4-((5-cyclopropyl-3-(2,6-dichlorophenyl)isoxazol-4-yl)methoxy)phenyl)cyclopropyl)-1-isopropyl-1H-pyrazole-3-carboxylic acid;

6-(2-(2-chloro-4-((5-cyclopropyl-3-(2,6-dichlorophenyl)isoxazol-4-yl)methoxy)phenyl)cyclopropyl)-1-isopropyl-1H-indazole-3-carboxylic acid;

4-(2-(2-chloro-4-((5-cyclopropyl-3-(2,6-dichlorophenyl)isoxazol-4-yl)methoxy)phenyl)cyclopropyl)-2,6-dimethylbenzoic acid;

4-(2-(2-chloro-4-((5-cyclopropyl-3-(2-(trifluoromethoxy)phenyl)isoxazol-4-yl)methoxy)phenyl)cyclopropyl)benzoic acid;

(+)-2-(4-(2-(2-chloro-4-((5-cyclopropyl-3-(2,6-dichlorophenyl)isoxazol-4-yl)methoxy)phenyl)cyclopropyl)benzamido)ethanesulfonic acid;

(−)-2-(4-(2-(2-chloro-4-((5-cyclopropyl-3-(2,6-dichlorophenyl)isoxazol-4-yl)methoxy)phenyl)cyclopropyl)benzamido)ethanesulfonic acid;

2-(4-(2-(2-chloro-4-((5-cyclopropyl-3-(2,6-dichlorophenyl)isoxazol-4-yl)methoxy)phenyl)cyclopropyl)benzamido)acetic acid; or 4-(2-(2-chloro-4-((4-(2,6-dichlorophenyl)-1-isopropyl-1H-1,2,3-triazol-5-yl)methoxy)phenyl)cyclopropyl)benzoic acid.

7. A pharmaceutical composition comprising a compound of claim 1, or an enantiomer, diastereomer, tautomer, solvate, prodrug or pharmaceutical acceptable salt thereof, and a pharmaceutically acceptable carrier.

8. A method for the treatment of a disease or condition mediated by FXR in a mammal, wherein the method comprises administering to the mammal a compound of claim 1, or an enantiomer, diastereomer, tautomer, solvate, prodrug or pharmaceutical acceptable salt thereof, or a pharmaceutical composition of claim 7, wherein the disease or condition is selected from extrahepatic cholestatic conditions, liver fibrosis resulting from chronic cholestatic conditions or acute intrahepatic cholestatic conditions, or cholestatic or fibrotic effects that are associated with alcohol-induced cirrhosis or with viral-borne forms of hepatitis.

9. A method for the treatment of a disease or condition mediated by FXR in a mammal, wherein the method comprises administering to the mammal a compound of claim 1, or an enantiomer, diastereomer, tautomer, solvate, prodrug or pharmaceutical acceptable salt thereof, or a pharmaceutical composition of claim 7, wherein the disease or condition is selected from non-alcoholic fatty liver disease or non-alcoholic steatohepatitis.

* * * * *